(12) United States Patent
Courtney et al.

(10) Patent No.: US 9,428,464 B2
(45) Date of Patent: Aug. 30, 2016

(54) KYNURENINE-3-MONOOXYGENASE INHIBITORS, PHARMACEUTICAL COMPOSITIONS, AND METHODS OF USE THEREOF

(75) Inventors: Stephen Martin Courtney, Oxfordshire (GB); Michael Prime, Oxfordshire (GB); William Mitchell, Lincolnshire (GB); Christopher John Brown, Abingdon (GB); Paula C. De Aguiar Pena, Oxfordshire (GB); Peter Johnson, Oxfordshire (GB); Celia Dominguez, Los Angeles, CA (US); Leticia M. Toledo-Sherman, Santa Monica, CA (US); Ignacio Muñoz-Sanjuan, West Hollywood, CA (US)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 14/241,699

(22) PCT Filed: Aug. 28, 2012

(86) PCT No.: PCT/US2012/052617
§ 371 (c)(1),
(2), (4) Date: May 28, 2014

(87) PCT Pub. No.: WO2013/033068
PCT Pub. Date: Mar. 7, 2013

(65) Prior Publication Data
US 2014/0329795 A1    Nov. 6, 2014

Related U.S. Application Data

(60) Provisional application No. 61/529,003, filed on Aug. 30, 2011.

(51) Int. Cl.
*C07D 239/52* (2006.01)
*A61K 31/506* (2006.01)
*C07D 239/28* (2006.01)
*C07D 403/12* (2006.01)
*C07D 403/06* (2006.01)
*C07D 405/12* (2006.01)
*C07D 413/12* (2006.01)
*C07D 491/048* (2006.01)
*C07D 239/42* (2006.01)
*C07D 401/04* (2006.01)
*C07D 401/12* (2006.01)
*C07D 417/12* (2006.01)
*C07D 471/04* (2006.01)
*C07D 487/04* (2006.01)

(52) U.S. Cl.
CPC ............ *C07D 239/28* (2013.01); *A61K 31/506* (2013.01); *C07D 239/42* (2013.01); *C07D 239/52* (2013.01); *C07D 401/04* (2013.01); *C07D 401/12* (2013.01); *C07D 403/06* (2013.01); *C07D 403/12* (2013.01); *C07D 405/12* (2013.01); *C07D 413/12* (2013.01); *C07D 417/12* (2013.01); *C07D 471/04* (2013.01); *C07D 487/04* (2013.01); *C07D 491/048* (2013.01)

(58) Field of Classification Search
CPC .......................... C07D 239/52; A61K 31/506
USPC .......................................... 544/335; 514/256
See application file for complete search history.

(56) References Cited

U.S. PATENT DOCUMENTS

| | | | |
|---|---|---|---|
| 3,707,560 | A | 12/1972 | De Angelis et al. |
| 3,908,012 | A | 9/1975 | De Angelis et al. |
| 3,935,202 | A | 1/1976 | Wei et al. |
| 3,950,525 | A | 4/1976 | De Angelis et al. |
| 4,634,689 | A | 1/1987 | Witkowski et al. |
| 4,824,846 | A | 4/1989 | Kampe et al. |
| 4,931,443 | A | 6/1990 | Nakao et al. |
| 5,064,832 | A | 11/1991 | Stanek et al. |

(Continued)

FOREIGN PATENT DOCUMENTS

| | | |
|---|---|---|
| CN | 1566065 | 1/2005 |
| EP | 1 679 309 A1 | 7/2006 |

(Continued)

OTHER PUBLICATIONS

Douglas, Jr. Introduction to Viral Diseases, Cecil Textbook of Medicine, 20th Edition, vol. 2, pp. 1739-1747, 1996.*

(Continued)

*Primary Examiner* — Deepak Rao
(74) *Attorney, Agent, or Firm* — Sheppard Mullin Richter & Hampton LLP

(57) ABSTRACT

Certain chemical entities are provided herein. Also provided are pharmaceutical compositions comprising at least one chemical entity and one or more pharmaceutically acceptable vehicle. Methods of treating patients suffering from certain diseases and disorders responsive to the inhibition of KMO activity are described, which comprise administering to such patients an amount of at least one chemical entity effective to reduce signs or symptoms of the disease or disorder are disclosed. These diseases include neurodegenerative disorders such as Huntington's disease. Also described are methods of treatment include administering at least one chemical entity as a single active agent or administering at least one chemical entity in combination with one or more other therapeutic agents. Also provided are methods for screening compounds capable of inhibiting KMO activity.

3 Claims, No Drawings

(56) References Cited

U.S. PATENT DOCUMENTS

| | | |
|---|---|---|
| 5,102,904 A | 4/1992 | Kameswaran |
| 5,334,720 A | 8/1994 | Schmiesing et al. |
| 5,338,739 A | 8/1994 | Wettlaufer et al. |
| 5,439,912 A | 8/1995 | Hubele |
| 5,446,067 A | 8/1995 | Benoit et al. |
| 5,726,185 A | 3/1998 | Alig et al. |
| 5,925,639 A | 7/1999 | Doll et al. |
| 5,948,780 A | 9/1999 | Peterson |
| 6,008,220 A | 12/1999 | Hupe et al. |
| 6,133,304 A | 10/2000 | Peterson et al. |
| 6,169,103 B1 | 1/2001 | Purchase et al. |
| 6,194,428 B1 | 2/2001 | Urbahns et al. |
| 6,211,214 B1 | 4/2001 | Kramer et al. |
| 6,214,822 B1 | 4/2001 | Treiber et al. |
| 6,239,288 B1 | 5/2001 | Purchase et al. |
| 6,248,765 B1 | 6/2001 | Schwartz et al. |
| 6,251,926 B1 | 6/2001 | Momose et al. |
| 6,288,063 B1 | 9/2001 | Kluender et al. |
| 6,340,709 B1 | 1/2002 | Bocan et al. |
| 6,399,612 B1 | 6/2002 | Purchase et al. |
| 6,518,435 B1 | 2/2003 | Yamane et al. |
| 6,541,521 B1 | 4/2003 | Purchase et al. |
| 6,624,196 B2 | 9/2003 | Purchase et al. |
| 7,022,725 B2 | 4/2006 | Momose et al. |
| 7,049,318 B2 | 5/2006 | Dominguez et al. |
| 7,105,549 B2 | 9/2006 | Shao et al. |
| 7,345,178 B2 | 3/2008 | Nunes et al. |
| 7,994,338 B2 | 8/2011 | Muchowski et al. |
| 8,071,631 B2 | 12/2011 | Muchowski et al. |
| 8,536,186 B2 * | 9/2013 | Wityak et al. .............. 514/256 |
| 8,883,785 B2 | 11/2014 | Dominguez et al. |
| 9,145,373 B2 * | 9/2015 | Wityak .............. C07D 213/79 |
| 2002/0049207 A1 | 4/2002 | McCarthy et al. |
| 2004/0077557 A1 | 4/2004 | Ali et al. |
| 2004/0204464 A1 | 10/2004 | Al-Abed |
| 2004/0214817 A1 | 10/2004 | Pierce et al. |
| 2005/0070584 A1 | 3/2005 | Havran |
| 2005/0239854 A1 | 10/2005 | Sugiyama et al. |
| 2005/0288308 A1 | 12/2005 | Amrien et al. |
| 2006/0052606 A1 | 3/2006 | Liebeschuetz et al. |
| 2006/0178388 A1 | 8/2006 | Wrobleski et al. |
| 2006/0189806 A1 | 8/2006 | Bernardini et al. |
| 2006/0223849 A1 | 10/2006 | Mjalli et al. |
| 2006/0252751 A1 | 11/2006 | Xue et al. |
| 2006/0293339 A1 | 12/2006 | Chakravarty et al. |
| 2007/0060573 A1 | 3/2007 | Wortmann et al. |
| 2008/0019915 A1 | 1/2008 | Hadida-Ruah et al. |
| 2008/0058391 A1 | 3/2008 | Johnson et al. |
| 2008/0070937 A1 | 3/2008 | Muchowski et al. |
| 2008/0077419 A1 | 3/2008 | Santiago et al. |
| 2008/0113997 A1 | 5/2008 | Sielecki-Dzurdz et al. |
| 2008/0187575 A1 | 8/2008 | Klebl et al. |
| 2008/0188452 A1 | 8/2008 | Altenbach et al. |
| 2011/0015232 A1 | 1/2011 | Charest et al. |
| 2011/0183957 A1 | 7/2011 | Wityak et al. |
| 2011/0230428 A1 | 9/2011 | Wityak et al. |
| 2012/0041009 A1 | 2/2012 | Mizuno |
| 2012/0329812 A1 | 12/2012 | Wityak et al. |
| 2013/0029988 A1 | 1/2013 | Dominguez et al. |
| 2013/0116216 A1 | 5/2013 | Dominguez et al. |
| 2013/0331370 A1 | 12/2013 | Wityak et al. |
| 2014/0329795 A1 | 11/2014 | Courtney et al. |
| 2014/0329816 A1 | 11/2014 | Dominguez et al. |
| 2015/0057238 A1 | 2/2015 | Toledo-Sherman et al. |

FOREIGN PATENT DOCUMENTS

| | | |
|---|---|---|
| EP | 1 783 116 B1 | 5/2007 |
| EP | 1 928 842 B1 | 6/2008 |
| FR | 2204406 | 5/1974 |
| JP | 01113377 | 5/1989 |
| JP | 07041459 | 2/1995 |
| JP | 2000198771 A | 7/2000 |
| JP | 2002241358 | 8/2002 |
| JP | 2007-230963 | 9/2007 |
| JP | 2009-280521 | 12/2009 |
| WO | WO-9523135 | 8/1995 |
| WO | WO-9921583 | 5/1999 |
| WO | WO-0134579 | 5/2001 |
| WO | WO-0160781 | 8/2001 |
| WO | WO 02/060877 | 8/2002 |
| WO | WO 03/002536 | 1/2003 |
| WO | WO 03/022276 A1 | 3/2003 |
| WO | WO 03/029210 | 4/2003 |
| WO | WO 03/051833 | 6/2003 |
| WO | WO 03/066623 A1 | 8/2003 |
| WO | WO 2004/014844 A2 | 2/2004 |
| WO | WO 2004/032933 A1 | 4/2004 |
| WO | WO-2004026833 | 4/2004 |
| WO | WO 2005/003123 A1 | 1/2005 |
| WO | WO 2005/042498 A2 | 5/2005 |
| WO | WO 2005/079800 | 9/2005 |
| WO | WO 2005/079801 | 9/2005 |
| WO | WO 2005/079802 | 9/2005 |
| WO | WO 2006/000371 | 1/2006 |
| WO | WO 2006/062093 A1 | 6/2006 |
| WO | WO 2006/086600 A1 | 8/2006 |
| WO | WO-2006133333 | 12/2006 |
| WO | WO 2007/017289 A2 | 2/2007 |
| WO | WO 2007/019416 A1 | 2/2007 |
| WO | WO 2007/024922 A1 | 3/2007 |
| WO | WO 2007/067836 A2 | 6/2007 |
| WO | WO 2007/070818 A1 | 6/2007 |
| WO | WO 2007/093542 A1 | 8/2007 |
| WO | WO-2007087637 | 8/2007 |
| WO | WO 2008/002576 A2 | 1/2008 |
| WO | WO 2008/022286 A2 | 2/2008 |
| WO | WO 2008/023720 A1 | 2/2008 |
| WO | WO 2008/034008 A2 | 3/2008 |
| WO | WO 2008/095852 A1 | 8/2008 |
| WO | WO 2008/121877 A2 | 10/2008 |
| WO | WO 2008/152099 A2 | 12/2008 |
| WO | WO 2009/006389 A2 | 1/2009 |
| WO | WO 2009/082346 A1 | 7/2009 |
| WO | WO 2009/148004 A1 | 12/2009 |
| WO | WO 2010/005783 A1 | 1/2010 |
| WO | WO 2010/017179 * | 2/2010 |
| WO | WO 2010/100475 A1 | 9/2010 |
| WO | WO 2010/117323 A1 | 10/2010 |
| WO | WO 2010/134478 A1 | 11/2010 |
| WO | WO 2011/008709 A1 | 1/2011 |
| WO | WO 2011/046771 A1 | 4/2011 |
| WO | WO 2011/050323 A1 | 4/2011 |
| WO | WO 2011/091153 A1 | 7/2011 |
| WO | WO 2011/104322 A1 | 9/2011 |
| WO | WO 2012/003387 A1 | 1/2012 |
| WO | WO 2012/035421 A2 | 3/2012 |
| WO | WO 2013/016488 A1 | 1/2013 |
| WO | WO 2013/033068 | 3/2013 |
| WO | WO 2013/033085 A1 | 3/2013 |
| WO | WO 2013/151707 | 10/2013 |

OTHER PUBLICATIONS

Gura et al., Systems for identifying new drugs are often faulty, Science, 278:1041-1042, 1997.*

Johnson et al., Relationships between drug activity in NCI preclinical in vitro and in vivo models and early clinical trials, British Journal of Cancer, 84(10):1424-1431,2001.*

Pearce et al., Failure modes in anticancer drug discovery and development, Cancer Drug Design and Discovery Edited by Stephen Neidle, Chapter 18, pp. 424-435 (2008).*

Simone, Oncology: Introduction, Cecil Textbook of Medicine, 20th Edition, vol. 1, pp. 1004-1010, 1995.*

Damasio, Alzheimer's Disease and Related Dementias, Cecil Textbook of Medicine, 20th Edition, vol. 2, pp. 1992-1996, 1996.*

Layzer, Degenerative Diseases of the Nervous System, Cecil Textbook of Medicine, 20th Edition, vol. 2, pp. 2050-2057, 1996.*

Sathyasaikumar et al., Dysfunctional Kynurenine Pathway Metabolism in the R6/2 Mouse Model of Huntington's Disease, J Neurochem. 113(6), pp. 1416-1425, Jun. 2010.*

Allen, "Pyrolysis of oximes of some γ-cyano and γ-nitro ketones," Canadian Journal of Chemistry (1965), 43(9), 2486-92.

(56) References Cited

OTHER PUBLICATIONS

Berthel, et al., "Identification of phenyl-pyridine-2-carboxylic acid derivatives as novel cell cycle inhibitors with increased selectivity for cancer cells." Anti-Cancer Drugs, 13:359-366 (2002).
Blomquist et al., "Many-membered carbon rings. XVII. A paracyclophane possessing two gem-dimethyl groups," Journal of the American Chemical Society (1958), 80, 3405-8.
Bredereck, et al., "Foramid-Reaktionen, VIII. Eine neue pyrimidinsynthese." Chemische Berichte 90:942-52 (1957).
Brown et al., "Product class 16: benzisothiazoles," Science of Synthesis (2002), 11, 573-625.
Bundgaard, Design of Prodrugs, Elsevier, 1985.
Chatterjea, et al., "Synthesis in 3-azafluorene group. Part III." J. Indian Chem. Soc., vol. LXI, 1028-1031 (1984).
Chemical Abstracts Service. CAS Reg. No. 1017484-83-1 (Apr. 27, 2008).
Chemical Abstracts Service. CAS Reg. No. 1017484-87-5 (Apr. 27, 2008).
Chemical Abstracts Service. CAS Reg. No. 1017484-91-1 (Apr. 27, 2008).
Chemical Abstracts Service. CAS Reg. No. 1017484-95-5 (Apr. 27, 2008).
Chemical Abstracts Service. CAS Reg. No. 1017394-18-1 (Apr. 25, 2008).
Chemical Abstracts Service. CAS Reg. No. 1017396-21-2 (Apr. 25, 2008).
Chemical Abstracts Service. CAS Reg. No. 1017396-26-7 (Apr. 25, 2008).
Chemical Abstracts Service. CAS Reg. No. 1017396-31-4 (Apr. 25, 2008).
Chemical Abstracts Service. CAS Reg. No. 1017438-20-8 (Apr. 25, 2008).
Chemical Abstracts Service. CAS Reg. No. 1017438-24-2 (Apr. 25, 2008).
Chemical Abstracts Service. CAS Reg. No. 1017438-28-6 (Apr. 25, 2008).
Chemical Abstracts Service. CAS Reg. No. 1017438-32-2 (Apr. 25, 2008).
Chemical Abstracts Service. CAS Reg. No. 1017438-36-6 (Apr. 25, 2008).
Chemical Abstracts Service. CAS Reg. No. 1017484-79-5 (Apr. 27, 2008).
Chemical Abstracts Service. CAS Reg. No. 1017484-99-9 (Apr. 27, 2008).
Chiarugi et al. J. Neurochem. 2001, 77, 1310-1318.
Child et al., "Fenbufen, a new anti-inflammatory analgesic: synthesis and structure-activity relations of analogs," Journal of Pharmaceutical Sciences (1977), 66(4), 466-76.
Clapham et al., Trifluoromethyl-substituted pyridyl- and pyrazolylboronic acids and esters: synthesis and Suzuki-Miyaura cross-coupling reactions, Organic & Biomolecular Chemistry, 7(10), pp. 2155-2161 (2009).
Dalal et al. "Substituted Butyro Lactones. Part III. Synthesis of γ-(4-alkoxy-3-chlorophenyl)butyro lactones." J. Ind. Chem. Soc. 1958, 35, 742.
Eglinton, et al., "The chemistry of fungi. Part XXXV. A preliminary investigation of ergoflavin." View Online/Journal Homepage, 1833-1842 (1958).
EP Application No. 09805426. Suppl. Search Report dated Feb. 2, 2012.
Filosa, et al., "Synthesis and antiproliferative properties of N3/8-disubstituted 3,8-diazabicyclo[3.2.1]octane analogues of 3,8-bis[2-(3,4,5-trimethoxyphenyl)pyridine-4-yl]methyl-piperazine." Eur. J. Med. Chem. 42:293-306 (2007).
Furuya et al. "Cyanuric Chloride as a Mild and Active Beckmann Rearrangement Catalyst ," Journal of the American Chemical Society (2005), 127(32), 11240-11241.
Goldfarb, CAPLUS Abstract 151:92839 (2009).
Hametner et al., CAPLUS Abstract 135:241866 (2001).

Han, et al., "Lead optimization studies on FimH antagonists: discovery of potent and orally bioavailable ortho-substituted biphenyl mannosides." J. Med. Chem. 55:3945-3959 (2012).
Hassner et al., "Cycloadditions. 43. Stereospecific synthesis of functionalized Cyclopentanes," Tetrahedron Letters (1989), 30(42), 5803-6.
Hoffman et al., CAPLUS Abstract 117:7954 (1992).
Imoto et al. "Studies on non-thiazolidinedione antidiabetic agents. 2. Novel oxyiminoalkanoic acid derivatives as potent glucose and lipid lowering agents," Chemical & Pharmaceutical Bulletin (2003), 51(2), 138-151.
Kato et al. CAPLUS Abstract 73:7794 (1970).
Kato et al., "The Vilsmeier reaction of methylpyrimidine derivatives." Yakugaku Zasshi 90(7):870-876 (1970).
Kemp et al., "N-Ethylbenzisoxazolium cation. I. Preparation and reactions with nucleophilic species," Tetrahedron (1965), 21(11), 3019-35.
Khachatryan et al. "Synthesis and heterocyclization of β-aroyl-α-diphenyl-phosphorylpropionic acids," Chemistry of Heterocyclic Compounds (New York, NY, United States) (Translation of Khimiya Geterotsiklicheskikh Soedinenii) (2004), 40(4), 446-451.
Khachikyan et al. "Reaction of β-Aroylacrylic Acids with Triphenylphosphine Hydrobromide and Certain Reactions of the Resulting Products," Russian Journal of General Chemistry (2005), 75(12), 1895-1898.
Kobayashi, et al., "A novel strategy for the synthesis of 2-arylpyridines using one-pot 6 π-azaelectrocyclization." Tetrahedron Ltrs., 49:4349-4351 (2008).
Kohler et al., "Isoxazoline oxides," Journal of the American Chemical Society (1926), 48, 2425-34.
Kori, et al., "Subtype-selective Nav1.8 sodium channel blockers: Identitication of potent orally active nicotinamide derivatives." Bioorg. & Med. Chem. Ltrs. 20:6812-6815 (2010).
Kulkarni, et al., "Design and synthesis of novel heterobiaryl amides as metabotropic glutamate receptor subtype 5 antagonists." Bioorg. & Med. Chem. Ltrs. 17:2074-2079 (2007).
Lafferty et al. "The preparation and properties of certain pyridylpyrimidines and bidiazines as potential chelating agents for Iron(II)" J. Org. Chem. 1967, 32, 1591-1596.
Li, et al., "Discovering novel chemical inhibitors of human cyclophilin A: virtual screening, synthesis, and bioassay." Bioorganic & Medicinal Chemistry, 14:2209-2224 (2006).
Masaki et al., "Dehydration of 4-oximinocarboxylic acids with dicyclohexylcarbodiimide," Journal of Heterocyclic Chemistry (1965), 2(4), 376-8.
Mason et al., "Some Aryl Substituted 2-(4-Nitrophenyl)-4-oxo-4-phenylbutanoates and 3-(4-Nitrophenyl)-1-phenyl-1,4-butanediols and Related Compounds as Inhibitors of Rat Liver Microsomal Retinoic Acid Metabolising Enzymes," Journal of Enzyme Inhibition and Medicinal Chemistry (2003), 18(6), 511-528.
Maurin et al., "Structure of (E)-4-benzoylbutyramide oxime," Acta Crystallographica, Section C: Crystal Structure Communications (1992), C48(10), 1819-20.
Maurin et al., "Structures of 4-hydroxyimino-4-phenylbutanoic acid, C10H11NO3 (I), and 5-hydroxyimino-5-phenylpentanoic acid, C11H13NO3 (II), at 223 K," Acta Crystallographica, Section C: Crystal Structure Communications (1994), C50(1), 78-81.
McKinnon et al., "Fused heterocycles from o-acylbenzenethiol derivatives," Canadian Journal of Chemistry (1988), 66(6), 1405-9.
Migliara et al., "A new route for the preparation of pyrazolo[3,4-c]pyridines," Journal of Heterocyclic Chemistry (1979), 16(3), 577-9.
Migliara et al., "Synthesis of 1-hydroxy-2,4-diphenylpyrrolo[2,3-d]pyridazin-7(6H)-one," Journal of Heterocyclic Chemistry (1979), 16(1), 203.
Mikhaleva et al., CAPLUS Abstract 91:107951 (1979).
Molina, et al., "Electrocylization of 3-azahexa-1,3,5-trienes: a convenient iminophosphorane-mediated preparation of 4-arylpyridines." Tetrahedron Ltrs. 34(23):3773-3776 (1993).
Molyneux, "The resorcinol-maleic anhydride condensation product. An unequivocal proof of structure," Journal of Organic Chemistry (1978), 43(13), 2730-1.

(56) References Cited

OTHER PUBLICATIONS

Nerurkar et al., "β-Arylglutaconic acids. IV. Synthesis of crotono- and valerolactones of β-arylglutaconic and glutaric acids," Journal of Organic Chemistry (1960), 25, 1491-5.
Oare et al., "Acyclic stereoselection. 46. Stereochemistry of the Michael addition of N,N-disubstituted amide and thioamide enolates to α,β-unsaturated ketones," Journal of Organic Chemistry (1990), 55(1), 132-57.
Osborne et al., "The chemistry of triazine derivatives II. The acylation of 2,4,6-trimethyl-s-triazine to triazinyl ketones and their facile isomerization to acetamidopyrimidines." J. Heterocyclic Chem. 1 (Jul. 1, 1964) pp. 145-150 (1964).
Overmars et al., "Fluvoxamine maleate: metabolism in man," European Journal of Drug Metabolism and Pharmacokinetics (1983), 8(3), 269-80.
Papet et al., CAPLUS Abstract 119:271098 (1993).
PCT/US2009/052667. International Search Report & Written Opinion dated Oct. 13, 2009.
PCT/US2011/021890. International Search Report dated Mar. 29, 2011.
Pimentel and McClellan, The Hydrogen Bond, Freeman, San Francisco, 1960.
Pratsch, et al., "Hydroxy- and aminophenyl radicals from arenediazonium salts." Chem. Eur. J. 17:4104-4108 (2011).
Proctor, et al., "Bridged-ring nitrogen compounds. part 5,1 synthesis of 2,6-methano-3-benzazonine ring-systems." JCS Perkin I, 1754-1762 (1981).
Sakaguchi, et al., "Library-directed solution- and solid-phase synthesis of 2,4-disubstituted pyridines: one-pot approach through 6 π-azaelectrocyclization." Chem. Asian. J. 4:1573-1577 (2009).
Sakamoto, et al. "Studies on pyrimidine derivatives. XV. Homolytic acylation and amidation of simply substituted pyrimidines." Chem. Pharm. Bull. 1980, 28, 202-207.
Sakamoto, et al., "Studies on pyrimidine derivatives. XVI. site selectivity in the homolytic substitution of simple pyrimidines." Chem. Pharm. Bull. 1980, 28, 571-577.
Saravanan et al., "Tandem Ring Opening and Oximation of Ethyl 3-Aroyl-1-cyano-4-hydroxy-2,4,6-triarylcyclohexanecarboxylate by Hydroxylamine," Synthetic Communications (2007), 37(20), 3635-3648.
Sasse et al. "New Histamine H3-Receptor Ligands of the Proxifan Series: Imoproxifan and Other Selective Antagonists with High Oral in Vivo Potency," Journal of Medicinal Chemistry (2000), 43(17), 3335-3343.
Savarin et al. "Novel Intramolecular Reactivity of Oximes: Synthesis of Cyclic and Spiro-Fused Imines," Organic Letters (2007), 9(6), 981-983.
Saygili et al., CAPLUS Abstract 141:7086 (2004).
Schilt et al., CAPLUS Abstract 85:186182 (2 pages) (1976).
Shao, et al., Phenoxyphenyl pyridines as novel state-dependent, high-potency sodium channel inhibitors. J. Med. Chem. 47:4277-4285 (2004).
Silverman, Prodrugs and Drug Delivery Systems, The Organic Chemistry of Drug Design and Drug action, Chapter 8, pp. 352-400, 1992.
Stevens et al., "Chemistry and structure of mitomycin C," Journal of Medicinal Chemistry (1965), 8(1), 1-10.
Tanimoto et al., "Synthesis of 6-alkoxy-3-aryl-6-(trimethylsilyloxy)-5,6-dihydro-4H-1,2-oxazines and their acid catalyzed hydrolysis leading to 3-aryl-5,6-dihydro-4H-1,2-oxazin-6-ones and (or) 4-aryl-4-(hydroxyimino)butyric acid esters," Journal of the Chemical Society, Perkin Transactions 1: Organic and Bio-Organic Chemistry (1972-1999) (1991), (12), 3153-7.
Tomoeda et al., "A synthesis of 5-benzyl-2-pyrrolidinone," Yakugaku Zasshi (1966), 86(12), 1213-16.
Van Der Zanden et al., "Action of BF3-ether upon methylchavicol, the oximes of γ-p-methoxy- and γ-p-ethoxybenzoylbutyric acids and the oxime of benzophenone," Recueil des Travaux Chimiques des Pays-Bas et de la Belgique (1942), 61, 280-4.
Van Der Zanden et al., "Reduction products of γ-anisoylbutyric acid, its oxime and the ethoxy homologs," Recueil des Travaux Chimiques des Pays-Bas et de la Belgique (1942), 61, 365-72.
Van Der Zanden, et al., "Polymers of methylchavicol. 1,5-Dianisyl-4-methyl-1-pentene," Recueil des Travaux Chimiques des Pays-Bas et de la Belgique (1943), 62, 383-92.
Wilkerson et al. (Eur. J. Med. Chem., 1992, 27(6), 595).
Wienhoefer et al., CAPLUS Abstract 81 :169509 (1974).
Written Opinion of the International Search Authority for PCT/US2009/004244, Jan. 22, 2011.
Van Muijlwijk-Koezen, et al., "Thiazole and thiadiazole analogues as a novel class of adenosine receptor antagonists." J. Med. Chem. 44:749-762 (2001).
Von Angerer, "Product class 12: pyrimidines." Science of Synthesis Houben-Weyl Methods of Molecular Transformations, Category 2, vol. 16 (2003).
Warshakoon, et al., "Design and synthesis of substituted pyridine derivatives as HIF-1α prolyl hydroxylase inhibitors." Bioorganic & Medicinal Chemistry Lett. 16:5616-5620 (2006).
Arzel, et al. A new synthesis of a-substituted 6-carbolines. Journal of Heterocyclic Chemistry vol. 34, Issue 4, pp. 1205-1210, 1997.
Database Registry, Chemical Library Supplier: Ambinte, Entered STN: Apr. 25, 2008. (RN No. 1017438-16-2).
PCT/US2009/052560, International Search Report and Written Opinion, mailed Sep. 29, 2009, 8 pages.
PCT/US2012/48254. International Search Report & Written Opinion dated Sep. 24, 2012.
PCT/US2012/052617. International Search Report & Written Opinion dated Oct. 22, 2012.
Chemical Abstracts Service. CAS Reg. No. 52565-56-7 (1984), 1p.
Chemical Abstracts Service. CAS Reg. No. 55240-51-2 (1984), 1 p.
Chemical Abstracts Service. CAS Reg. No. 887407-77-4 (2006), 1 p.
WO2013/033085 International Search Report dated Jul. 13, 2013.
WO2011091153 (PCT/US2011/021890) International Preliminary Report on Patentability dated Jul. 31, 2012.

* cited by examiner

KYNURENINE-3-MONOOXYGENASE INHIBITORS, PHARMACEUTICAL COMPOSITIONS, AND METHODS OF USE THEREOF

This applications claims the benefit under 35 U.S.C. §371 of PCT International Application No. PCT/US12/52617, filed Aug. 28, 2012, which in turn claims the benefit of priority of U.S. Application No. 61/529,003, filed Aug. 30, 2011, which is incorporated herein in its entirety for all purposes.

Provided herein are certain kynurenine-3-monooxygenase inhibitors, pharmaceutical compositions thereof, and methods of their use.

Kynurenine-3-monooxygenase (KMO) is an enzyme in the tryptophan degradation pathway that catalyzes the conversion of kynurenine (KYN) into 3-hydroxykynurenine (3-HK), which is further degraded to the excitotoxic NMDA receptor agonist QUIN (3-hydroxyanthranilate oxygenase). 3-OH-KYN and QUIN act synergistically, i.e. 3-OH-KYN significantly potentiates the excitotoxic actions of QUIN. Studies from several laboratories have provided evidence that the shift of KYN pathway metabolism away from the 3-OH-KYN/QUIN branch to increase the formation of the neuroprotectant KYNA in the brain leads to neuroprotection. In addition to having effects in the brain, the inhibition of KMO is further contemplated to impact peripheral tissues. Thus, the inhibition of KMO may be useful in the treatment of peripheral diseases as well as diseases of the brain. Furthermore, the relationship between KMO inhibition and elevations in AA (Anthranilic acid) could also have significant biological effects.

It has also been reported that KMO expression increases in inflammatory conditions or after immune stimulation. 3-OH-KYN, the product of its activity, accumulates in the brain of vitamin B-6 deficient neonatal rats and it causes cytotoxicity when added to neuronal cells in primary cultures or when locally injected into the brain. Recently, it was reported that relatively low concentrations (nanomolar) of 3-OH-KYN may cause apoptotic cell death of neurons in primary neuronal cultures. Structure-activity studies have in fact shown that 3-OH-KYN, and other o-amino phenols, may be subject to oxidative reactions initiated by their conversion to quinoneimines, a process associated with concomitant production of oxygen-derived free radicals. The involvement of these reactive species in the pathogenesis of ischemic neuronal death has been widely studied in the last several years and it has been shown that oxygen derived free radicals and glutamate mediated neurotransmission co-operate in the development of ischemic neuronal death.

It was also recently demonstrated that KMO activity is particularly elevated in the iris-ciliary body and that neo-formed 3-OH-KYN is secreted into the fluid of the lens. An excessive accumulation of 3-OH-KYN in the lens may cause cataracts.

QUIN is an agonist of a subgroup of NMDA receptors and when directly injected into brain areas it destroys most neuronal cell bodies sparing fibers en passant and neuronal terminals. QUIN is a relatively poor agonist of the NMDA receptor complex containing either NR2C or NR2D subunits, while it interacts with relatively high affinity with the NMDA receptor complex containing NR2A and NR2B subunits. The neurotoxicity profile found after intrastriatal injection of QUIN resembles that found in the basal nuclei of Huntington's disease patients: while most of the intrinsic striatal neurons are destroyed, NADH-diaphorase-staining neurons (which are now considered able to express nitric oxide synthetase) and neurons containing neuropeptide Y seem to be spared together with axon terminals and fiber en passant.

In vivo-infusion of KYNA has shown to modulate synaptic release of critical neurotransmitters implicated in cognitive processes and affective mental faculties, such as Acetylcholine, dopamine, and glutamate; therefore elevation of KYNA in brain can have effects in cognitive disorders and disorders arising from, or influenced by, changes in the levels of the neurotransmitters glutamate, dopamine, or Ach (such as Alzheimers, MCI, PD, schizophrenia, HD, OCD, Tourette's).

In vitro, the neurotoxic effects of the compound have been studied in different model systems with variable results: chronic exposure of organotypic cortico-striatal cultures to submicromolar concentration of QUIN causes histological signs of pathology, similar results have been obtained after chronic exposure of cultured neuronal cells.

In models of inflammatory neurological disorders such as experimental allergic encephalitis, bacterial and viral infections, forebrain global ischemia or spinal trauma, brain QUIN levels are extremely elevated. This increased brain QUIN concentration could be due to either an elevated circulating concentration of the excitotoxin or to an increased de novo synthesis in activated microglia or in infiltrating macrophages. In retrovirus-infected macaques, it has been proposed that most of the increased content of brain QUIN (approximately 98%) is due to local production. In fact, a robust increase in the activities of IDO, KMO and kynureninase has been found in areas of brain inflammation.

Previous studies have shown that agents able to increase brain KYNA content cause sedation, mild analgesia, increase in the convulsive threshold and neuroprotection against excitotoxic or ischemic damage. In addition to the above reported evidences, it has been recently demonstrated that a number of compounds able to increase brain KYNA formation may cause a robust decrease in glutamate (GLU) mediated neurotransmission by reducing GLU concentrations in brain extracellular spaces.

There remains a need for compounds that are effective inhibitors of KMO and may be used in treating neurodegenerative disorders.

Provided is at least one chemical entity chosen from compounds of Formula I, II, or III or the compounds of Table 1 or 2, or a pharmaceutically acceptable salt or prodrug thereof.

Also provided is a pharmaceutical composition comprising at least one chemical entity described herein and at least one pharmaceutically acceptable excipient.

Also provided is a method of treating a condition or disorder mediated by Kynurenine 3-mono-oxygenase activity in a subject in need of such a treatment which method comprises administering to the subject a therapeutically effective amount of at least one chemical entity described herein.

Also provided is a method of treating a condition or disorder mediated by Kynurenine 3-mono-oxygenase activity in a subject in need of such a treatment which method comprises administering to the subject a therapeutically effective amount of at least one chemical entity described herein.

Also provided is a packaged pharmaceutical composition comprising at least one pharmaceutical composition described herein and instructions for using the composition to treat a subject suffering from a condition or disorder mediated by Kynurenine 3-mono-oxygenase activity.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. An alkoxy group is further meant to encompass a cycloalkyl group, as defined above, that is likewise attached through an oxygen bridge. Alkoxy groups will usually have from 1 to 6 carbon atoms attached through the oxygen bridge. "Lower alkoxy" refers to alkoxy groups having 1 to 4 carbons.

"Aryl" encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

"Heteroaryl" encompasses:
5- to 7-membered aromatic, monocyclic rings containing one or more, for example, from 1 to 4, or In some embodiments, from 1 to 3, heteroatoms chosen from N, O, and S, with the remaining ring atoms being carbon; and
bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For example, heteroaryl also includes a 5- or 6-membered heterocycloalkyl, aromatic ring fused to a 5- to 7-membered aryl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolyl, isoxazolinyl, oxazolyl, oxazolinyl, oxadiazolyl, thiazolinyl, thiadiazolinyl, tetrazolyl, thienyl, benzothiophenyl, furanyl, benzofuranyl, benzoimidazolinyl, benzooxazolyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O$^-$) substituents, such as pyridinyl N-oxides.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycloalkyl" also refers to 5- and 6-membered carbocyclic aromatic rings fused to a 5- to 7-membered heterocycloalkyl ring containing 1 or more heteroatoms chosen from N, O, and S, provided that the point of attachment is at the heterocycloalkyl ring. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl (including without limitation phenyl), heterocycloalkyl (including without limitation morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl), and heteroaryl (including without limitation pyridinyl), unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1-C_2$ alkyl)$O$— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1-C_6$ alkyl, optionally substituted cycloalkyl, optionally substituted aryl, optionally substituted heterocycloalkyl, and optionally substituted heteroaryl;

$R^b$ is chosen from H, optionally substituted $C_1-C_6$ alkyl, optionally substituted cycloalkyl, optionally substituted aryl, optionally substituted heterocycloalkyl, and optionally substituted heteroaryl; and $R^c$ is chosen from hydrogen and optionally substituted $C_1-C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1-C_4$ alkyl, cycloalkyl, aryl, heterocycloalkyl, heteroaryl, aryl-$C_1-C_4$ alkyl-, heteroaryl-$C_1-C_4$ alkyl-, $C_1-C_4$ haloalkyl-, —$OC_1-C_4$ alkyl, —$OC_1-C_4$ alkylphenyl, —$C_1-C_4$ alkyl-OH, —$C_1-C_4$ alkyl-O—$C_1-C_4$ alkyl, —$OC_1-C_4$ haloalkyl, halo, —OH, —$NH_2$, —$C_1-C_4$ alkyl-$NH_2$, —$N(C_1-C_4$ alkyl)($C_1$-$C_4$ alkyl), —$NH(C_1-C_4$ alkyl), —$N(C_1-C_4$ alkyl)($C_1-C_4$ alkylphenyl), —$NH(C_1-C_4$ alkylphenyl), cyano, nitro, oxo (as a substituent for heteroaryl), —$CO_2H$, —$C(O)OC_1-C_4$ alkyl, —$CON(C_1-C_4$ alkyl)($C_1-C_4$ alkyl), —$CONH(C_1-C_4$ alkyl), —$CONH_2$, —$NHC(O)(C_1-C_4$ alkyl), —$NHC(O)$(phenyl), —$N(C_1-C_4$ alkyl)$C(O)(C_1-C_4$ alkyl), —$N(C_1-C_4$ alkyl)$C(O)$(phenyl), —$C(O)C_1-C_4$ alkyl, —$C(O)C_1-C_4$ phenyl, —$C(O)C_1-C_4$ haloalkyl, —$OC(O)C_1-C_4$ alkyl, —$SO_2(C_1-C_4$ alkyl), —$SO_2$(phenyl), —$SO_2(C_1-C_4$ haloalkyl), —$SO_2NH_2$, —$SO_2NH(C_1-C_4$ alkyl), —$SO_2NH$(phenyl), —$NHSO_2(C_1-C_4$ alkyl), —$NHSO_2$(phenyl), and —$NHSO_2$ ($C_1-C_4$ haloalkyl).

The term "substituted alkoxy" refers to alkoxy wherein the alkyl constituent is substituted (i.e., —O-(substituted alkyl)) wherein "substituted alkyl" is as described herein. "Substituted alkoxy" also includes glycosides (i.e., glycosyl groups) and derivatives of ascorbic acid.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O)(optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

By "alkoxycarbonyl" is meant an ester group of the formula (alkoxy)(C=O)— attached through the carbonyl carbon wherein the alkoxy group has the indicated number of carbon atoms. Thus a $C_1-C_6$alkoxycarbonyl group is an alkoxy group having from 1 to 6 carbon atoms attached through its oxygen to a carbonyl linker.

By "amino" is meant the group —$NH_2$.

The term "sulfinyl" includes the groups: —S(O)-(optionally substituted $(C_1-C_6)$alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups —$S(O_2)$-(optionally substituted $(C_1-C_6)$alkyl), —$S(O_2)$-optionally substituted aryl), —S(O$_2$)-optionally substituted heteroaryl), —S(O$_2$)-(optionally substituted heterocycloalkyl), —S(O$_2$)-(optionally substituted alkoxy), —S(O$_2$)-optionally substituted aryloxy), —S(O$_2$)-optionally substituted heteroaryloxy), —S(O$_2$)-(optionally substituted heterocyclyloxy); and —S(O$_2$)-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxycarbonyl" refers to the group (substituted alkyl)-O—C(O)— wherein the group is attached to the parent structure through the carbonyl functionality and wherein substituted alkyl is as described herein.

"Glycosides" refer to any of a number of sugar derivatives that contain a non-sugar group bonded to an oxygen or nitrogen atom of a sugar and that on hydrolysis yield that sugar. An example of a glycosyl group is glucosyl.

"Derivatives of ascorbic acid" or "ascorbic acid derivatives" refer to any of a number of derivatives that contain a non-sugar group bonded to an oxygen or nitrogen atom of ascorbic acid and that on hydrolysis yield ascorbic acid (i.e., (R)-5-((S)-1,2-dihydroxyethyl)-3,4-dihydroxyfuran-2(5H)-one).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

Chemical entities include, but are not limited to compounds described herein and all pharmaceutically acceptable forms thereof. Pharmaceutically acceptable forms of the compounds recited herein include pharmaceutically acceptable salts, prodrugs, and mixtures thereof. In some embodiments, the compounds described herein are in the form of pharmaceutically acceptable salts and prodrugs. Hence, the terms "chemical entity" and "chemical entities" also encompass pharmaceutically acceptable salts, prodrugs, and mixtures thereof.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities described herein. In some embodiments, the "prodrugs" described herein include any compound that becomes a compound of Formula I-III when administered to a patient, e.g., upon metabolic processing of the prodrug. Examples of prodrugs include derivatives of functional groups, such as a carboxylic acid group, in the compounds of Formula I-III. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include NH$_2$, primary, and secondary amines such as NHR$^x$, and NR$^x$R$^y$, wherein R$^x$ is hydrogen, (C$_1$-C$_{18}$)-alkyl, (C$_3$-C$_7$)-cycloalkyl, (C$_3$-C$_7$)-cycloalkyl-(C$_1$-C$_4$)-alkyl-, (C$_6$-C$_{14}$)-aryl which is unsubstituted or substituted by a residue (C$_1$-C$_2$)-alkyl, (C$_1$-C$_2$)-alkoxy, fluoro, or chloro; heteroaryl-, (C$_6$-C$_{14}$)-aryl-(C$_1$-C$_4$)-alkyl- where aryl is unsubstituted or substituted by a residue (C$_1$-C$_2$)-alkyl, (C$_1$-C$_2$)-alkoxy, fluoro, or chloro; or heteroaryl-(C$_1$-C$_4$)-alkyl- and in which R$^y$ has the meanings indicated for R$^x$ with the exception of hydrogen or wherein R$^x$ and R$^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen-.group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a chemical entity which has biological activity. In some embodiments, an "active agent" is a compound having pharmaceutical utility. For example an active agent may be an anti-neurodegenerative therapeutic.

The term "therapeutically effective amount" of a chemical entity described herein means an amount effective, when administered to a human or non-human subject, to provide a therapeutic benefit such as amelioration of symptoms, slowing of disease progression, or prevention of disease e.g., a therapeutically effective amount may be an amount sufficient to decrease the symptoms of a disease responsive to inhibition of KMO activity and modulation of kynurenine pathway metabolites (such as kynurenine, kynurenic acid, anthranilic acid, 3-OH-kynurenine, 3-OH anthranilic acid, or quinolinic acid). In some embodiments, a therapeutically effective amount is an amount sufficient to treat the symptoms of neurodegenerative pathway or disease. In some embodiments a therapeutically effective amount is an amount sufficient to reduce the signs or side effects of a neurodegenerative disease. In some embodiments, a therapeutically effective amount of a chemical entity is an amount sufficient to prevent a significant increase or significantly reduce the level of neuronal cell death. In some embodiments, a therapeutically effective amount of a chemical entity is an amount sufficient to prevent a significant increase or significantly reduce the level of QUIN associated with neuronal cell death. In some embodiments, a therapeutically effective amount of a chemical entity is an amount sufficient to effect an increase in the level of KYNA associated with neuronal cell health. In some embodiments, a therapeutically effective amount of a chemical entity is an amount sufficient to increase the anticonvulsant and neuroprotective properties associated with lowered levels of QUIN and increased levels of KYNA. In some embodiments, a therapeutically effective amount is an amount sufficient to modulate an inflammatory process in the body, including but not limited to inflammation in the brain, spinal cord, and peripheral nervous system, or meninges. In some embodiments, a therapeutically effective amount is an amount sufficient to modulate the production of cytokines responsible for mounting an effective immune response (such as IL-1 beta or TNF-alpha) or an amount sufficient to affect monocyte/macrophage pro-inflammatory activity in the periphery or in the brain in conditions where the blood-brain barrier is compromised, such as in multiple sclerosis).

In methods described herein for treating a neurodegenerative disorder, a therapeutically effective amount may also be an amount sufficient, when administered to a patient, to detectably slow the progression of the neurodegenerative disease, or prevent the patient to whom the chemical entity is given from presenting symptoms of the neurodegenerative disease. In some methods described herein for treating a neurodegenerative disease, a therapeutically effective amount may also be an amount sufficient to produce a detectable decrease in the level of neuronal cell death. For example, in some embodiments a therapeutically effective amount is an amount of a chemical entity described herein sufficient to significantly decrease the level of neuronal death by effecting a detectable decrease in the amount of QUIN, and an increase in the amount of kynurenine, KYNA, or anthranilic acid.

In addition, an amount is considered to be a therapeutically effective amount if it is characterized as such by at least one of the above criteria or experimental conditions, regardless of any inconsistent or contradictory results under a different set of criteria or experimental conditions.

The term "inhibition" indicates a significant decrease in the baseline activity of a biological activity or process. "Inhibition of KMO activity" refers to a decrease in KMO activity as a direct or indirect response to the presence of at least one chemical entity described herein, relative to the activity of KMO in the absence of at least one chemical entity. The decrease in activity may be due to the direct interaction of the compound with KMO, or due to the interaction of the chemical entity(ies) described herein with one or more other factors that in turn affect KMO activity. For example, the presence of the chemical entity(ies) may decrease KMO activity by directly binding to the KMO, by causing (directly or indirectly) another factor to decrease KMO activity, or by (directly or indirectly) decreasing the amount of KMO present in the cell or organism.

"Inhibition of KMO activity" refers to a decrease in KMO activity as a direct or indirect response to the presence of at least one chemical entity described herein, relative to the activity of KMO in the absence of the at least one chemical entity. The decrease in activity may be due to the direct interaction of the compound with KMO or with one or more other factors that in turn affect KMO activity.

Inhibition of KMO activity also refers to an observable inhibition of 3-HK and QUIN production in a standard assay such as the assay described below. The inhibition of KMO activity also refers to an observable increase in the production of KYNA. In some embodiments, the chemical entity described herein has an $IC_{50}$ value less than or equal to 1 micromolar. In some embodiments, the chemical entity has an $IC_{50}$ value less than or equal to less than 100 micromolar. In some embodiments, the chemical entity has an $IC_{50}$ value less than or equal to 10 nanomolar.

"KMO activity" also includes activation, redistribution, reorganization, or capping of one or more various KMO membrane-associated proteins (such as those receptors found in the mitochondria), or binding sites can undergo redistribution and capping that can initiate signal transduction. KMO activity also can modulate the availability of kynurenine, which can effect the synthesis or production of QUIN, KYNA, anthranilic acid, and/or 3-HK.

A "disease responsive to inhibition of KMO activity" is a disease in which inhibiting KMO provides a therapeutic benefit such as an amelioration of symptoms, decrease in disease progression, prevention or delay of disease onset, prevention or amelioration of an inflammatory response, or inhibition of aberrant activity and/or death of certain cell-types (such as neuronal cells).

"Treatment" or "treating" means any treatment of a disease in a patient, including:
a) preventing the disease, that is, causing the clinical symptoms of the disease not to develop;
b) inhibiting the progression of the disease;
c) slowing or arresting the development of clinical symptoms; and/or
d) relieving the disease, that is, causing the regression of clinical symptoms.

"Subject" or "patient' refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is at least one chemical entity chosen from compounds of Formula I

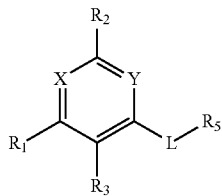

Formula I and pharmaceutically acceptable salts and prodrugs thereof wherein:
X and Y are independently chosen from —N— and —CH—, provided that at least one of X and Y is —N—;
$R_1$ is chosen from optionally substituted aryl and optionally substituted heteroaryl;
$R_2$ is chosen from hydrogen and optionally substituted lower alkyl;
$R_3$ is chosen from hydrogen, halo, optionally substituted lower alkyl, hydroxyl, optionally substituted lower alkoxy, and optionally substituted amino, or $R_1$ and $R_3$, taken together with intervening atoms form a bicyclic ring of the formula

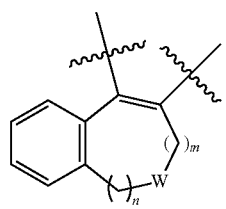

which is optionally substituted where m is 0 or 1 and n is 0 or 1, provided that at least one of m and n is 1 and W is —O—, or —N($R_8$)— where $R_8$ is hydrogen or lower alkyl;
L is chosen from —C(O)O—, —C(O)N($R_4$)—, —N($R_4$)S(O)$_2$—S(O)$_2$N($R_4$), —C(O)N($R_4$)S(O)$_2$—, —C(O)—, and —C(=N)—OR$_7$— where $R_7$ is hydrogen or lower alkyl, provided that if L is —C(O)N($R_4$)—, then $R_5$ also can be lower alkoxy; and
$R_4$ and $R_5$ taken together with the nitrogen to which they are bound form an optionally substituted 4- to 7-membered heterocycloalkyl ring, which is optionally fused to an optionally substituted cycloalkyl, optionally substituted heterocycloalkyl, optionally substituted aryl or optionally substituted heteroaryl ring.

At least one chemical entity chosen from compounds of Formula II

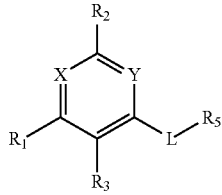

Formula II and pharmaceutically acceptable salts and prodrugs thereof wherein:
X and Y are independently chosen from —N— and —CH—, provided that at least one of X and Y is —N—;
$R_1$ is chosen from optionally substituted aryl and optionally substituted heteroaryl;
$R_2$ is chosen from hydrogen and optionally substituted lower alkyl;
$R_3$ is chosen from hydrogen, halo, optionally substituted lower alkyl, hydroxyl, optionally substituted lower alkoxy, and optionally substituted amino, or $R_1$ and $R_3$, taken together with intervening atoms form a bicyclic ring of the formula

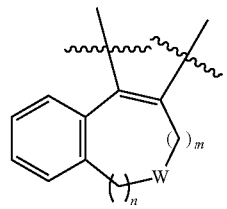

which is optionally substituted where m is 0 or 1 and n is 0 or 1, provided that at least one of m and n is 1 and W is —O—, or —N($R_8$)— where $R_8$ is hydrogen or lower alkyl;
L is chosen from —C(O)N($R_4$)S(O)$_2$—, —C(O)—, —C(=N)—OR$_7$ and

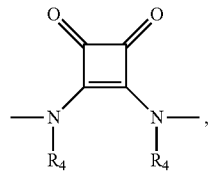

where $R_7$ is hydrogen or lower alkyl; and
$R_4$ is chosen from hydrogen and lower alkyl;
$R_5$ is chosen from hydrogen, optionally substituted lower alkyl, optionally substituted aryl, optionally substituted heteroaryl, optionally substituted cycloalkyl, and optionally substituted heterocycloalkyl; provided that when L is —C(O)N($R_4$)S(O)$_2$—, then $R_5$ is not hydrogen, or $R_4$ and $R_5$ taken together with the nitrogen to which they are bound form an optionally substituted 4- to 7-membered heterocycloalkyl ring, which is optionally fused to an optionally substituted cycloalkyl, optionally substituted heterocycloalkyl, optionally substituted aryl or optionally substituted heteroaryl ring, or $R_3$ and $R_5$, taken together with the intervening atoms, form an optionally substituted 5- to 7-membered ring.

Also provided is at least one chemical entity chosen from compounds of Formula III

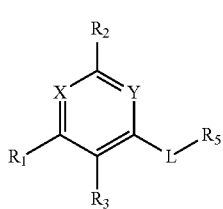

Formula III and pharmaceutically acceptable salts and prodrugs thereof wherein:

X and Y are independently chosen from —N— and —CH—, provided that at least one of X and Y is —N—;

$R_1$ is chosen from optionally substituted aryl and optionally substituted heteroaryl;

$R_2$ is chosen from hydrogen and optionally substituted lower alkyl;

$R_3$ is chosen from optionally substituted amino and lower alkyl substituted with hydroxyl or lower alkoxy, or $R_1$ and $R_3$, taken together with intervening atoms form a bicyclic ring of the formula

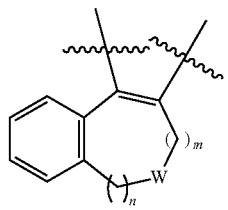

which is optionally substituted where m is 0 or 1 and n is 0 or 1, provided that at least one of m and n is 1 and W is —O—, or —N($R_8$)— where $R_8$ is hydrogen or lower alkyl, L is chosen from —C(O)O—, —C(O)N($R_4$)—, —N($R_4$)S(O)$_2$—, S(O)$_2$N($R_4$)—, —C(O)N($R_4$)S(O)$_2$—, —C(O)—, and —C(=N)—O$R_7$— where $R_7$ is hydrogen or lower alkyl, provided that if L is —C(O)N ($R_4$)—, then $R_5$ also can be lower alkoxy; and $R_4$ is chosen from hydrogen and lower alkyl;

$R_5$ is chosen from hydrogen, optionally substituted lower alkyl, optionally substituted aryl, optionally substituted heteroaryl, optionally substituted cycloalkyl, and optionally substituted heterocycloalkyl; provided that when L is —N($R_4$)S(O)$_{2-5}$ then $R_5$ is not hydrogen, or $R_3$ and $R_5$, taken together with the intervening atoms, form an optionally substituted 5- to 7-membered ring, or $R_4$ and $R_5$ taken together with the nitrogen to which they are bound form an optionally substituted 4- to 7-membered heterocycloalkyl ring, which is optionally fused to an optionally substituted cycloalkyl, optionally substituted heterocycloalkyl, optionally substituted aryl or optionally substituted heteroaryl ring.

In some embodiments of Formula I, II, or III, X is —N—.

In some embodiments of Formula I, II, or III, Y is —N—.

In some embodiments of Formula I, II, or III, X and Y are —N—.

In some embodiments of Formula I, II, or III, $R_1$ is chosen from aryl and heteroaryl, each of which is optionally substituted with one, two, or three groups independent chosen from —$R^a$, —$OR^b$, —$SR^b$, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCO$-$NR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted cycloalkyl, optionally substituted aryl, optionally substituted heterocycloalkyl, and optionally substituted heteroaryl;

$R^b$ is chosen from H, optionally substituted $C_1$-$C_6$ alkyl, optionally substituted cycloalkyl, optionally substituted aryl, optionally substituted heterocycloalkyl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, cycloalkyl, aryl, heterocycloalkyl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —NH$SO_2$($C_1$-$C_4$ alkyl), —NH$SO_2$(phenyl), and —NH$SO_2$($C_1$-$C_4$ haloalkyl).

In some embodiments of Formula I, II, or III, $R_1$ is chosen from aryl and heteroaryl, each of which is substituted with one, two, or three groups chosen from halo, optionally substituted lower alkyl, optionally substituted lower alkoxy, optionally substituted amino, optionally substituted heterocycloalkyl, optionally substituted heteroaryl, and hydroxyl.

In some embodiments of Formula I, II, or III, $R_1$ is phenyl optionally substituted with one, two, or three groups chosen from halo, optionally substituted lower alkyl, optionally substituted lower alkoxy, optionally substituted amino, optionally substituted heterocycloalkyl, optionally substituted heteroaryl, and hydroxy.

In some embodiments of Formula I, II, or III, $R_1$ is phenyl optionally substituted with one, two, or three groups chosen from halo, optionally substituted lower alkyl, optionally substituted lower alkoxy, and hydroxy.

In some embodiments of Formula I, II, or III, $R_1$ is phenyl optionally substituted with one, two, or three groups chosen from halo, lower alkyl, trifluoromethyl, lower alkoxy, and hydroxy.

In some embodiments of Formula I, II, or III, $R_1$ is phenyl optionally substituted with one, two, or three groups chosen from halo, lower alkyl, and trifluoromethyl.

In some embodiments of Formula I, II, or III, $R_1$ is chosen from phenyl, 2,4-difluorophenyl, 3-chloro-2-fluorophenyl, 3-chloro-4-trifluoromethylphenyl, 2-fluoro-5-trifluoromethylphenyl, 3-fluoro-5-trifluoromethylphenyl, 3-trifluoromethylphenyl, 4-fluoro-3-trifluoromethylphenyl, 2-trifluoromethylphenyl, 3,4-dichlorophenyl, 3-chlorophenyl, 4-chlorophenyl, 3,5-dichlorophenyl, 4-chloro-3-fluoro-phenyl, 4-chloro-2-fluoro-phenyl, 3,4-difluoro-phenyl, 5-chloro-2-fluoro-phenyl, 3-fluoro-phenyl, 3-chloro-4-fluoro-phenyl, 3-chloro-6-fluoro-phenyl, 3-chloro-4-methyl-phenyl, 3-bromo-phenyl, and 3-fluoro-phenyl.

In some embodiments of Formula I, II, or III, $R_1$ is chosen from 2-trifluoromethylphenyl, 3,4-dichlorophenyl, 3-chlorophenyl, 4-chlorophenyl, and 3,5-dichlorophenyl.

In some embodiments of Formula I, II, or III, $R_1$ is pyridin-3-yl optionally substituted with one, two, or three groups chosen from halo, lower alkyl, lower alkoxy, optionally substituted amino, optionally substituted heterocycloalkyl, optionally substituted heteroaryl, and hydroxy.

In some embodiments of Formula I, II, or III, $R_1$ is pyridin-3-yl optionally substituted with one, two, or three groups chosen from halo, optionally substituted lower alkyl, optionally substituted lower alkoxy, and hydroxy.

In some embodiments of Formula I, II, or III, $R_1$ is pyridin-3-yl optionally substituted with one, two, or three groups chosen from halo, lower alkyl, trifluoromethyl, lower alkoxy, and hydroxy.

In some embodiments of Formula I, II, or III, $R_1$ is pyridin-3-yl optionally substituted with one, two, or three groups chosen from halo, lower alkyl, and trifluoromethyl.

In some embodiments of Formula I, II, or III, $R_1$ is chosen from pyridin-3-yl, 5-fluoropyridin-3-yl, and 5-chloropyridin-3-yl.

In some embodiments Formula I, II, or III, $R_2$ is hydrogen.

In some embodiments of Formula I, II, or III, $R_2$ is lower alkyl.

In some embodiments of Formula I, II, or III, $R_2$ is methyl or ethyl.

In some embodiments of Formula I, II, or III, $R_2$ is methyl.

In some embodiments of Formula I, II, or III, $R_3$ is —CH$_2$OH.

In some embodiments of Formula I, II, or III, $R_3$ is —NH$_2$.

In some embodiments of Formula I, II, or III, $R_3$ is —CH$_2$OCH$_3$.

In some embodiments of Formula I or II, $R_3$ is hydrogen.

In some embodiments of Formula I or II, $R_3$ is fluoro.

In some embodiments of Formula I or II, $R_3$ is methyl.

In some embodiments, $R_1$ and $R_3$, taken together with intervening atoms form a bicyclic ring of the formula

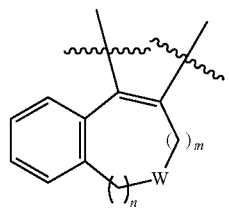

which is optionally substituted where m is 0 or 1 and n is 0 or 1, provided that at least one of m and n is 1 and W is —O—, or —N(R$_8$)— where R$_8$ is hydrogen or lower alkyl.

In some embodiments, W is —O—. In some embodiments, W is —N(R$_8$)— where R$_8$ is hydrogen or lower alkyl. In some embodiments, m is 1. In some embodiments, n is 1. In some embodiments, m and n are each 1.

In some embodiments, the compound of Formula III is chosen from compounds of Formula IV

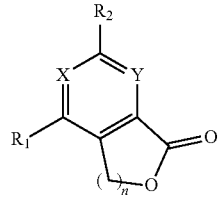

Formula IV wherein n is chosen from 1 and 2 and X, Y, $R_1$ and $R_2$ are as described for compounds of Formula III.

In some embodiments of Formula IV, n is 1.

In some embodiments of Formula IV, n is 2.

In some embodiments of Formula I or III, L is —C(O)O—.

In some embodiments of Formula I or III, L is —C(O)N(R$_4$)—.

In some embodiments of Formula I or III, L is —N(R$_4$)S(O)$_2$—.

In some embodiments of Formula I, II, or III, L is —C(O)N(R$_4$)S(O)$_2$—.

In some embodiments of Formula I, II, or III, L is —C(O)—.

In some embodiments of Formula I, II, or III, L is —C(=N)—OR$_7$—.

In some embodiments of Formula II or III, $R_4$ is hydrogen.

In some embodiments of Formula II or III, $R_5$ is lower alkyl.

In some embodiments of Formula II or III, $R_5$ is hydrogen.

In some embodiments of Formula I, II, or III, $R_4$ and $R_5$ taken together with the nitrogen to which they are bound form an optionally substituted 5- to 7-membered heterocycloalkyl ring. In some embodiments, $R_4$ and $R_5$ taken together with the nitrogen to which they are bound form a ring chosen from 3-oxopiperazin-1-yl, 5,6-dihydro-[1,2,4]triazolo[4,3-a]pyrazin-7(8H)-yl, 4-oxohexahydropyrrolo[3,4-c]pyrrol-2(1H)-yl, piperidin-1-yl, azetidin-3-yl, 5-oxo-1,4-diazepan-1-yl, 1,4-diazepan-1-yl, 5,6-dihydroimidazo[1,2-a]pyrazin-7(8H)-yl, 3-oxo-3,4-dihydroquinoxalin-1(2H)-yl, 7,8-dihydro-1,6-naphthyridin-6(5H)-yl, 4-oxohexahydropyrrolo[1,2-a]pyrazin-2(1H)-yl, 4-oxodihydro-1H-pyrido[1,2-a]pyrazin-2(6H,7H,8H,9H,9aH)-yl, pyrrolidin-1-yl, 1,1-dioxido-1,2,5-thiadiazinan-5-yl, 5,7-dihydro-6H-pyrrolo[3,4-d]pyrimidin-6-yl, 5,7-dihydro-6H-pyrrolo[3,4-b]pyridin-6-yl, and 2,4,5,7-tetrahydro-6H-pyrazolo[3,4-c]pyridin-6-yl, each of which is optionally substituted.

Also provided is at least one chemical entity chosen from the compounds listed in Table 1 or 2 below or a pharmaceutically acceptable salt or prodrug thereof.

TABLE 1

| Structure | IUPAC name |
|---|---|
| 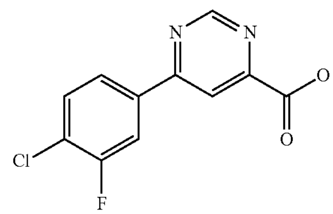 [SMILES: O=C(O)c1cc(-c2ccc(Cl)c(F)c2)ncn1] | 6-(4-Chloro-3-fluoro-phenyl)-pyrimidine-4-carboxylic acid |
| 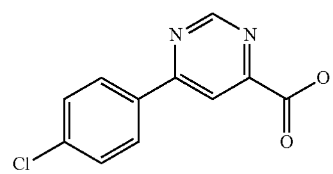 [SMILES: O=C(O)c1cc(-c2ccc(Cl)cc2)ncn1] | 6-(4-Chloro-phenyl)-pyrimidine-4-carboxylic acid |
| 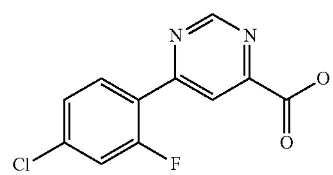 [SMILES: O=C(O)c1cc(-c2ccc(Cl)cc2F)ncn1] | 6-(4-Chloro-2-fluoro-phenyl)-pyrimidine-4-carboxylic acid |
| 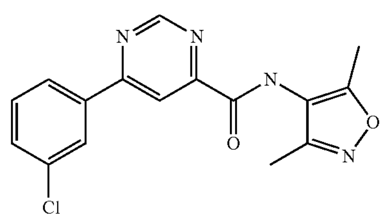 [SMILES: Cc1noc(C)c1NC(=O)c1cc(-c2cccc(Cl)c2)ncn1] | 6-(3-Chloro-phenyl)-pyrimidine-4-carboxylic acid (3,5-dimethyl-isoxazol-4-yl)-amide |
| 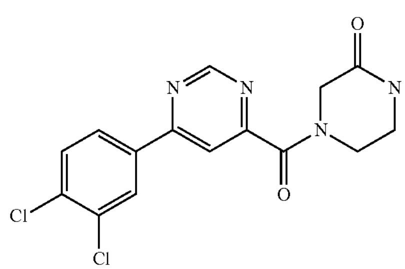 [SMILES: O=C1CN(C(=O)c2cc(-c3ccc(Cl)c(Cl)c3)ncn2)CCN1] | 4-[6-(3,4-Dichloro-phenyl)-pyrimidine-4-carbonyl]-piperazin-2-one |
| 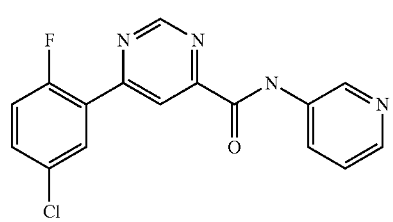 [SMILES: O=C(Nc1cccnc1)c1cc(-c2cc(Cl)ccc2F)ncn1] | 6-(5-Chloro-2-fluoro-phenyl)-pyrimidine-4-carboxylic acid pyridin-3-yl-amide |
| 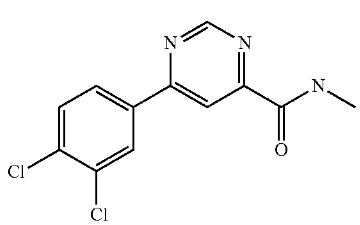 | 6-(3,4-Dichloro-phenyl)-pyrimidine-4-carboxylic acid methylamide |

TABLE 1-continued

| Structure | IUPAC name |
|---|---|
| 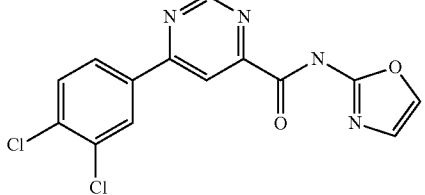 | 6-(3,4-Dichloro-phenyl)-pyrimidine-4-carboxylic acid oxazol-2-yl-amide |
| 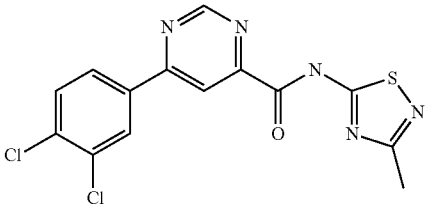 [SMILES: Cc1nsc(NC(=O)c2cc(-c3ccc(Cl)c(Cl)c3)ncn2)n1] | 6-(3,4-Dichloro-phenyl)-pyrimidine-4-carboxylic acid (3-methyl-[1,2,4]-thiadiazol-5-yl)-amide |
| 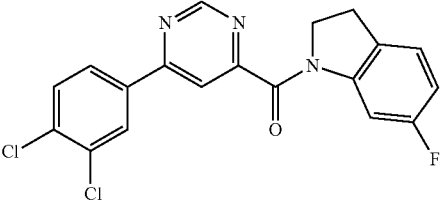 [SMILES: O=C(c1cc(-c2ccc(Cl)c(Cl)c2)ncn1)N1CCc2ccc(F)cc21] | [6-(3,4-Dichloro-phenyl)-pyrimidin-4-yl]-(6-fluoro-2,3-dihydro-indol-1-yl)-methanone |
| 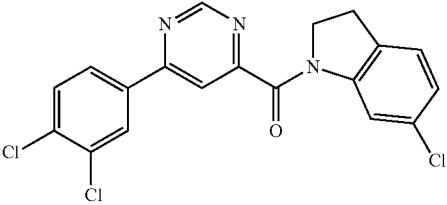 [SMILES: O=C(c1cc(-c2ccc(Cl)c(Cl)c2)ncn1)N1CCc2ccc(Cl)cc21] | (6-Chloro-2,3-dihydro-indol-1-yl)-[6-(3,4-dichloro-phenyl)-pyrimidin-4-yl]-methanone |
| 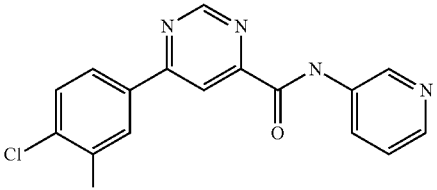 | 6-(4-Chloro-3-fluoro-phenyl)-pyrimidine-4-carboxylic acid pyridin-3-yl-amide |
| 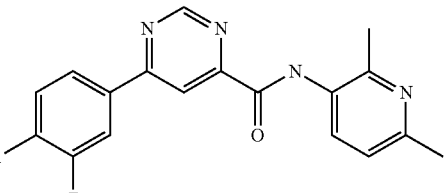 | 6-(4-Chloro-3-fluoro-phenyl)-pyrimidine-4-carboxylic acid (2,6-dimethyl-pyridin-3-yl)-amide |
| 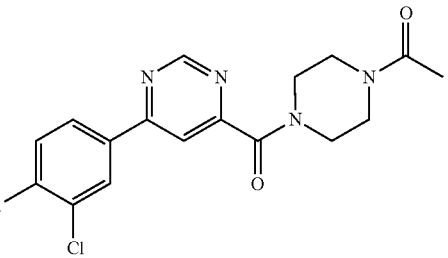 | 1-{4-[6-(3,4-Dichloro-phenyl)-pyrimidine-4-carbonyl]-piperazin-1-yl}-ethanone |

TABLE 1-continued

| Structure | IUPAC name |
| --- | --- |
| 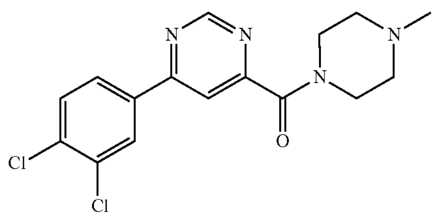 [SMILES: CN1CCN(C(=O)c2cc(-c3ccc(Cl)c(Cl)c3)ncn2)CC1] | [6-(3,4-Dichloro-phenyl)-pyrimidin-4-yl]-(4-methyl-piperazin-1-yl)-methanone |
| 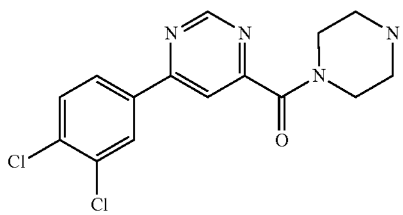 [SMILES: O=C(c1cc(-c2ccc(Cl)c(Cl)c2)ncn1)N1CCNCC1] | [6-(3,4-Dichloro-phenyl)-pyrimidin-4-yl]-piperazin-1-yl-methanone |
| 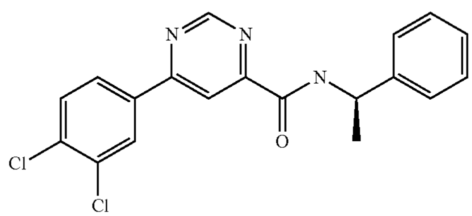 [SMILES: C[C@@H](NC(=O)c1cc(-c2ccc(Cl)c(Cl)c2)ncn1)c1ccccc1] | 6-(3,4-Dichloro-phenyl)-pyrimidine-4-carboxylic acid ((R)-1-phenyl-ethyl)-amide |
| 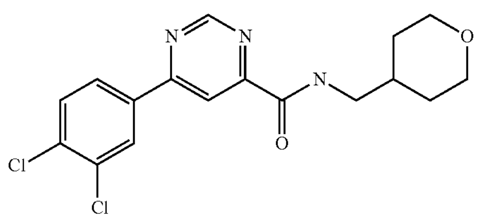 [SMILES: O=C(NCC1CCOCC1)c1cc(-c2ccc(Cl)c(Cl)c2)ncn1] | 6-(3,4-Dichloro-phenyl)-pyrimidine-4-carboxylic acid (tetrahydro-pyran-4-ylmethyl)-amide |
| 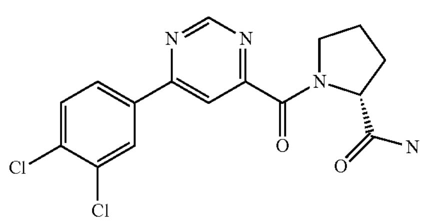 [SMILES: NC(=O)[C@H]1CCCN1C(=O)c1cc(-c2ccc(Cl)c(Cl)c2)ncn1] | (R)-1-[6-(3,4-Dichloro-phenyl)-pyrimidine-4-carbonyl]-pyrrolidine-2-carboxylic acid amide |
| 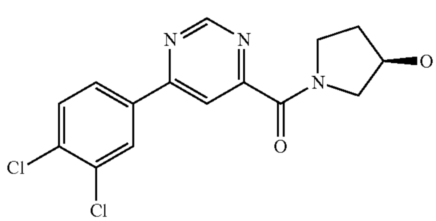 [SMILES: O=C(c1cc(-c2ccc(Cl)c(Cl)c2)ncn1)N1CC[C@@H](O)C1] | [6-(3,4-Dichloro-phenyl)-pyrimidin-4-yl]-((R)-3-hydroxy-pyrrolidin-1-yl)-methanone |
| 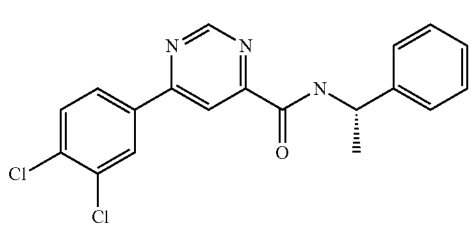 [SMILES: C[C@H](NC(=O)c1cc(-c2ccc(Cl)c(Cl)c2)ncn1)c1ccccc1] | 6-(3,4-Dichloro-phenyl)-pyrimidine-4-carboxylic acid ((S)-1-phenyl-ethyl)-amide |

TABLE 1-continued

| Structure | IUPAC name |
|---|---|
| 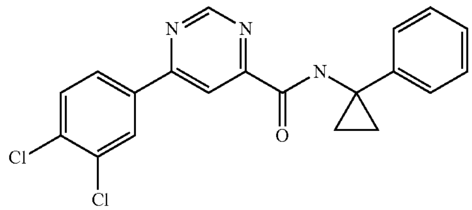 [SMILES: O=C(NC1(c2ccccc2)CC1)c1cc(-c2ccc(Cl)c(Cl)c2)ncn1] | 6-(3,4-Dichloro-phenyl)-pyrimidine-4-carboxylic acid (1-phenyl-cyclopropyl)-amide |
| 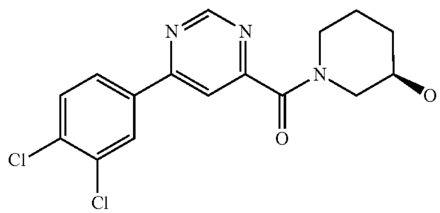 [SMILES: O=C(c1cc(-c2ccc(Cl)c(Cl)c2)ncn1)N1CCC[C@@H](O)C1] | [6-(3,4-Dichloro-phenyl)-pyrimidin-4-yl]-((R)-3-hydroxy-piperidin-1-yl)-methanone |
| 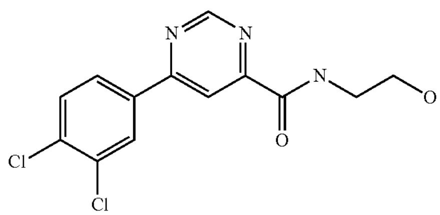 [SMILES: O=C(NCCO)c1cc(-c2ccc(Cl)c(Cl)c2)ncn1] | 6-(3,4-Dichloro-phenyl)-pyrimidine-4-carboxylic acid (2-hydroxy-ethyl)-amide |
| 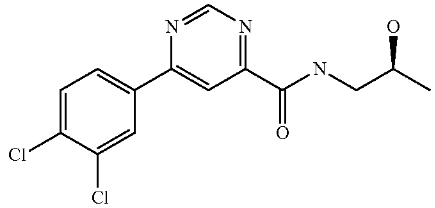 [SMILES: C[C@H](O)CNC(=O)c1cc(-c2ccc(Cl)c(Cl)c2)ncn1] | 6-(3,4-Dichloro-phenyl)-pyrimidine-4-carboxylic acid ((S)-2-hydroxy-propyl)-amide |
| 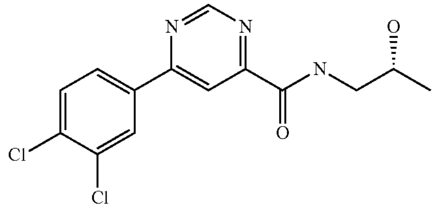 [SMILES: C[C@@H](O)CNC(=O)c1cc(-c2ccc(Cl)c(Cl)c2)ncn1] | 6-(3,4-Dichloro-phenyl)-pyrimidine-4-carboxylic acid ((R)-2-hydroxy-propyl)-amide |
| 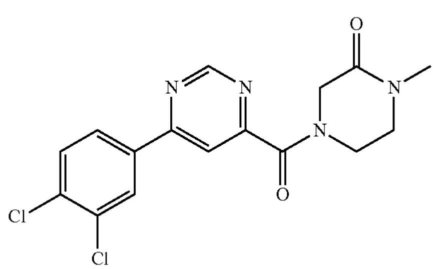 [SMILES: CN1CCN(C(=O)c2cc(-c3ccc(Cl)c(Cl)c3)ncn2)CC1=O] | 4-[6-(3,4-Dichloro-phenyl)-pyrimidine-4-carbonyl]-1-methyl-piperazin-2-one |
| 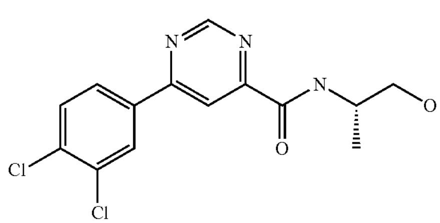 [SMILES: C[C@@H](CO)NC(=O)c1cc(-c2ccc(Cl)c(Cl)c2)ncn1] | 6-(3,4-Dichloro-phenyl)-pyrimidine-4-carboxylic acid ((S)-2-hydroxy-1-methyl-ethyl)-amide |

TABLE 1-continued

| Structure | IUPAC name |
|---|---|
| 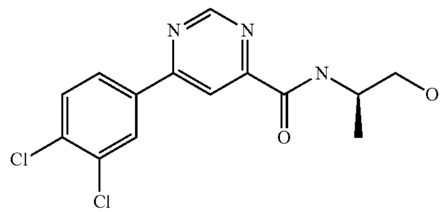 [SMILES: C[C@H](CO)NC(=O)c1cc(-c2ccc(Cl)c(Cl)c2)ncn1] | 6-(3,4-Dichloro-phenyl)-pyrimidine-4-carboxylic acid ((R)-2-hydroxy-1-methyl-ethyl)-amide |
| 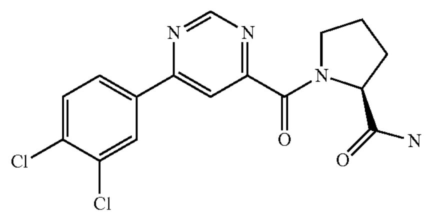 [SMILES: NC(=O)[C@@H]1CCCN1C(=O)c1cc(-c2ccc(Cl)c(Cl)c2)ncn1] | (S)-1-[6-(3,4-Dichloro-phenyl)-pyrimidine-4-carbonyl]-pyrrolidine-2-carboxylic acid amide |
| 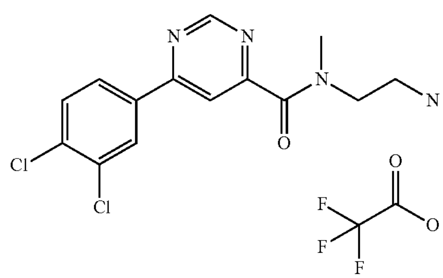 [SMILES: CN(CCN)C(=O)c1cc(-c2ccc(Cl)c(Cl)c2)ncn1 ; O=C(O)C(F)(F)F] | 6-(3,4-Dichloro-phenyl)-pyrimidine-4-carboxylic acid (2-amino-ethyl)-methyl-amide, trifluoro-acetic acid salt |
| 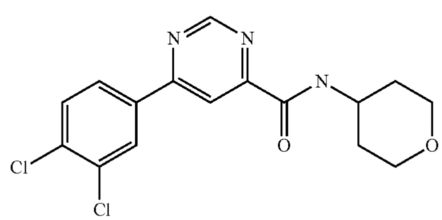 [SMILES: O=C(NC1CCOCC1)c1cc(-c2ccc(Cl)c(Cl)c2)ncn1] | 6-(3,4-Dichloro-phenyl)-pyrimidine-4-carboxylic acid (tetrahydro-pyran-4-yl)-amide |
| 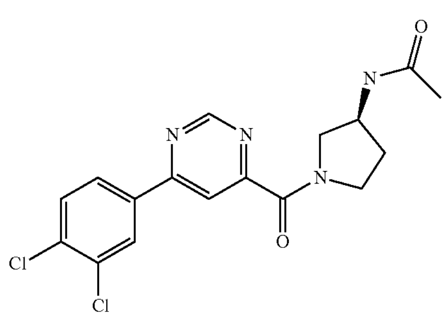 [SMILES: CC(=O)N[C@H]1CCN(C(=O)c2cc(-c3ccc(Cl)c(Cl)c3)ncn2)C1] | N-{(S)-1-[6-(3,4-Dichloro-phenyl)-pyrimidine-4-carbonyl]-pyrrolidin-3-yl}-acetamide |
| 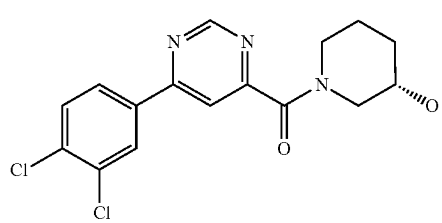 [SMILES: O=C(c1cc(-c2ccc(Cl)c(Cl)c2)ncn1)N1CCC[C@H](O)C1] | [6-(3,4-Dichloro-phenyl)-pyrimidin-4-yl]-((S)-3-hydroxy-piperidin-1-yl)-methanone |

TABLE 1-continued

| Structure | IUPAC name |
|---|---|
| 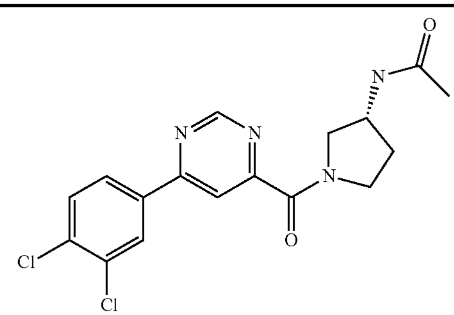 | N-{(R)-1-[6-(3,4-Dichloro-phenyl)-pyrimidine-4-carbonyl]-pyrrolidin-3-yl}-acetamide |
| 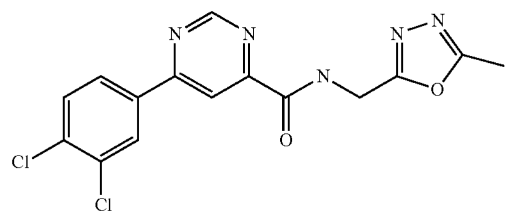 [SMILES: Cc1nnc(CNC(=O)c2cc(-c3ccc(Cl)c(Cl)c3)ncn2)o1] | 6-(3,4-Dichloro-phenyl)-pyrimidine-4-carboxylic acid (5-methyl-[1,3,4]oxadiazol-2-ylmethyl)-amide |
| 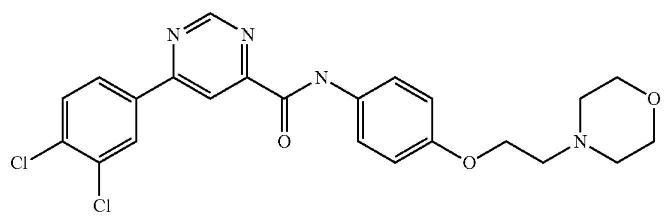 [SMILES: O=C(Nc1ccc(OCCN2CCOCC2)cc1)c1cc(-c2ccc(Cl)c(Cl)c2)ncn1] | 6-(3,4-Dichloro-phenyl)-pyrimidine-4-carboxylic acid [4-(2-morpholin-4-yl-ethoxy)-phenyl]-amide |
| 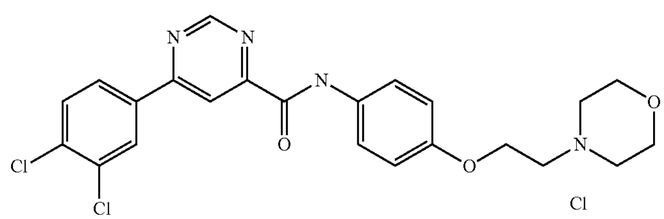 [SMILES: O=C(Nc1ccc(OCCN2CCOCC2)cc1)c1cc(-c2ccc(Cl)c(Cl)c2)ncn1 ; Cl] | 6-(3,4-Dichloro-phenyl)-pyrimidine-4-carboxylic acid [4-(2-morpholin-4-yl-ethoxy)-phenyl]-amide hydrochloride salt |
| 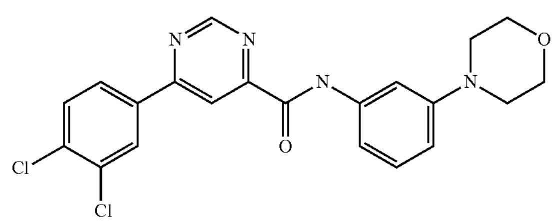 [SMILES: O=C(Nc1cccc(N2CCOCC2)c1)c1cc(-c2ccc(Cl)c(Cl)c2)ncn1] | 6-(3,4-Dichloro-phenyl)-pyrimidine-4-carboxylic acid (3-morpholin-4-yl-phenyl)-amide |
| 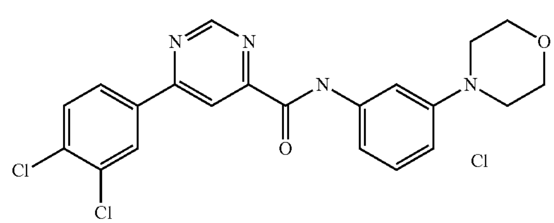 [SMILES: O=C(Nc1cccc(N2CCOCC2)c1)c1cc(-c2ccc(Cl)c(Cl)c2)ncn1 ; Cl] | 6-(3,4-Dichloro-phenyl)-pyrimidine-4-carboxylic acid (3-morpholin-4-yl-phenyl)-amide hydrochloride salt |
| 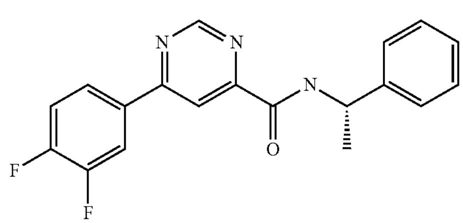 | 6-(3,4-Difluoro-phenyl)-pyrimidine-4-carboxylic acid ((S)-1-phenyl-ethyl)-amide |

TABLE 1-continued

| Structure | IUPAC name |
|---|---|
| 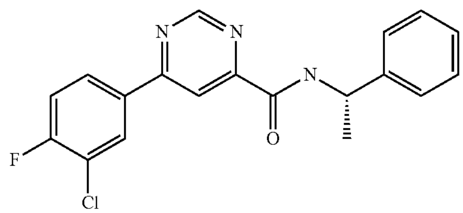 | 6-(3-Chloro-4-fluoro-phenyl)-pyrimidine-4-carboxylic acid ((S)-1-phenyl-ethyl)-amide |
| 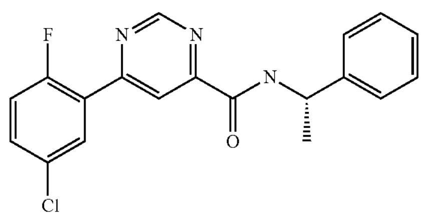 [SMILES: C[C@H](NC(=O)c1cc(-c2cc(Cl)ccc2F)ncn1)c1ccccc1] | 6-(5-Chloro-2-fluoro-phenyl)-pyrimidine-4-carboxylic acid ((S)-1-phenyl-ethyl)-amide |
| 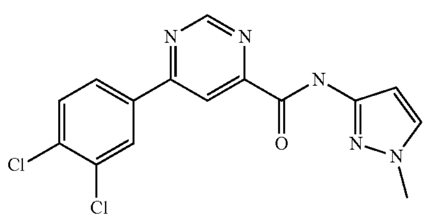 [SMILES: Cn1ccc(NC(=O)c2cc(-c3ccc(Cl)c(Cl)c3)ncn2)n1] | 6-(3,4-Dichloro-phenyl)-pyrimidine-4-carboxylic acid (1-methyl-1H-pyrazol-3-yl)-amide |
| 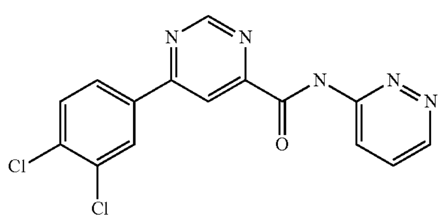 [SMILES: O=C(Nc1cccnn1)c1cc(-c2ccc(Cl)c(Cl)c2)ncn1] | 6-(3,4-Dichloro-phenyl)-pyrimidine-4-carboxylic acid pyridazin-3-yl-amide |
| 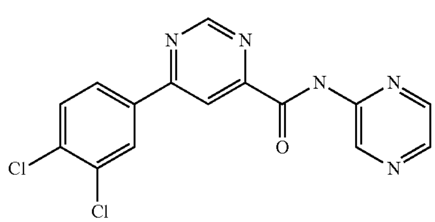 [SMILES: O=C(Nc1cnccn1)c1cc(-c2ccc(Cl)c(Cl)c2)ncn1] | 6-(3,4-Dichloro-phenyl)-pyrimidine-4-carboxylic acid pyrazin-2-yl-amide |
| 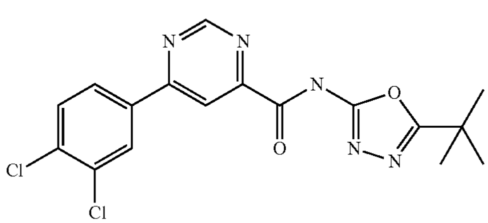 [SMILES: CC(C)(C)c1nnc(NC(=O)c2cc(-c3ccc(Cl)c(Cl)c3)ncn2)o1] | 6-(3,4-Dichloro-phenyl)-pyrimidine-4-carboxylic acid (5-tert-butyl-[1,3,4]oxadiazol-2-yl)-amide |
| 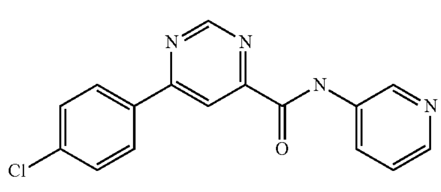 [SMILES: O=C(Nc1cccnc1)c1cc(-c2ccc(Cl)cc2)ncn1] | 6-(4-Chloro-phenyl)-pyrimidine-4-carboxylic acid pyridin-3-yl-amide |

TABLE 1-continued

| Structure | IUPAC name |
|---|---|
| 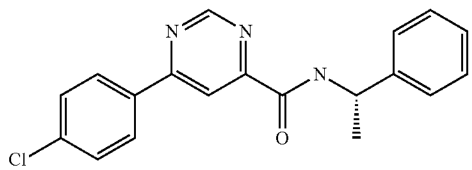 [SMILES: C[C@H](NC(=O)c1cc(-c2ccc(Cl)cc2)ncn1)c1ccccc1] | 6-(4-Chloro-phenyl)-pyrimidine-4-carboxylic acid ((S)-1-phenyl-ethyl)-amide |
| 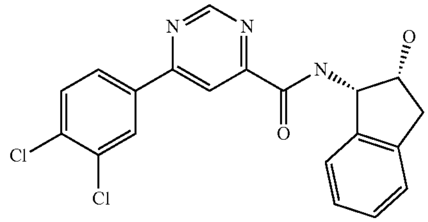 [SMILES: O=C(N[C@H]1c2ccccc2C[C@H]1O)c1cc(-c2ccc(Cl)c(Cl)c2)ncn1] | 6-(3,4-Dichloro-phenyl)-pyrimidine-4-carboxylic acid ((1S,2R)-2-hydroxy-indan-1-yl)-amide |
| 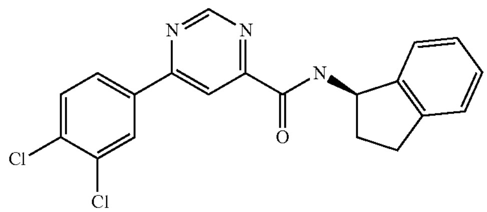 [SMILES: O=C(N[C@@H]1CCc2ccccc21)c1cc(-c2ccc(Cl)c(Cl)c2)ncn1] | 6-(3,4-Dichloro-phenyl)-pyrimidine-4-carboxylic acid (R)-indan-1-ylamide |
| 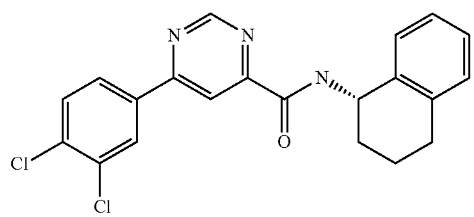 [SMILES: O=C(N[C@H]1CCCc2ccccc21)c1cc(-c2ccc(Cl)c(Cl)c2)ncn1] | 6-(3,4-Dichloro-phenyl)-pyrimidine-4-carboxylic acid (1,2,3,4-tetrahydro-naphthalen-1S-yl)-amide |
| 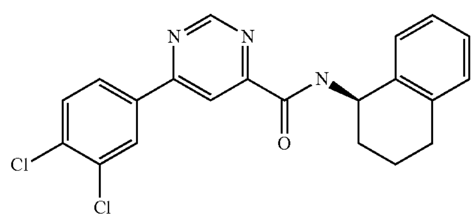 [SMILES: O=C(N[C@@H]1CCCc2ccccc21)c1cc(-c2ccc(Cl)c(Cl)c2)ncn1] | 6-(3,4-Dichloro-phenyl)-pyrimidine-4-carboxylic acid (1,2,3,4-tetrahydro-naphthalen-1R-yl)-amide |
| 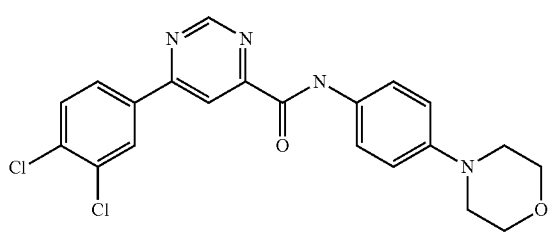 | 6-(3,4-Dichloro-phenyl)-pyrimidine-4-carboxylic acid (4-morpholin-4-yl-phenyl)-amide |
| 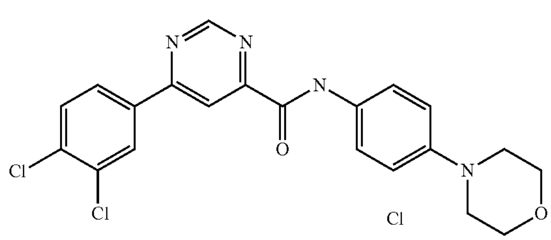 | 6-(3,4-Dichloro-phenyl)-pyrimidine-4-carboxylic acid (4-morpholin-4-yl-phenyl)-amide hydrochloride salt |

TABLE 1-continued

| Structure | IUPAC name |
|---|---|
| 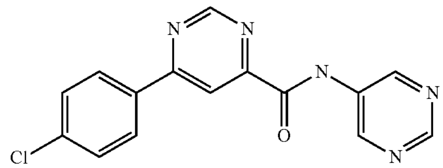 [SMILES: O=C(Nc1cncnc1)c1cc(-c2ccc(Cl)cc2)ncn1] | 6-(4-Chloro-phenyl)-pyrimidine-4-carboxylic acid pyrimidin-5-ylamide |
| 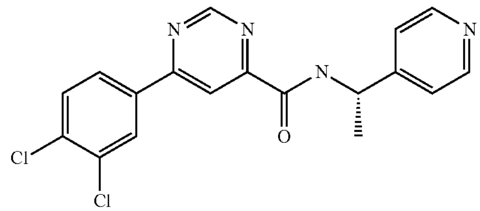 [SMILES: C[C@H](NC(=O)c1cc(-c2ccc(Cl)c(Cl)c2)ncn1)c1ccncc1] | 6-(3,4-Dichloro-phenyl)-pyrimidine-4-carboxylic acid ((S)-1-pyridin-4-yl-ethyl)-amide |
| 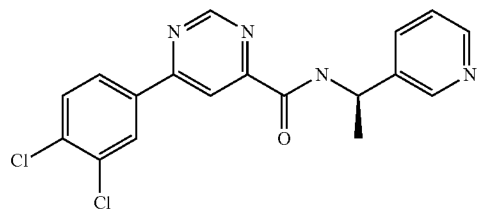 [SMILES: C[C@@H](NC(=O)c1cc(-c2ccc(Cl)c(Cl)c2)ncn1)c1cccnc1] | 6-(3,4-Dichloro-phenyl)-pyrimidine-4-carboxylic acid ((R)-1-pyridin-3-yl-ethyl)-amide |
| 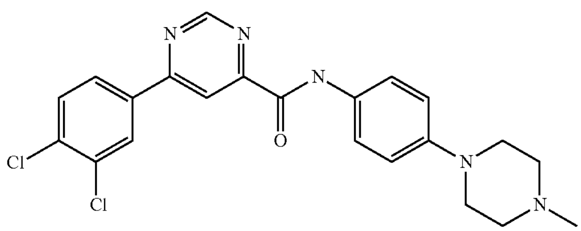 [SMILES: CN1CCN(c2ccc(NC(=O)c3cc(-c4ccc(Cl)c(Cl)c4)ncn3)cc2)CC1] | 6-(3,4-Dichloro-phenyl)-pyrimidine-4-carboxylic acid [4-(4-methyl-piperazin-1-yl)-phenyl]-amide |
| 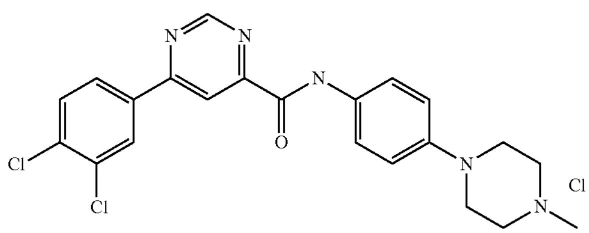 [SMILES: CN1CCN(c2ccc(NC(=O)c3cc(-c4ccc(Cl)c(Cl)c4)ncn3)cc2)CC1 ; Cl] | 6-(3,4-Dichloro-phenyl)-pyrimidine-4-carboxylic acid [4-(4-methyl-piperazin-1-yl)-phenyl]-amide hydrochloride salt |
| 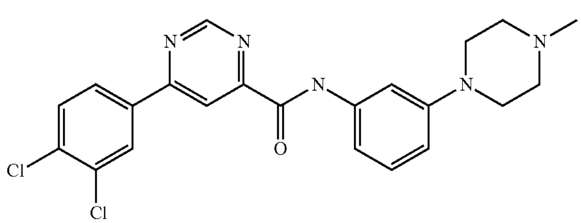 [SMILES: CN1CCN(c2cccc(NC(=O)c3cc(-c4ccc(Cl)c(Cl)c4)ncn3)c2)CC1] | 6-(3,4-Dichloro-phenyl)-pyrimidine-4-carboxylic acid [3-(4-methyl-piperazin-1-yl)-phenyl]-amide |
| 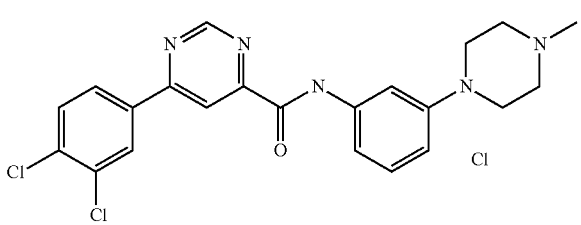 [SMILES: CN1CCN(c2cccc(NC(=O)c3cc(-c4ccc(Cl)c(Cl)c4)ncn3)c2)CC1 ; Cl] | 6-(3,4-Dichloro-phenyl)-pyrimidine-4-carboxylic acid [3-(4-methyl-piperazin-1-yl)-phenyl]-amide hydrochloride salt |

TABLE 1-continued

| Structure | IUPAC name |
|---|---|
| 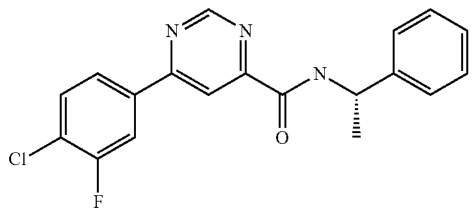 [SMILES: C[C@H](NC(=O)c1cc(-c2ccc(Cl)c(F)c2)ncn1)c1ccccc1] | 6-(4-Chloro-3-fluoro-phenyl)-pyrimidine-4-carboxylic acid ((S)-1-phenyl-ethyl)-amide |
| 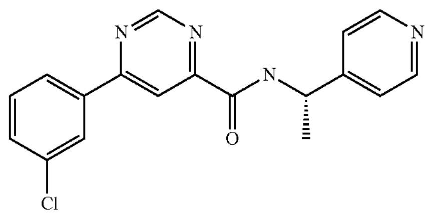 [SMILES: C[C@H](NC(=O)c1cc(-c2cccc(Cl)c2)ncn1)c1ccncc1] | 6-(3-Chloro-phenyl)-pyrimidine-4-carboxylic acid ((S)-1-pyridin-4-yl-ethyl)-amide |
| 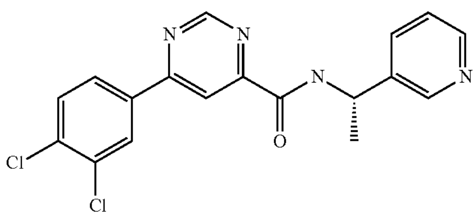 [SMILES: C[C@H](NC(=O)c1cc(-c2ccc(Cl)c(Cl)c2)ncn1)c1cccnc1] | 6-(3,4-Dichloro-phenyl)-pyrimidine-4-carboxylic acid ((S)-1-pyridin-3-yl-ethyl)-amide |
| 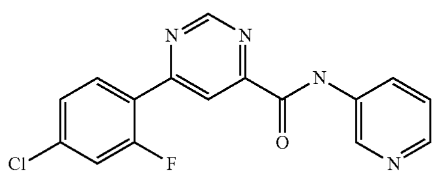 [SMILES: O=C(Nc1cccnc1)c1cc(-c2ccc(Cl)cc2F)ncn1] | 6-(4-Chloro-2-fluoro-phenyl)-pyrimidine-4-carboxylic acid pyridin-3-yl-amide |
| 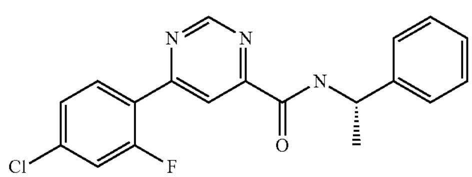 [SMILES: C[C@H](NC(=O)c1cc(-c2ccc(Cl)cc2F)ncn1)c1ccccc1] | 6-(4-Chloro-2-fluoro-phenyl)-pyrimidine-4-carboxylic acid ((S)-1-phenyl-ethyl)-amide |
| 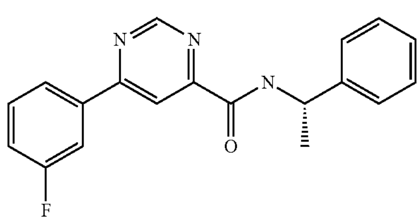 [SMILES: C[C@H](NC(=O)c1cc(-c2cccc(F)c2)ncn1)c1ccccc1] | 6-(3-Fluoro-phenyl)-pyrimidine-4-carboxylic acid ((S)-1-phenyl-ethyl)-amide |
| 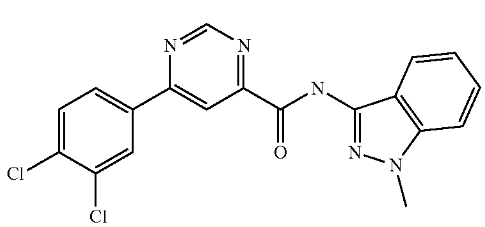 [SMILES: Cn1nc(NC(=O)c2cc(-c3ccc(Cl)c(Cl)c3)ncn2)c2ccccc21] | 6-(3,4-Dichloro-phenyl)-pyrimidine-4-carboxylic acid (1-methyl-1H-indazol-3-yl)-amide |

TABLE 1-continued

| Structure | IUPAC name |
| --- | --- |
| 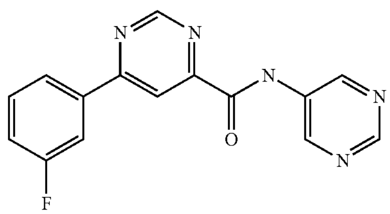 [SMILES: O=C(Nc1cncnc1)c1cc(-c2cccc(F)c2)ncn1] | 6-(3-Fluoro-phenyl)-pyrimidine-4-carboxylic acid pyrimidin-5-yl-amide |
| 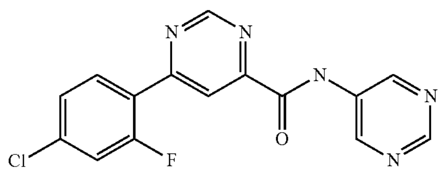 [SMILES: O=C(Nc1cncnc1)c1cc(-c2ccc(Cl)cc2F)ncn1] | 6-(4-Chloro-2-fluoro-phenyl)-pyrimidine-4-carboxylic acid pyrimidin-5-yl-amide |
| 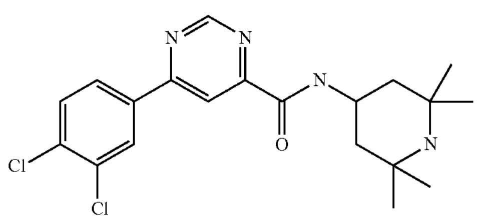 [SMILES: CC1(C)CC(NC(=O)c2cc(-c3ccc(Cl)c(Cl)c3)ncn2)CC(C)(C)N1] | 6-(3,4-Dichloro-phenyl)-pyrimidine-4-carboxylic acid (2,2,6,6-tetramethyl-piperidin-4-yl)-amide |
| 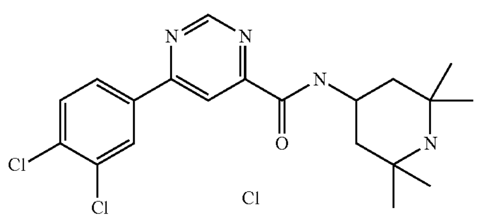 [SMILES: CC1(C)CC(NC(=O)c2cc(-c3ccc(Cl)c(Cl)c3)ncn2)CC(C)(C)N1 ; Cl] | 6-(3,4-Dichloro-phenyl)-pyrimidine-4-carboxylic acid (2,2,6,6-tetramethyl-piperidin-4-yl)-amide hydrochloride salt |
| 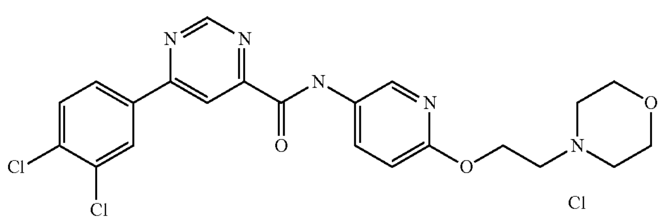 [SMILES: O=C(Nc1ccc(OCCN2CCOCC2)nc1)c1cc(-c2ccc(Cl)c(Cl)c2)ncn1 ; Cl] | 6-(3,4-Dichloro-phenyl)-pyrimidine-4-carboxylic acid [6-(2-morpholin-4-yl-ethoxy)-pyridin-3-yl]-amide hydrochloride salt |
| 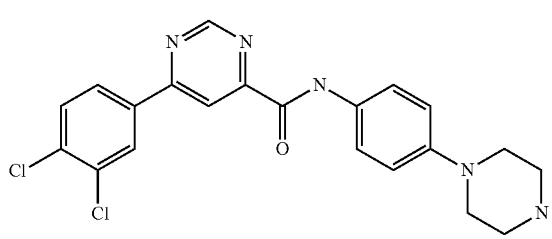 [SMILES: O=C(Nc1ccc(N2CCNCC2)cc1)c1cc(-c2ccc(Cl)c(Cl)c2)ncn1] | 6-(3,4-Dichloro-phenyl)-pyrimidine-4-carboxylic acid (4-piperazin-1-yl-phenyl)-amide |
| 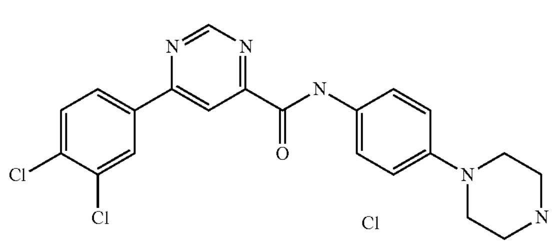 [SMILES: O=C(Nc1ccc(N2CCNCC2)cc1)c1cc(-c2ccc(Cl)c(Cl)c2)ncn1 ; Cl] | 6-(3,4-Dichloro-phenyl)-pyrimidine-4-carboxylic acid (4-piperazin-1-yl-phenyl)-amide hydrochloride salt |

TABLE 1-continued

| Structure | IUPAC name |
|---|---|
| 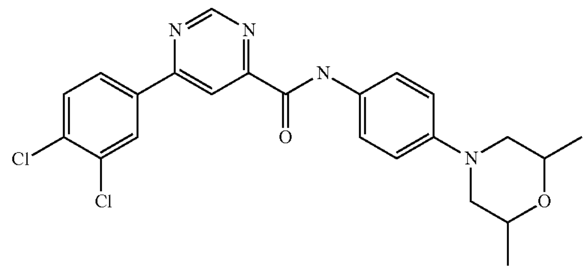 [SMILES: CC1CN(c2ccc(NC(=O)c3cc(-c4ccc(Cl)c(Cl)c4)ncn3)cc2)CC(C)O1] | 6-(3,4-Dichloro-phenyl)-pyrimidine-4-carboxylic acid [4-(2,6-dimethyl-morpholin-4-yl)-phenyl]-amide |
| 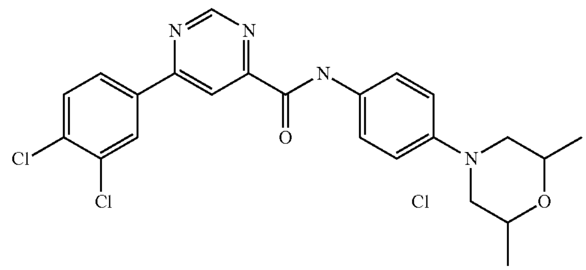 [SMILES: CC1CN(c2ccc(NC(=O)c3cc(-c4ccc(Cl)c(Cl)c4)ncn3)cc2)CC(C)O1 ; Cl] | 6-(3,4-Dichloro-phenyl)-pyrimidine-4-carboxylic acid [4-(2,6-dimethyl-morpholin-4-yl)-phenyl]-amide hydrochloride salt |
| 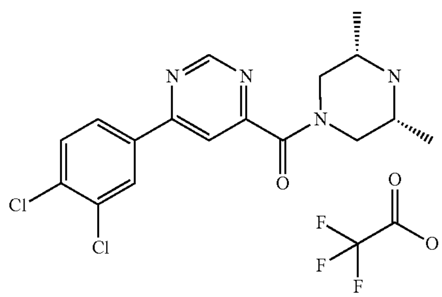 | [6-(3,4-Dichloro-phenyl)-pyrimidin-4-yl]-((3S,5R)-3,5 dimethyl-piperazin-1-yl)-methanone, trifluoro-acetic acid salt |
| 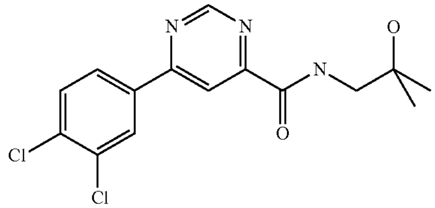 [SMILES: CC(C)(O)CNC(=O)c1cc(-c2ccc(Cl)c(Cl)c2)ncn1] | 6-(3,4-Dichloro-phenyl)-pyrimidine-4-carboxylic acid (2-hydroxy-2-methyl-propyl)-amide |
| 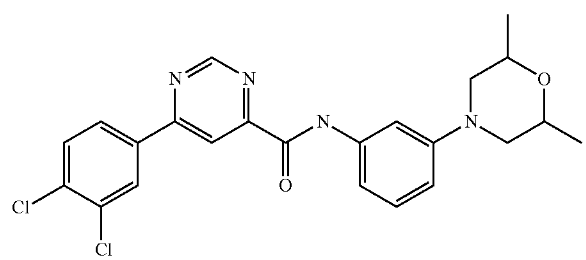 [SMILES: CC1CN(c2cccc(NC(=O)c3cc(-c4ccc(Cl)c(Cl)c4)ncn3)c2)CC(C)O1] | 6-(3,4-Dichloro-phenyl)-pyrimidine-4-carboxylic acid [3-(2,6-dimethyl-morpholin-4-yl)-phenyl]-amide |
| 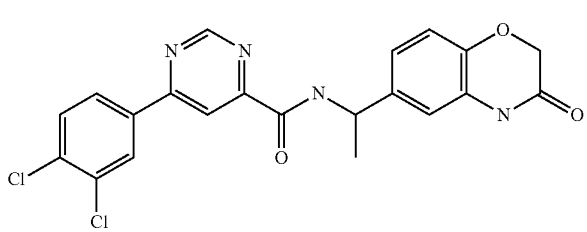 [SMILES: CC(NC(=O)c1cc(-c2ccc(Cl)c(Cl)c2)ncn1)c1ccc2c(c1)NC(=O)CO2] | 6-(3,4-Dichloro-phenyl)-pyrimidine-4-carboxylic acid [1-(3-oxo-3,4-dihydro-2H-benzo[1,4]oxazin-6-yl)-ethyl]-amide |

TABLE 1-continued

| Structure | IUPAC name |
|---|---|
| 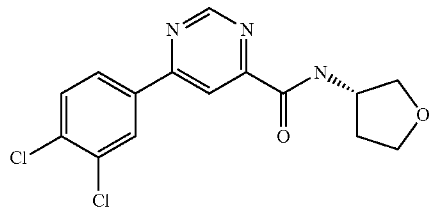 [SMILES: O=C(N[C@H]1CCOC1)c1cc(-c2ccc(Cl)c(Cl)c2)ncn1] | 6-(3,4-Dichloro-phenyl)-pyrimidine-4-carboxylic acid (tetrahydro-furan-3S-yl)-amide |
| 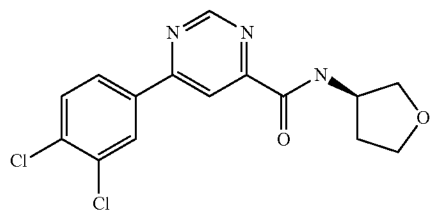 [SMILES: O=C(N[C@@H]1CCOC1)c1cc(-c2ccc(Cl)c(Cl)c2)ncn1] | 6-(3,4-Dichloro-phenyl)-pyrimidine-4-carboxylic acid (tetrahydro-furan-3R-yl)-amide |
| 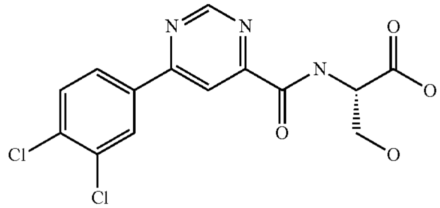 [SMILES: O=C(N[C@@H](CO)C(=O)O)c1cc(-c2ccc(Cl)c(Cl)c2)ncn1] | (S)-2-{[6-(3,4-Dichloro-phenyl)-pyrimidine-4-carbonyl]-amino}-3-hydroxy-propionic acid |
| 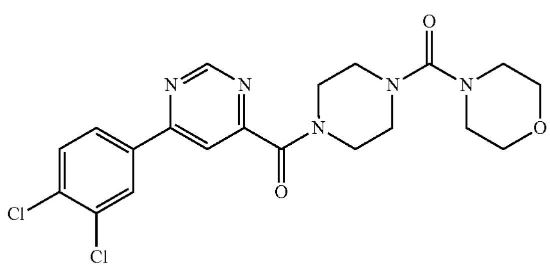 [SMILES: O=C(c1cc(-c2ccc(Cl)c(Cl)c2)ncn1)N1CCN(C(=O)N2CCOCC2)CC1] | [6-(3,4-Dichloro-phenyl)-pyrimidin-4-yl]-[4-(morpholine-4-carbonyl)-piperazin-1-yl]-methanone |
| 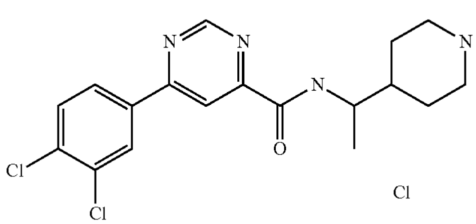 [SMILES: CC(NC(=O)c1cc(-c2ccc(Cl)c(Cl)c2)ncn1)C1CCNCC1 ; Cl] | 6-(3,4-Dichloro-phenyl)-pyrimidine-4-carboxylic acid (1-piperidin-4-yl-ethyl)-amide hydrochloride salt |
| 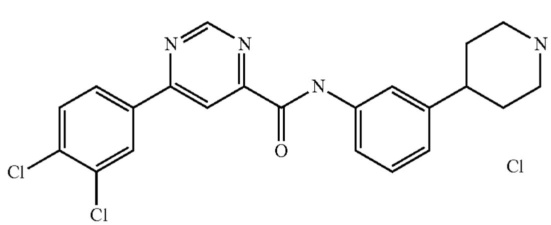 [SMILES: O=C(Nc1cccc(C2CCNCC2)c1)c1cc(-c2ccc(Cl)c(Cl)c2)ncn1 ; Cl] | 6-(3,4-Dichloro-phenyl)-pyrimidine-4-carboxylic acid (3-piperidin-4-yl-phenyl)-amide hydrochloride salt |

TABLE 1-continued

| Structure | IUPAC name |
|---|---|
| 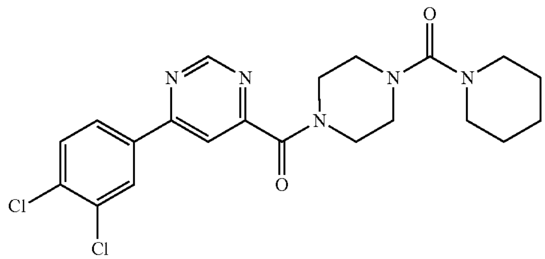 [SMILES: O=C(c1cc(-c2ccc(Cl)c(Cl)c2)ncn1)N1CCN(C(=O)N2CCCCC2)CC1] | [6-(3,4-Dichloro-phenyl)-pyrimidin-4-yl]-[4-(piperidine-1-carbonyl)-piperazin-1-yl]-methanone |
| 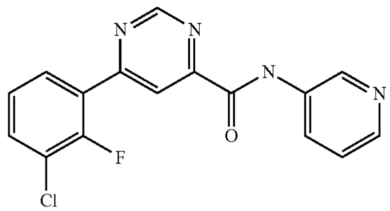 [SMILES: O=C(Nc1cccnc1)c1cc(-c2cccc(Cl)c2F)ncn1] | 6-(3-Chloro-2-fluoro-phenyl)-pyrimidine-4-carboxylic acid pyridin-3-yl-amide |
| 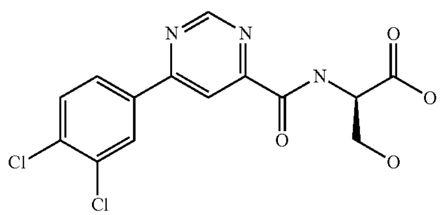 [SMILES: O=C(N[C@H](CO)C(=O)O)c1cc(-c2ccc(Cl)c(Cl)c2)ncn1] | (R)-2-{[6-(3,4-Dichloro-phenyl)-pyrimidine-4-carbonyl]-amino}-3-hydroxy-propionic acid |
| 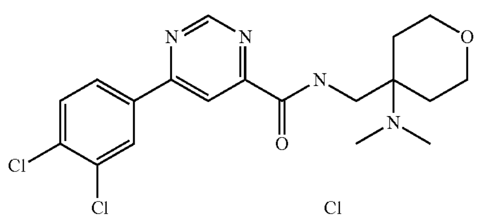 [SMILES: CN(C)C1(CNC(=O)c2cc(-c3ccc(Cl)c(Cl)c3)ncn2)CCOCC1 ; Cl] | 6-(3,4-Dichloro-phenyl)-pyrimidine-4-carboxylic acid (4-dimethylamino-tetrahydro-pyran-4-ylmethyl)-amide hydrochloride salt |
| 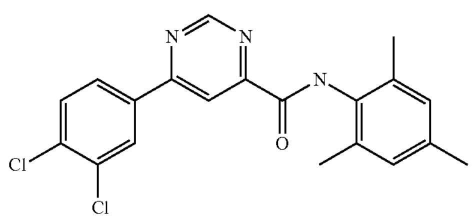 [SMILES: Cc1cc(C)c(NC(=O)c2cc(-c3ccc(Cl)c(Cl)c3)ncn2)c(C)c1] | 6-(3,4-Dichloro-phenyl)-pyrimidine-4-carboxylic acid (2,4,6-trimethyl-phenyl)-amide |
| 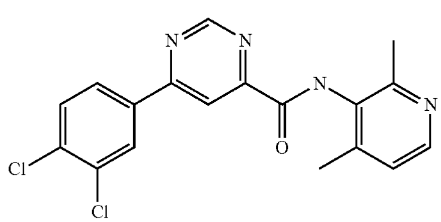 [SMILES: Cc1ccnc(C)c1NC(=O)c1cc(-c2ccc(Cl)c(Cl)c2)ncn1] | 6-(3,4-Dichloro-phenyl)-pyrimidine-4-carboxylic acid (2,4-dimethyl-pyridin-3-yl)-amide |
| 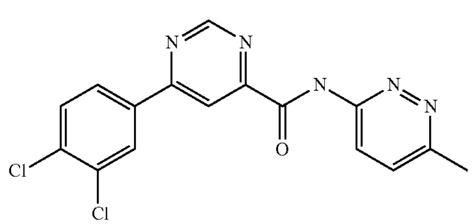 [SMILES: Cc1ccc(NC(=O)c2cc(-c3ccc(Cl)c(Cl)c3)ncn2)nn1] | 6-(3,4-Dichloro-phenyl)-pyrimidine-4-carboxylic acid (6-methyl-pyridazin-3-yl)-amide |

TABLE 1-continued

| Structure | IUPAC name |
|---|---|
| 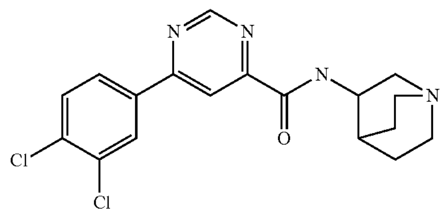 [SMILES: O=C(NC1CN2CCC1CC2)c1cc(-c2ccc(Cl)c(Cl)c2)ncn1] | 6-(3,4-Dichloro-phenyl)-pyrimidine-4-carboxylic acid (1-aza-bicyclo[2.2.2]oct-3-yl)-amide |
| 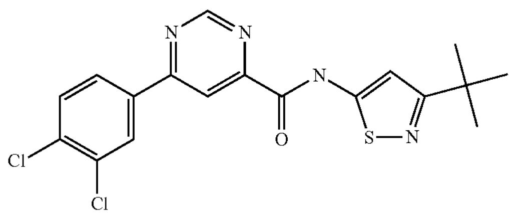 [SMILES: CC(C)(C)c1cc(NC(=O)c2cc(-c3ccc(Cl)c(Cl)c3)ncn2)sn1] | 6-(3,4-Dichloro-phenyl)-pyrimidine-4-carboxylic acid (3-tert-butyl-isothiazol-5-yl)-amide |
| 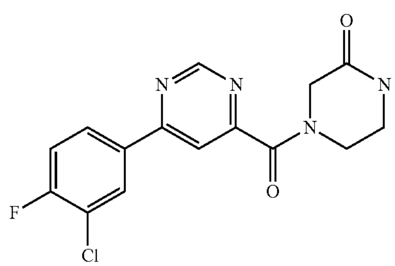 [SMILES: O=C1CN(C(=O)c2cc(-c3ccc(F)c(Cl)c3)ncn2)CCN1] | 4-[6-(3-Chloro-4-fluoro-phenyl)-pyrimidine-4-carbonyl]-piperazin-2-one |
| 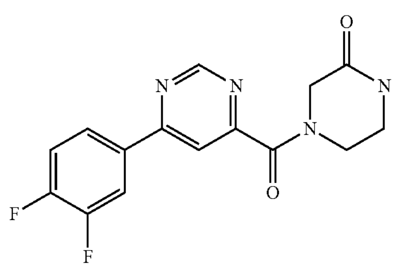 [SMILES: O=C1CN(C(=O)c2cc(-c3ccc(F)c(F)c3)ncn2)CCN1] | 4-[6-(3,4-Difluoro-phenyl)-pyrimidine-4-carbonyl]-piperazin-2-one |
| 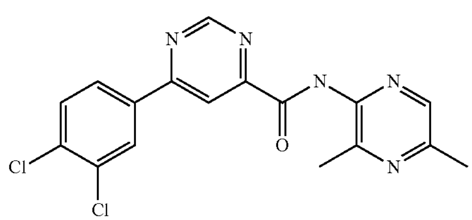 [SMILES: Cc1cnc(NC(=O)c2cc(-c3ccc(Cl)c(Cl)c3)ncn2)c(C)n1] | 6-(3,4-Dichloro-phenyl)-pyrimidine-4-carboxylic acid (3,5-dimethyl-pyrazin-2-yl)-amide |
| 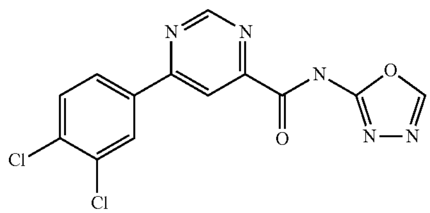 [SMILES: O=C(Nc1nnco1)c1cc(-c2ccc(Cl)c(Cl)c2)ncn1] | 6-(3,4-Dichloro-phenyl)-pyrimidine-4-carboxylic acid [1,3,4]oxadiazol-2-ylamide |

TABLE 1-continued

| Structure | IUPAC name |
|---|---|
| 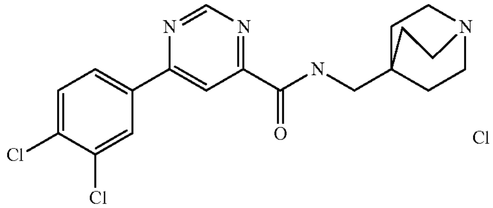 [SMILES: O=C(NCC12CCN(CC1)CC2)c1cc(-c2ccc(Cl)c(Cl)c2)ncn1 ; Cl] | 6-(3,4-Dichloro-phenyl)-pyrimidine-4-carboxylic acid (1-aza-bicyclo[2.2.2]oct-4-ylmethyl)-amide hydrochloride salt |
| 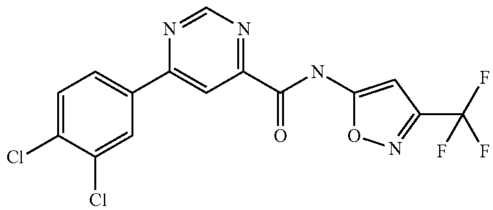 [SMILES: O=C(Nc1cc(C(F)(F)F)no1)c1cc(-c2ccc(Cl)c(Cl)c2)ncn1] | 6-(3,4-Dichloro-phenyl)-pyrimidine-4-carboxylic acid (3-trifluoromethyl-isoxazol-5-yl)-amide |
| 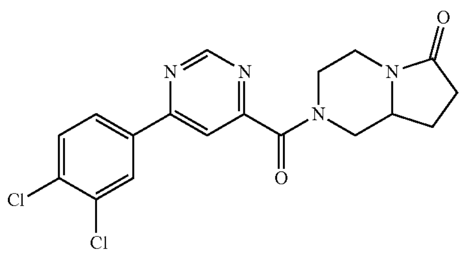 [SMILES: O=C(c1cc(-c2ccc(Cl)c(Cl)c2)ncn1)N1CCN2C(=O)CCC2C1] | 2-[6-(3,4-Dichloro-phenyl)-pyrimidine-4-carbonyl] hexahydro-pyrrolo[1,2-a]pyrazin-6-one |
| 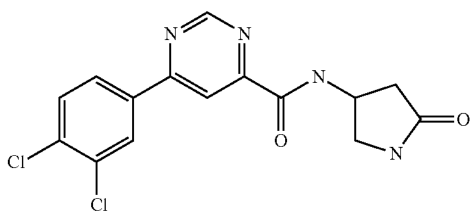 [SMILES: O=C1CC(NC(=O)c2cc(-c3ccc(Cl)c(Cl)c3)ncn2)CN1] | 6-(3,4-Dichloro-phenyl)-pyrimidine-4-carboxylic acid (5-oxo-pyrrolidin-3-yl)-amide |
| 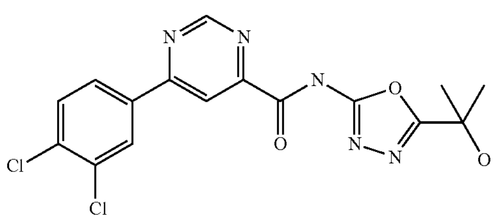 [SMILES: CC(C)(O)c1nnc(NC(=O)c2cc(-c3ccc(Cl)c(Cl)c3)ncn2)o1] | 6-(3,4-Dichloro-phenyl)-pyrimidine-4-carboxylic acid [5-(1-hydroxy-1-methyl-ethyl)-[1,3,4]oxadiazol-2-yl]-amide |
| 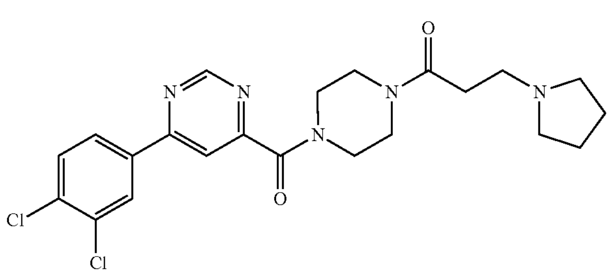 [SMILES: O=C(CCN1CCCC1)N1CCN(C(=O)c2cc(-c3ccc(Cl)c(Cl)c3)ncn2)CC1] | 1-{4-[6-(3,4-Dichloro-phenyl)-pyrimidine-4-carbonyl] piperazin-1-yl}-3-pyrrolidin-1-yl-propan-1-one |

TABLE 1-continued

| Structure | IUPAC name |
|---|---|
| 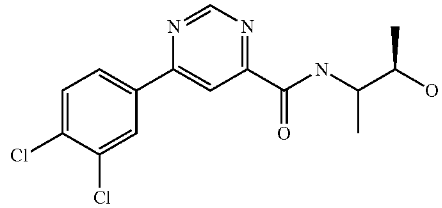 [SMILES: CC(NC(=O)c1cc(-c2ccc(Cl)c(Cl)c2)ncn1)[C@@H](C)O] | 6-(3,4-Dichloro-phenyl)-pyrimidine-4-carboxylic acid ((R)-2-hydroxy-1-methyl-propyl)-amide |
| 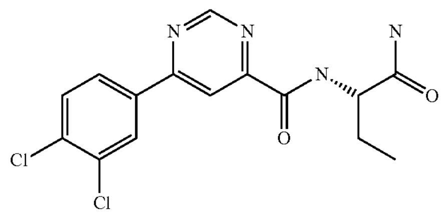 | 6-(3,4-Dichloro-phenyl)-pyrimidine-4-carboxylic acid ((S)-1-carbamoyl-propyl)-amide |
| 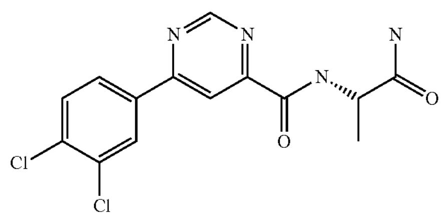 | 6-(3,4-Dichloro-phenyl)-pyrimidine-4-carboxylic acid ((S)-1-carbamoyl-ethyl)-amide |
| 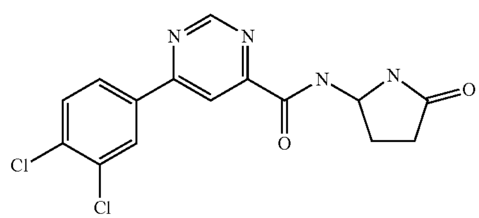 [SMILES: O=C1CCC(NC(=O)c2cc(-c3ccc(Cl)c(Cl)c3)ncn2)N1] | 6-(3,4-Dichloro-phenyl)-pyrimidine-4-carboxylic acid (5-oxo-pyrrolidin-2-yl)-amide |
| 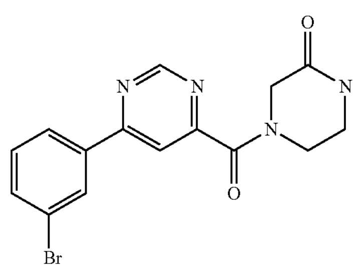 [SMILES: O=C1CN(C(=O)c2cc(-c3cccc(Br)c3)ncn2)CCN1] | 4-[6-(3-Bromo-phenyl)-pyrimidine-4-carbonyl]-piperazin-2-one |
| 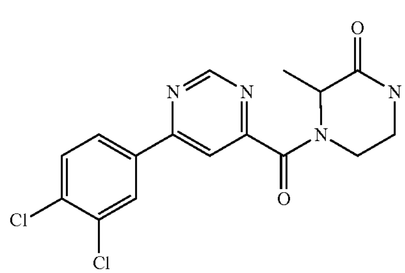 [SMILES: CC1C(=O)NCCN1C(=O)c1cc(-c2ccc(Cl)c(Cl)c2)ncn1] | 4-[6-(3,4-Dichloro-phenyl)-pyrimidine-4-carbonyl]-3-methyl-piperazin-2-one |

TABLE 1-continued

| Structure | IUPAC name |
|---|---|
| 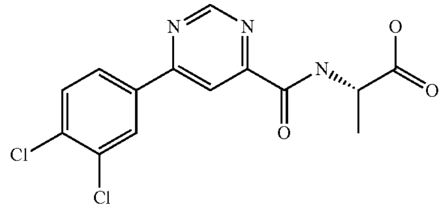 [SMILES: C[C@H](NC(=O)c1cc(-c2ccc(Cl)c(Cl)c2)ncn1)C(=O)O] | (S)-2-{[6-(3,4-Dichloro-phenyl)-pyrimidine-4-carbonyl]-amino}-propionic acid |
| 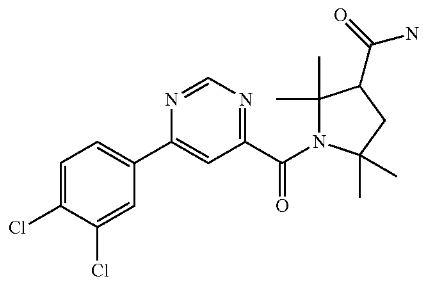 [SMILES: CC1(C)CC(C(N)=O)C(C)(C)N1C(=O)c1cc(-c2ccc(Cl)c(Cl)c2)ncn1] | 1-[6-(3,4-Dichloro-phenyl)-pyrimidine-4-carbonyl]-2,2,5,5-tetramethyl-pyrrolidine-3-carboxylic acid amide |
| 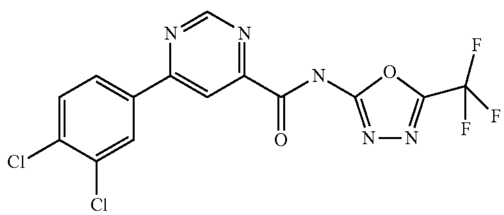 [SMILES: O=C(Nc1nnc(C(F)(F)F)o1)c1cc(-c2ccc(Cl)c(Cl)c2)ncn1] | 6-(3,4-Dichloro-phenyl)-pyrimidine-4-carboxylic acid (5-trifluoromethyl-[1,3,4]oxadiazol-2-yl)-amide |
| 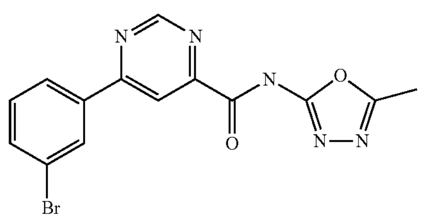 [SMILES: Cc1nnc(NC(=O)c2cc(-c3cccc(Br)c3)ncn2)o1] | 6-(3-Bromo-phenyl)-pyrimidine-4-carboxylic acid (5-methyl-[1,3,4]oxadiazol-2-yl)-amide |
| 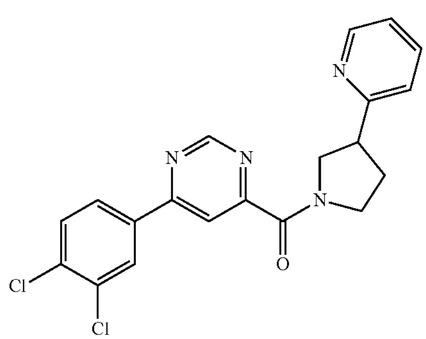 [SMILES: O=C(c1cc(-c2ccc(Cl)c(Cl)c2)ncn1)N1CCC(c2ccccn2)C1] | 6-(3,4-Dichloro-phenyl)-pyrimidine-4-carboxylic acid ((S)-1-acetyl-pyrrolidin-3-yl)-amide |
| 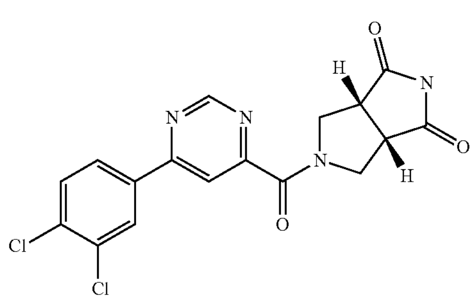 [SMILES: O=C1NC(=O)[C@@H]2CN(C(=O)c3cc(-c4ccc(Cl)c(Cl)c4)ncn3)C[C@H]12] | (3aS,6aR)-5-[6-(3,4-Dichloro-phenyl)-pyrimidine-4-carbonyl]-tetrahydro-pyrrolo[3,4-c]pyrrole-1,3-dione |

TABLE 1-continued

| Structure | IUPAC name |
|---|---|
| 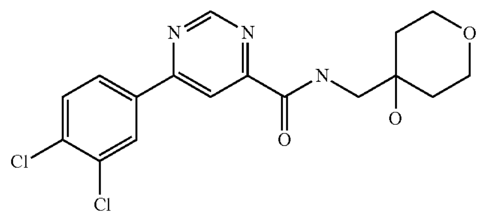 [SMILES: O=C(NCC1(O)CCOCC1)c1cc(-c2ccc(Cl)c(Cl)c2)ncn1] | 6-(3,4-Dichloro-phenyl)-pyrimidine-4-carboxylic acid (4-hydroxy-tetrahydro-pyran-4-ylmethyl)-amide |
| 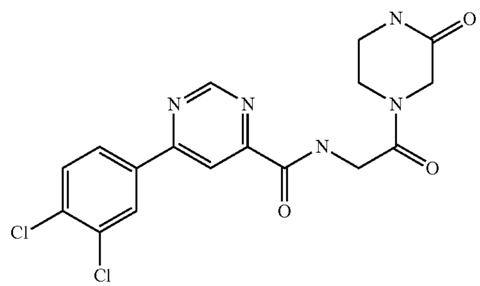 [SMILES: O=C1CN(C(=O)CNC(=O)c2cc(-c3ccc(Cl)c(Cl)c3)ncn2)CCN1] | 6-(3,4-Dichloro-phenyl)-pyrimidine-4-carboxylic acid [2-oxo-2-(3-oxo-piperazin-1-yl)-ethyl]-amide |
| 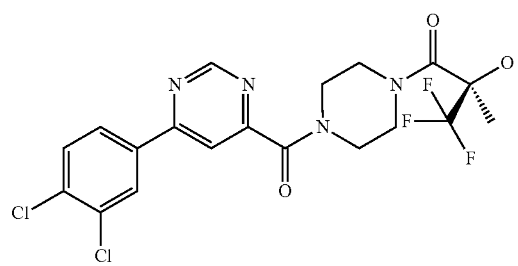 [SMILES: C[C@@](O)(C(=O)N1CCN(C(=O)c2cc(-c3ccc(Cl)c(Cl)c3)ncn2)CC1)C(F)(F)F] | (R)-1-{4-[6-(3,4-Dichloro-phenyl)-pyrimidine-4-carbonyl]-piperazin-1-yl}-3,3,3-trifluoro-2-hydroxy-2-methyl-propan-1-one |
| 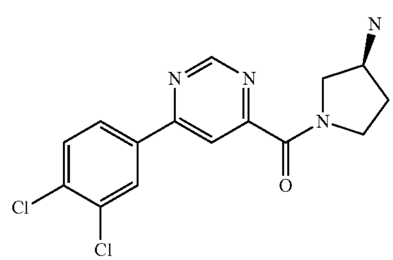 [SMILES: N[C@H]1CCN(C(=O)c2cc(-c3ccc(Cl)c(Cl)c3)ncn2)C1] | ((S)-3-Amino-pyrrolidin-1-yl)-[6-(3,4-dichloro-phenyl)-pyrimidin-4-yl]-methanone |
| 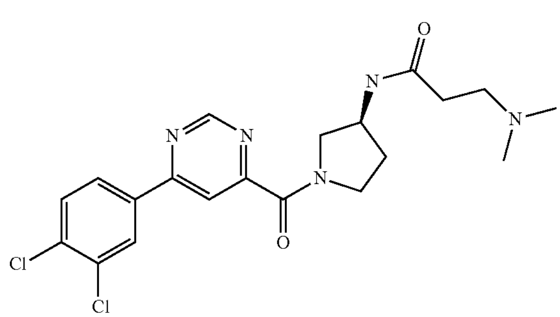 [SMILES: CN(C)CCC(=O)N[C@H]1CCN(C(=O)c2cc(-c3ccc(Cl)c(Cl)c3)ncn2)C1] | N-{(S)-1-[6-(3,4-Dichloro-phenyl)-pyrimidine-4-carbonyl]-pyrrolidin-3-yl}-3-dimethylamino-propionamide |
| 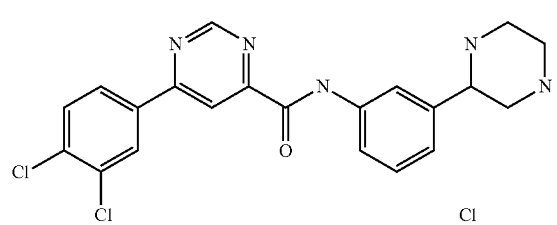 [SMILES: O=C(Nc1cccc(C2CNCCN2)c1)c1cc(-c2ccc(Cl)c(Cl)c2)ncn1 ; Cl] | 6-(3,4-Dichloro-phenyl)-pyrimidine-4-carboxylic acid (3-piperazin-2-yl-phenyl)-amide hydrochloride salt |

TABLE 1-continued

| Structure | IUPAC name |
|---|---|
| 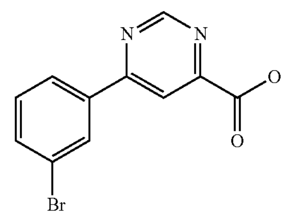 | 6-(3-Bromo-phenyl)-pyrimidine-4-carboxylic acid |
| 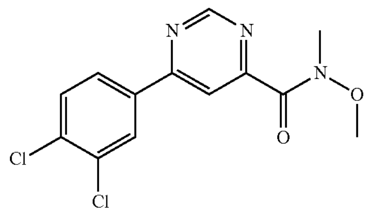 [SMILES: CON(C)C(=O)c1cc(-c2ccc(Cl)c(Cl)c2)ncn1] | 6-(3,4-Dichloro-phenyl)-pyrimidine-4-carboxylic acid methoxy-methyl-amide |
| 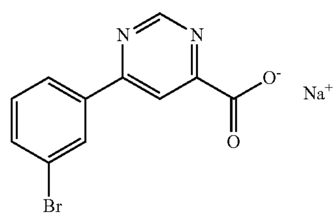 [SMILES: O=C([O-])c1cc(-c2cccc(Br)c2)ncn1 ; [Na+]] | 6-(3-Bromo-phenyl)-pyrimidine-4-carboxylic acid sodium salt |
| 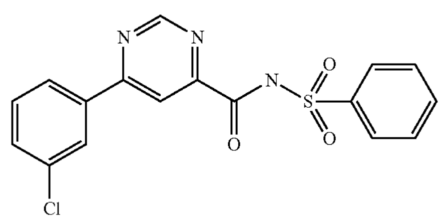 [SMILES: O=C(NS(=O)(=O)c1ccccc1)c1cc(-c2cccc(Cl)c2)ncn1] | N-[6-(3-Chloro-phenyl)-pyrimidine-4-carbonyl]-benzenesulfonamide |
| 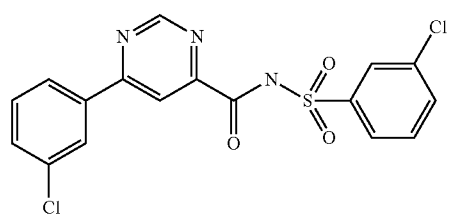 [SMILES: O=C(NS(=O)(=O)c1cccc(Cl)c1)c1cc(-c2cccc(Cl)c2)ncn1] | 3-Chloro-N-[6-(3-chloro-phenyl)-pyrimidine-4-carbonyl]-benzenesulfonamide |
| 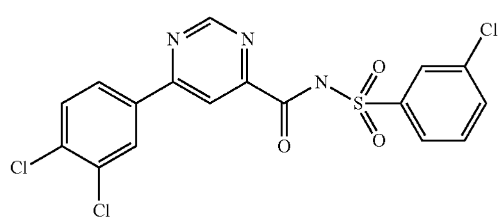 [SMILES: O=C(NS(=O)(=O)c1cccc(Cl)c1)c1cc(-c2ccc(Cl)c(Cl)c2)ncn1] | 3-Chloro-N-[6-(3,4-dichloro-phenyl)-pyrimidine-4-carbonyl]-benzenesulfonamide |
| 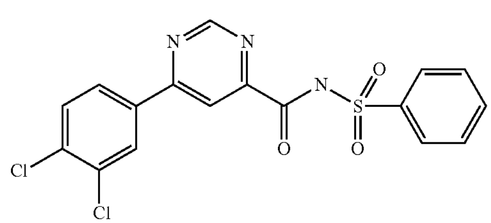 [SMILES: O=C(NS(=O)(=O)c1ccccc1)c1cc(-c2ccc(Cl)c(Cl)c2)ncn1] | N-[6-(3,4-Dichloro-phenyl)-pyrimidine-4-carbonyl]-benzenesulfonamide |

TABLE 1-continued

| Structure | IUPAC name |
|---|---|
| 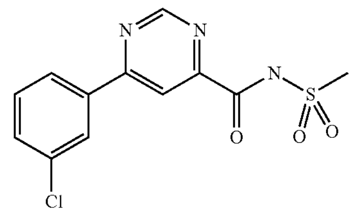 [SMILES: CS(=O)(=O)NC(=O)c1cc(-c2cccc(Cl)c2)ncn1] | N-[6-(3-Chloro-phenyl)-pyrimidine-4-carbonyl]-methanesulfonamide |
| 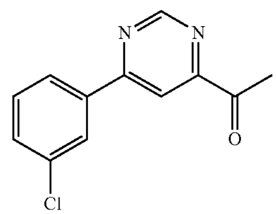 [SMILES: CC(=O)c1cc(-c2cccc(Cl)c2)ncn1] | 1-[6-(3-Chloro-phenyl)-pyrimidin-4-yl]-ethanone |
| 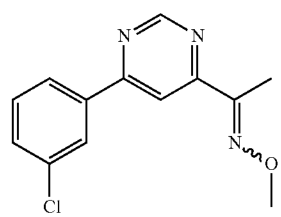 [SMILES: CON=C(C)c1cc(-c2cccc(Cl)c2)ncn1] | 1-[6-(3-Chloro-phenyl)-pyrimidin-4-yl]-ethanone O-methyl-oxime |
| 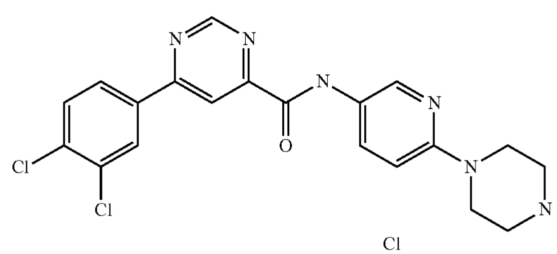 [SMILES: O=C(Nc1ccc(N2CCNCC2)nc1)c1cc(-c2ccc(Cl)c(Cl)c2)ncn1 ; Cl] | 6-(3,4-Dichloro-phenyl)-pyrimidine-4-carboxylic acid (6-piperazin-1-yl-pyridin-3-yl)-amide hydrochloride salt |
| 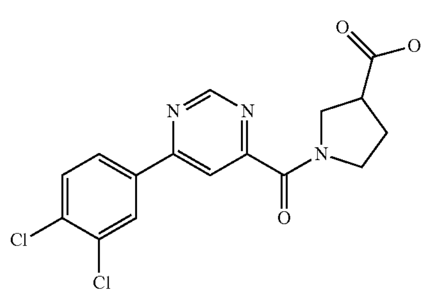 | 1-[6-(3,4-Dichloro-phenyl)-pyrimidine-4-carbonyl]-pyrrolidine-3-carboxylic acid |
| 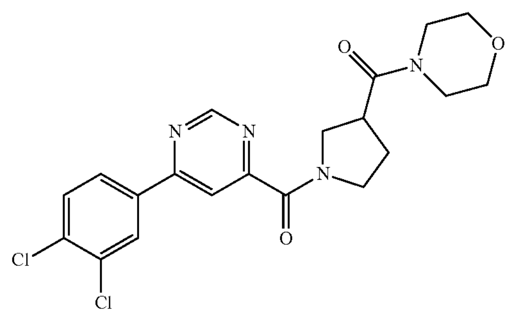 [SMILES: O=C(c1cc(-c2ccc(Cl)c(Cl)c2)ncn1)N1CCC(C(=O)N2CCOCC2)C1] | [6-(3,4-Dichloro-phenyl)-pyrimidin-4-yl]-[3-(morpholine-4-carbonyl)-pyrrolidin-1-yl]-methanone |

TABLE 1-continued

| Structure | IUPAC name |
| --- | --- |
| 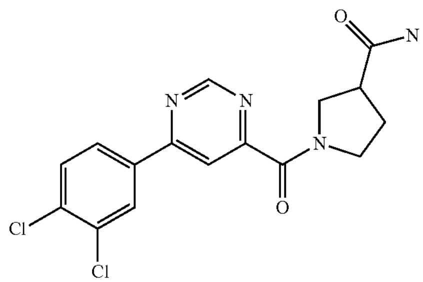 [SMILES: NC(=O)C1CCN(C(=O)c2cc(-c3ccc(Cl)c(Cl)c3)ncn2)C1] | 1-[6-(3,4-Dichloro-phenyl)-pyrimidine-4-carbonyl]-pyrrolidine-3-carboxylic acid amide |
| 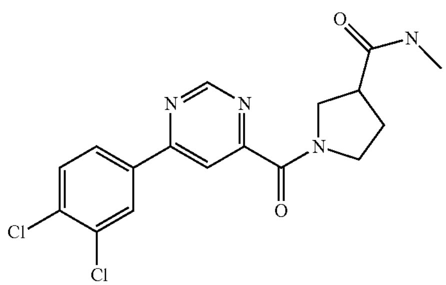 [SMILES: CNC(=O)C1CCN(C(=O)c2cc(-c3ccc(Cl)c(Cl)c3)ncn2)C1] | 1-[6-(3,4-Dichloro-phenyl)-pyrimidine-4-carbonyl]-pyrrolidine-3-carboxylic acid methylamide |
| 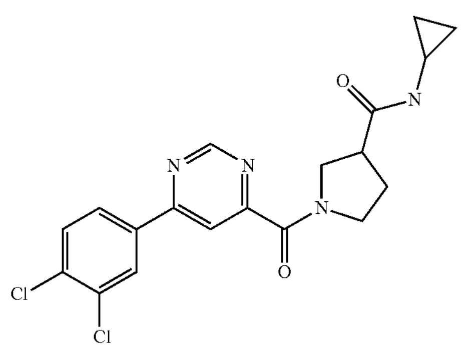 [SMILES: O=C(NC1CC1)C1CCN(C(=O)c2cc(-c3ccc(Cl)c(Cl)c3)ncn2)C1] | 1-[6-(3,4-Dichloro-phenyl)-pyrimidine-4-carbonyl]-pyrrolidine-3-carboxylic acid cyclopropylamide |
| 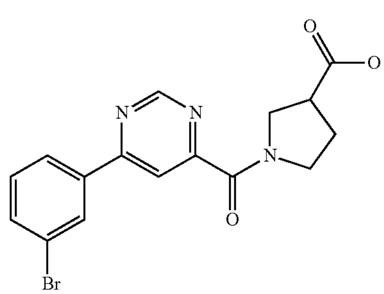 [SMILES: O=C(O)C1CCN(C(=O)c2cc(-c3cccc(Br)c3)ncn2)C1] | 1-[6-(3-Bromo-phenyl)-pyrimidine-4-carbonyl]-pyrrolidine-3-carboxylic acid |
| 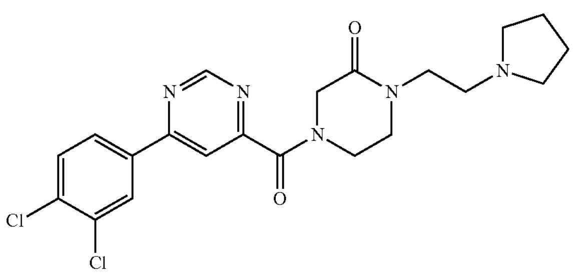 [SMILES: O=C1CN(C(=O)c2cc(-c3ccc(Cl)c(Cl)c3)ncn2)CCN1CCN1CCCC1] | 4-[6-(3,4-Dichloro-phenyl)-pyrimidine-4-carbonyl]-1-(2-pyrrolidin-1-yl-ethyl)-piperazin-2-one |

TABLE 1-continued

| Structure | IUPAC name |
|---|---|
| 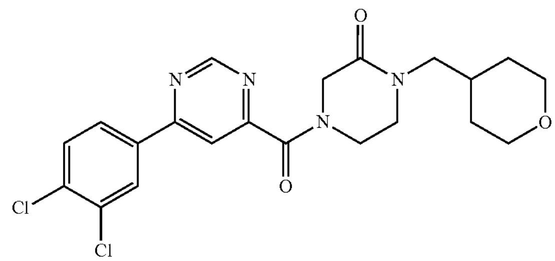 [SMILES: O=C1CN(C(=O)c2cc(-c3ccc(Cl)c(Cl)c3)ncn2)CCN1CC1CCOCC1] | 4-[6-(3,4-Dichloro-phenyl)-pyrimidine-4-carbonyl]-1-(tetrahydro-pyran-4-ylmethyl)-piperazin-2-one |
| 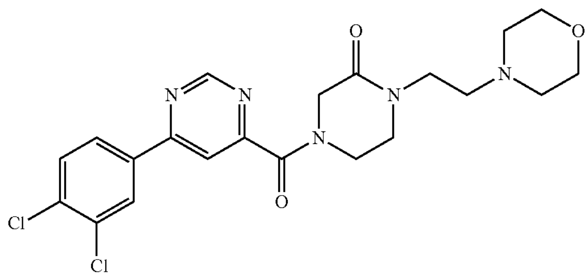 [SMILES: O=C1CN(C(=O)c2cc(-c3ccc(Cl)c(Cl)c3)ncn2)CCN1CCN1CCOCC1] | 4-[6-(3,4-Dichloro-phenyl)-pyrimidine-4-carbonyl]-1-(2-morpholin-4-yl-ethyl)-piperazin-2-one |
| 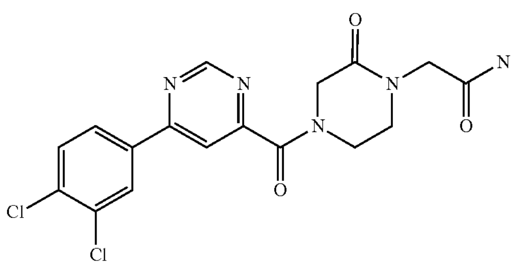 [SMILES: NC(=O)CN1CCN(C(=O)c2cc(-c3ccc(Cl)c(Cl)c3)ncn2)CC1=O] | 2-{4-[6-(3,4-Dichloro-phenyl)-pyrimidine-4-carbonyl]-2-oxo-piperazin-1-yl}-acetamide |
| 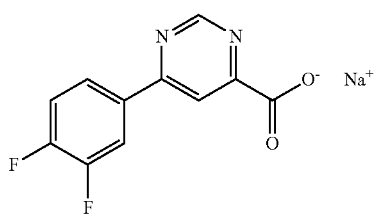 [SMILES: O=C([O-])c1cc(-c2ccc(F)c(F)c2)ncn1 ; [Na+]] | 6-(3,4-Difluoro-phenyl)-pyrimidine-4-carboxylic acid anion, sodium salt |
| 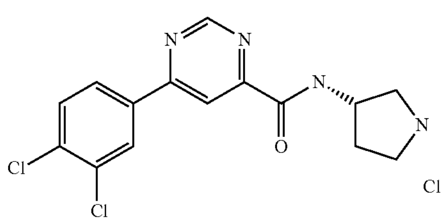 | 6-(3,4-Dichloro-phenyl)-pyrimidine-4-carboxylic acid (S)-pyrrolidin-3-ylamide hydrochloride salt |
| 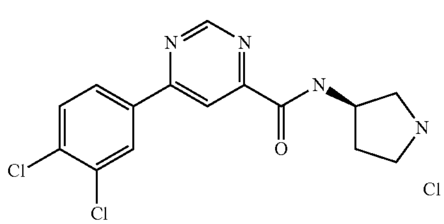 [SMILES: O=C(N[C@@H]1CCNC1)c1cc(-c2ccc(Cl)c(Cl)c2)ncn1 ; Cl] | 6-(3,4-Dichloro-phenyl)-pyrimidine-4-carboxylic acid (R)-pyrrolidin-3-ylamide hydrochloride salt |

TABLE 1-continued

| Structure | IUPAC name |
|---|---|
| 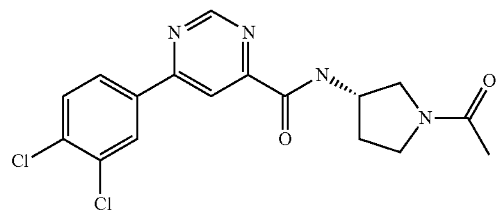 [SMILES: CC(=O)N1CC[C@H](NC(=O)c2cc(-c3ccc(Cl)c(Cl)c3)ncn2)C1] | 6-(3,4-Dichloro-phenyl)-pyrimidine-4-carboxylic acid ((S)-1-acetyl-pyrrolidin-3-yl)-amide |
| 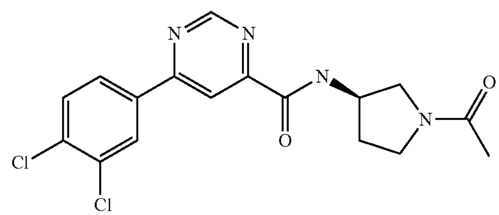 [SMILES: CC(=O)N1CC[C@@H](NC(=O)c2cc(-c3ccc(Cl)c(Cl)c3)ncn2)C1] | 6-(3,4-Dichloro-phenyl)-pyrimidine-4-carboxylic acid ((R)-1-acetyl-pyrrolidin-3-yl)-amide |
| 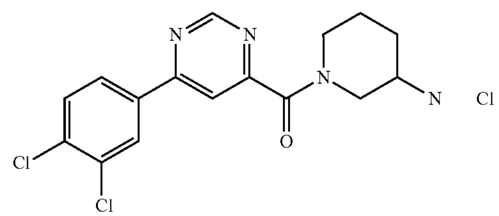 [SMILES: NC1CCCN(C(=O)c2cc(-c3ccc(Cl)c(Cl)c3)ncn2)C1 ; Cl] | (3-Amino-piperidin-1-yl)-[6-(3,4-dichloro-phenyl)-pyrimidin-4-yl]-methanone |
| 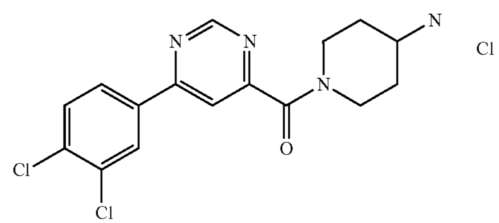 [SMILES: NC1CCN(C(=O)c2cc(-c3ccc(Cl)c(Cl)c3)ncn2)CC1 ; Cl] | (4-Amino-piperidin-1-yl)-[6-(3,4-dichloro-phenyl)-pyrimidin-4-yl]-methanone |
| 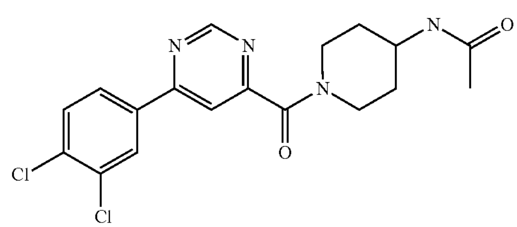 [SMILES: CC(=O)NC1CCN(C(=O)c2cc(-c3ccc(Cl)c(Cl)c3)ncn2)CC1] | N-{1-[6-(3,4-Dichloro-phenyl)-pyrimidine-4-carbonyl]-piperidin-4-yl}-acetamide |
| 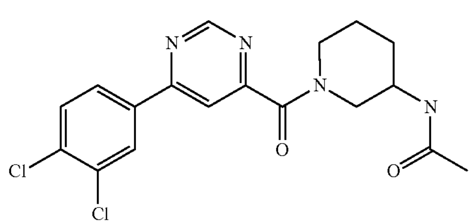 [SMILES: CC(=O)NC1CCCN(C(=O)c2cc(-c3ccc(Cl)c(Cl)c3)ncn2)C1] | N-{1-[6-(3,4-Dichloro-phenyl)-pyrimidine-4-carbonyl]-piperidin-3-yl}-acetamide |
| 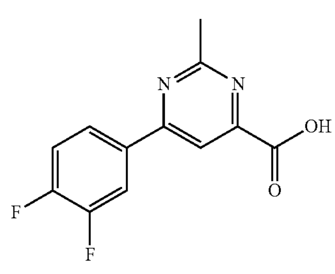 [SMILES: Cc1nc(C(=O)O)cc(-c2ccc(F)c(F)c2)n1] | 6-(3,4-Difluoro-phenyl)-2-methyl-pyrimidine-4-carboxylic acid |

TABLE 1-continued

| Structure | IUPAC name |
| --- | --- |
| 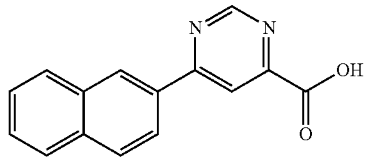 [SMILES: O=C(O)c1cc(-c2ccc3ccccc3c2)ncn1] | 6-Naphthalen-2-yl-pyrimidine-4-carboxylic acid |
| 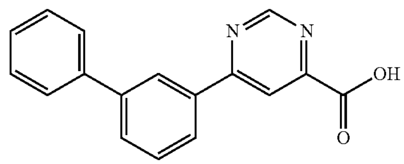 [SMILES: O=C(O)c1cc(-c2cccc(-c3ccccc3)c2)ncn1] | 6-Biphenyl-3-yl-pyrimidine-4-carboxylic acid |
| 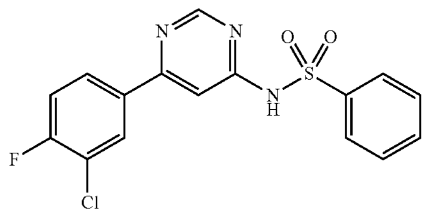 [SMILES: O=S(=O)(Nc1cc(-c2ccc(F)c(Cl)c2)ncn1)c1ccccc1] | N-[6-(3-Chloro-4-fluoro-phenyl)-pyrimidin-4-yl]-benzenesulfonamide |
| 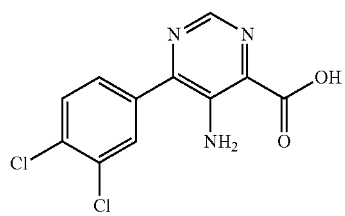 [SMILES: Nc1c(C(=O)O)ncnc1-c1ccc(Cl)c(Cl)c1] | 5-amino-6-(3,4-dichlorophenyl)pyrimidine-4-carboxylate |
| 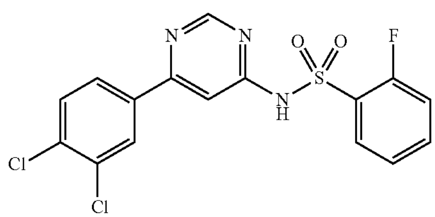 [SMILES: O=S(=O)(Nc1cc(-c2ccc(Cl)c(Cl)c2)ncn1)c1ccccc1F] | N-[6-(3,4-dichlorophenyl)pyrimidin-4-yl]-2-fluorobenzene-1-sulfonamide |
| 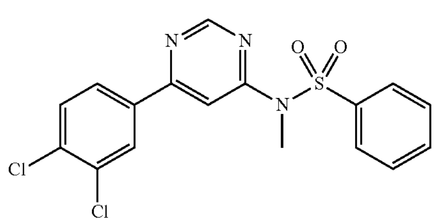 [SMILES: CN(c1cc(-c2ccc(Cl)c(Cl)c2)ncn1)S(=O)(=O)c1ccccc1] | N-[6-(3,4-dichlorophenyl)pyrimidin-4-yl]-N-methylbenzenesulfonamide |
| 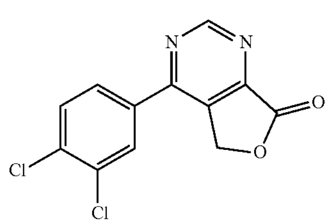 [SMILES: O=C1OCc2c1ncnc2-c1ccc(Cl)c(Cl)c1] | 4-(3,4-dichlorophenyl)-5H,7H-furo[3,4-d]pyrimidin-7-one |

TABLE 1-continued

| Structure | IUPAC name |
|---|---|
| 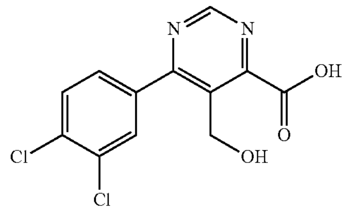 [SMILES: O=C(O)c1ncnc(-c2ccc(Cl)c(Cl)c2)c1CO] | 6-(3,4-dichlorophenyl)-5-(hydroxymethyl)pyrimidine-4-carboxylate |
| 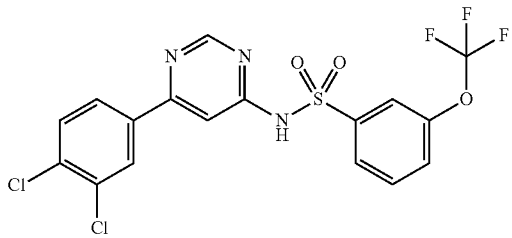 [SMILES: O=S(=O)(Nc1cc(-c2ccc(Cl)c(Cl)c2)ncn1)c1cccc(OC(F)(F)F)c1] | N-[6-(3,4-dichlorophenyl)pyrimidin-4-yl]-3-(trifluoromethoxy)benzene-1-sulfonamide |
| 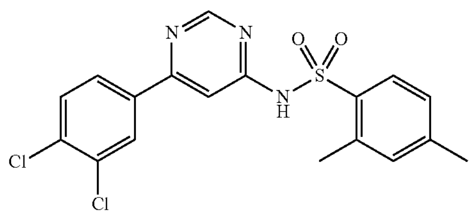 [SMILES: Cc1ccc(S(=O)(=O)Nc2cc(-c3ccc(Cl)c(Cl)c3)ncn2)c(C)c1] | N-[6-(3,4-dichlorophenyl)pyrimidin-4-yl]-2,4-dimethylbenzene-1-sulfonamide |
| 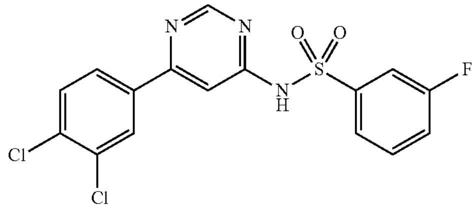 [SMILES: O=S(=O)(Nc1cc(-c2ccc(Cl)c(Cl)c2)ncn1)c1cccc(F)c1] | N-[6-(3,4-dichlorophenyl)pyrimidin-4-yl]-3-fluorobenzene-1-sulfonamide |
| 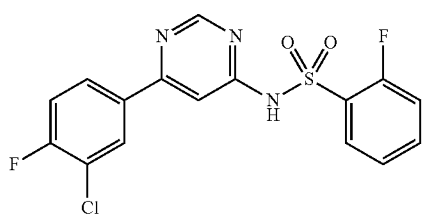 [SMILES: O=S(=O)(Nc1cc(-c2ccc(F)c(Cl)c2)ncn1)c1ccccc1F] | N-[6-(3-chloro-4-fluorophenyl)pyrimidin-4-yl]-2-fluorobenzene-1-sulfonamide |
| 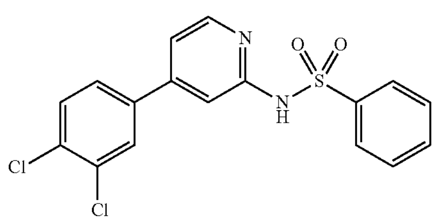 [SMILES: O=S(=O)(Nc1cc(-c2ccc(Cl)c(Cl)c2)ccn1)c1ccccc1] | N-[4-(3,4-dichlorophenyl)pyridin-2-yl]benzenesulfonamide |
| 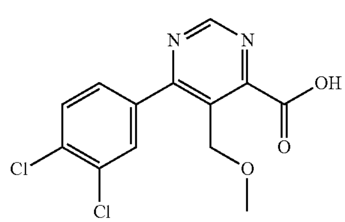 [SMILES: COCc1c(C(=O)O)ncnc1-c1ccc(Cl)c(Cl)c1] | 6-(3,4-dichlorophenyl)-5-(methoxymethyl)pyrimidine-4-carboxylate |

TABLE 1-continued

| Structure | IUPAC name |
| --- | --- |
| 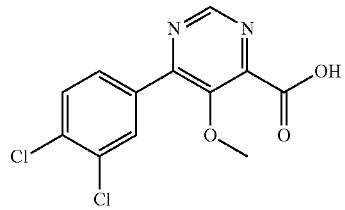 [SMILES: COc1c(C(=O)O)ncnc1-c1ccc(Cl)c(Cl)c1] | 6-(3,4-dichlorophenyl)-5-methoxypyrimidine-4-carboxylate |
| 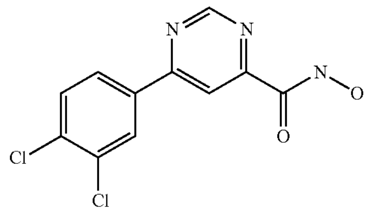 [SMILES: O=C(NO)c1cc(-c2ccc(Cl)c(Cl)c2)ncn1] | 6-(3,4-dichlorophenyl)-N-hydroxypyrimidine-4-carboxamide |
| 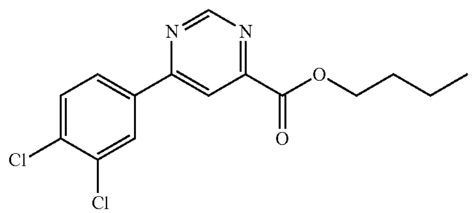 [SMILES: CCCCOC(=O)c1cc(-c2ccc(Cl)c(Cl)c2)ncn1] | butyl 6-(3,4-dichlorophenyl)pyrimidine-4-carboxylate |
| 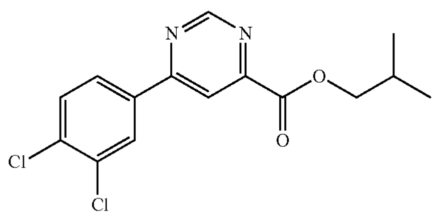 [SMILES: CC(C)COC(=O)c1cc(-c2ccc(Cl)c(Cl)c2)ncn1] | 2-methylpropyl 6-(3,4-dichlorophenyl)pyrimidine-4-carboxylate |
| 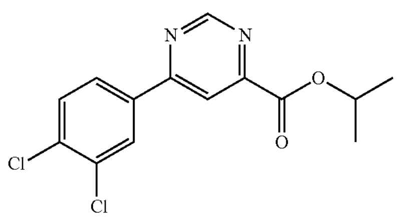 [SMILES: CC(C)OC(=O)c1cc(-c2ccc(Cl)c(Cl)c2)ncn1] | propan-2-yl 6-(3,4-dichlorophenyl)pyrimidine-4-carboxylate |
| 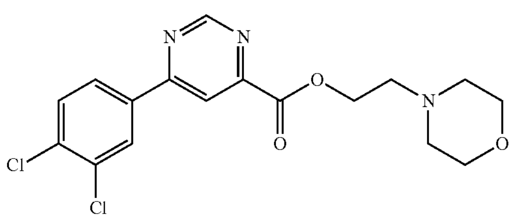 [SMILES: O=C(OCCN1CCOCC1)c1cc(-c2ccc(Cl)c(Cl)c2)ncn1] | 2-(morpholin-4-yl)ethyl 6-(3,4-dichlorophenyl)pyrimidine-4-carboxylate |
| 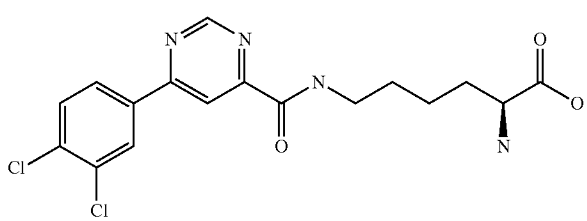 [SMILES: N[C@@H](CCCCNC(=O)c1cc(-c2ccc(Cl)c(Cl)c2)ncn1)C(=O)O] | (2S)-2-amino-6-{[6-(3,4-dichlorophenyl)pyrimidin-4-yl]formamido}hexanoic acid |

Methods for obtaining the chemical entities described herein will be apparent to those of ordinary skill in the art, suitable procedures being described, for example, in examples below, and in the references cited herein.

Provided is a method of inhibiting the catalytic activity of KMO, comprising contacting said KMO with an effective amount of at least one chemical entity described herein.

Also provided is a method of treating a condition or disorder mediated by KMO activity in a subject in need of such a treatment, comprising administering to the subject a therapeutically effective amount of at least one chemical entity described herein.

Also provided is a method of treating a neurodegenerative pathology mediated by KMO activity in a subject in need of such a treatment, comprising administering to the subject a therapeutically effective amount of at least one chemical entity described herein.

Also provided is a method for treating disorders mediated by (or at least in part by) the presence 3-OH-KYN, QUIN and/or KYNA. Also provided is a method of treating a degenerative or inflammatory condition in which an increased synthesis in the brain of QUIN, 3-OH-KYN or increased release of GLU are involved and which may cause neuronal damage.

Such diseases include, for example, Huntington's disease and other polyglutamine disorders such as spinocerebellar ataxias neurodegenerative diseases, psychiatric of neurological diseases or disorders, Alzheimer's disease, Parkinson's disease, amyotropic lateral sclerosis, Creutzfeld-Jacob disease, trauma-induced neurodegeneration, high-pressure neurological syndrome, dystonia, olivopontocerebellar atrophy, amyotrophic lateral sclerosis, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, Dementia such as senile dementia and AIDS-dementia complex, AIDS-induced encephalopathy, other infection related encephalopathy, viral or bacterial meningitis, infectious diseases caused by viral, bacterial and other parasites, for example, general central nervous system (CNS) infections such as viral, bacterial or parasites, for example, poliomyelitis, Lyme disease (*Borrelia burgdorferi* infection) septic shock, and malaria, cancers, cancers with cerebral localization, hepatic encephalopathy, systemic lupus, analgesia and opiate withdrawal symptoms, feeding behavior, psychiatric disorders, such as insomnia, depression, schizophrenia, severe deficit in working memory, severe deficit in long term memory storage, decrease in cognition, severe deficit in attention, severe deficit in executive functioning, sloweness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, and complications thereof, Tourette's syndrome, Fragile X syndrome, autism spectrum disorders, disorders that cause severe and pervasive impairment in thinking feeling, language and the ability to relate to others, mood disorders, psychological disorders characterized by abnormalities of emotional state, such as without limitation, bipolar disorder, unipolar depression, major depression, ondougenous depression, involutional depression, reactive depression, psychotic depression, depression caused by underlying medical conditions, depressive disorders, cyclothymic disorders, dysthymic disorders, mood disorders due to general medical condition, mood disorders not otherwise specified and substance-induced mood disorders. Such disease also include, for example, Acute necrotizing Pancreatitis, AIDS (disease), Analgesia, Aseptic meningitis, Brain disease, for example, Gilles de la Tourette syndrome, Asperger syndrome, Rett syndrome, pervasive developmental disorders, aging-related Brain disease, and developmental Brain disease, burnout syndrome, carbon monoxide poisoning, cardiac arrest or insufficiency and hemorrhagic shock (global brain ischemia), cataract formation and aging of the eye, Central nervous system disease, Cerebrovascular disease, chronic fatigue syndrome, Chronic Stress, Cognitive disorders, convulsive Disorders, such as variants of Grand mal and petit mal epilepsy and Partial Complex Epilepsy, Diabetes mellitus, Disease of the nervous system (e.g., dyskinesia, L-DOPA induced movement disorders, drug addiction, pain and cataract), Drug dependence, Drug withdrawal, feeding disorders, Guillain Barr Syndrome and other neurophaties, Hepatic encephalopathy, Immune disease, immunitary disorders and therapeutic treatment aimed at modifying biological responses (for instance administrations of interferons or interleukins), Inflammation (systemic inflammatory response syndrome), inflammatory disorders of the central and/or peripheral nervous system, Injury (trauma, polytrauma), Mental and behavioral disorders, Metabolic disease, pain disease, or disorder selected from a group of inflammatory pain, neurophathic pain or migraine, allodynia, hyperalgesis pain, phantom pain, neurophatic pain related to diabetic neuropathy, Multiple organ failure, near drowning, Necrosis, neoplasms of the brain, neoplastic disorders including lymphomas and other malignant blood disorders, Nervous system disease (high-pressure neurol. Syndrome, infection), nicotine addiction and other addictive disorders including alcoholism, cannabis, benzodiazepine, barbiturate, morphine and cocaine dependence, change in appetite, sleep disorders, changes in sleep pattern, lack of energy, fatigue, low self steam, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, as a Neuroprotective agents, Pain, Post-traumatic stress disorder, Sepsis, Spinal cord disease, Spinocerebellar ataxia, Systemic lupus erythematosis, traumatic damage to the brain and spinal cord, and tremor syndromes and different movement disorders (diskynesia). Poor balance, brakykinesia, rigidity, tremor, change in speech, loss of facial expression, micrographia, difficulty swallowing, drooling, dementia, confusion, fear, sexual disfunction, language impairment, impairment in decision making, violent outbursts, aggression, hallucination, apathy, impairment in abstract thinking.

Such diseases include, for example, cardiovascular diseases, which refers to diseases and disorders of the heart and circulatory system. These diseases are often associated with dyslipoproteinemias and/or dyslipidemias. Cardiovascular diseases include but are not limited to cardiomegaly, atherosclerosis, myocardial infarction, and congestive heart failure, coronary heart disease, hypertension and hypotension.

Other such diseases include hyperproliferative diseases of benign or malignant behaviour, in which cells of various tissues and organs exhibit aberrant patterns of growth, proliferation, migration, signaling, senescence, and death. Generally hyperpoliferative disease refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, Age-related Macular Degeneration and various retinopaties, as well as the proliferation of ECs and smooth muscle cells that cause restenosis as a consequence of stenting in the treatment of atherosclerosis. Hyperproliferative disorders involving fibroblasts (i.e., fibrogenesis) include but are not limited to disorders of excessive scaring (i.e., fibrosis) such as Age-related Macular Degeneration, cardiac remodeling and failure associated with myocardial infarction, excessive wound healing such as commonly occurs as a consequence of surgery or injury, keloids, and fibroid tumors and stenting.

Additional diseases include transplant rejection (suppression of T-cells) and graft vs host disease, chronic kidney disease, systemic inflammatory disorders, brain inflammatory disorders including malaria and African trypanosomiasis, stroke, and pneumococcal meningitis.

Also provided are methods of treatment in which at least one chemical entity described herein is the only active agent given to the subject and also includes methods of treatment in which at least one chemical entity described herein is given to the subject in combination with one or more additional active agents.

In general, the chemical entities described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, such as once or twice a day.

In some embodiments, the chemical entities described herein are administered as a pharmaceutical composition. Accordingly, provided are pharmaceutical compositions comprising at least one chemical entity described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the chemical entity is sufficient to provide a practical quantity of material for administration per unit dose of the chemical entity.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the chemical entity described herein.

Effective concentrations of at least one chemical entity described herein are mixed with a suitable pharmaceutically acceptable vehicle. In instances in which the chemical entity exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a chemical entity described herein, the resulting mixture may be a solution, suspension, emulsion or the like. The form of the resulting mixture depends upon a number of factors, including the intended mode of administration and the solubility of the chemical entity in the chosen vehicle. The effective concentration sufficient for ameliorating the symptoms of the disease treated may be empirically determined.

Chemical entities described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one chemical entity described herein. In some embodiments, oral pharmaceutical compositions contain at least 5% (weight %) of at least one chemical entity described herein. Some embodiments contain from 25% to 50% or from 5% to 75% of at least one chemical entity described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

Chemical entities described herein can be incorporated into oral liquid preparations such as aqueous or oily suspensions, solutions, emulsions, syrups, or elixirs, for example. Moreover, pharmaceutical compositions containing these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n- propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the chemical entity is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Chemical entities described herein may be administered parenterally in a sterile medium. Parenteral administration includes subcutaneous injections, intravenous, intramuscular, intrathecal injection or infusion techniques. Chemical entities described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Chemical entities described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Chemical entities described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. Chemical entities described herein may also be formulated for transdermal administration as a transdermal patch.

Topical pharmaceutical compositions comprising at least one chemical entity described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The chemical entities described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the chemical entity include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the chemical entities described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one chemical entity described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one chemical entity described herein, and instructions for using the composition to treat a subject (typically a human patient). In some embodiments, the instructions are for using the pharmaceutical composition to treat a subject suffering a condition or disorder mediated by Kynurenine 3-mono-oxygenase activity. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the chemical entities can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one chemical entity described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one chemical entity described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one chemical entity described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating Parkinson's disease, including treating memory and/or cognitive impairment associated with Parkinson's disease, comprising administering to a subject, simultaneously or sequentially, at least one chemical entity described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one chemical entity described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one chemical entity described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

Also provided are methods for treating memory and/or cognitive impairment associated with Alzheimer's disease, comprising administering to a subject, simultaneously or sequentially, at least one chemical entity described herein and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. Also provided are pharmaceutical compositions comprising at least one chemical entity described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, also provided are packaged pharmaceutical compositions containing a pharmaceutical composition comprising at least one chemical entity described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

Also provided are methods for treating memory and/or cognitive impairment associated with dementia or cognitive impairment comprising administering to a subject, simultaneously or sequentially, at least one chemical entity and one or more additional agents used in the treatment of dementia such as, but not limited to, Thioridazine, Haloperidol, Risperidone, Cognex, Aricept, and Exelon. In methods using simultaneous administration, the agents can be present in a combined composition or can be administered separately. Also provided are pharmaceutical compositions comprising at least one chemical entity described herein, and one or more additional pharmaceutical agents used in the treatment of dementia such as, but not limited to, Thioridazine, Haloperidol, Risperidone, Cognex, Aricept, and Exelon. Also provided are packaged pharmaceutical compositions containing a pharmaceutical composition comprising at least one chemical entity described herein, and another composition comprising one or more additional pharmaceutical agents used in the treatment of dementia such as, but not limited to, Thioridazine, Haloperidol, Risperidone, Cognex, Aricept, and Exelon.

Also provided are methods for treating memory and/or cognitive impairment associated with epilepsy comprising administering to a subject, simultaneously or sequentially, at least one chemical entity described herein and one or more additional agents used in the treatment of epilepsy such as, but not limited to, Dilantin, Luminol, Tegretol, Depakote, Depakene, Zarontin, Neurontin, Barbita, Solfeton, and Felbatol. In methods using simultaneous administration, the agents can be present in a combined composition or can be administered separately. Also provided are pharmaceutical compositions comprising at least one chemical entity described herein, and one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol. Also provided are packaged pharmaceutical compositions containing a pharmaceutical composition comprising at least one chemical entity described herein, and another composition comprising one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol.

Also provided are methods for treating memory and/or cognitive impairment associated with multiple sclerosis comprising administering to a subject, simultaneously or sequentially, at least one chemical entity described herein and one or more additional agents used in the treatment of multiple sclerosis such as, but not limited to, Detrol, Ditropan XL, OxyContin, Betaseron, Avonex, Azothioprine, Methotrexate, and Copaxone. In methods using simultaneous administration, the agents can be present in a combined composition or can be administered separately. Also provided are pharmaceutical compositions comprising at least one chemical entity described herein, and one or more additional pharmaceutical agents used in the treatment of multiple sclerosis such as, but not limited to, Detrol, Ditropan XL, OxyContin, Betaseron, Avonex, Azothioprine, Methotrexate, and Copaxone. Also provided are packaged pharmaceutical compositions containing a pharmaceutical composition comprising at least one chemical entity described herein, and another composition comprising one or more additional pharmaceutical agents used in the treatment of multiple sclerosis such as, but not limited to, Detrol, Ditropan XL, OxyContin, Betaseron, Avonex, Azothioprine, Methotrexate, and Copaxone.

When used in combination with one or more additional pharmaceutical agent or agents, the described herein may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The chemical entities described herein are typically administered at dosage levels and in a manner customary for KMO inhibitors. For example, the chemical entities can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one chemical entity described herein, for example, 0.1-50 mg of at least one chemical entity described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one chemical entity described herein.

A labeled form of a chemical entity described herein can be used as a diagnostic for identifying and/or obtaining compounds that have the function of modulating an activity of KMO as described herein. The chemical entities described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The chemical entities, compositions, and methods described herein are further illustrated by the following non-limiting examples.

As used herein, the following abbreviations have the following meanings. If an abbreviation is not defined, it has its generally accepted meaning.

CDI=carbonyldiimidazole
DCM=dichloromethane
DME=dimethyl ether
DMEM=Dulbecco's modified Eagle's medium
DMF=N,N-dimethylformamide
DMSO=dimethylsulfoxide
EDC.HCl=1-Ethyl-3-(3-dimethylaminopropyl)carbodiimide hydrochloride
EtOH=ethanol
Et$_2$O=diethylether
EtOAc=ethyl acetate
g=gram
hr=hour
hrs=hours
HOBt=1-Hydroxybenzotriazol
LiHMDS=lithium hexamethyl-disilazide
LC/MS=liquid chromatography/mass spectrometry
mg=milligram
min=minutes
mL=milliliter
mmol=millimoles
mM=millimolar
ng=nanogram
nm=nanometer
nM=nanomolar
PBS=phosphate buffered saline
rt=room temperature
TBME=t-butyl methyl ether
THF=tetrahydrofuran
TMOF=trimethylorthoformate
μL=microliter
μM=micromolar
1 g/1 ml=1 vol Experimental Commercially available reagents and solvents (HPLC grade) were used without further purification.

Thin-layer chromatography (TLC) analysis was performed with Kieselgel 60 F$_{254}$ (Merck) plates and visualized using UV light. Microwave reactions were carried out using CEM focussed microwaves.

Analytical HPLC-MS was performed on Agilent HP1100 and Shimadzu 2010, systems using reverse phase Atlantis dC18 columns (5 μm, 2.1×50 mm), gradient 5-100% B (A=water/0.1% formic acid, B=acetonitrile/0.1% formic acid) over 3 min, injection volume 3 μl, flow=1.0 ml/min. UV spectra were recorded at 215 nm using a Waters 2487 dual wavelength UV detector or the Shimadzu 2010 system. Mass spectra were obtained over the range m/z 150 to 850 at a sampling rate of 2 scans per second using Waters ZMD and over m/z 100 to 1000 at a sampling rate of 2 Hz using Electrospray ionisation, by a Shimadzu 2010 LC-MS system or analytical HPLC-MS was performed on Agilent HP1100 and Shimadzu 2010, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array or on the Shimadzu 2010 system. Mass spectra were obtained over the range m/z 150 to 850 at a sampling rate of 2 scans per second using Waters ZQ and over m/z 100 to 1000 at a sampling rate of 2 Hz using Electrospray ionisation, by a Shimadzu 2010 LC-MS system. Data were integrated and reported using OpenLynx and OpenLynx Browser software or via Shimadzu PsiPort software.

General Procedures

Method A. Amide coupling. To a solution of carboxylic acid (1 eq) in DMF were added EDC.HCl (1 eq) and HOBt (1 to 1.2 eq) or HATU (1 to 1.2 eq). The reaction mixture was stirred at ambient temperature for 30 minutes after which time the appropriate amine (1 eq) was added. The reaction was monitored by LCMS to completion whereupon the reaction mixture was poured into water. The resultant precipitate was filtered, washed with water (×2), heptane (×2) and dried in vacuo to yield the target compound. If a precipitate was not formed the reaction mixture was extracted with EtOAc (×3) and the combined organic layers were washed with water (×2), saturated aqueous NaCl (×2), dried (Na$_2$SO$_4$ or MgSO$_4$) and the solvent removed in vacuo to afford the crude product. Purification was carried out by flash column chromatography, prep HPLC, or a combination of both.

Method B. Amide coupling. To a solution of carboxylic acid (1 eq) in DCM (20 vol) under nitrogen were added oxalyl chloride (3 eq) and 1 drop of DMF (cat.). The reaction mixture was stirred at ambient temperature for 30 minutes after which time the solvents were removed in vacuo. DCM (20 vol) or THF (20 vol) was added, followed by the required amine (1 to 3 eq) and triethylamine (2 eq) or DIPEA (1.5 eq). The reaction mixture was stirred at ambient temperature. The reaction was monitored by LCMS to completion whereupon water was added. The reaction mixture was then extracted with DCM and the organic layer was washed with water, saturated aqueous NaCl, dried over Na₂SO₄ or MgSO₄ and the solvent removed in vacuo to afford the crude product. Purification was carried out by flash column chromatography, prep HPLC, a combination of both or by trituration with an appropriate solvent.

Method C. Amide coupling. To a solution of carboxylic acid (1 eq) in DMF were added EDC.HCl (1 eq) and HOBt (1 eq). The reaction mixture was stirred at ambient temperature for 30 minutes after which time the appropriate amine was added. The reaction was monitored by LCMS. After completion the reaction mixture was poured into water after which a precipitate came out of solution and was filtered, washed with water, heptane and dried in vacuo to yield the target compound or if a precipitate was not formed the reaction mixture was extracted with EtOAc (3×) and the combined organic layers were washed with water, saturated aqueous NaCl, dried (Na₂SO₄ or MgSO₄) and the solvent removed in vacuo to afford the crude product. Purification was carried out by flash column chromatography, prep HPLC, or a combination of both.

Method D. Amide coupling. To a solution of carboxylic acid (1 eq) in DCM (20 vol) under nitrogen were added oxalyl chloride (3 eq) and DMF (cat). The reaction mixture was stirred at ambient temperature for 30 minutes after which time the solvents were removed in vacuo. DCM (20 vol) or THF (20 vol) was added, followed by the required amine (1 to 3 eq) and triethylamine (2 eq) and the reaction mixture was stirred at ambient temperature. The reaction was monitored by LCMS to completion whereupon water was added. The reaction mixture was then extracted with DCM and the organic layer was washed with water, saturated aqueous NaCl, dried over Na₂SO₄ or MgSO₄ and the solvent removed in vacuo to afford the crude product. Purification was carried out by flash column chromatography, prep HPLC, a combination of both or by trituration with an appropriate solvent.

Example 1

Reaction Scheme 1

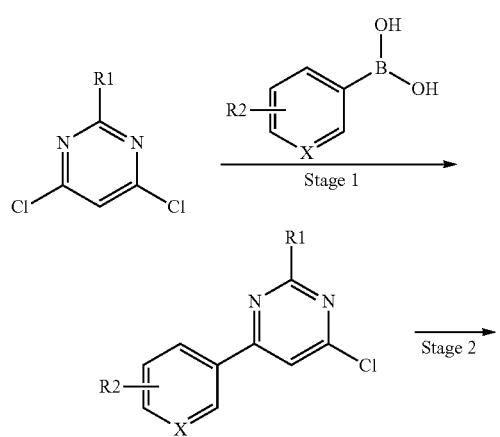

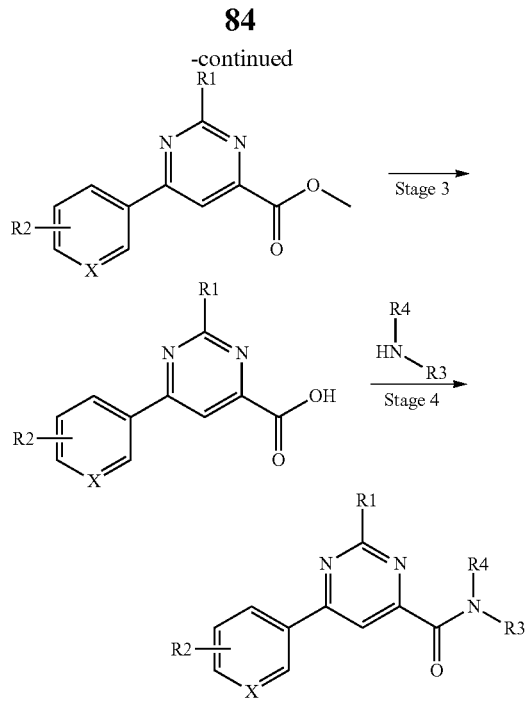

Referring to Reaction Scheme 1, Stage 1, to a stirred suspension of dichloropyrimidine (1 eq) in 1,4-dioxane (15 vol) was added boronic acid (0.7 eq) and Pd(PPh₃)₄ (0.025 eq). A 2M K₂CO₃ solution (7.5 vol) was added to the resulting mixture, which was heated at 90° C. overnight under an atmosphere of N₂. The reaction mixture was cooled to room temperature and concentrated in vacuo. The residue was dissolved in EtOAc:water (1:1) (100 vol) and the resulting solution filtered through celite. The organic layer was separated and the aqueous layer further extracted with EtOAc (50 vol). The combined organic layers were washed with saturated aqueous NaCl (20 vol), dried over Na₂SO₄, filtered and the solvent removed in vacuo. The resulting residue was purified by flash column chromatography (eluent: [0:1 to 1:19] EtOAc:heptane) to afford the required target compounds.

Referring to Reaction Scheme 1, Stage 2, 4-chloro-6-substituted-phenyl-pyrimidine (1 eq), PdCl₂(dppf).DCM (0.05 eq) and triethylamine (2 eq) were suspended in degassed MeOH (50 vol) in a bomb fitted with a magnetic stirrer bar. The atmosphere in the reaction vessel was replaced with N₂ by successive evacuation and charging with N₂ gas (this process was repeated three times). The bomb was then flushed with CO by successive charging with CO and evacuation. The vessel was pressurised to 5 bar of CO and heated at 50° C. with stirring for 5 hours. The reaction vessel was allowed to cool to room temperature before venting CO and flushing with N₂. The reaction mixture was concentrated in vacuo and the resulting residue dissolved in EtOAc (30 vol) and water (30 vol). The solution was filtered through cotton wool and the organic layer was separated, washed with saturated aqueous NaCl (15 vol), dried over Na₂SO₄, filtered and concentrated under reduced pressure. Purification by flash column chromatography (eluent: [0:1 to 1:9] EtOAc:heptane) yielded the target compounds.

Referring to Reaction Scheme 1, Stage 3, 6-substituted-phenyl-pyrimidine-4-carboxylic acid methyl ester (1 eq) was suspended in MeOH (20 vol), 1M NaOH solution (20 vol) and stirred at room temperature for 4 hours. The reaction mixture was acidified with 2M HCl. Soluble products were extracted with DCM (2×20 vol) and the combined organic layers were dried over MgSO₄, filtered and concentration under reduced pressure afforded the target compounds. Insoluble products were filtered, washed with water (3×10 vol) and heptane (3×10 vol) before drying in vacuo to yield the target compounds.

Referring to Reaction Scheme 1, Stage 4, the required amide analogues were prepared following the procedures described in method A, B, C or D.

The following compounds were prepared substantially as described above.

| Structure | Molecular Weight | Mass Spec Result |
|---|---|---|
| 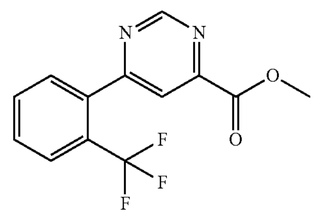 [SMILES: COC(=O)c1cc(-c2ccccc2C(F)(F)F)ncn1] | 282.22 | [M + H]⁺ = 283, 94% @ rt = 3.90 min |
| | 283.12 | [M + H]⁺ = 283, 100% @ rt = 4.47 min |
| 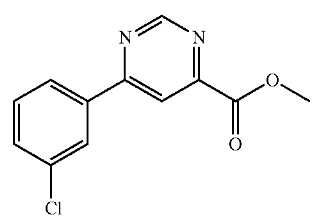 [SMILES: COC(=O)c1cc(-c2cccc(Cl)c2)ncn1] | 248.67 | [M + H]⁺ = 249, 97% @ rt = 3.98 min |
| | 283.12 | [M + H]⁺ = 283/285, 99% @ rt = 4.58 min |
| 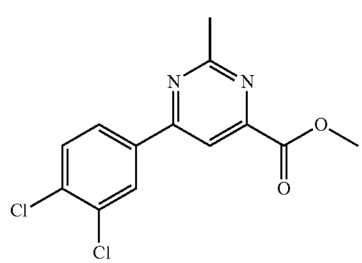 [SMILES: COC(=O)c1cc(-c2ccc(Cl)c(Cl)c2)nc(C)n1] | 297.14 | [M + H]⁺ = 297, 100% @ rt = 4.78 min |
| 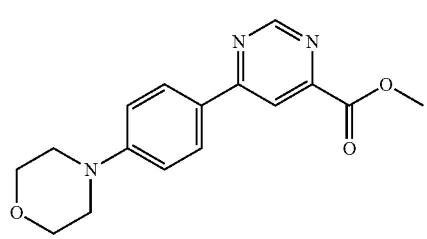 [SMILES: COC(=O)c1cc(-c2ccc(N3CCOCC3)cc2)ncn1] | 299.33 | [M + H]⁺ = 300, 96% @ rt = 3.61 min |

| Structure | Molecular Weight | Mass Spec Result |
|---|---|---|
| | 300.21 | [M + H]+ = 301, 95% @ rt = 4.39 min |
| 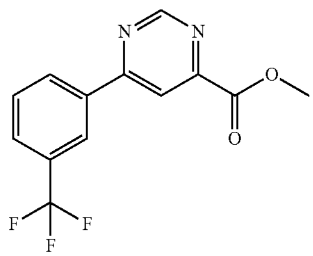 [SMILES: COC(=O)c1cc(-c2cccc(C(F)(F)F)c2)ncn1] | 282.22 | [M + H]+ = 283, 97% @ rt = 4.16 min |
| | 300.21 | [M + H]+ = 301, 100% @ rt = 4.52 min |
| 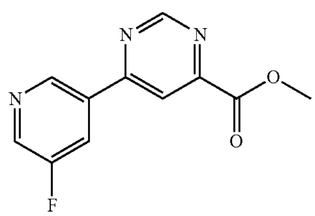 [SMILES: COC(=O)c1cc(-c2cncc(F)c2)ncn1] | 233.20 | [M + H]+ = 234, 100% @ rt = 2.96 min |
| 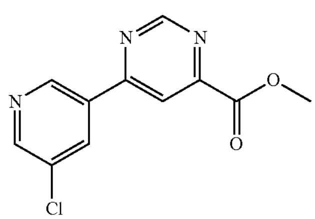 [SMILES: COC(=O)c1cc(-c2cncc(Cl)c2)ncn1] | 249.66 | [M + H]+ = 250, 100% @ rt = 3.30 min |
| | 300.21 | [M + 23]+ = 301, 100% @ rt = 4.17 min |
| 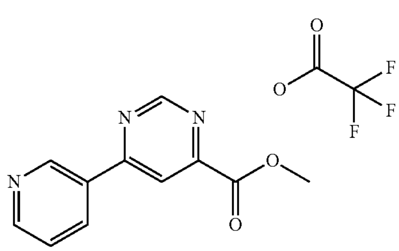 [SMILES: COC(=O)c1cc(-c2cccnc2)ncn1 ; O=C(O)C(F)(F)F] | 329.24 | [M + H]+ = 216, 100% @ rt = 2.27 min |

-continued
| Structure | Molecular Weight | Mass Spec Result |
|---|---|---|
| 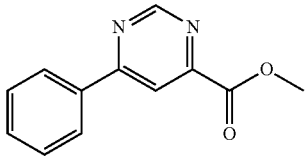 [SMILES: COC(=O)c1cc(-c2ccccc2)ncn1] | 214.23 | [M + H]⁺ = 215, 99% @ rt = 3.55 min |
| 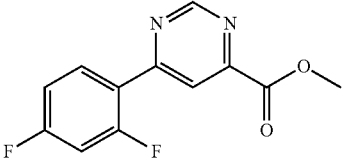 [SMILES: COC(=O)c1cc(-c2ccc(F)cc2F)ncn1] | 250.21 | [M + H]⁺ = 251, 98% @ rt = 3.76 min |
| 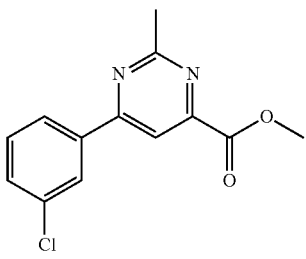 [SMILES: COC(=O)c1cc(-c2cccc(Cl)c2)nc(C)n1] | 262.70 | [M + H]⁺ = 263, 99% @ rt = 4.48 min |
| 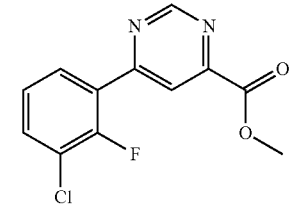 [SMILES: COC(=O)c1cc(-c2cccc(Cl)c2F)ncn1] | 266.66 | [M + H]⁺ = 267, 100% @ rt = 3.99 min |
| 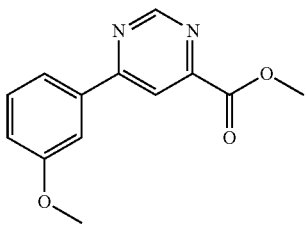 [SMILES: COC(=O)c1cc(-c2cccc(OC)c2)ncn1] | 244.25 | [M + H]⁺ = 245, 99% @ rt = 3.80 min |
| 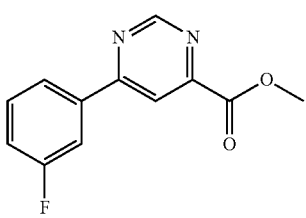 [SMILES: COC(=O)c1cc(-c2cccc(F)c2)ncn1] | 232.22 | [M + H]⁺ = 233, 100% @ rt = 3.87 min |
| 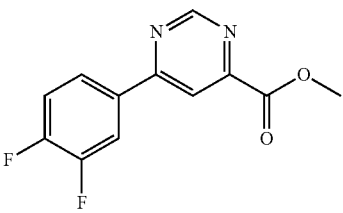 [SMILES: COC(=O)c1cc(-c2ccc(F)c(F)c2)ncn1] | 250.21 | [M + H]⁺ = 251, 100% @ rt = 4.11 min |

| Structure | Molecular Weight | Mass Spec Result |
|---|---|---|
| methyl 6-(5-chloro-2-fluorophenyl)pyrimidine-4-carboxylate | 266.66 | [M + H]⁺ = 267, 100% @ rt = 4.31 min |
| methyl 6-(m-tolyl)pyrimidine-4-carboxylate | 228.25 | [M + H]⁺ = 229, 100% @ rt = 4.06 min |
| methyl 6-(3-chloro-4-(trifluoromethyl)phenyl)pyrimidine-4-carboxylate | 316.67 | [M + H]⁺ = 317, 99% @ rt = 4.62 min |
| methyl 6-(3-chloro-4-methylphenyl)pyrimidine-4-carboxylate | 262.70 | [M + H]⁺ = 263, 99.8% @ rt = 4.36 min |
| methyl 6-(3-chloro-4-fluorophenyl)pyrimidine-4-carboxylate | 266.66 | [M + H]⁺ = 267, 100% @ rt = 4.35 min |
| 6-(2-(trifluoromethyl)phenyl)pyrimidine-4-carboxylate | 268.20 | [M + H]⁺ = 269, 100% @ rt = 3.34 min |
| 6-(3-chlorophenyl)pyrimidine-4-carboxylate | 234.64 | [M + H]⁺ = 235, 100% @ rt = 3.66 min |

| Structure | Molecular Weight | Mass Spec Result |
|---|---|---|
| | 269.09 | [M + H]⁺ = 269, 100% @ rt = 4.04 min |
| | 269.09 | [M + H]⁺ = 269, 99% @ rt = 4.30 min |
| 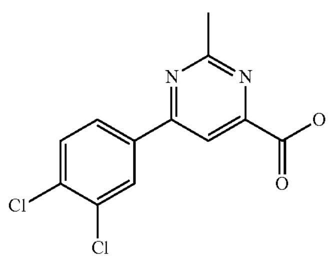 [SMILES: Cc1nc(C(=O)O)cc(-c2ccc(Cl)c(Cl)c2)n1] | 283.12 | [M + H]⁺ = 283, 99% @ rt = 4.43 min |
| 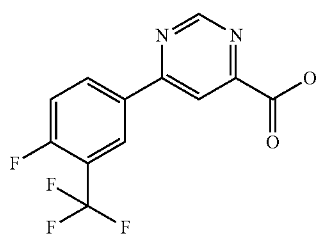 [SMILES: O=C(O)c1cc(-c2ccc(F)c(C(F)(F)F)c2)ncn1] | 286.19 | [M + H]⁺ = 287, 100% @ rt = 4.07 min |
| 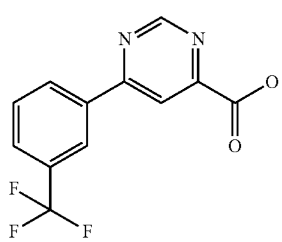 [SMILES: O=C(O)c1cc(-c2cccc(C(F)(F)F)c2)ncn1] | 268.20 | [M + H]⁺ = 269, 100% @ rt = 3.78 min |
| 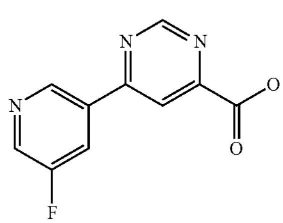 [SMILES: O=C(O)c1cc(-c2cncc(F)c2)ncn1] | 219.18 | [M + H]⁺ = 220, 99% @ rt = 2.66 min |

| Structure | Molecular Weight | Mass Spec Result |
|---|---|---|
| [3-(trifluoromethyl)-5-fluorophenyl pyrimidine-4-carboxylate] | 286.19 | [M + H]⁺ = 287, 97% @ rt = 4.26 min |
| [5-chloropyridin-3-yl pyrimidine-4-carboxylate] | 235.63 | [M + H]⁺ = 236, 100% @ rt = 2.92 min |
| [6-phenylpyrimidine-4-carboxylate] | 200.20 | [M + H]⁺ = 201, 100% @ rt = 3.29 min |
| [2-fluoro-5-(trifluoromethyl)phenyl pyrimidine-4-carboxylate] | 286.19 | [M + H]⁺ = 287, 100% @ rt = 4.03 min |
| [2,4-difluorophenyl pyrimidine-4-carboxylate] | 236.18 | [M + H]⁺ = 237, 100% @ rt = 3.41 min |
| [3-chloro-2-fluorophenyl pyrimidine-4-carboxylate] | 252.63 | [M + H]⁺ = 253, 97% @ rt = 3.96 min |
| [3-chlorophenyl-2-methylpyrimidine-4-carboxylate] | 248.67 | [M + H]¹⁺ = 249, 100% @ rt = 3.88 min |

| Structure | Molecular Weight | Mass Spec Result |
|---|---|---|
| 6-(3-methoxyphenyl)pyrimidine-4-carboxylic acid | 230.23 | [M + H]⁺ = 231, 100% @ rt = 3.20 min |
| 6-(m-tolyl)pyrimidine-4-carboxylic acid | 214.23 | [M + H]⁺ = 215, 100% @ rt = 3.90 min |
| 6-(4-methoxyphenyl)pyrimidine-4-carboxylic acid | 230.23 | [M + H]⁺ = 231, 100% @ rt = 3.52 min |
| 6-(3,4-difluorophenyl)pyrimidine-4-carboxylic acid | 236.18 | [M + H]⁺ = 237, 100% @ rt = 3.74 min |
| 6-(3-fluorophenyl)pyrimidine-4-carboxylic acid | 218.19 | [M + H]⁺ = 219, 100% @ rt = 3.54 min |
| 6-(3-chloro-4-(trifluoromethyl)phenyl)pyrimidine-4-carboxylic acid | 302.64 | [M + H]⁺ = 303, 100% @ rt = 4.38 min |
| 6-(5-chloro-2-fluorophenyl)pyrimidine-4-carboxylic acid | 252.63 | [M + H]⁺ = 253, 100% @ rt = 3.64–3.93 min |

-continued

| Structure | Molecular Weight | Mass Spec Result |
|---|---|---|
| 6-(3-chloro-4-methoxyphenyl)pyrimidine-4-carboxylic acid | 264.67 | [M + H]⁺ = 265, 100% @ rt = 3.73-4.10 min |
| 6-(3-chloro-4-fluorophenyl)pyrimidine-4-carboxylic acid | 252.63 | [M + H]⁺ = 293, 100% @ rt = 3.92-4.23 min |
| 6-(3-chloro-4-methylphenyl)pyrimidine-4-carboxylic acid | 248.67 | [M + H]⁺ = 249, 100% @ rt = 4.21 min |
| 6-(4-chloro-3-fluorophenyl)pyrimidine-4-carboxylic acid | 252.63 | [M + H]⁺ = 253, 100% @ rt = 4.06 min |
| 6-(4-chlorophenyl)pyrimidine-4-carboxylic acid | 234.64 | [M + H]⁺ = 235/237, 66% @ rt = 3.47 min + 34% @ rt = 3.65 min |
| 6-(4-chloro-2-fluorophenyl)pyrimidine-4-carboxylic acid | 252.63 | [M + H]⁺ = 253/255, 100% @ rt = 3.40 min |
| 6-(3-chlorophenyl)-N-(pyridin-3-yl)pyrimidine-4-carboxamide | 310.75 | [M + H]⁺ = 311, 100% @ rt = 3.74 min |

-continued

| Structure | Molecular Weight | Mass Spec Result |
|---|---|---|
| 3,4-dichlorophenyl-2-methylpyrimidine-N-(pyridin-3-yl)carboxamide | 359.22 | [M + H]⁺ = 359/361, 100% @ rt = 4.50 min |
| 3-chlorophenyl-pyrimidine-N-(2,6-dimethylpyridin-3-yl)carboxamide | 338.80 | [M + H]⁺ = 339/341, 100% @ rt = 3.17 min |
| 3-chlorophenyl-pyrimidine-N-(pyrimidin-5-yl)carboxamide | 311.73 | [M + H]⁺ = 312, 98% @ rt = 4.00 min |
| 3-(trifluoromethyl)phenyl-pyrimidine-N-(pyridin-2-yl)carboxamide | 344.30 | [M + H]⁺ = 345, 100% @ rt = 4.92 min |
| 4-fluoro-3-(trifluoromethyl)phenyl-pyrimidine-N-(pyridin-3-yl)carboxamide | 362.29 | [M + H]⁺ = 363, 99% @ rt = 4.06 min |
| 3,5-dichlorophenyl-pyrimidine-N-(pyridin-3-yl)carboxamide | 345.19 | [M + H]⁺ = 344, 100% @ rt = 4.38 min |

-continued
| Structure | Molecular Weight | Mass Spec Result |
|---|---|---|
| 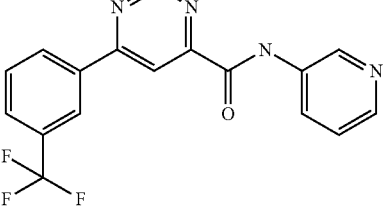 | 344.30 | [M + H]⁺ = 345, 100% @ rt = 3.89 min |
| 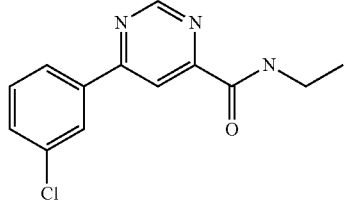 [SMILES: CCNC(=O)c1cc(-c2cccc(Cl)c2)ncn1] | 261.71 | [M + H]⁺ = 262, 99% @ rt = 4.34 min |
| 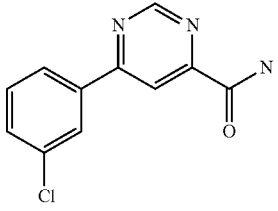 [SMILES: NC(=O)c1cc(-c2cccc(Cl)c2)ncn1] | 233.66 | [M + H]⁺ = 234, 100% @ rt = 3.60 min |
| 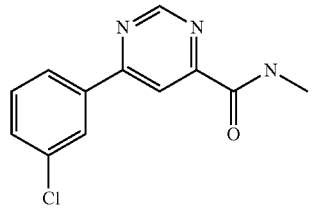 [SMILES: CNC(=O)c1cc(-c2cccc(Cl)c2)ncn1] | 247.69 | [M + H]⁺ = 248, 100% @ rt = 3.85 min |
| 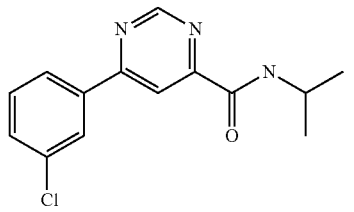 [SMILES: CC(C)NC(=O)c1cc(-c2cccc(Cl)c2)ncn1] | 275.74 | [M + H]⁺ = 276, 99% @ rt = 4.68 min |
| 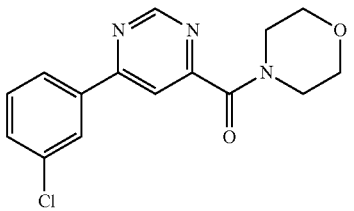 [SMILES: O=C(c1cc(-c2cccc(Cl)c2)ncn1)N1CCOCC1] | 303.75 | [M + H]⁺ = 304, 100% @ rt = 3.64 min |
| 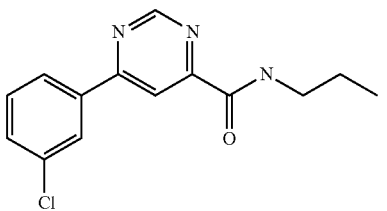 [SMILES: CCCNC(=O)c1cc(-c2cccc(Cl)c2)ncn1] | 275.74 | [M + H]⁺ = 276, 100% @ rt = 4.39 min |

-continued

| Structure | Molecular Weight | Mass Spec Result |
|---|---|---|
| [6-(3-chlorophenyl)pyrimidin-4-yl]-N-phenyl carboxamide | 309.76 | [M + H]⁺ = 310, 100% @ rt = 5.17 min |
| [6-(3-chlorophenyl)pyrimidin-4-yl]-N-(2-methylphenyl) carboxamide | 323.78 | [M + H]⁺ = 324, 100% @ rt = 5.08 min |
| [6-(3-chlorophenyl)pyrimidin-4-yl]-N-(4-methylphenyl) carboxamide | 323.78 | [M + H]⁺ = 324, 100% @ rt = 5.40 min |
| [6-(3-chlorophenyl)pyrimidin-4-yl]-(3,4-dihydroquinolin-1(2H)-yl)methanone | 349.82 | [M + H]⁺ = 350/352, 100% @ rt = 4.57 min |
| [6-(3-chlorophenyl)pyrimidin-4-yl]-N-(6-methoxypyridin-3-yl) carboxamide | 340.77 | [M + H]⁺ = 341, 100% @ rt = 4.53 min |
| [6-(3-chlorophenyl)pyrimidin-4-yl]-(2,3-dihydroindol-1-yl)methanone | 335.80 | [M + H]⁺ = 336, 100% @ rt = 4.57 min |
| [6-(3-chlorophenyl)pyrimidin-4-yl]-N-(3-methylphenyl) carboxamide | 323.78 | [M + H]⁺ = 324, 100% @ rt = 5.25 min |

-continued

| Structure | Molecular Weight | Mass Spec Result |
|---|---|---|
| | 340.77 | [M + H]⁺ = 342, 100% @ rt = 4.15 min |
| 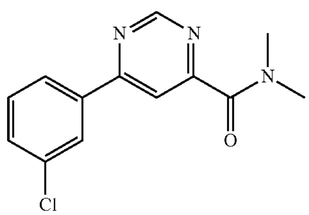 | 261.71 | [M + H]⁺ = 262, 100% @ rt = 3.73 min |
| 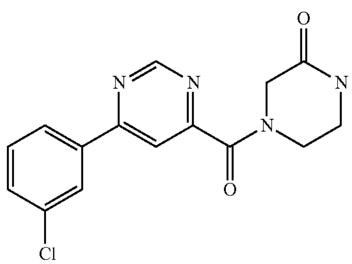 [SMILES: O=C1CN(C(=O)c2cc(-c3cccc(Cl)c3)ncn2)CCN1] | 316.75 | [M + H]⁺ = 317, 100% @ rt = 3.30 min |
| 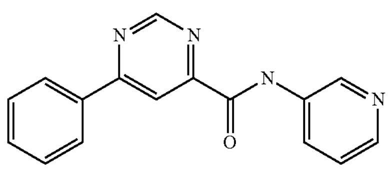 [SMILES: O=C(Nc1cccnc1)c1cc(-c2ccccc2)ncn1] | 276.30 | [M + H]⁺ = 277, 100% @ rt = 3.30 min |
| | 340.77 | [M + H]⁺ = 341, 99% @ rt = 3.19 min |
| 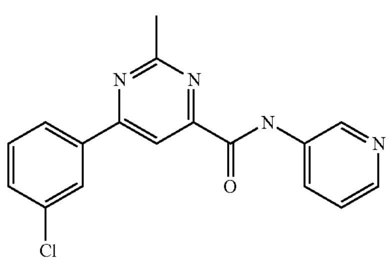 [SMILES: Cc1nc(C(=O)Nc2cccnc2)cc(-c2cccc(Cl)c2)n1] | 324.77 | [M + H]⁺ = 325, 100% @ rt = 4.14 min |
| 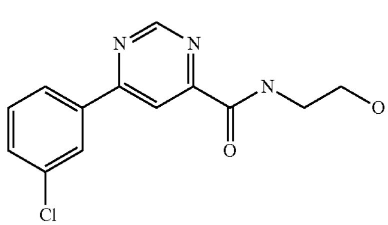 [SMILES: O=C(NCCO)c1cc(-c2cccc(Cl)c2)ncn1] | 277.71 | [M + H]⁺ = 278, 100% @ rt = 3.56 min |

| Structure | Molecular Weight | Mass Spec Result |
|---|---|---|
| (6-(3-chlorophenyl)pyrimidin-4-yl)(4-hydroxypiperidin-1-yl)methanone | 317.78 | [M + H]⁺ = 318, 100% @ rt = 3.42 min |
| N-benzyl-6-(3-chlorophenyl)pyrimidine-4-carboxamide | 323.78 | [M + H]⁺ = 324, 100% @ rt = 4.97 min |
| (6-(3-chlorophenyl)pyrimidin-4-yl)(4-methylpiperazin-1-yl)methanone | 316.79 | [M + H]⁺ = 317, 100% @ rt = 2.66 min |
| (6-(3-chlorophenyl)pyrimidin-4-yl)(pyrrolidin-1-yl)methanone | 287.75 | [M + H]⁺ = 288, 100% @ rt = 4.56 min |
| 6-(3-chlorophenyl)-N-((S)-2-hydroxypropyl)pyrimidine-4-carboxamide | 291.74 | [M + H]⁺ = 292, 100% @ rt = 3.78 min |
| (4-acetylpiperazin-1-yl)(6-(3-chlorophenyl)pyrimidin-4-yl)methanone | 344.80 | [M + H]⁺ = 345, 100% @ rt = 3.51 min |

| Structure | Molecular Weight | Mass Spec Result |
|---|---|---|
| 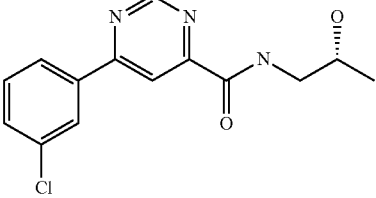 | 291.74 | [M + H]⁺ = 292, 100% @ rt = 3.77 min |
| 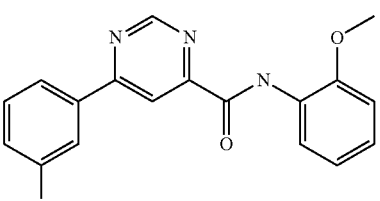 | 339.78 | [M + H]⁺ = 340, 100% @ rt = 5.45 min |
| 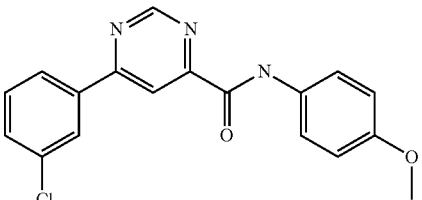 | 339.78 | [M + H]⁺ = 340, 100% @ rt = 5.43 min |
| 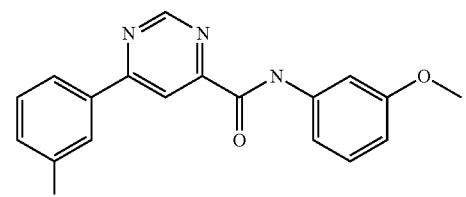 | 339.78 | [M + H]⁺ = 340, 100% @ rt = 5.16 min |
| 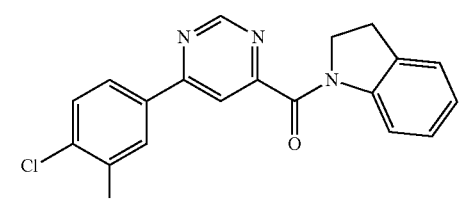 | 370.24 | [M + H]⁺ = 370, 100% @ rt = 5.38 min |
| 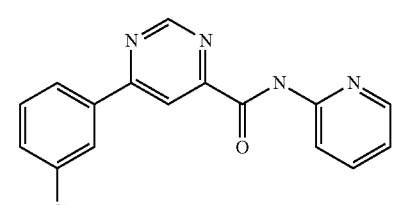 | 310.75 | [M + H]⁺ = 311, 100% @ rt = 4.98 min |
| 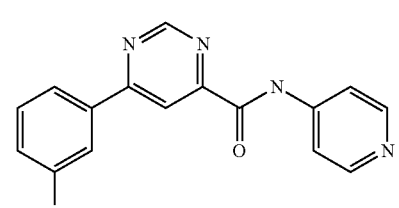 | 310.75 | [M + H]⁺ = 311, 100% @ rt = 3.08 min |

-continued

| Structure | Molecular Weight | Mass Spec Result |
|---|---|---|
| 6-(3-chlorophenyl)-N-(pyridin-4-ylmethyl)pyrimidine-4-carboxamide | 324.77 | [M + H]⁺ = 325, 97% @ rt = 2.98 min |
| 6-(3-chlorophenyl)-pyrimidin-4-yl(4-methylpiperidin-1-yl)methanone | 315.81 | [M + H]⁺ = 316, 97% @ rt = 4.64 min |
| (S)-(6-(3-chlorophenyl)pyrimidin-4-yl)(3-hydroxypyrrolidin-1-yl)methanone | 303.75 | [M + H]⁺ = 304, 100% @ rt = 3.48 min |
| 6-(3-chlorophenyl)-N-(1,3,4-thiadiazol-2-yl)pyrimidine-4-carboxamide | 317.76 | [M + H]⁺ = 318, 100% @ rt = 4.18 min |
| 6-(3-chlorophenyl)-N-(isoxazol-3-yl)pyrimidine-4-carboxamide | 300.71 | [M + H]⁺ = 301, 93% @ rt = 4.48 min |
| (R)-6-(3-chlorophenyl)-N-(1-phenylethyl)pyrimidine-4-carboxamide | 337.81 | [M + H]⁺ = 338, 100% @ rt = 5.11 min |
| (S)-6-(3-chlorophenyl)-N-(1-phenylethyl)pyrimidine-4-carboxamide | 337.81 | [M + H]⁺ = 338, 100% @ rt = 5.10 min |

| Structure | Molecular Weight | Mass Spec Result |
|---|---|---|
| 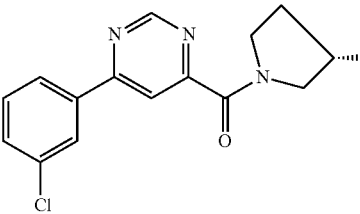 | 303.75 | [M + H]⁺ = 304, 100% @ rt = 3.48 min |
| 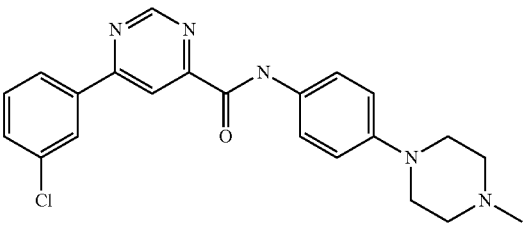 [SMILES: CN1CCN(c2ccc(NC(=O)c3cc(-c4cccc(Cl)c4)ncn3)cc2)CC1] | 407.91 | [M + H]⁺ = 408, 99% @ rt = 3.30 min |
| 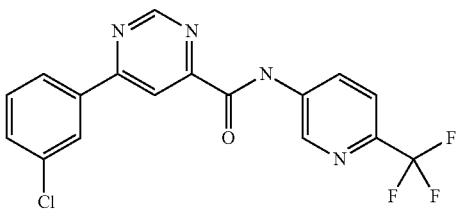 [SMILES: O=C(Nc1ccc(C(F)(F)F)nc1)c1cc(-c2cccc(Cl)c2)ncn1] | 378.74 | [M + H]⁺ = 379, 100% @ rt = 5.13 min |
| 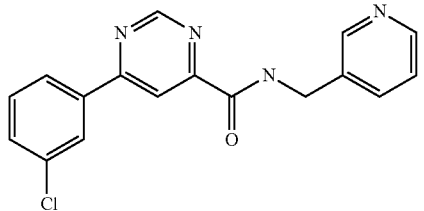 [SMILES: O=C(NCc1cccnc1)c1cc(-c2cccc(Cl)c2)ncn1] | 324.77 | [M + H]⁺ = 325, 100% @ rt = 3.15 min |
| 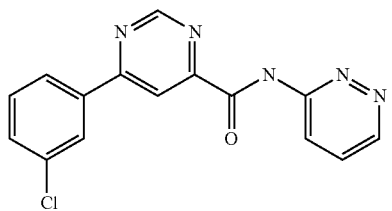 [SMILES: O=C(Nc1cccnn1)c1cc(-c2cccc(Cl)c2)ncn1] | 311.73 | [M + H]⁺ = 311, 100% @ rt = 4.36 min |
| 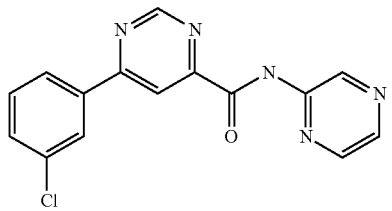 [SMILES: O=C(Nc1cnccn1)c1cc(-c2cccc(Cl)c2)ncn1] | 311.73 | [M + H]⁺ = 311, 98% @ rt = 4.67 min |
| 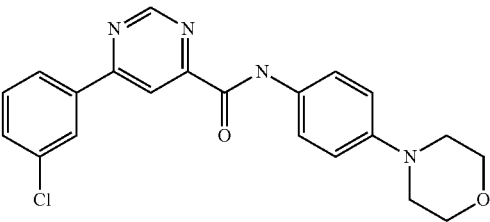 [SMILES: O=C(Nc1ccc(N2CCOCC2)cc1)c1cc(-c2cccc(Cl)c2)ncn1] | 394.86 | [M + H]⁺ = 395, 100% @ rt = 4.91 min |

-continued

| Structure | Molecular Weight | Mass Spec Result |
|---|---|---|
| | 330.78 | [M + H]⁺ = 331, 100% @ rt = 3.39 min |
| | 330.78 | [M + H]⁺ = 331, 99% @ rt = 3.41 min |
| 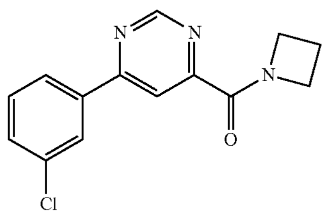 [SMILES: O=C(c1cc(-c2cccc(Cl)c2)ncn1)N1CCC1] | 273.72 | [M + H]⁺ = 274, 100% @ rt = 4.25 min |
| 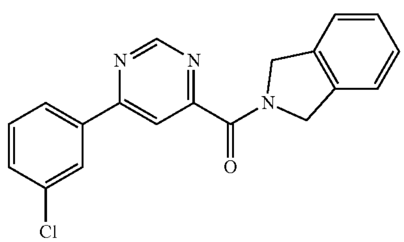 [SMILES: O=C(c1cc(-c2cccc(Cl)c2)ncn1)N1Cc2ccccc2C1] | 335.80 | [M + H]⁺ = 336, 100% @ rt = 5.32 min |
| 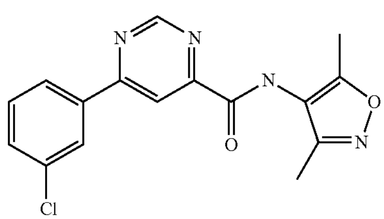 [SMILES: Cc1noc(C)c1NC(=O)c1cc(-c2cccc(Cl)c2)ncn1] | 328.76 | [M + H]⁺ = 329, 100% @ rt = 4.83 min |
| 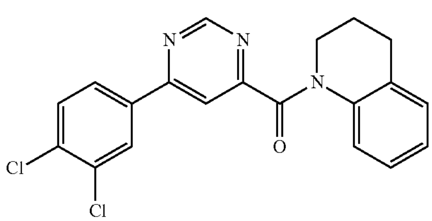 [SMILES: O=C(c1cc(-c2ccc(Cl)c(Cl)c2)ncn1)N1CCCc2ccccc21] | 384.27 | [M + H]⁺ = 384, 100% @ rt = 5.13 min |
| 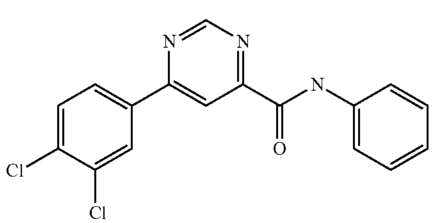 [SMILES: O=C(Nc1ccccc1)c1cc(-c2ccc(Cl)c(Cl)c2)ncn1] | 344.20 | [M + H]⁺ = 344, 100% @ rt = 5.41 min |

-continued

| Structure | Molecular Weight | Mass Spec Result |
|---|---|---|
| 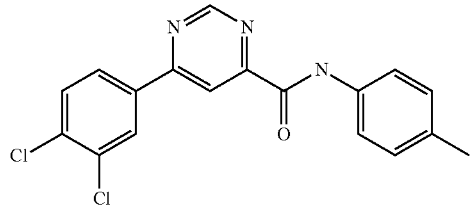 [SMILES: Cc1ccc(NC(=O)c2cc(-c3ccc(Cl)c(Cl)c3)ncn2)cc1] | 358.23 | [M + H]⁺ = 358, 100% @ rt = 5.61 min |
| 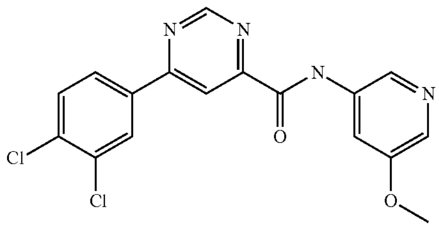 [SMILES: COc1cncc(NC(=O)c2cc(-c3ccc(Cl)c(Cl)c3)ncn2)c1] | 375.22 | [M + H]⁺ = 375, 100% @ rt = 4.67 min |
| 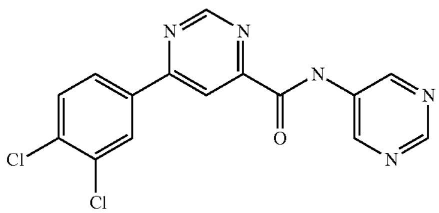 [SMILES: O=C(Nc1cncnc1)c1cc(-c2ccc(Cl)c(Cl)c2)ncn1] | 346.18 | [M + H]⁺ = 346, 100% @ rt = 4.47 min |
| | 359.22 | [M + H]⁺ = 361, 100% @ rt = 3.82 min |
| | 359.22 | [M + H]⁺ = 361, 100% @ rt = 4.09 min |
| 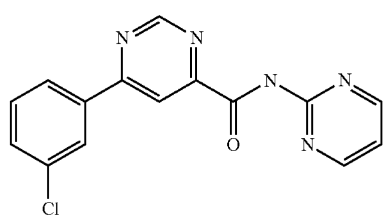 | 311.73 | [M + H]⁺ = 312, 100% @ rt = 4.12 min |
| 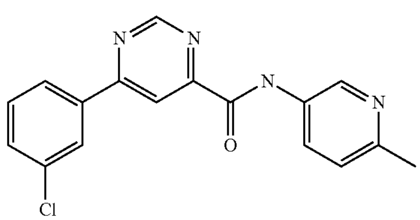 [SMILES: Cc1ccc(NC(=O)c2cc(-c3cccc(Cl)c3)ncn2)cn1] | 324.77 | [M + H]⁺ = 325, 100% @ rt = 3.39 min |

-continued

| Structure | Molecular Weight | Mass Spec Result |
|---|---|---|
| 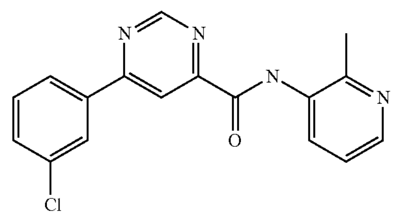 [SMILES: Cc1ncccc1NC(=O)c1cc(-c2cccc(Cl)c2)ncn1] | 324.77 | [M + H]⁺ = 325, 100% @ rt = 3.63 min |
| 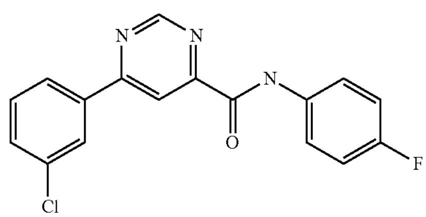 [SMILES: O=C(Nc1ccc(F)cc1)c1cc(-c2cccc(Cl)c2)ncn1] | 327.75 | [M + H]⁺ = 328, 100% @ rt = 5.25 min |
| 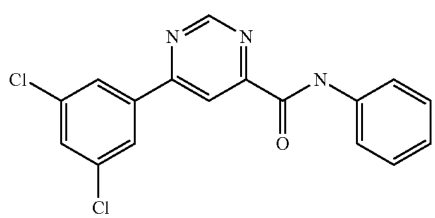 [SMILES: O=C(Nc1ccccc1)c1cc(-c2cc(Cl)cc(Cl)c2)ncn1] | 344.20 | [M + H]⁺ = 344, 100% @ rt = 5.47 min |
| 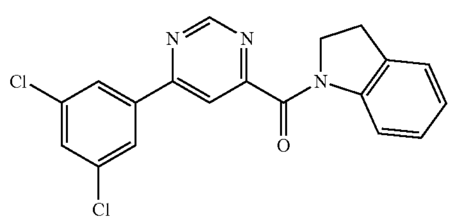 [SMILES: O=C(c1cc(-c2cc(Cl)cc(Cl)c2)ncn1)N1CCc2ccccc21] | 370.24 | [M + H]⁺ = 370, 100% @ rt = 5.38 min |
| 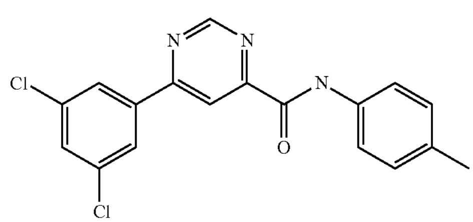 | 358.23 | [M + H]⁺ = 358, 100% @ rt = 5.67 min |
| 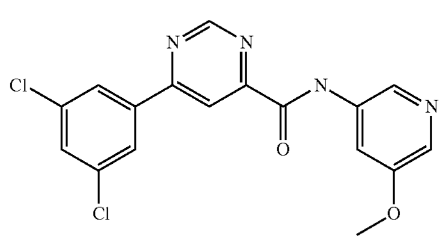 [SMILES: COc1cncc(NC(=O)c2cc(-c3cc(Cl)cc(Cl)c3)ncn2)c1] | 375.22 | [M + H]⁺ = 375, 100% @ rt = 4.75 min |
| 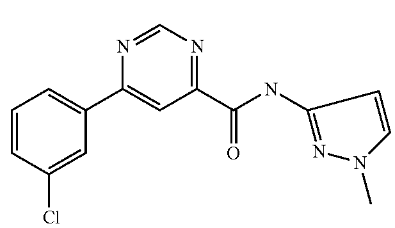 [SMILES: Cn1ccc(NC(=O)c2cc(-c3cccc(Cl)c3)ncn2)n1] | 313.75 | [M + H]⁺ = 314, 100% @ rt = 4.39 min |

| Structure | Molecular Weight | Mass Spec Result |
|---|---|---|
| 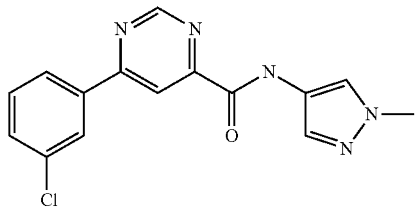 [SMILES: Cn1cc(NC(=O)c2cc(-c3cccc(Cl)c3)ncn2)cn1] | 313.75 | [M + H]⁺ = 313, 99% @ rt = 4.15 min |
| 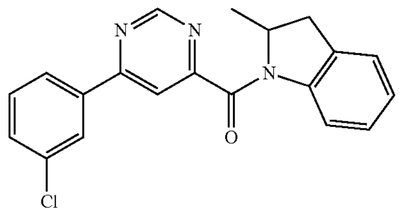 [SMILES: CC1Cc2ccccc2N1C(=O)c1cc(-c2cccc(Cl)c2)ncn1] | 349.82 | [M + H]⁺ = 350, 100% @ rt = 5.28 min |
| 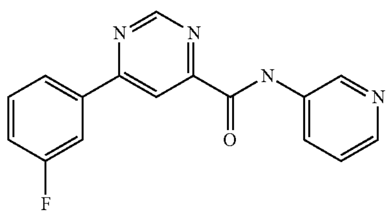 [SMILES: O=C(Nc1cccnc1)c1cc(-c2cccc(F)c2)ncn1] | 294.29 | [M + H]⁺ = 295, 100% @ rt = 3.61 min |
| 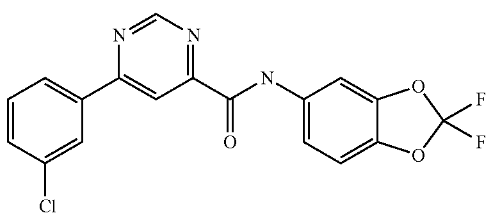 [SMILES: O=C(Nc1ccc2c(c1)OC(F)(F)O2)c1cc(-c2cccc(Cl)c2)ncn1] | 389.75 | [M + H]⁺ = 390, 100% @ rt = 5.43 min |
| 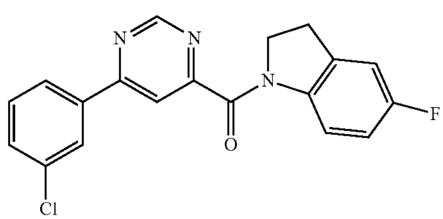 [SMILES: O=C(c1cc(-c2cccc(Cl)c2)ncn1)N1CCc2cc(F)ccc21] | 353.79 | [M + H]⁺ = 354, 100% @ rt = 5.04 min |
| 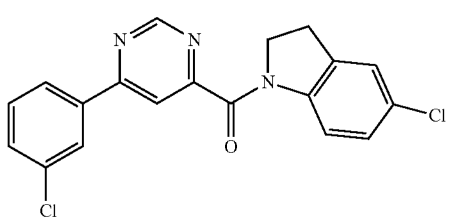 [SMILES: O=C(c1cc(-c2cccc(Cl)c2)ncn1)N1CCc2cc(Cl)ccc21] | 370.24 | [M + H]⁺ = 370, 100% @ rt = 5.31 min |
| 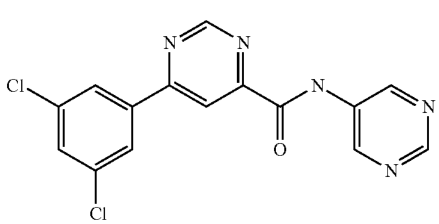 [SMILES: O=C(Nc1cncnc1)c1cc(-c2cc(Cl)cc(Cl)c2)ncn1] | 346.18 | [M + H]⁺ = 345, 97% @ rt = 4.56 min |

| Structure | Molecular Weight | Mass Spec Result |
|---|---|---|
| (6-(3-chloro-4-(trifluoromethyl)phenyl)pyrimidin-4-yl)-N-(pyridin-3-yl)carboxamide | 378.74 | [M + H]⁺ = 379, 100% @ rt = 4.34 min |
| (6-(3-chlorophenyl)pyrimidin-4-yl)(2,3-dihydro-1H-pyrrolo[3,2-c]pyridin-1-yl)methanone | 336.78 | [M + H]⁺ = 337/339, 100% @ rt = 3.24 min |
| 6-(3-chlorophenyl)-N-(thiazol-2-yl)pyrimidine-4-carboxamide | 316.77 | [M + H]⁺ = 317, 100% @ rt = 4.75 min |
| 6-(3-chlorophenyl)-N-(3-methylisoxazol-5-yl)pyrimidine-4-carboxamide | 314.73 | [M + H]⁺ = 315/317, 100% @ rt = 4.69 min |
| 6-(3-chlorophenyl)-N-(5-methyl-1,3,4-oxadiazol-2-yl)pyrimidine-4-carboxamide | 315.72 | [M + H]⁺ = 316/318, 100% @ rt = 3.92 min |
| 6-(3-chlorophenyl)-N-(oxazol-2-yl)pyrimidine-4-carboxamide | 300.71 | [M + H]⁺ = 301/303, 100% @ rt = 4.08 min |
| 6-(3-chlorophenyl)-N-(3-methyl-1,2,4-thiadiazol-5-yl)pyrimidine-4-carboxamide | 331.79 | [M + H]⁺ = 332, 99% @ rt = 4.59 min |

-continued
| Structure | Molecular Weight | Mass Spec Result |
|---|---|---|
| 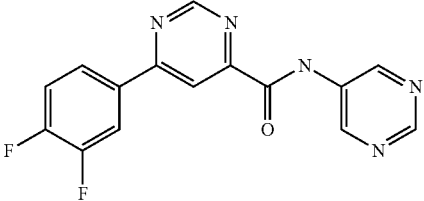 [SMILES: O=C(Nc1cncnc1)c1cc(-c2ccc(F)c(F)c2)ncn1] | 313.27 | [M + H]⁺ = 314, 98% @ rt = 4.09 min |
| 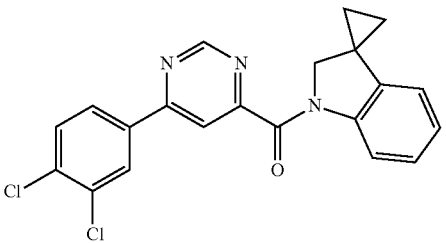 [SMILES: O=C(c1cc(-c2ccc(Cl)c(Cl)c2)ncn1)N1CC2(CC2)c2ccccc21] | 396.28 | [M + H]⁺ = 396, 100% @ rt = 5.69 min |
| 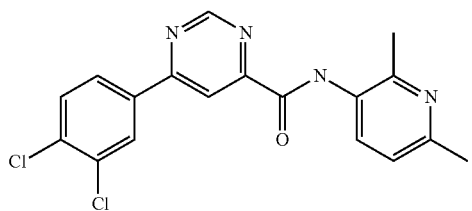 [SMILES: Cc1ccc(NC(=O)c2cc(-c3ccc(Cl)c(Cl)c3)ncn2)c(C)n1] | 373.24 | [M + H]⁺ = 374, 100% @ rt = 3.69 min |
| 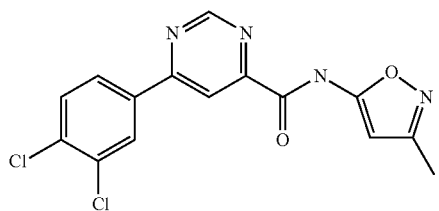 [SMILES: Cc1cc(NC(=O)c2cc(-c3ccc(Cl)c(Cl)c3)ncn2)on1] | 349.18 | [M + H]⁺ = 349, 100% @ rt = 5.13 min |
| 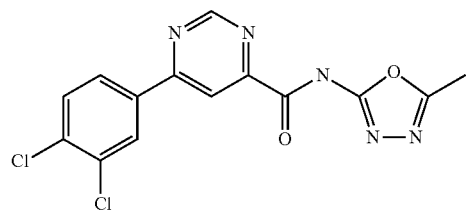 [SMILES: Cc1nnc(NC(=O)c2cc(-c3ccc(Cl)c(Cl)c3)ncn2)o1] | 350.17 | [M + H]⁺ = 350, 99% @ rt = 4.19 min |
| 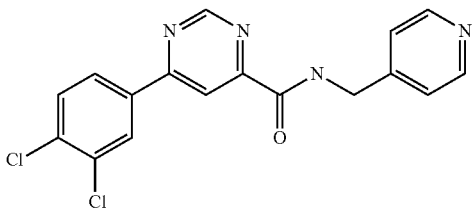 [SMILES: O=C(NCc1ccncc1)c1cc(-c2ccc(Cl)c(Cl)c2)ncn1] | 359.22 | [M + H]⁺ = 360, 100% @ rt = 3.46 min |
| 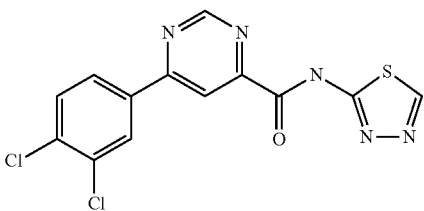 | 352.20 | [M + H]⁺ = 352, 100% @ rt = 4.42 min |

| Structure | Molecular Weight | Mass Spec Result |
|---|---|---|
| 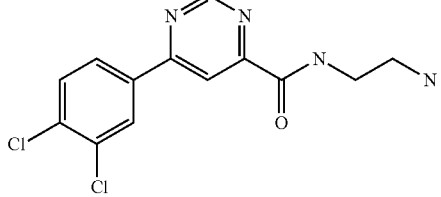 | 311.17 | [M + H]⁺ = 312, 96% @ rt = 3.18 min |
| 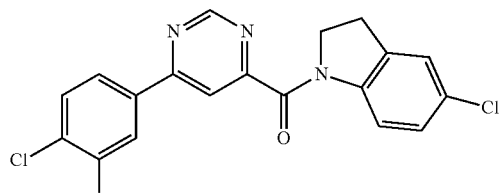 | 404.69 | [M + H]⁺ = 406, 100% @ rt = 5.44 min |
| 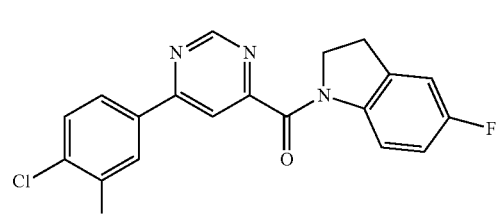 | 388.23 | [M + H]⁺ = 388, 100% @ rt = 5.46 min |
| 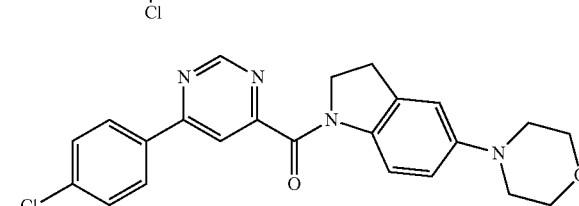 | 455.35 | [M + H]⁺ = 455, 100% @ rt = 5.17 min |
| 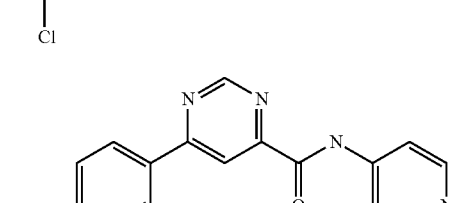 | 345.19 | [M + H]⁺ = 346, 100% @ rt = 3.33 min |
| 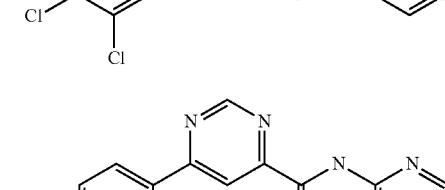 | 345.19 | [M + H]⁺ = 345, 100% @ rt = 5.19 min |
| 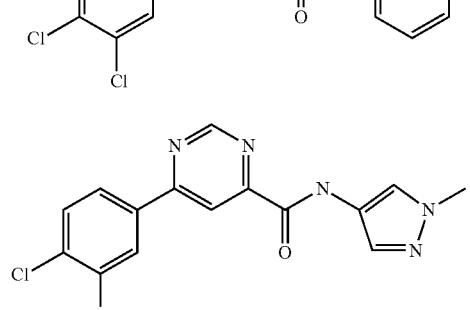 | 348.19 | [M + H]⁺ = 348, 98% @ rt = 4.40 min |

-continued

| Structure | Molecular Weight | Mass Spec Result |
|---|---|---|
| 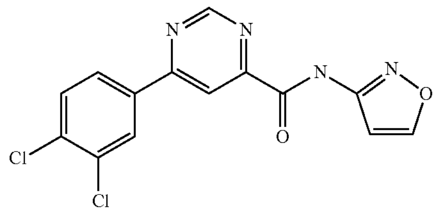 [SMILES: O=C(Nc1ccon1)c1cc(-c2ccc(Cl)c(Cl)c2)ncn1] | 335.15 | [M + H]⁺ = 335, 100% @ rt = 4.68 min |
| 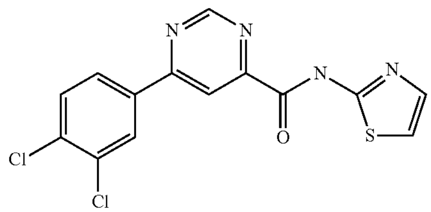 [SMILES: O=C(Nc1nccs1)c1cc(-c2ccc(Cl)c(Cl)c2)ncn1] | 351.22 | [M + H]⁺ = 351, 100% @ rt = 4.87 min |
| 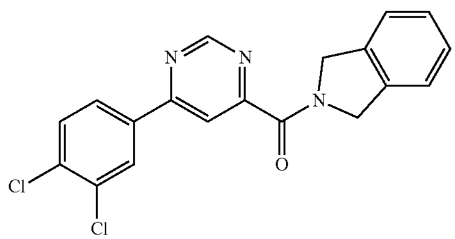 [SMILES: O=C(c1cc(-c2ccc(Cl)c(Cl)c2)ncn1)N1Cc2ccccc2C1] | 370.24 | [M + H]⁺ = 370, 100% @ rt = 5.25 min |
| 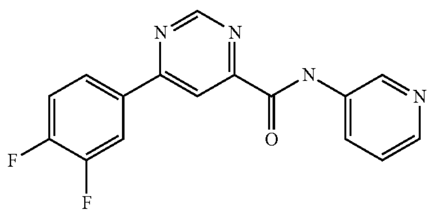 [SMILES: O=C(Nc1cccnc1)c1cc(-c2ccc(F)c(F)c2)ncn1] | 312.28 | [M + H]⁺ = 313, 100% @ rt = 3.82 min |
| 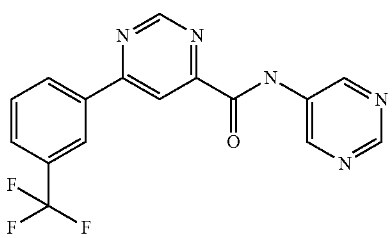 [SMILES: O=C(Nc1cncnc1)c1cc(-c2cccc(C(F)(F)F)c2)ncn1] | 345.29 | [M + H]⁺ = 346, 100% @ rt = 4.23 min |
| 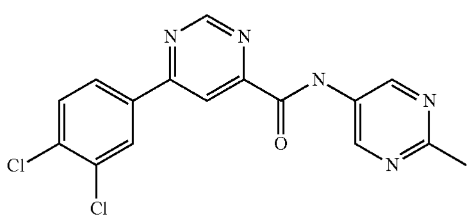 [SMILES: Cc1ncc(NC(=O)c2cc(-c3ccc(Cl)c(Cl)c3)ncn2)cn1] | 360.20 | [M + H]⁺ = 360, 100% @ rt = 4.47 min |
| 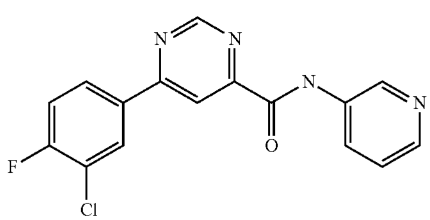 | 328.74 | [M + H]⁺ = 329, 100% @ rt = 3.96 min |

| Structure | Molecular Weight | Mass Spec Result |
|---|---|---|
| [6-(3-chloro-4-fluorophenyl)pyrimidine-4-carboxamide with 2,6-dimethylpyridin-3-yl] | 356.79 | [M + H]⁺ = 358, 100% @ rt = 3.27 min |
| [6-(3,4-dichlorophenyl)pyrimidine-4-carboxamide with N-(2-acetamidoethyl)] | 353.21 | [M + H]⁺ = 355, 100% @ rt = 3.83 min |
| [6-(3,4-dichlorophenyl)pyrimidine-4-carbonyl with 3,3-dimethylindoline] | 398.30 | [M + H]⁺ = 398, 100% @ rt = 5.45 min |
| [6-(3,4-dichlorophenyl)pyrimidine-4-carbonyl with 4-hydroxypiperidine] | 352.22 | [M + H]⁺ = 352, 100% @ rt = 3.88 min |
| [6-(3,4-dichlorophenyl)pyrimidine-4-carbonyl with morpholine] | 338.20 | [M + H]⁺ = 338, 100% @ rt = 4.21 min |
| [6-(3-chloro-4-fluorophenyl)pyrimidine-4-carboxamide with pyrimidin-5-yl] | 329.72 | [M + H]⁺ = 330, 100% @ rt = 4.21 min |
| [6-(3,4-dichlorophenyl)pyrimidine-4-carboxamide with 2-methylpyrimidin-5-yl] | 360.20 | [M + H]⁺ = 326, 100% @ rt = 4.16 min |

-continued

| Structure | Molecular Weight | Mass Spec Result |
|---|---|---|
| 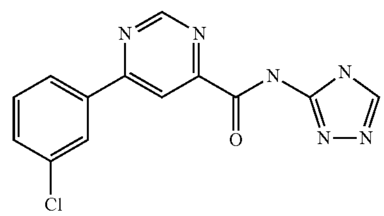 [SMILES: O=C(Nc1nnc[nH]1)c1cc(-c2cccc(Cl)c2)ncn1] | 300.71 | |
| | 335.15 | |
| 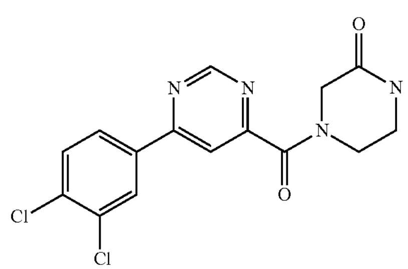 [SMILES: O=C1CN(C(=O)c2cc(-c3ccc(Cl)c(Cl)c3)ncn2)CCN1] | 351.19 | [M + H]⁺ = 351, 100% @ rt = 3.74 min |
| 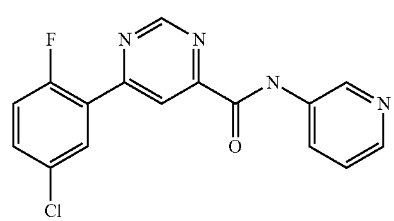 [SMILES: O=C(Nc1cccnc1)c1cc(-c2cc(Cl)ccc2F)ncn1] | 328.74 | [M + H]⁺ = 329, 100% @ rt = 3.82 min |
| 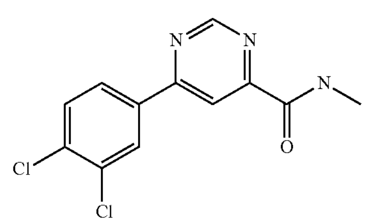 [SMILES: CNC(=O)c1cc(-c2ccc(Cl)c(Cl)c2)ncn1] | 282.13 | [M + H]⁺ = 282, 99% @ rt = 4.28 min |
| | 335.15 | [M + H]⁺ = 335, 100% @ rt = 4.25 min |

-continued

| Structure | Molecular Weight | Mass Spec Result |
|---|---|---|
| [6-(3-chloro-4-methoxyphenyl)pyrimidin-4-yl]-C(=O)-NH-(pyridin-3-yl) | 340.77 | [M + H]⁺ = 341, 100% @ rt = 3.67 min |
| [6-(3,4-dichlorophenyl)pyrimidin-4-yl]-C(=O)-NH-(3-methyl-1,2,4-thiadiazol-5-yl) | 366.23 | [M + Na]⁺ = 388, 100% @ rt = 4.94 min |
| [6-(3,4-dichlorophenyl)pyrimidin-4-yl]-C(=O)-N-(6-fluoroindolin-1-yl) | 388.23 | [M + H]⁺ = 388, 100% @ rt = 5.24 min |
| [6-(3,4-dichlorophenyl)pyrimidin-4-yl]-C(=O)-N-(6-chloroindolin-1-yl) | 404.69 | [M + H]⁺ = 405, 100% @ rt = 5.45 min |
| [6-(4-chloro-3-fluorophenyl)pyrimidin-4-yl]-C(=O)-NH-(pyridin-3-yl) | 328.74 | [M + H]⁺ = 330, 100% @ rt = 3.80 min |
| [6-(4-chloro-3-fluorophenyl)pyrimidin-4-yl]-C(=O)-NH-(2,6-dimethylpyridin-3-yl) | 356.79 | [M + H]⁺ = 359, 100% @ rt = 3.30 min |
| [6-(3,4-dichlorophenyl)pyrimidin-4-yl]-C(=O)-N-(4-acetylpiperazin-1-yl) | 379.25 | [M + H]⁺ = 379/381, 99% @ rt = 3.94 min |

-continued

| Structure | Molecular Weight | Mass Spec Result |
|---|---|---|
| 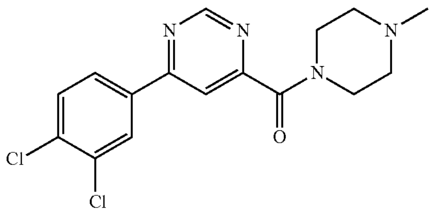 [SMILES: CN1CCN(C(=O)c2cc(-c3ccc(Cl)c(Cl)c3)ncn2)CC1] | 351.24 | [M + H]⁺ = 351/353, 100% @ rt = 2.94 min |
| 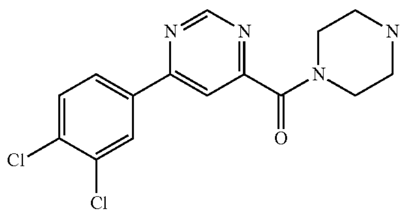 [SMILES: O=C(c1cc(-c2ccc(Cl)c(Cl)c2)ncn1)N1CCNCC1] | 337.21 | [M + H]⁺ = 337/339, 100% @ rt = 2.92 min |
| | 372.26 | [M + H]⁺ = 372/374, 100% @ rt = 5.33 min |
| 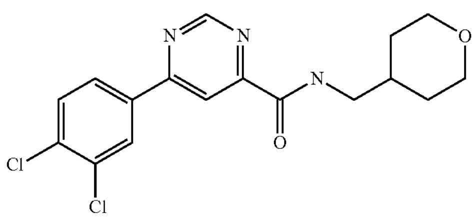 [SMILES: O=C(NCC1CCOCC1)c1cc(-c2ccc(Cl)c(Cl)c2)ncn1] | 366.25 | [M + H]⁺ = 366/368, 100% @ rt = 4.56 min |
| 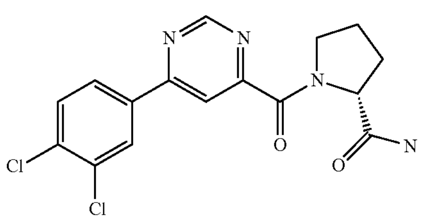 [SMILES: NC(=O)[C@H]1CCCN1C(=O)c1cc(-c2ccc(Cl)c(Cl)c2)ncn1] | 365.22 | [M + H]⁺ = 365/367, 100% @ rt = 3.34 min |
| 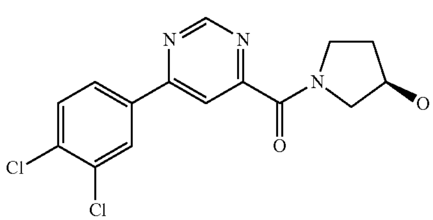 [SMILES: O=C(c1cc(-c2ccc(Cl)c(Cl)c2)ncn1)N1CC[C@@H](O)C1] | 338.20 | [M + H]⁺ = 338/339, 100% @ rt = 3.84 min |
| | 372.26 | [M + H]⁺ = 372/374, 100% @ rt = 5.33 min |

-continued

| Structure | Molecular Weight | Mass Spec Result |
|---|---|---|
| 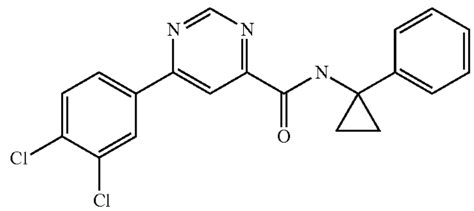 [SMILES: O=C(NC1(c2ccccc2)CC1)c1cc(-c2ccc(Cl)c(Cl)c2)ncn1] | 384.27 | [M + H]⁺ = 384/386, 100% @ rt = 5.10 min |
| 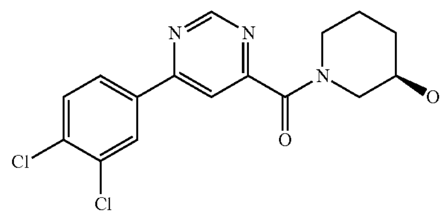 [SMILES: O=C(c1cc(-c2ccc(Cl)c(Cl)c2)ncn1)N1CCC[C@@H](O)C1] | 352.22 | [M + H]⁺ = 352/354, 100% @ rt = 3.83 min |
| 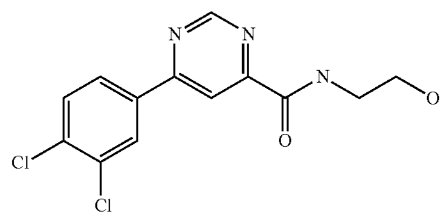 | 312.16 | [M + H]⁺ = 311/313, 99% @ rt = 3.83 min |
| | 326.18 | [M + H]⁺ = 325/327, 100% @ rt = 4.00 min |
| | 326.18 | [M + H]⁺ = 325/327, 100% @ rt = 4.00 min |
| 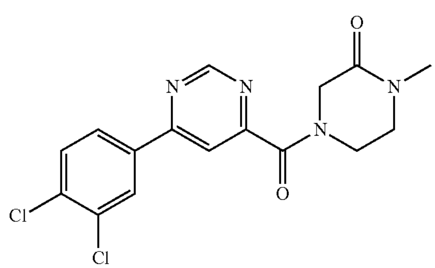 [SMILES: CN1CCN(C(=O)c2cc(-c3ccc(Cl)c(Cl)c3)ncn2)CC1=O] | 365.22 | [M + H]⁺ = 365/367, 95% @ rt = 3.81 min |
| | 326.18 | [M + H]⁺ = 325/327, 99% @ rt = 4.02 min |

| Structure | Molecular Weight | Mass Spec Result |
|---|---|---|
| 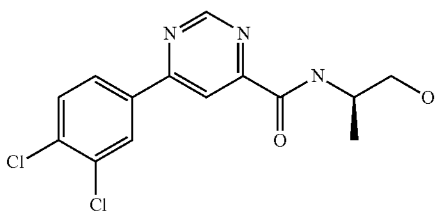 [SMILES: C[C@H](CO)NC(=O)c1cc(-c2ccc(Cl)c(Cl)c2)ncn1] | 326.18 | [M + H]⁺ = 325/327, 99% @ rt = 4.02 min |
| 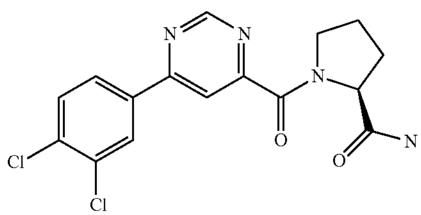 [SMILES: NC(=O)[C@@H]1CCCN1C(=O)c1cc(-c2ccc(Cl)c(Cl)c2)ncn1] | 365.22 | [M + H]⁺ = 365/367, 99% @ rt = 3.88 min |
| 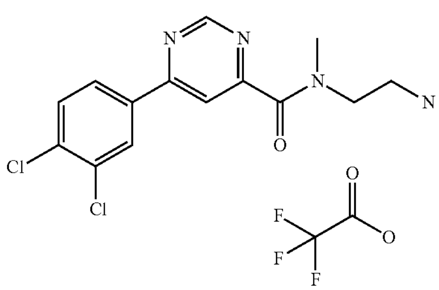 [SMILES: CN(CCN)C(=O)c1cc(-c2ccc(Cl)c(Cl)c2)ncn1 ; O=C(O)C(F)(F)F] | 439.22 | [M + H]⁺ = 324/326, 100% @ rt = 2.94 min |
| | 352.22 | [M + H]⁺ = 352/354, 100% @ rt = 4.40 min |
| 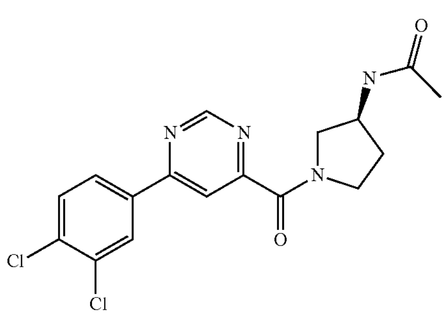 [SMILES: CC(=O)N[C@H]1CCN(C(=O)c2cc(-c3ccc(Cl)c(Cl)c3)ncn2)C1] | 379.25 | [M + H]⁺ = 379/381, 100% @ rt = 3.74 min |
| | 352.22 | [M + H]⁺ = 352/354, 100% @ rt = 3.81 min |

-continued

| Structure | Molecular Weight | Mass Spec Result |
|---|---|---|
| 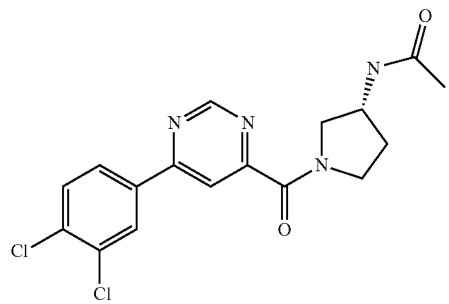 [SMILES: CC(=O)N[C@@H]1CCN(C(=O)c2cc(-c3ccc(Cl)c(Cl)c3)ncn2)C1] | 379.25 | [M + H]⁺ = 379/381, 100% @ rt = 3.73 min |
| 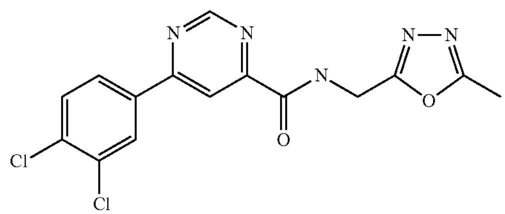 [SMILES: Cc1nnc(CNC(=O)c2cc(-c3ccc(Cl)c(Cl)c3)ncn2)o1] | 364.19 | [M + H]⁺ = 363/365, 100% @ rt = 4.07 min |
| 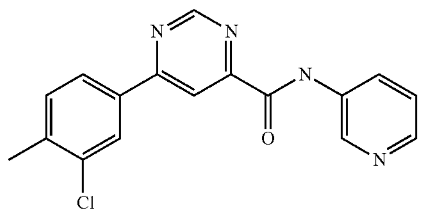 [SMILES: Cc1ccc(-c2cc(C(=O)Nc3cccnc3)ncn2)cc1Cl] | 324.77 | [M + H]⁺ = 325/327, 100% @ rt = 4.06 min |
| 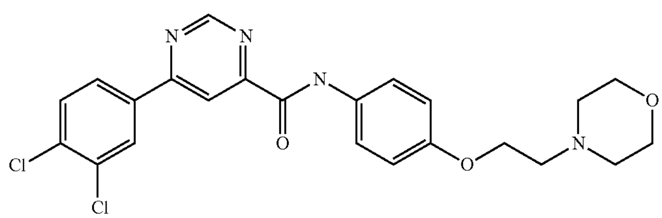 [SMILES: O=C(Nc1ccc(OCCN2CCOCC2)cc1)c1cc(-c2ccc(Cl)c(Cl)c2)ncn1] | 473.36 | [M + H]⁺ = 473/475, 100% @ rt = 3.62 min |
| 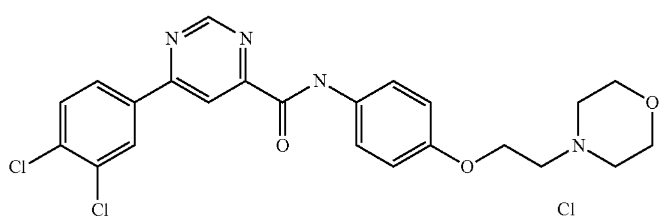 [SMILES: O=C(Nc1ccc(OCCN2CCOCC2)cc1)c1cc(-c2ccc(Cl)c(Cl)c2)ncn1 ; Cl] | 509.82 | [M + H]⁺ = 473/475, 100% @ rt = 3.42 min |
| 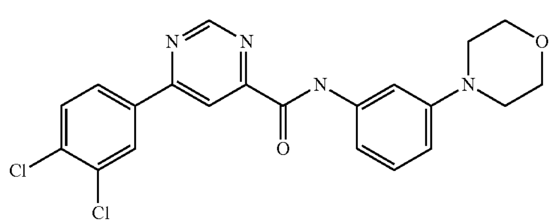 [SMILES: O=C(Nc1cccc(N2CCOCC2)c1)c1cc(-c2ccc(Cl)c(Cl)c2)ncn1] | 429.31 | [M + H]⁺ = 429/431, 99% @ rt = 5.28 min |

-continued

| Structure | Molecular Weight | Mass Spec Result |
|---|---|---|
| 3,4-dichlorophenyl-pyrimidine-carboxamide-N-(3-morpholinophenyl) | 465.77 | [M + H]⁺ = 429/430, 100% @ rt = 5.29 min |
| 3,4-difluorophenyl-pyrimidine-carboxamide-N-(1-phenylethyl) | 339.35 | [M + H]⁺ = 340, 100% @ rt = 4.73 min |
| 3-chloro-4-fluorophenyl-pyrimidine-carboxamide-N-(1-phenylethyl) | 355.80 | [M + H]⁺ = 356, 100% @ rt = 4.95 min |
| 5-chloro-2-fluorophenyl-pyrimidine-carboxamide-N-(1-phenylethyl) | 355.80 | [M + H]⁺ = 356/358, 97% @ rt = 4.91 min |
| 3,4-dichlorophenyl-pyrimidine-carboxamide-N-(1-methylpyrazol-3-yl) | 348.19 | [M + H]⁺ = 348, 100% @ rt = 4.62 min |
| 3,4-dichlorophenyl-pyrimidine-carboxamide-N-(pyridazin-3-yl) | 346.18 | [M + H]⁺ = 346/348, 96% @ rt = 4.63 min |
| 3,4-dichlorophenyl-pyrimidine-carboxamide-N-(pyrazin-2-yl) | 346.18 | no LCMS-Insoluble in an appropriate solvent |

| Structure | Molecular Weight | Mass Spec Result |
|---|---|---|
| 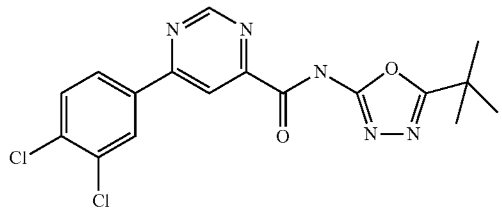 [SMILES: CC(C)(C)c1nnc(NC(=O)c2cc(-c3ccc(Cl)c(Cl)c3)ncn2)o1] | 392.25 | [M + H]⁺ = 392/394, 100% @ rt = 4.76 min |
| 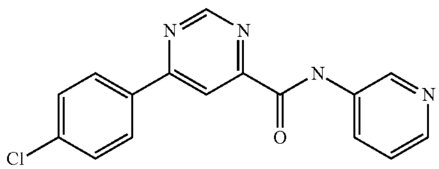 [SMILES: O=C(Nc1cccnc1)c1cc(-c2ccc(Cl)cc2)ncn1] | 310.75 | [M + H]⁺ = 311/313, 100% @ rt = 3.76 min |
| 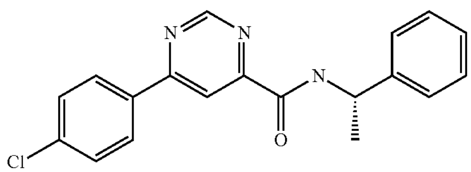 [SMILES: C[C@H](NC(=O)c1cc(-c2ccc(Cl)cc2)ncn1)c1ccccc1] | 337.81 | [M + H]⁺ = 338/340, 99% @ rt = 4.87 min |
| 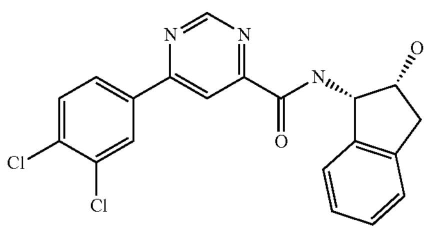 [SMILES: O=C(N[C@H]1c2ccccc2C[C@H]1O)c1cc(-c2ccc(Cl)c(Cl)c2)ncn1] | 400.27 | [M + H]⁺ = 400/402, 99% @ rt = 4.74 min |
| 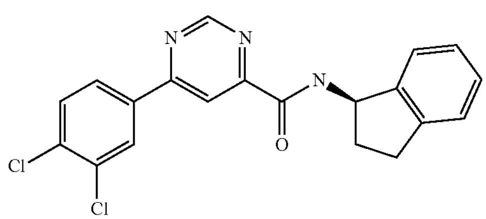 [SMILES: O=C(N[C@@H]1CCc2ccccc21)c1cc(-c2ccc(Cl)c(Cl)c2)ncn1] | 384.27 | [M + H]⁺ = 384/386, 99% @ rt = 5.36 min |
| | 398.30 | [M + H]⁺ = 398/400, 100% @ rt = 5.59 min |
| | 398.30 | [M + H]⁺ = 398/400, 100% @ rt = 5.59 min |

| Structure | Molecular Weight | Mass Spec Result |
|---|---|---|
| [pyrimidine-C(=O)NH-phenyl-morpholine with 3,4-dichlorophenyl] | 429.31 | [M + H]+ = 429/431, 100% @ rt = 5.07 min |
| [pyrimidine-C(=O)NH-phenyl-morpholine with 3,4-dichlorophenyl and Cl] | 465.77 | [M + H]+ = 429/431, 100% @ rt = 5.18 min |
| [pyrimidine-C(=O)NH-pyrimidine with 4-chlorophenyl] | 311.73 | [M + H]+ = 312/314, 100% @ rt = 4.07 min |
| [pyrimidine-C(=O)NH-CH(CH3)-4-pyridyl with 3,4-dichlorophenyl] | 373.24 | [M + H]+ = 373/375, 100% @ rt = 3.58 min |
| [pyrimidine-C(=O)NH-CH(CH3)-3-pyridyl with 3,4-dichlorophenyl] | 373.24 | [M + H]+ = 373/375, 100% @ rt = 3.58 min |
| [pyrimidine-C(=O)NH-phenyl-N-methylpiperazine with 3,4-dichlorophenyl] | 442.35 | [M + H]+ = 442/444, 100% @ rt = 3.61 min |
| [pyrimidine-C(=O)NH-phenyl-N-methylpiperazine with 3,4-dichlorophenyl and Cl] | 478.81 | [M + H]+ = 441/443, 100% @ rt = 3.39 min |

-continued

| Structure | Molecular Weight | Mass Spec Result |
|---|---|---|
| 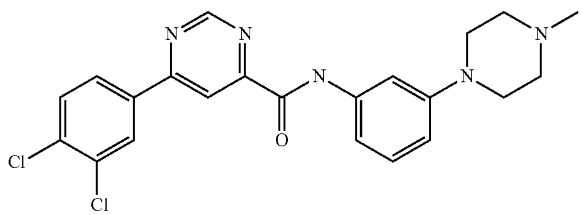 [SMILES: CN1CCN(c2cccc(NC(=O)c3cc(-c4ccc(Cl)c(Cl)c4)ncn3)c2)CC1] | 442.35 | [M + H]⁺ = 442/444, 100% @ rt = 3.64 min |
| 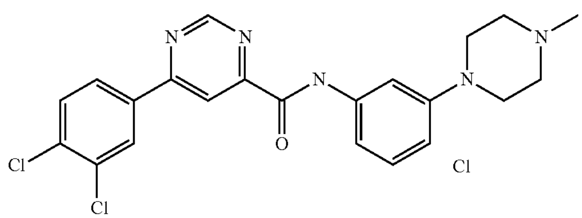 [SMILES: CN1CCN(c2cccc(NC(=O)c3cc(-c4ccc(Cl)c(Cl)c4)ncn3)c2)CC1 ; Cl] | 478.81 | [M + H]⁺ = 441/443, 100% @ rt = 3.50 min |
| | 355.80 | [M + H]⁺ = 356/358, 100% @ rt = 4.91 min |
| 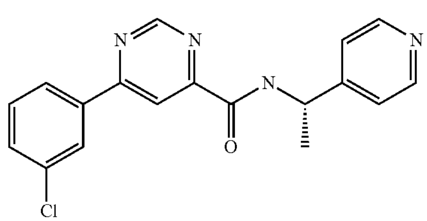 [SMILES: C[C@H](NC(=O)c1cc(-c2cccc(Cl)c2)ncn1)c1ccncc1] | 338.80 | [M + H]⁺ = 339/341, 99% @ rt = 3.86 min |
| 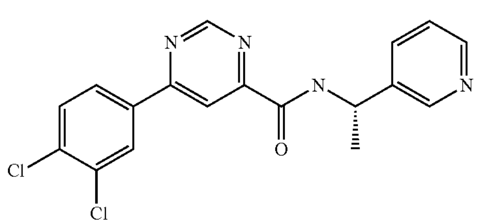 [SMILES: C[C@H](NC(=O)c1cc(-c2ccc(Cl)c(Cl)c2)ncn1)c1cccnc1] | 373.24 | [M + H]⁺ = 373/375, 100% @ rt = 4.21 min |
| 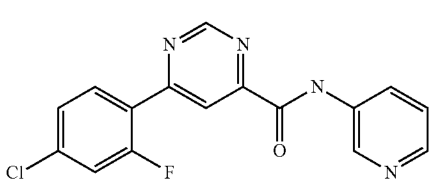 [SMILES: O=C(Nc1cccnc1)c1cc(-c2ccc(Cl)cc2F)ncn1] | 328.74 | [M + H]⁺ = 329/331, 100% @ rt = 3.75 min |
| | 355.80 | [M + H]⁺ = 356/358, 100% @ rt = 5.70 min |

| Structure | Molecular Weight | Mass Spec Result |
|---|---|---|
| 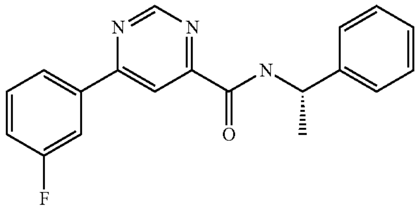 [SMILES: C[C@H](NC(=O)c1cc(-c2cccc(F)c2)ncn1)c1ccccc1] | 321.36 | [M + H]+ = 322, 100% @ rt = 5.57 min |
| 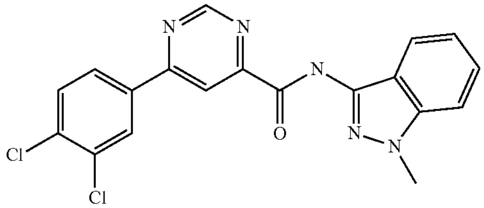 [SMILES: Cn1nc(NC(=O)c2cc(-c3ccc(Cl)c(Cl)c3)ncn2)c2ccccc21] | 398.25 | [M + H]+ = 397/399, 100% @ rt = 5.76 min |
| 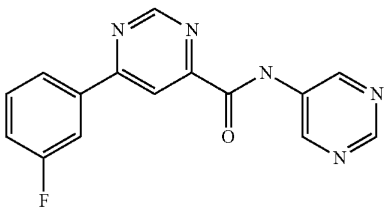 [SMILES: O=C(Nc1cncnc1)c1cc(-c2cccc(F)c2)ncn1] | 295.28 | [M + H]+ = 296, 94% @ rt = 3.58 min |
| 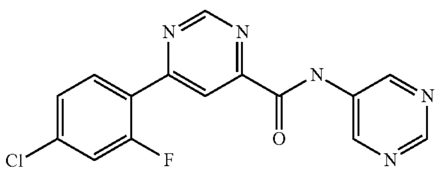 [SMILES: O=C(Nc1cncnc1)c1cc(-c2ccc(Cl)cc2F)ncn1] | 329.72 | [M + H]+ = 329, 100% @ rt = 3.92 min |
| 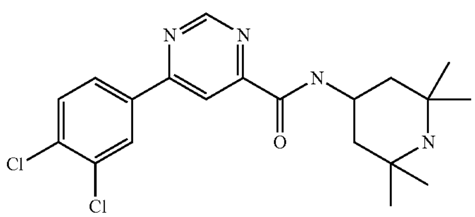 [SMILES: CC1(C)CC(NC(=O)c2cc(-c3ccc(Cl)c(Cl)c3)ncn2)CC(C)(C)N1] | 407.35 | [M + H]+ = 407/409, 100% @ rt = 3.19 min |
| 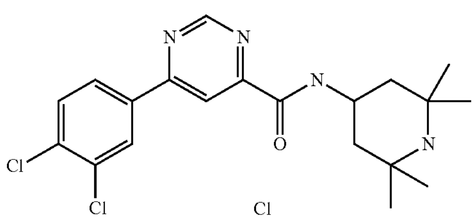 [SMILES: CC1(C)CC(NC(=O)c2cc(-c3ccc(Cl)c(Cl)c3)ncn2)CC(C)(C)N1 ; Cl] | 443.81 | [M + H]+ = 407/409, 100% @ rt = 3.24 min |
| 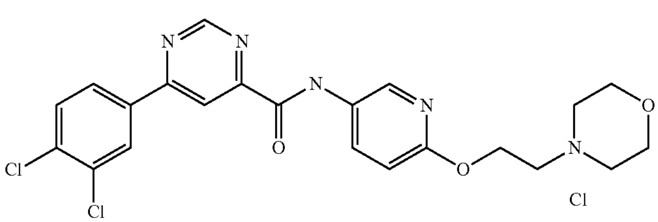 [SMILES: O=C(Nc1ccc(OCCN2CCOCC2)nc1)c1cc(-c2ccc(Cl)c(Cl)c2)ncn1 ; Cl] | 510.81 | [M + H]+ = 474/476, 96% @ rt = 3.43 min |

-continued

| Structure | Molecular Weight | Mass Spec Result |
|---|---|---|
| 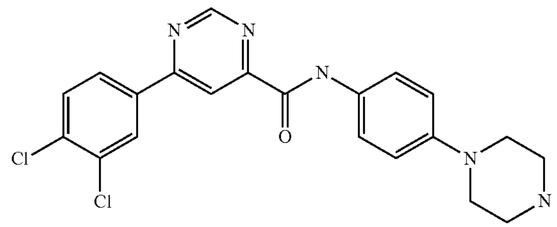 [SMILES: O=C(Nc1ccc(N2CCNCC2)cc1)c1cc(-c2ccc(Cl)c(Cl)c2)ncn1] | 428.32 | [M + H]⁺ = 428/430, 100% @ rt = 3.18 min |
| 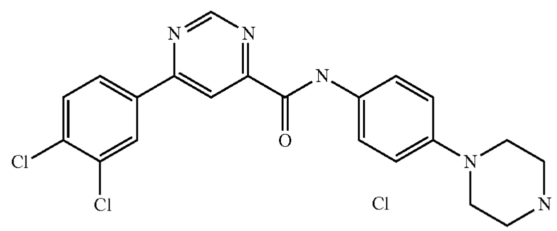 [SMILES: O=C(Nc1ccc(N2CCNCC2)cc1)c1cc(-c2ccc(Cl)c(Cl)c2)ncn1 ; Cl] | 464.79 | [M + H]⁺ = 428/430, 100% @ rt = 3.14 min |
| 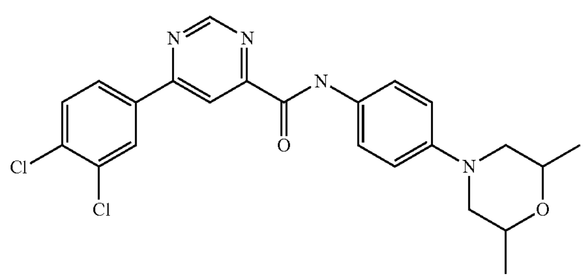 [SMILES: CC1CN(c2ccc(NC(=O)c3cc(-c4ccc(Cl)c(Cl)c4)ncn3)cc2)CC(C)O1] | 457.36 | [M + H]⁺ = 457/459, 100% @ rt = 5.23 min |
| 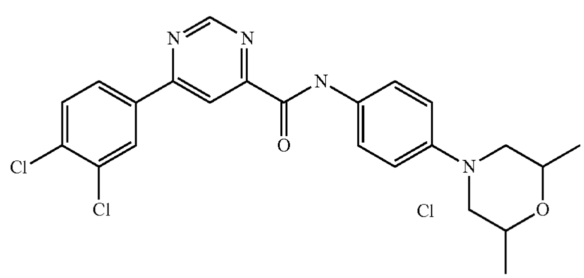 [SMILES: CC1CN(c2ccc(NC(=O)c3cc(-c4ccc(Cl)c(Cl)c4)ncn3)cc2)CC(C)O1 ; Cl] | 493.82 | [M + H]⁺ = 457/459, 100% @ rt = 5.58 min |
| 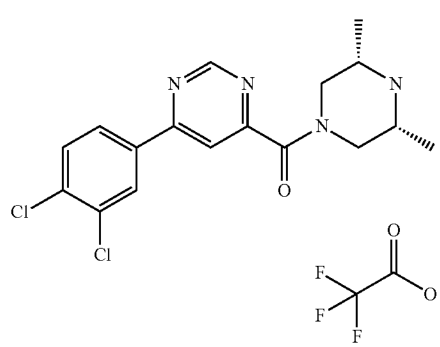 [SMILES: C[C@@H]1CN(C(=O)c2cc(-c3ccc(Cl)c(Cl)c3)ncn2)C[C@H](C)N1 ; O=C(O)C(F)(F)F] | 479.29 | [M + H]⁺ = 365/367, 100% @ rt = 2.63 min |
| 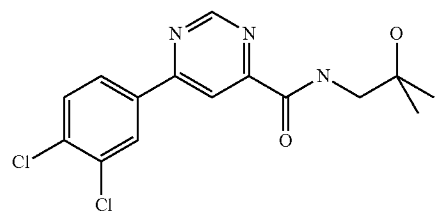 [SMILES: CC(C)(O)CNC(=O)c1cc(-c2ccc(Cl)c(Cl)c2)ncn1] | 340.21 | [M + H]⁺ = 340/342, 100% @ rt = 4.17 min |

-continued

| Structure | Molecular Weight | Mass Spec Result |
|---|---|---|
| 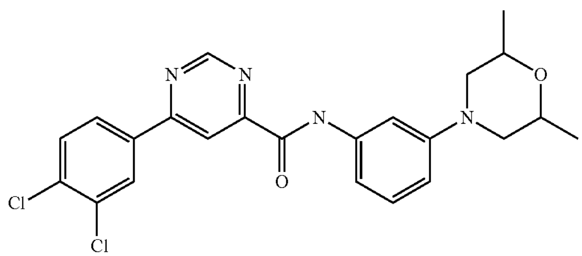 [SMILES: CC1CN(c2cccc(NC(=O)c3cc(-c4ccc(Cl)c(Cl)c4)ncn3)c2)CC(C)O1] | 457.36 | [M + H]⁺ = 457/459, 100% @ rt = 5.57 min |
| 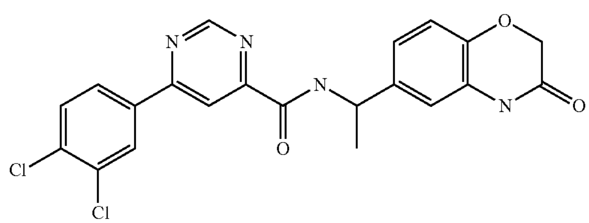 [SMILES: CC(NC(=O)c1cc(-c2ccc(Cl)c(Cl)c2)ncn1)c1ccc2c(c1)NC(=O)CO2] | 443.29 | [M + H]⁺ = 443/445, 100% @ rt = 4.67 min |
| | 338.20 | [M + H]⁺ = 338/340, 99% @ rt = 4.40 min |
| | 338.20 | [M + H]⁺ = 338/340, 99% @ rt = 4.40 min |
| 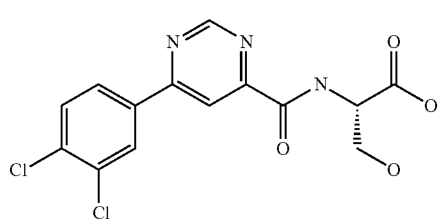 [SMILES: O=C(N[C@@H](CO)C(=O)O)c1cc(-c2ccc(Cl)c(Cl)c2)ncn1] | 356.17 | [M + H]⁺ = 356/358, 99% @ rt = 3.84 min |
| 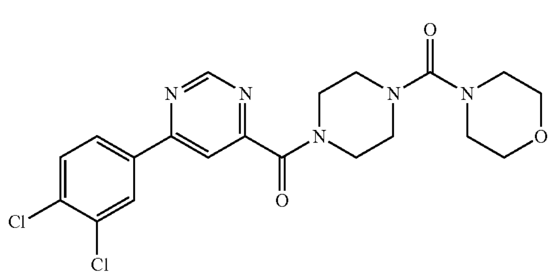 [SMILES: O=C(c1cc(-c2ccc(Cl)c(Cl)c2)ncn1)N1CCN(C(=O)N2CCOCC2)CC1] | 450.33 | [M + H]⁺ = 450/452, 100% @ rt = 4.00 min |

| Structure | Molecular Weight | Mass Spec Result |
|---|---|---|
| 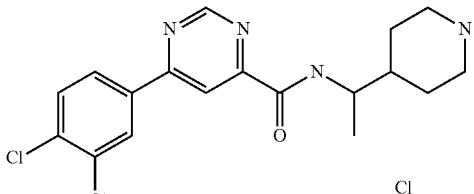 | 415.75 | [M + H]⁺ = 379/381, 100% @ rt = 3.12 min |
| 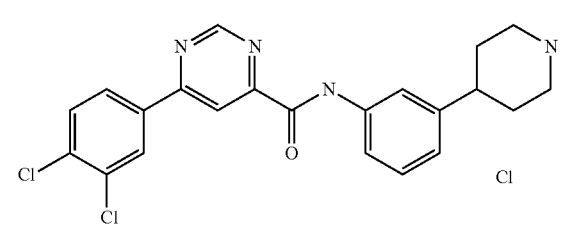 [SMILES: O=C(Nc1cccc(C2CCNCC2)c1)c1cc(-c2ccc(Cl)c(Cl)c2)ncn1 ; Cl] | 463.80 | [M + H]⁺ = 427/429, 100% @ rt = 3.45 min |
| 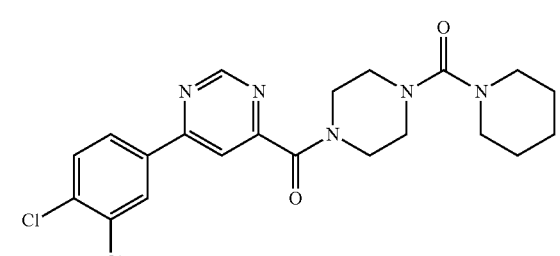 | 448.36 | [M + H]⁺ = 448/450, 100% @ rt = 4.53 min |
| 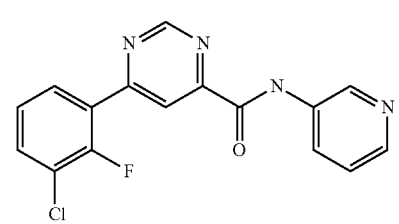 [SMILES: O=C(Nc1cccnc1)c1cc(-c2cccc(Cl)c2F)ncn1] | 328.74 | [M + H]⁺ = 329/331, 100% @ rt = 3.67 min |
| 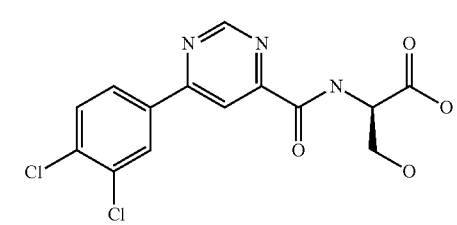 [SMILES: O=C(N[C@H](CO)C(=O)O)c1cc(-c2ccc(Cl)c(Cl)c2)ncn1] | 356.17 | [M + H]⁺ = 356/358, 100% @ rt = 3.82 min |
| 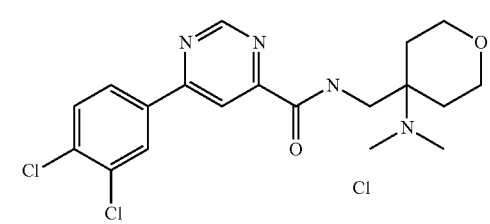 [SMILES: CN(C)C1(CNC(=O)c2cc(-c3ccc(Cl)c(Cl)c3)ncn2)CCOCC1 ; Cl] | 445.78 | [M + H]⁺ = 409/411, 100% @ rt = 3.07 min |
| 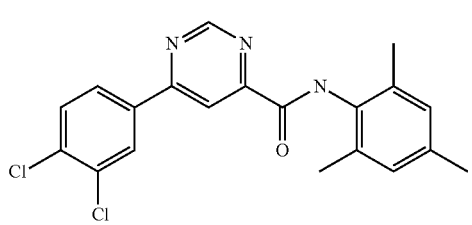 [SMILES: Cc1cc(C)c(NC(=O)c2cc(-c3ccc(Cl)c(Cl)c3)ncn2)c(C)c1] | 386.28 | [M + H]⁺ = 386/388, 100% @ rt = 5.55 min |

| Structure | Molecular Weight | Mass Spec Result |
|---|---|---|
| (3,4-dichlorophenyl-pyrimidine carboxamide with 2,4-dimethylpyridin-3-yl) | 373.24 | [M + H]⁺ = 373/375, 100% @ rt = 3.41 min |
| (3,4-dichlorophenyl-pyrimidine carboxamide with 6-methylpyridazin-3-yl) | 360.20 | [M + H]⁺ = 360/362, 100% @ rt = 4.73 min |
| (3,4-dichlorophenyl-pyrimidine carboxamide with quinuclidin-3-yl) | 377.28 | [M + H]⁺ = 377/379, 100% @ rt = 3.13 min |
| (3,4-dichlorophenyl-pyrimidine carboxamide with 3-tert-butylisothiazol-5-yl) | 407.32 | [M + H]⁺ = 407/409, 100% @ rt = 5.48 min |
| (3-chloro-4-fluorophenyl-pyrimidine with 3-oxopiperazinyl) | 334.74 | [M + H]⁺ = 335, 100% @ rt = 3.37 min |
| (3,4-difluorophenyl-pyrimidine with 3-oxopiperazinyl) | 318.29 | [M + H]⁺ = 319, 98% @ rt = 3.19 min |

| Structure | Molecular Weight | Mass Spec Result |
|---|---|---|
| 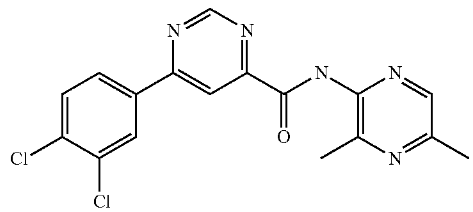 [SMILES: Cc1cnc(NC(=O)c2cc(-c3ccc(Cl)c(Cl)c3)ncn2)c(C)n1] | 374.23 | [M + H]⁺ = 374/376, 98% @ rt = 4.63 min |
| 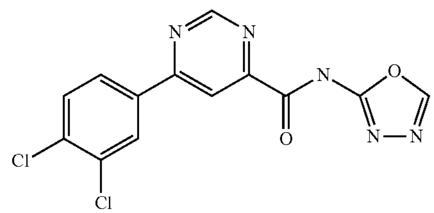 [SMILES: O=C(Nc1nnco1)c1cc(-c2ccc(Cl)c(Cl)c2)ncn1] | 336.14 | [M + H]⁺ = 336/338, 100% @ rt = 4.04 min |
| 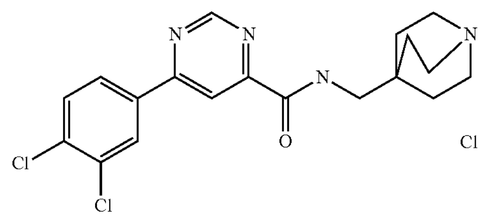 [SMILES: O=C(NCC12CCN(CC1)CC2)c1cc(-c2ccc(Cl)c(Cl)c2)ncn1 ; Cl] | 427.76 | [M + H]⁺ = 391/393, 100% @ rt = 3.12 min |
| 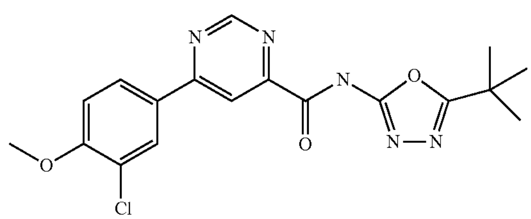 [SMILES: COc1ccc(-c2cc(C(=O)Nc3nnc(C(C)(C)C)o3)ncn2)cc1Cl] | 387.83 | [M + H]⁺ = 388/390, 100% @ rt = 4.38 min |
| 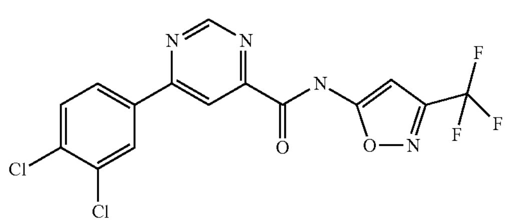 [SMILES: O=C(Nc1cc(C(F)(F)F)no1)c1cc(-c2ccc(Cl)c(Cl)c2)ncn1] | 403.15 | [M + H]⁺ = 403/405, 100% @ rt = 5.35 min |
| 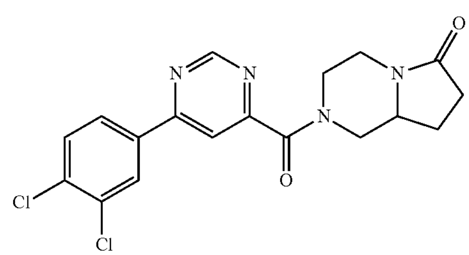 [SMILES: O=C(c1cc(-c2ccc(Cl)c(Cl)c2)ncn1)N1CCN2C(=O)CCC2C1] | 391.26 | [M + H]⁺ = 391/393, 100% @ rt = 3.86 min |
| 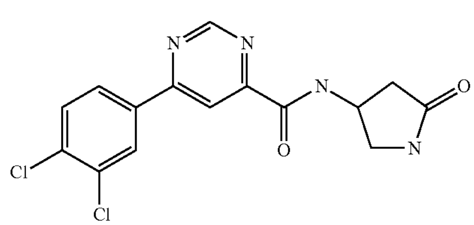 [SMILES: O=C1CC(NC(=O)c2cc(-c3ccc(Cl)c(Cl)c3)ncn2)CN1] | 351.19 | [M + H]⁺ = 351/353, 100% @ rt = 3.78 min |

| Structure | Molecular Weight | Mass Spec Result |
|---|---|---|
| 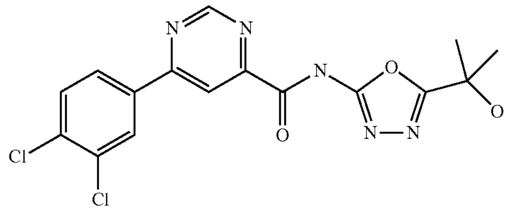 [SMILES: CC(C)(O)c1nnc(NC(=O)c2cc(-c3ccc(Cl)c(Cl)c3)ncn2)o1] | 394.22 | [M + H]⁺ = 394/396, 100% @ rt = 3.99 min |
| 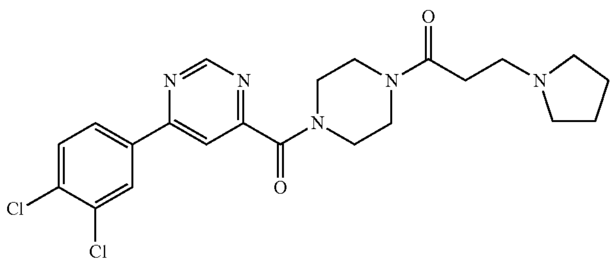 [SMILES: O=C(CCN1CCCC1)N1CCN(C(=O)c2cc(-c3ccc(Cl)c(Cl)c3)ncn2)CC1] | 462.38 | [M + H]⁺ = 462/464, 100% @ rt = 3.04 min |
| 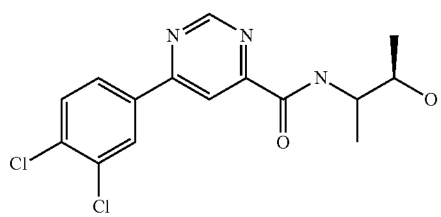 [SMILES: CC(NC(=O)c1cc(-c2ccc(Cl)c(Cl)c2)ncn1)[C@@H](C)O] | 340.21 | [M + H]⁺ = 340/342, 100% @ rt = 4.28 min |
| 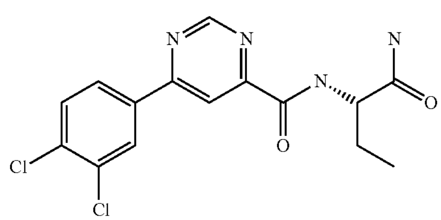 | 353.21 | [M + H]⁺ = 353/355, 100% @ rt = 4.10 min |
| 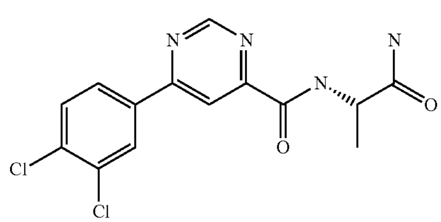 | 339.18 | [M + H]⁺ = 339/341, 100% @ rt = 3.90 min |
| 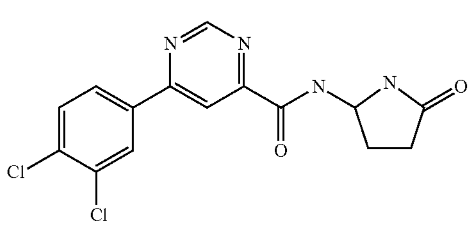 [SMILES: O=C1CCC(NC(=O)c2cc(-c3ccc(Cl)c(Cl)c3)ncn2)N1] | 351.19 | [M − C4H4NO]⁺ = 268/270, 100% @ rt = 3.88 min |

-continued

| Structure | Molecular Weight | Mass Spec Result |
|---|---|---|
| *(3-bromophenyl pyrimidinyl carbonyl - oxopiperazine)* | 361.20 | [M + H]⁺ = 361/363, 100% @ rt = 3.38 min |
| *(3,4-dichlorophenyl pyrimidinyl carbonyl - methyl-oxopiperazine)* | 365.22 | [M + H]⁺ = 365/367, 100% @ rt = 3.80 min |
| *(3,4-dichlorophenyl pyrimidinyl carbonyl-alanine)* | 340.17 | [M + H]⁺ = 340/342, 100% @ rt = 4.20 min |
| *(3,4-dichlorophenyl pyrimidinyl carbonyl tetramethyl pyrrolidine carboxamide)* | 421.33 | [M + H]⁺ = 421/423, 100% @ rt = 4.13 min |
| *(3,4-dichlorophenyl pyrimidinyl carboxamide trifluoromethyl-oxadiazole)* | 404.14 | [M + H]⁺ = 404/406, 100% @ rt = 4.94 min |
| *(3-bromophenyl pyrimidinyl carboxamide methyl-oxadiazole)* | 360.17 | [M + H]⁺ = 360/362, 100% @ rt = 3.70 min |

| Structure | Molecular Weight | Mass Spec Result |
|---|---|---|
| 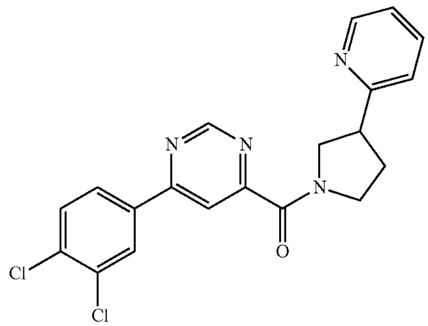 [SMILES: O=C(c1cc(-c2ccc(Cl)c(Cl)c2)ncn1)N1CCC(c2ccccn2)C1] | 399.28 | [M + H]⁺ = 399/401, 100% @ rt = 3.98 min |
| 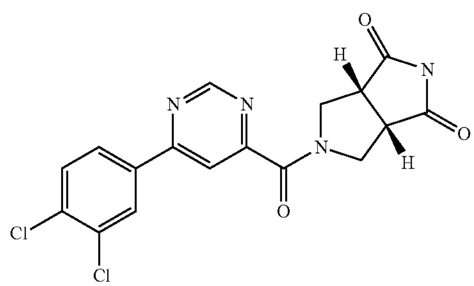 [SMILES: O=C1NC(=O)[C@@H]2CN(C(=O)c3cc(-c4ccc(Cl)c(Cl)c4)ncn3)C[C@H]12] | 391.22 | [M + H]⁺ = 391/393, 100% @ rt = 3.59 min |

Example 2

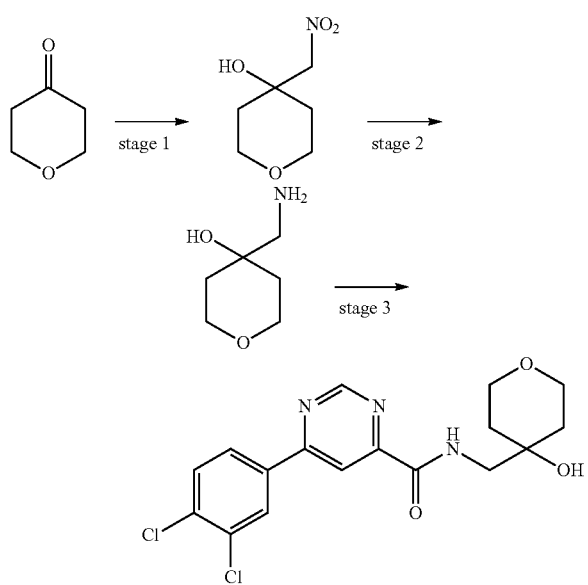

Reaction Scheme 2

Referring to Reaction Scheme 2, Stage 1, to a stirred solution of pyran-4-one (1 eq) and nitromethane (1 eq) in methanol (10 vol) externally cooled to −10° C. under an atmosphere of nitrogen gas, was added, over a five minute period, a 30% w/w solution of sodium methoxide in methanol (2.10 vol). The mixture was then stirred for 1 hour at 0° C. and after 2 hours at 10° C., acetic acid (0.75 vol) was added and the solvent evaporated under reduced pressure. Water (25 vol) was added to the residue and the organics were extracted with DCM (4×50 vol). The combined organic layers were dried (Na₂SO₄), filtered off and concentrated under reduced pressure. The crude residue was purified by flash column chromatography (2:3 EtOAc:heptane) to afford the target compound as white solid crystals.

Referring to Reaction Scheme 2, Stage 2, to a stirred solution of 4-nitromethyl-tetrahydro-pyran-4-ol (1 eq) in ethanol (24 vol) and water (0.3 vol) was added 10% palladium on carbon (0.29 wt eq). The mixture was stirred under hydrogen gas for 22 hours at RT. The mixture was filtered through Kieselguhr and the filtrate was evaporated. The residue was then azeodried with toluene (2×10 vol) and ethanol (2×10 vol) to give the target compound as a dark oil.

Referring to Reaction Scheme 2, Stage 3, to a stirred solution of 6-(3,4-dichloro-phenyl)-pyrimidine-4-carbonyl chloride (1 eq) externally cooled to 0° C. under an atmosphere of nitrogen gas was added a mixture of 4-aminomethyl-tetrahydro-pyran-4-ol (1.5 eq) and DIPEA (1.5 eq) in dry THF (16 vol). The reaction mixture was warmed to RT and stirred for 18 hours. The solvent was evaporated under reduced pressure; a saturated solution of NaHCO₃ (80 vol) was added and the organics extracted with ethyl acetate (4×120 vol). The combined organic layers were dried (Na₂SO₄), filtered off and concentrated under reduced pressure. The crude residue was purified by dry flash column chromatography (gradient 3:7 to 7:3 EtOAc:heptane) to afford the target compound as a white crystalline solid.

| Structure | Molecular Weight | Mass Spec Result |
|---|---|---|
| 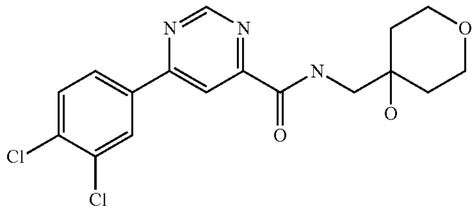 | 382.25 | [M + H]⁺ = 382/384, 100% @ rt = 4.06 min |

Example 3

Reaction Scheme 3

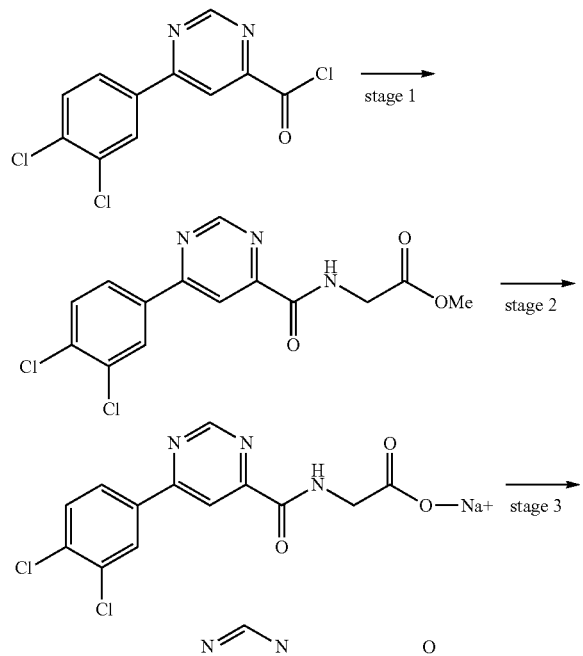

Referring to Reaction Scheme 3, Stage 1, a mixture of 6-(3,4-dichloro-phenyl)-pyrimidine-4-carbonyl chloride (1 eq), glycine methyl ester hydrochloride (1.2 eq) and DIPEA (2.4 eq) in DCM (25 vol) was stirred overnight at room temperature. A saturated solution of NaHCO$_3$ was then added and the organic layer extracted with DCM (25 vol). The organic layer was washed with brine and concentrated under reduced pressure to afford the target compound.

Referring to Reaction Scheme 3, Stage 2, to a stirred solution of {[6-(3,4-dichloro-phenyl)-pyrimidine-4-carbonyl]-amino}-acetic acid methyl ester (1 eq) in THF (20 vol) was added 2N NaOH (3.70 vol) and the mixture stirred for 3 hours. The precipitate was then filtered off, washed with diethyl ether and EtOAc, and dried to afford the crude target compound.

Referring to Reaction Scheme 3, Stage 3, to a stirred suspension of the sodium salt of {[6-(3,4-dichloro-phenyl)-pyrimidine-4-carbonyl]-amino}-acetic acid (1 eq) and piperazin-2-one (1.2 eq) in DMF (50 vol) was added HATU (1.2 eq), EDCI (1.2 eq) and DIPEA (1.2 eq), and the mixture stirred for 2 hours. A saturated solution of NaHCO$_3$ was then added and the organics extracted with DCM. The organic layer was dried (Na$_2$SO$_4$), filtered and concentrated under reduced pressure. The crude solid was triturated in EtOAc, filtered off, washed with heptane and dried to afford the target compound.

| Structure | Molecular Weight | Mass Spec Result |
|---|---|---|
| 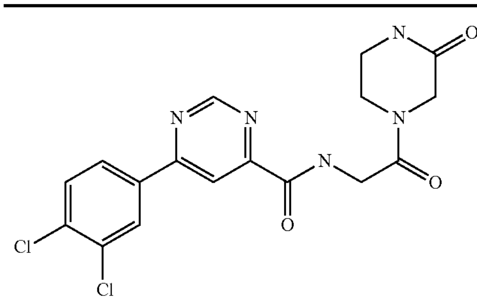 | 408.25 | [M + H]⁺ = 408/410, 99% @ rt = 3.72 min |

Example 4

Reaction Scheme 4

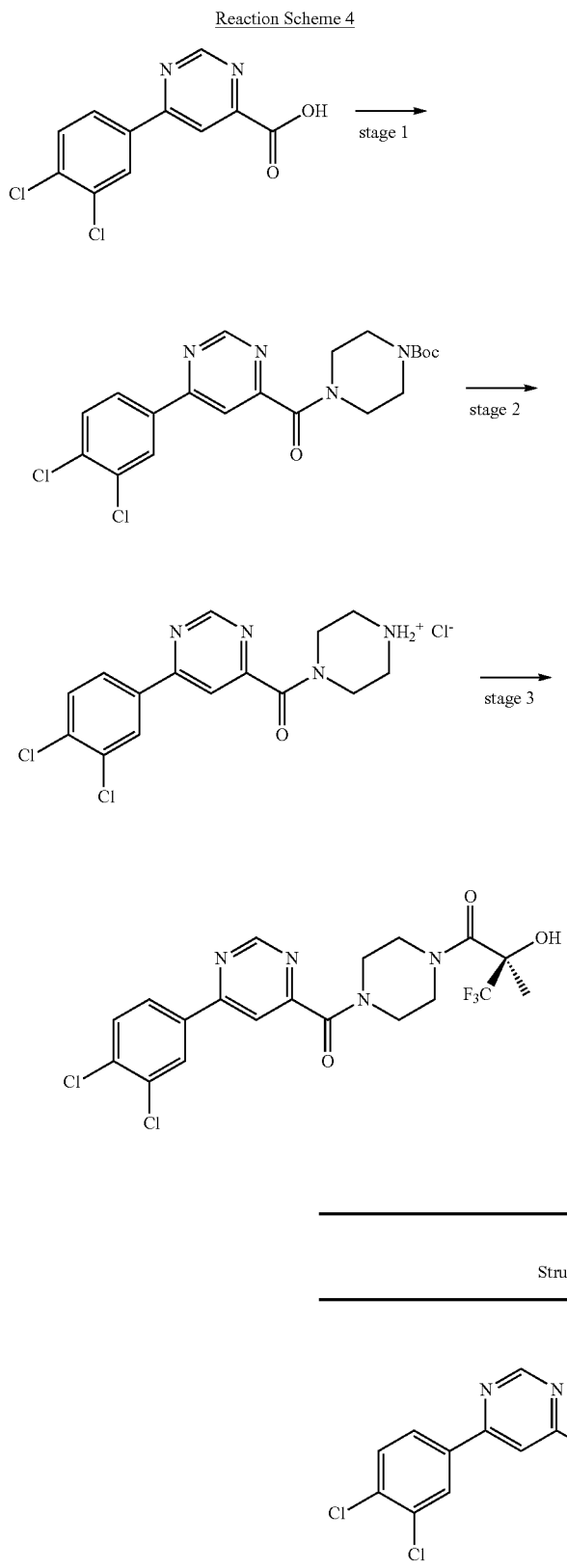

Referring to Reaction Scheme 4, Stage 1, the required amide analogues were prepared following the procedures described in method B.

Referring to Reaction Scheme 4, Stage 2, to a solution of 4M HCl in 1,4-dioxane (21 vol) was slowly added 4-[6-(3,4-dichloro-phenyl)-pyrimidine-4-carbonyl]-piperazine-1-carboxylic acid tert-butyl ester (1 eq) portion wise. The resultant thick reaction mixture was stirred for 3 days and then the solvent was concentrated under reduced pressure. The residue was azeodried with DCM (×5) to afford the target compound as the hydrochloride salt.

Referring to Reaction Scheme 4, Stage 3, to a stirred solution of (R)-3,3,3-trifluoro-2-hydroxy-2-methyl-propionic acid (1 eq) was dissolved in DCM (47 vol). Oxalyl chloride (3 eq) and DMF (0.09 vol) were then added and the reaction mixture stirred at room temperature for 2 hours. The solvent was concentrated under reduced pressure and azeodried with DCM (×2) to afford the acid chloride as a clear liquid.

To a stirred suspension of [6-(3,4-dichloro-phenyl)-pyrimidin-4-yl]-piperazin-1-yl-methanone hydrochloride (1.2 eq) in DCM (42 vol) was added triethylamine (4 eq) and the mixture stirred of 15 minutes. To the resultant solution was slowly added the acid chloride (1 eq) dissolved in DCM drop wise at room temperature. After stirring overnight at room temperature, water was added to the reaction mixture. The organic phase was then washed with water (1×2100 vol), 2N HCl (1×850 vol), water (2×850 vol), brine (1×850 vol), dried (MgSO$_4$), filtered off and concentrated under reduced pressure. The clear oil was semi-purified by flash column chromatography (using a gradient 0 to 5% MeOH:DCM). The solid was then dissolved in the minimum of EtOAc and precipitated with heptane, filtered and dried. This process was repeated. The solid was heated in the minimum of EtOAc and precipitated with an excess of heptane, filtered and dried to afford the target compound.

| Structure | Molecular Weight | Mass Spec Result |
|---|---|---|
| 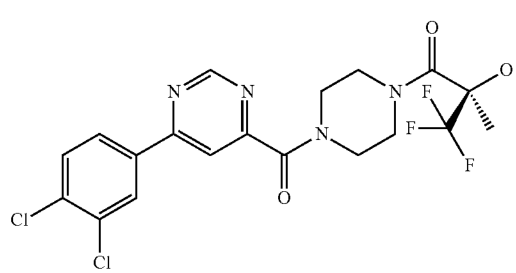 [SMILES: C[C@@](O)(C(=O)N1CCN(C(=O)c2cc(-c3ccc(Cl)c(Cl)c3)ncn2)CC1)C(F)(F)F] | 477.27 | [M + H]$^+$ = 477/479, 100% @ rt = 4.24 min |

Example 5

Reaction Scheme 5

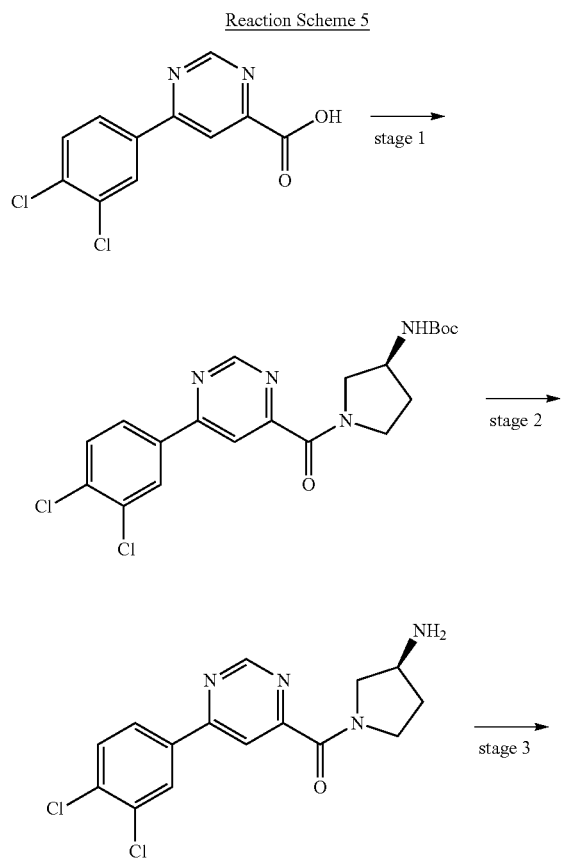

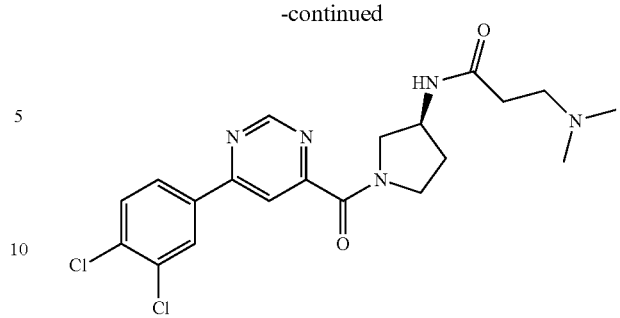

Referring to Reaction Scheme 5, Stage 1, the required amide analogues were prepared following the procedures described in method B.

Referring to Reaction Scheme 5, Stage 2, to a stirred solution of {(S)-1-[6-(3,4-dichloro-phenyl)-pyrimidine-4-carbonyl]-pyrrolidin-3-yl}-carbamic acid tert-butyl ester (1 eq) in DCM (21 vol) was added TFA (2.1 vol) at RT. After stirring at RT for 2 hours, more TFA (2.1 vol) was added and the reaction stirring overnight. A solution of saturated NaHCO$_3$ was added slowly until the pH 8. The organic phase was then dried (Na$_2$SO$_4$), filtered off and concentrated under reduced pressure to afford the target compound.

Referring to Reaction Scheme 5, Stage 3, to a stirred suspension of ((S)-3-amino-pyrrolidin-1-yl)-[6-(3,4-dichloro-phenyl)-pyrimidin-4-yl]-methanone (1 eq) and 3-dimethylamino propionic acid hydrochloride (1.2 eq) in DMF (42 vol) was added HATU (1.2 eq), DIPEA (1.2 eq) and EDCI (1.2 eq) at RT. After stirring for 2 hours, a saturated solution of NaHCO$_3$ was added and the precipitate that resulted was filtered off. The filtrate was extracted with EtOAc, dried (Na$_2$SO$_4$), filtered off and concentrated under reduced pressure. The solid was then triturated in diethyl ether and then heptane. Finally the solid was triturated in the minimum of EtOAc, filtered off and dried to afford the target compound.

The following compounds were prepared substantially as described above.

| Structure | Molecular Weight | Mass Spec Result |
|---|---|---|
| 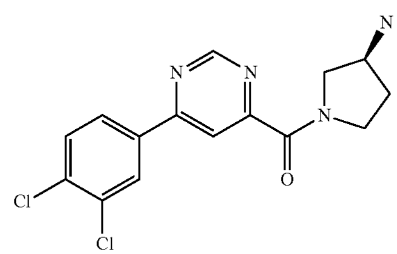 [SMILES: N[C@H]1CCN(C(=O)c2cc(-c3ccc(Cl)c(Cl)c3)ncn2)C1] | 337.21 | [M + H]$^+$ = 337/339, 99% @ rt = 2.84 min |
| 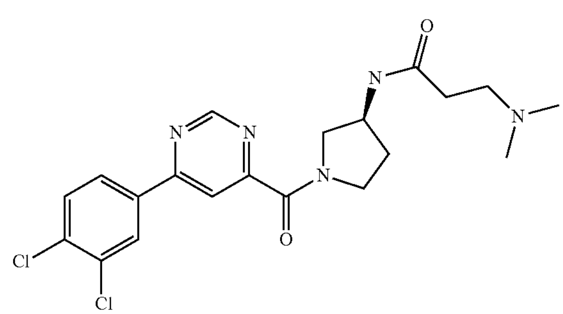 [SMILES: CN(C)CCC(=O)N[C@H]1CCN(C(=O)c2cc(-c3ccc(Cl)c(Cl)c3)ncn2)C1] | 436.34 | [M + H]$^+$ = 436/438, 99% @ rt = 2.98 min |

Example 6

Reaction Scheme 6

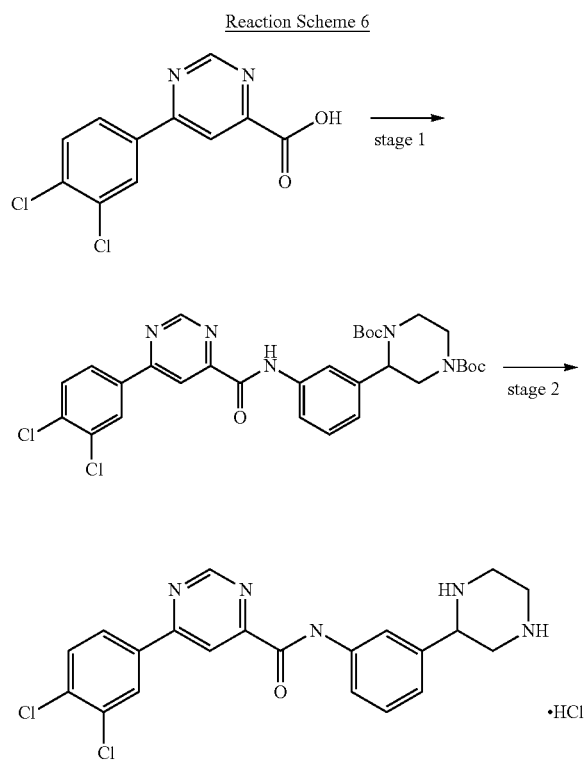 [SMILES: O=C(O)c1cc(-c2ccc(Cl)c(Cl)c2)ncn1 ; CC(C)(C)OC(=O)N1CCN(C(=O)OC(C)(C)C)C(c2cccc(NC(=O)c3cc(-c4ccc(Cl)c(Cl)c4)ncn3)c2)C1 ; O=C(Nc1cccc(C2CNCCN2)c1)c1cc(-c2ccc(Cl)c(Cl)c2)ncn1 ; Cl]

Example 7

Reaction Scheme 7

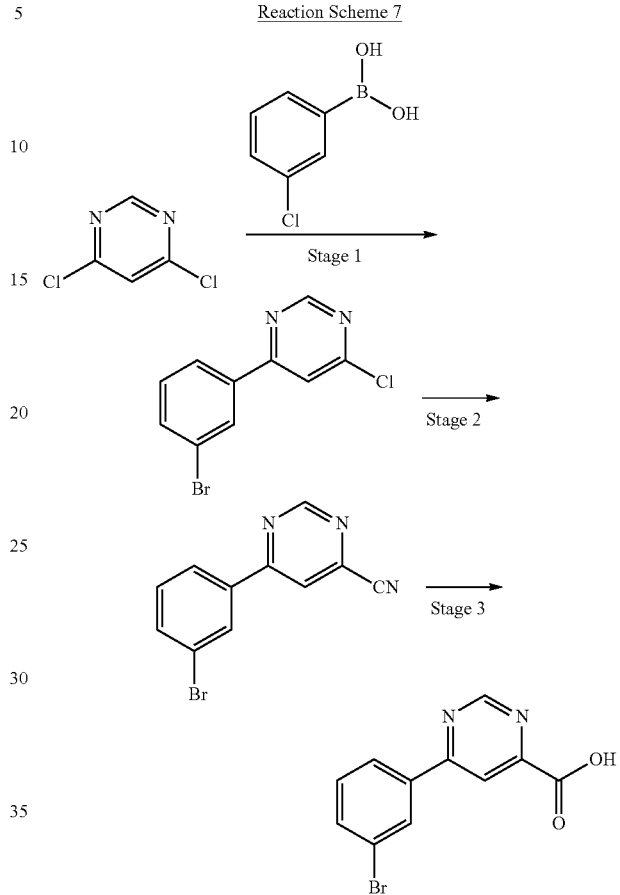

Referring to Reaction Scheme 6, Stage 1, the required amide analogues were prepared following the procedures described in method B.

Referring to Reaction Scheme 6, Stage 2, to a stirred solution of 2-(3-{[6-(3,4-dichloro-phenyl)-pyrimidine-4-carbonyl]-amino}-phenyl)-piperazine-1,4-dicarboxylic acid di-tert-butyl ester (1 eq) in MeOH (208 vol) under an atmosphere of nitrogen gas was added 4M HCl in 1,4-dioxane (5 eq) at RT. After 30 minutes more methanol was added to aid solubility. After stirring at RT overnight, more 4M HCl in 1,4-dioxane (10 vol) was added and the reaction mixture was again stirred overnight. The precipitated salt was filtered off, washed with heptane (1250 vol) and dried to afford the target compound.

Referring to Reaction Scheme 7, Stage 1, to a stirred suspension of dichloropyrimidine (1 eq) in 1,4-dioxane (20 vol) was added boronic acid (0.7 eq) and Pd(PPh$_3$)$_4$ (0.05 eq). A 2M K$_2$CO$_3$ solution (10 vol) was added to the resulting mixture, which was heated at 90° C. for 3 hours under an atmosphere of N$_2$. The reaction mixture was cooled to room temperature and concentrated in vacuo. The residue was dissolved in EtOAc:water (1:1) (100 vol) and the resulting solution filtered through celite. The organic layer was separated and the aqueous layer further extracted with EtOAc (50 vol). The combined organic layers were washed with saturated aqueous NaCl (20 vol), dried over Na$_2$SO$_4$, filtered and the solvent removed in vacuo. The resulting residue was purified by flash column chromatography (elu-

| Structure | Molecular Weight | Mass Spec Result |
|---|---|---|
| | 464.79 | [M + H]$^+$ = 428/430, 99% @ rt = 2.86 min | ent: [1:10] EtOAc:heptane) to afford the required target compound (8.38 g, 62%) as a pale yellow solid.

Referring to Reaction Scheme 7, Stage 2, to a degassed stirred mixture of 4-Chloro-6-substituted-phenyl-pyrimidine (1 eq) and Pd(PPh$_3$)$_4$ (0.05 eq) in DMF (20 vol) was added Zn(CN)$_2$ (1 eq). The reaction mixture was then heated at 100° C. with stirring for 3 hours. The reaction mixture was allowed to cool to room temperature. EtOAc (50 vol) was added and the organic phase was washed with water (3×40 vol). The organic layer was washed with saturated aqueous NaCl (20 vol), dried over Na$_2$SO$_4$, filtered and the solvent removed in vacuo. The resulting residue was purified by flash column chromatography (eluent: [1:10] EtOAc:heptane) to afford the required target compound (5.8 g, 75%) as a white solid.

Referring to Reaction Scheme 7, Stage 3, a suspension of 4-cyano-6-substituted-phenyl-pyrimidine (1 eq) in acetic acid (12 vol) and concentrated (12M) HCl (12 vol) was heated at 100° C. with stirring for 3 hours. The reaction mixture was allowed to cool to room temperature. Water (20 vol) was added to the reaction mixture and the resulting precipitate was filtered and washed with water and dried under vacuum. The crude solid was triturated with TBME, filtered and dried in vacuo to yield the target compound 5.5 g (88%).

| Structure | Molecular Weight | Mass Spec Result |
|---|---|---|
| 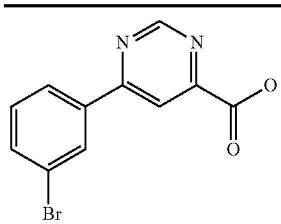 | 279.09 | [M + H]$^+$ = 279/281, 100% @ rt = 3.94 min |

Example 8

Reaction Scheme 8

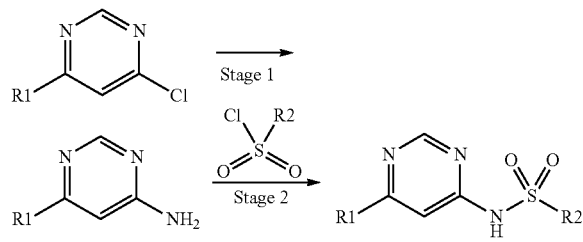

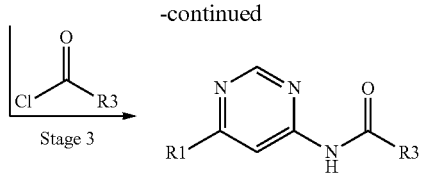

Referring to Reaction Scheme 8, Stage 1, 4-(chloro-6-substituted)-phenyl-pyrimidine (1 eq) was suspended in 1,4-dioxane (3 vol) and ammonium hydroxide (6 vol) was added to the suspension. The reaction mixture was heated at 95° C. in a pressure tube for 16 hours with stirring. The reaction mixture was cooled to room temperature and the precipitate was filtered off and washed with water to yield the target compound.

Referring to Reaction Scheme 8, Stage 2, 6-(substituted-phenyl)-pyrimidin-4-ylamine (1 eq) was suspended in 1,4-dioxane (20 vol). Sodium hydride (6 eq) was added and the suspension was stirred for 1 hour at ambient temperature. 3-Pyridinesulfonyl chloride or benzenesulfonyl chloride (1.2 eq) were added and the reaction mixture was stirred at 80° C. for 24 hours. In the case of pyridinesulfonyl chloride derivative, the reaction was quenched by the addition of water and the solvent was removed in vacuo. Purification by flash column chromatography (eluent: [0:1 to 1:4] MeOH:EtOAc) afforded the target compound. In the case of benzenesulfonyl chloride derivative, acetonitrile/water was added and the solid filtered off. The filtrate was concentrated in vacuo and the residue was triturated in EtOAc to furnish the sodium salt as a powder. The sodium salt was then washed with a citric acid aqueous solution followed by water and dried to furnish the desired compound.

Referring to Reaction Scheme 8, Stage 3, 6-substituted-phenyl-pyrimidin-4-ylamine (1 eq) was suspended in 1,4-dioxane or DMF (20 vol). Sodium hydride (3 eq) was added and the suspension stirred for 10 to 60 minutes at room temperature. The appropriate acid chloride (1.5 eq) was added and the reaction mixture stirred at room temperature for 1 hour. The reaction was monitored by LCMS. If the reaction was not complete, sodium hydride (1 eq) was added to the reaction mixture, which was then heated at 50° C. for 16 hours. Upon completion, the reaction was quenched with water. If precipitation occurred, the precipitate was filtered and purified further by flash column chromatography using an appropriate eluent, if not the desired material was extracted with EtOAc. The organic layer was washed with saturated aqueous NaCl solution, dried with MgSO$_4$, filtered and the solvent removed in vacuo. The desired compound was further purified either by trituration or prep HPLC when required.

The following compounds were prepared substantially as described above.

| Structure | Molecular Weight | Mass Spec Result |
|---|---|---|
| 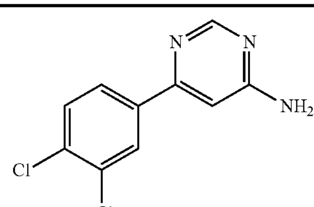 | 240.09 | [M + H]$^+$ = 240, 99% @ rt = 3.18 min |

-continued

| Structure | Molecular Weight | Mass Spec Result |
|---|---|---|
| (3,4-dichlorophenyl)-pyrimidinyl-N-phenylsulfonamide | 380.25 | [M + H]⁺ = 380/382, 100% @ rt = 4.62 min |
| (3,4-dichlorophenyl)-pyrimidinyl-N-phenylsulfonamide sodium salt | 402.24 | [M + H]⁺ = 381, 99% @ rt = 4.46 min |
| (3,4-dichlorophenyl)-pyrimidinyl-N-pyridinylsulfonamide | 381.24 | [M + H]⁺ = 381/383, 97% @ rt = 4.11 min |
| (2-trifluoromethylphenyl)-pyrimidinyl-N-methylsulfonamide | 317.29 | [M + H]⁺ = 318, 94% @ rt = 3.39 min |
| (3,4-dichlorophenyl)-pyrimidinyl-N-methylsulfonamide | 318.18 | [M + H]⁺ = 318/320, 98% @ rt = 3.92 min |
| (2-trifluoromethylphenyl)-pyrimidinyl-N-(3,4-dimethoxyphenyl)sulfonamide | 439.42 | [M + H]⁺ = 440, 100% @ rt = 3.88 min |
| (3,4-dichlorophenyl)-pyrimidinyl-N-(3,4-dimethoxyphenyl)sulfonamide | 440.31 | [M + H]⁺ = 440, 100% @ rt = 4.41 min |

| Structure | Molecular Weight | Mass Spec Result |
|---|---|---|
| 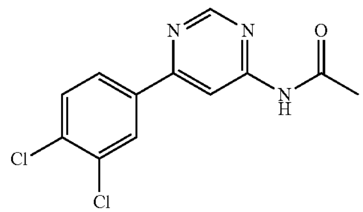 [SMILES: CC(=O)Nc1cc(-c2ccc(Cl)c(Cl)c2)ncn1] | 282.13 | [M + H]⁺ = 282/284, 99% @ rt = 4.33 min |
| 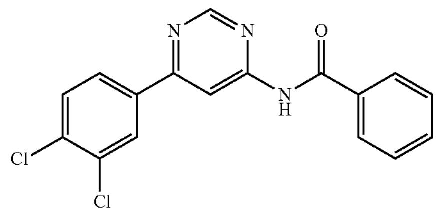 [SMILES: O=C(Nc1cc(-c2ccc(Cl)c(Cl)c2)ncn1)c1ccccc1] | 344.20 | [M + H]⁺ = 343/345, 95% @ rt = 5.62 min |
| 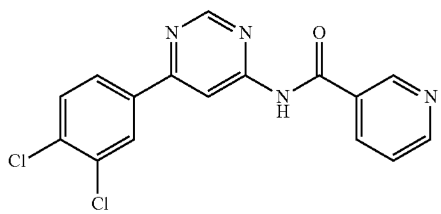 [SMILES: O=C(Nc1cc(-c2ccc(Cl)c(Cl)c2)ncn1)c1cccnc1] | 345.19 | [M + H]⁺ = 344/346, 96% @ rt = 4.41 min |
| 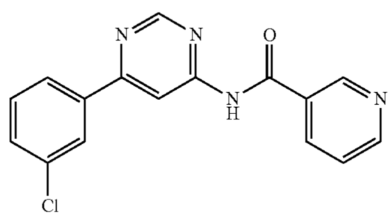 [SMILES: O=C(Nc1cc(-c2cccc(Cl)c2)ncn1)c1cccnc1] | 310.74 | [M + H]⁺ = 318, 94% @ rt = 3.39 min |
| 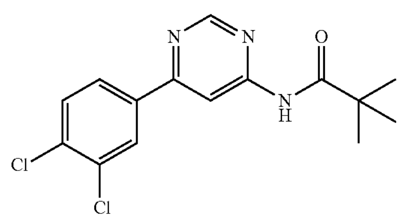 [SMILES: CC(C)(C)C(=O)Nc1cc(-c2ccc(Cl)c(Cl)c2)ncn1] | 324.21 | [M + H]+ = 324, 100% @ rt = 5.18 min |
| 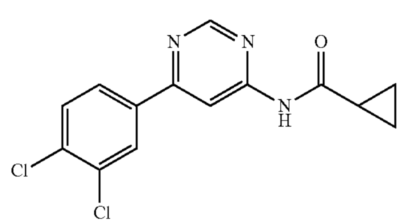 [SMILES: O=C(Nc1cc(-c2ccc(Cl)c(Cl)c2)ncn1)C1CC1] | 308.17 | [M + H]+ = 308, 98.8% @ rt = 4.73 min |
| 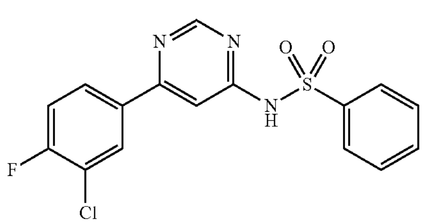 [SMILES: O=S(=O)(Nc1cc(-c2ccc(F)c(Cl)c2)ncn1)c1ccccc1] | 363.8 | [M + H]+ = 364, 99.2% @ rt = 4.35 min |

| Structure | Molecular Weight | Mass Spec Result |
|---|---|---|
| (6-(3,4-dichlorophenyl)pyrimidin-4-yl / 2-fluorophenyl sulfonamide) | 398.25 | [M + H]+ = 398/399, 100% @ rt = 4.69 min |
| (6-(3,4-dichlorophenyl)pyrimidin-4-yl / N-methyl phenyl sulfonamide) | 394.28 | [M + H]+ = 394/395, 99% @ rt = 5.35 min |
| (6-(3,4-dichlorophenyl)pyrimidin-4-yl / 3-(trifluoromethoxy)phenyl sulfonamide) | 464.25 | [M + H]+ = 464/465, 100% @ rt = 5.12 min |
| (6-(3,4-dichlorophenyl)pyrimidin-4-yl / 2,4-dimethylphenyl sulfonamide) | 408.31 | [M + H]+ = 408/409, 100% @ rt = 4.90 min |
| (6-(3,4-dichlorophenyl)pyrimidin-4-yl / 3-fluorophenyl sulfonamide) | 398.25 | [M + H]+ = 398/399, 98% @ rt = 4.76 min |
| (6-(3-chloro-4-fluorophenyl)pyrimidin-4-yl / 2-fluorophenyl sulfonamide) | 381.784 | [M + H]+ = 382/384, 99% @ rt = 4.31 min |

-continued

| Structure | Molecular Weight | Mass Spec Result |
|---|---|---|
| 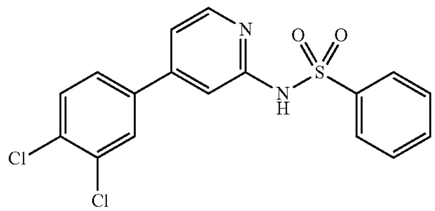 [SMILES: O=S(=O)(Nc1cc(-c2ccc(Cl)c(Cl)c2)ccn1)c1ccccc1] | 379.27 | [M + H]+ = 379/380/381, 95% @ rt = 4.52 min |

Example 9

Example 10

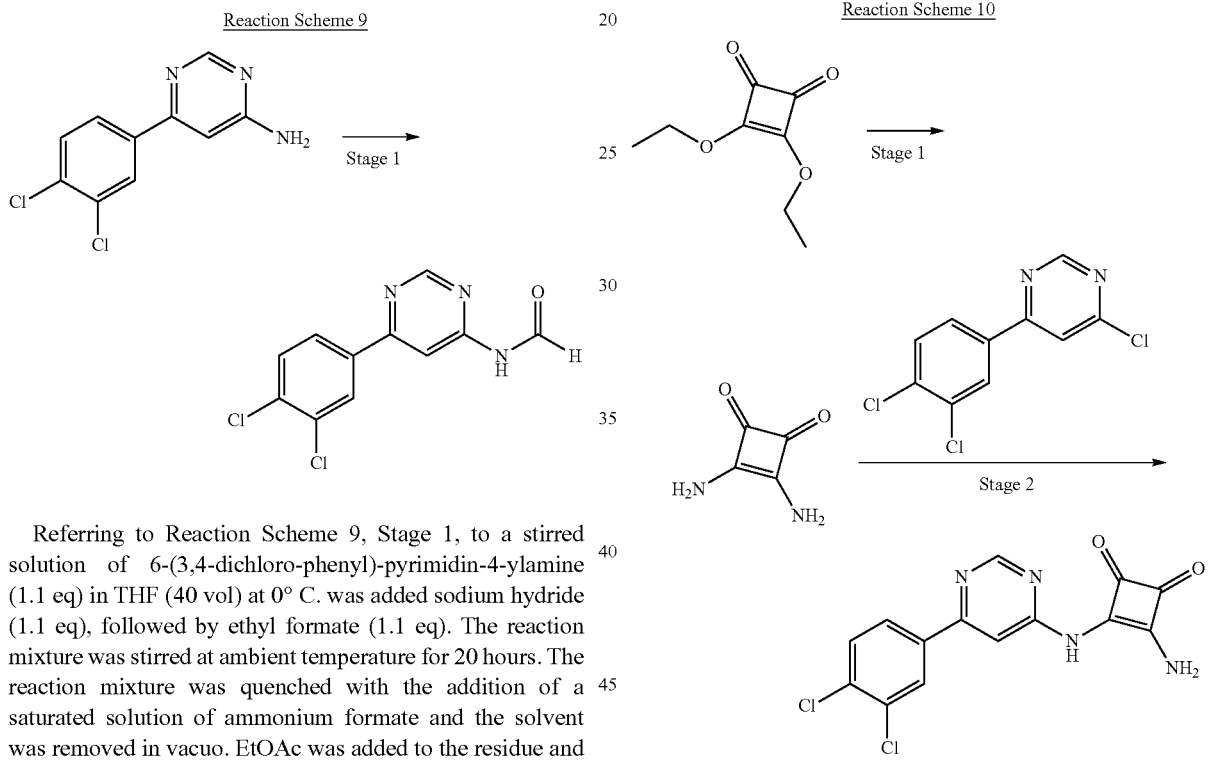

Referring to Reaction Scheme 9, Stage 1, to a stirred solution of 6-(3,4-dichloro-phenyl)-pyrimidin-4-ylamine (1.1 eq) in THF (40 vol) at 0° C. was added sodium hydride (1.1 eq), followed by ethyl formate (1.1 eq). The reaction mixture was stirred at ambient temperature for 20 hours. The reaction mixture was quenched with the addition of a saturated solution of ammonium formate and the solvent was removed in vacuo. EtOAc was added to the residue and the solid was filtered off. The filtrate was dried with MgSO$_4$, filtered and the solvent removed in vacuo to furnish the desired compound.

| Structure | Molecular Weight | Mass Spec Result |
|---|---|---|
| 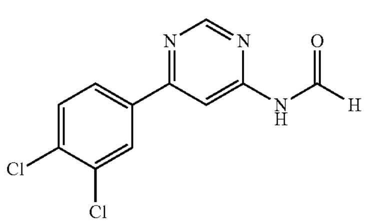 [SMILES: O=CNc1cc(-c2ccc(Cl)c(Cl)c2)ncn1] | 268.10 | [M + H]$^+$ = 267, 100% @ rt = 4.06 min |

Referring to Reaction Scheme 10, Stage 1, to a solution of 3,4-diethoxy-cyclobut-3-ene-1,2-dione (1 eq) in methanol (3 vol) was added a solution of ammonia in methanol (7N, 25 vol) at 0° C. The reaction mixture was left to warm up to room temperature and the precipitate was filtered off and washed with acetone and diethyl ether. The crude material was used without further purification in the next stage.

Referring to Reaction Scheme 10, Stage 2, to a solution of 3,4-diamino-cyclobut-3-ene-1,2-dione (1 eq) in DMF (20 vol) was added sodium hydride (1.5 eq) and the reaction mixture was stirred at ambient temperature for 5 minutes. 4-Chloro-6-(3,4-dichloro-phenyl)-pyrimidine (1.5 eq) was added to the reaction mixture, which was heated at 90° C. in a microwave for 5 minutes. To the cool mixture were added EtOAc and water. The organic layer was separated and dried with Na$_2$SO$_4$, filtered and evaporated to dryness. Purification by flash column chromatography using a suitable solvent afforded the target compound.

| Structure | Molecular Weight | Mass Spec Result |
|---|---|---|
| (structure) | 335.15 | [M + H]⁺ = 335/337, 100% @ rt = 3.93 min |

Example 11

Reaction Scheme 11

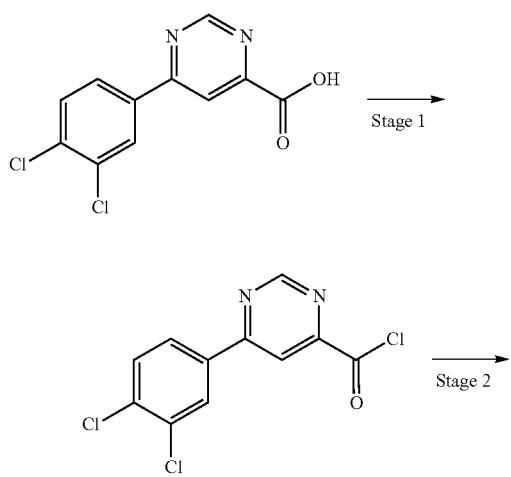

Referring to Reaction Scheme 11, Stage 1, to a stirred solution of 6-(3,4-dichloro-phenyl)-pyrimidine-4-carboxylic acid (1 eq) in DCM (20 vol) under an atmosphere of nitrogen were added oxalyl chloride (3 eq) and DMF (catalytic amount). The reaction mixture was stirred at ambient temperature for 30 minutes after which time the solvents were removed in vacuo. The resulting residue was used in the next stage without further purification.

Referring to Reaction Scheme 11, Stage 2, the resulting residue was dissolved in THF (10 vol). Triethylamine (1.5 eq) and N,O-dimethylhydroxylamine hydrochloride (1.1 eq) were added to the reaction mixture, which was stirred at ambient temperature for 48 hours followed by 2 hours at 45° C. The solvent was removed in vacuo and the resulting residue was partitioned between DCM and water. The organic phase was separated and washed with water, a saturated solution of NaCl, dried with MgSO₄, filtered and the solvent removed in vacuo. Purification by flash column chromatography (eluent: [0:1] to [1:4] EtOAc:heptane) furnished the desired target compound.

| Structure | Molecular Weight | Mass Spec Result |
|---|---|---|
| 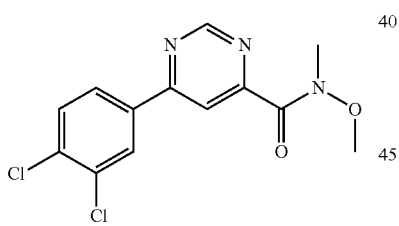 | 312.16 | [M + H]⁺ = 312/314, 100% @ rt = 4.24 min |

Example 12

Reaction Scheme 12

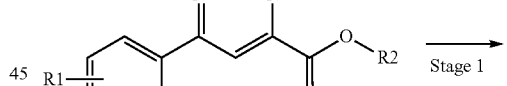

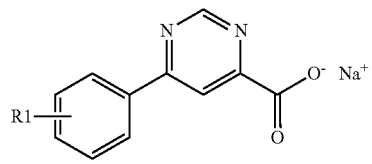

Referring to Reaction Scheme 12, Stage 1, to a stirred solution of 6-(3-chloro-phenyl)-pyrimidine-4-carboxylic acid (1 eq) or 6-(3,4-dichloro-phenyl)-pyrimidine-4-carboxylic acid methyl ester in THF (20 vol) was added dropwise a 1M NaOH solution. The mixture was stirred at ambient temperature and the resulting precipitate was filtered and washed with water/THF or with water then heptane to furnish the described salts.

| Structure | Molecular Weight | Mass Spec Result |
|---|---|---|
| 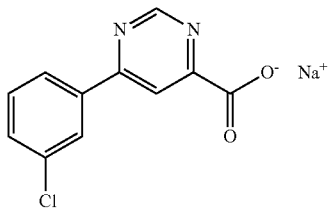 [SMILES: O=C([O-])c1cc(-c2cccc(Cl)c2)ncn1 ; [Na+]] | 256.63 | [M + H]⁺ = 235, 89% @ rt = 3.93 min |
| 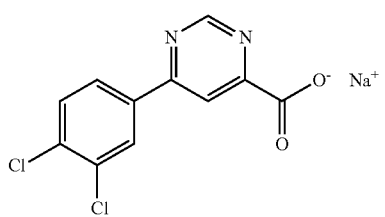 [SMILES: O=C([O-])c1cc(-c2ccc(Cl)c(Cl)c2)ncn1 ; [Na+]] | 291.07 | [M + H]⁺ = 269/271, 100% @ rt = 4.17 min |
| 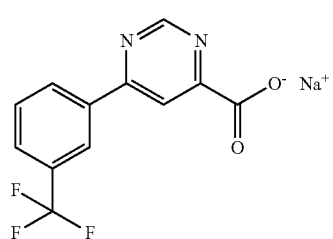 [SMILES: O=C([O-])c1cc(-c2cccc(C(F)(F)F)c2)ncn1 ; [Na+]] | 290.18 | [M + H]⁺ = 268, 100% @ rt = 4.10 min |
| 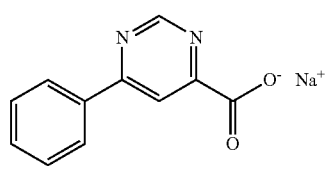 [SMILES: O=C([O-])c1cc(-c2ccccc2)ncn1 ; [Na+]] | 222.18 | [M + H]⁺ = 201, 100% @ rt = 3.27 min |
| 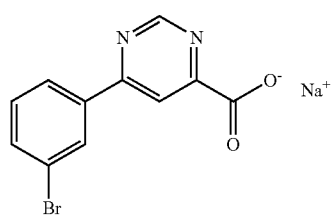 [SMILES: O=C([O-])c1cc(-c2cccc(Br)c2)ncn1 ; [Na+]] | 301.08 | [M + H]⁺ = 278/280, 100% @ rt = 3.59-3.70 min |

-continued

| Structure | Molecular Weight | Mass Spec Result |
|---|---|---|
| 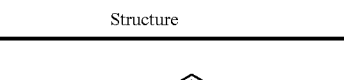 | 307.29 | [M + H]⁺ = 286, 91% @ rt = 3.43 min |

Example 13

Example 14

Reaction Scheme 13

Reaction Scheme 14

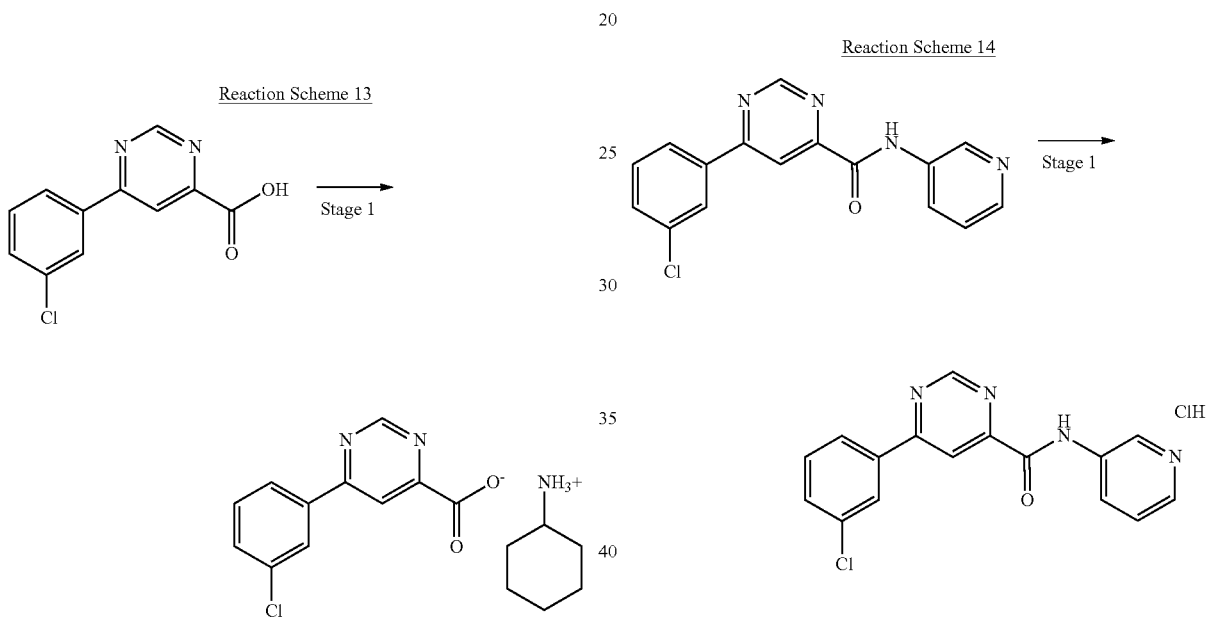

Referring to Reaction Scheme 13, Stage 1, to a stirred solution of 6-(3-chloro-phenyl)-pyrimidine-4-carboxylic acid (1 eq) dissolved in the minimum amount of THF was added cyclohexylamine. The mixture was stirred at ambient temperature for 1 hour and the resulting precipitate was filtered and washed with THF to furnish the described salt.

Referring to Reaction Scheme 14, to a stirred suspension of 6-(3-chloro-phenyl)-pyrimidine-4-carboxylic acid pyridin-3-ylamide (1 eq) in methanol was added 6N HCl at ambient temperature. After complete dissolution was observed, the solvents were removed in vacuo and the resulting salt was purified by successive trituration with acetone and tert-butylmethylether. Re-crystallisation from ethanol afforded the desired compound.

| Structure | Molecular Weight | Mass Spec Result |
|---|---|---|
| 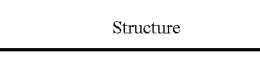 | 333.82 | [M + H]⁺ = 235, 92% @ rt = 3.84 min |

| Structure | Molecular Weight | Mass Spec Result |
|---|---|---|
| (3-chlorophenyl)-pyrimidine-N-(pyridin-3-yl)carboxamide structure | 347.21 | [M + H]$^+$ = 311, 100% @ rt = 3.73 min |

Example 15

Reaction Scheme 15

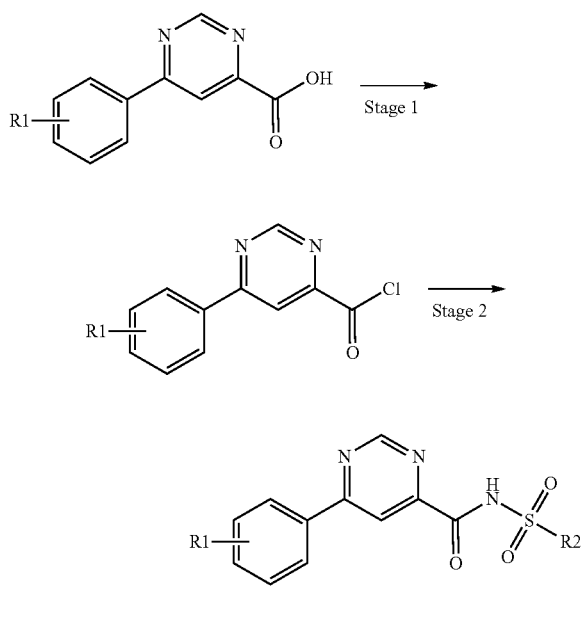

Referring to Reaction Scheme 15, Stage 1, to a stirred solution of 6-(substituted-phenyl)-pyrimidine-4-carboxylic acid (1 eq) in DCM (20 vol) under an atmosphere of nitrogen were added oxalyl chloride (3 eq) and 1 drop of DMF (cat.). The reaction mixture was stirred at ambient temperature for 30 minutes after which time the solvents were removed in vacuo. The resulting residue was used in the next stage without further purification.

Referring to Reaction Scheme 15, Stage 2, the resulting residue was dissolved in THF (10 vol). Triethylamine (1 eq) and the appropriate sulfonamide (1.5 eq) were added to the reaction mixture, which was stirred at ambient temperature for 4 to 16 hours. The solvent was removed in vacuo and the resulting residue was purified by trituration with water and diethyl ether. The solid was filtered and washed with water and DCM. When precipitation did not happen, the solvent was removed in vacuo and DCM was added. The organic phase was washed with a saturated solution of sodium bicarbonate followed by a 2M solution of citric acid, dried with Na$_2$SO$_4$, filtered and the solvent removed in vacuo to furnish the crude compound, which was purified by flash column chromatography (eluent: [1:10] to [1:0] EtOAc:heptane) to furnish the desired target compound.

| Structure | Molecular Weight | Mass Spec Result |
|---|---|---|
| phenylsulfonyl carboxamide structure | 373.82 | [M + H]$^+$ = 374, 100% @ rt = 4.66 min |
| 3-chlorophenylsulfonyl carboxamide structure | 408.27 | [M + H]$^+$ = 408, 100% @ rt = 5.09 min |

-continued
| Structure | Molecular Weight | Mass Spec Result |
|---|---|---|
| 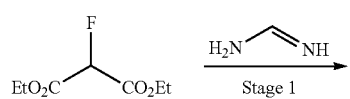 | 442.71 | [M + H]⁺ = 442/444, 95% @ rt = 5.47 min |
| 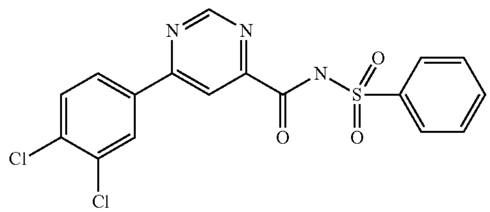 [SMILES: O=C(NS(=O)(=O)c1ccccc1)c1cc(-c2ccc(Cl)c(Cl)c2)ncn1] | 408.27 | [M + H]⁺ = 408, 94% @ rt = 5.06 min |
| 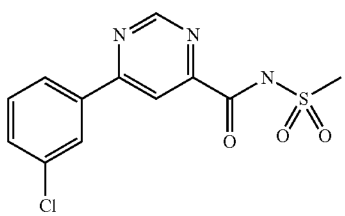 [SMILES: CS(=O)(=O)NC(=O)c1cc(-c2cccc(Cl)c2)ncn1] | 311.75 | [M + H]⁺ = 312/314, 100% @ rt = 4.08 min |
Example 16
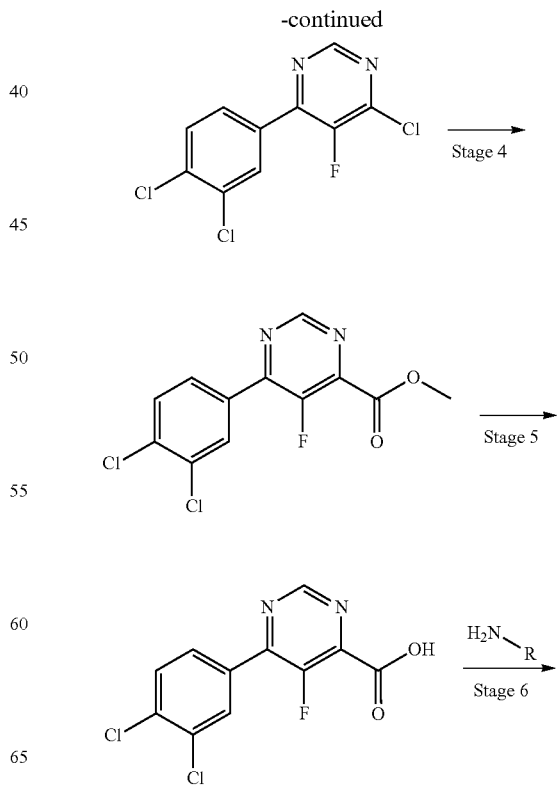

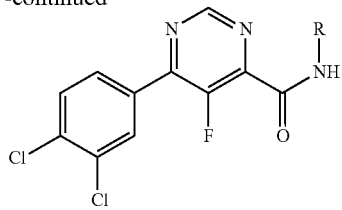

Referring to Reaction Scheme 16, Stage 1, to a stirred solution of formamidine acetate (1 eq) in ethanol (50 vol) was added a solution of sodium ethoxide in ethanol (2% w/w) (3 eq) at 0° C. and the reaction mixture was stirred at that temperature for 30 minutes. To the resulting mixture was added a solution of diethyl fluoromalonate (1 eq) in ethanol (5 vol) and the reaction mixture was stirred at ambient temperature for 72 hours. The reaction mixture was cooled to 0° C. and concentrated HCl (3 vol) was added to adjust the pH of the reaction mixture to pH6. The resulting precipitate was filtered, washed with isopropanol, diethylether and hexane to furnish the desired intermediate, which was used in the next stage without further purification Referring to Reaction Scheme 16, Stage 2, to a stirred solution of N,N-dimethylaniline (1 eq) in phosphorous oxychloride (4 vol) was added 5-fluoro-pyrimidine-4,6-diol (1 eq) and the reaction mixture was heated at reflux for 16 hours. After cooling to room temperature the solvent was removed in vacuo and the resulting residue was poured into ice. The desired intermediate was then extracted with EtOAc. The organic layer was dried with MgSO$_4$, filtered and the solvent removed in vacuo to furnish the desired intermediate, which was used in the next stage without further purification.

Referring to Reaction Scheme 16, Stage 3, 4,6-dichloro-5-fluoro-pyrimidine (1 eq), 3,4-dichlorophenyl boronic acid (0.7 eq) and Pd(PPh$_3$)$_4$ (0.05 eq) were suspended in 1,4-dioxane (20 vol). A 2M K$_2$CO$_3$ solution (6.75 vol) was added and the reaction mixture was heated at 90° C. with stirring for 2 hours under an atmosphere of N$_2$. The reaction mixture was cooled to room temperature and concentrated in vacuo. The residue was dissolved in EtOAc and water. The mixture was partitioned and the aqueous layer further extracted with EtOAc. The combined organic layers were washed with saturated aqueous NaCl, dried over Na$_2$SO$_4$, filtered and the solvent removed in vacuo. The resulting residue was purified by flash column chromatography (eluent: [1:15] EtOAc:heptane) to afford the required target compound.

Referring to Reaction Scheme 16, Stage 4, 4-chloro-6-(3,4-dichloro-phenyl)-5-fluoro-pyrimidine (1 eq), PdCl$_2$(dppf).DCM (0.05 eq) and triethylamine (2 eq) were suspended in degassed MeOH (50 vol) in a bomb fitted with a magnetic stirrer bar. The atmosphere in the reaction vessel was replaced with N$_2$ by successive evacuation and charging with N$_2$ gas (this process was repeated three times). The bomb was then flushed with CO by successive charging with CO and evacuation. The vessel was pressurised to 5 bar of CO and heated at 50° C. with stirring for 5 hours. The reaction vessel was allowed to cool to room temperature before venting CO and flushing with N$_2$. The reaction mixture was concentrated in vacuo. Purification of the residue by flash column chromatography (eluent: [1:15] EtOAc:heptane) yielded the target compound.

Referring to Reaction Scheme 16, Stage 5, 6-(3,4-dichloro-phenyl)-5-fluoro-pyrimidine-4-carboxylic acid methyl ester (1 eq) was suspended in THF (30 vol), 2M NaOH solution (5 eq) and stirred at room temperature for 3 hours. The reaction mixture was concentrated in vacuo. The resulting residue was dissolved in EtOAc and water. The aqueous layer was separated and the precipitate removed by filtration. The aqueous layer was acidified with conc. HCl and the resulting precipitate was filtered and washed with water to furnish the desired target compound.

Referring to Reaction Scheme 16, Stage 6, the required amide analogues were prepared following the procedure described in method B and were purified by trituration in acetonitrile/water (1/1).

| Structure | Molecular Weight | Mass Spec Result |
|---|---|---|
| 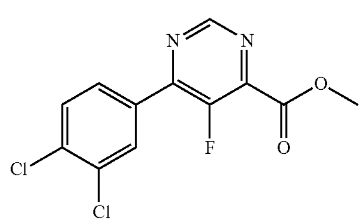 [SMILES: COC(=O)c1ncnc(-c2ccc(Cl)c(Cl)c2)c1F] | 301.11 | [M + H]$^+$ = 303, 98% @ rt = 4.63 min |
| 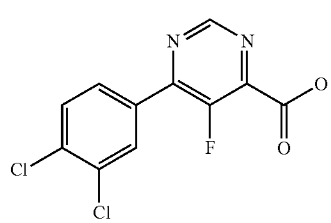 [SMILES: O=C(O)c1ncnc(-c2ccc(Cl)c(Cl)c2)c1F] | 287.08 | [M + H]$^+$ = 287, 100% @ rt = 3.85 min |

| Structure | Molecular Weight | Mass Spec Result |
|---|---|---|
| (3,4-dichlorophenyl-fluoro-pyrimidine-carboxamide-N-pyridin-3-yl) | 363.18 | [M + H]⁺ = 364, 99% @ rt = 4.07 min |
| (3,4-dichlorophenyl-fluoro-pyrimidine-carboxamide-N-(2,6-dimethylpyridin-3-yl)) | 391.23 | [M + H]⁺ = 391, 98% @ rt = 3.51 min |
| (3,4-dichlorophenyl-fluoro-pyrimidine-carboxamide-N-pyrimidin-5-yl) | 364.17 | [M + H]⁺ = 363, 100% @ rt = 4.34 min |

Example 17

Reaction Scheme 17

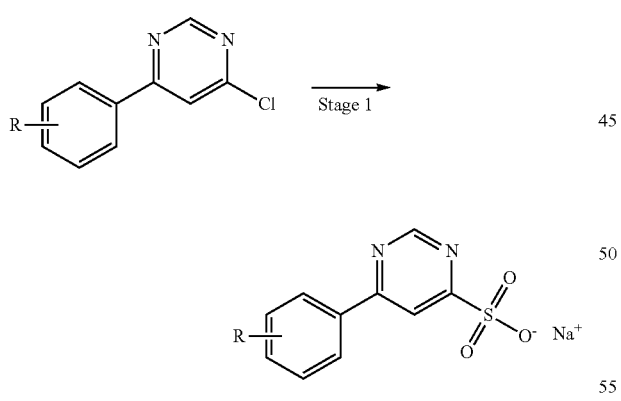

Referring to Reaction Scheme 17, Stage 1, to a stirred solution of 4-chloro-6-(substituted-phenyl)-pyrimidine (1 eq) in acetonitrile (9 vol) was added a 1M solution of sodium sulfite (2 eq) and the reaction mixture was heated at 90° C. with stirring for 16 hours. The reaction mixture was allowed to cool to room temperature and the precipitate was filtered. In the case of 4-chloro-6-(3-chlorophenyl)-pyrimidine, the precipitate was washed with acetonitrile/water and dried in a vacuum oven to furnish the desired compound. In the case of 4-chloro-6-(3,4-dichlorophenyl)-pyrimidine, the precipitate was triturated in hot acetonitrile/water and hot filtration was carried out. The filtrate was collected, allowed to cool to room temperature and the solvents removed in vacuo to furnish the desired compound.

| Structure | Molecular Weight | Mass Spec Result |
|---|---|---|
| (3-chlorophenyl-pyrimidine-sulfonate sodium) | 292.68 | [M + H]⁺ = 271, 97% @ rt = 3.13 min |
| (3,4-dichlorophenyl-pyrimidine-sulfonate sodium) | 327.12 | [M + H]⁺ = 305, 99% @ rt = 3.88 min |

Example 18

Reaction Scheme 18

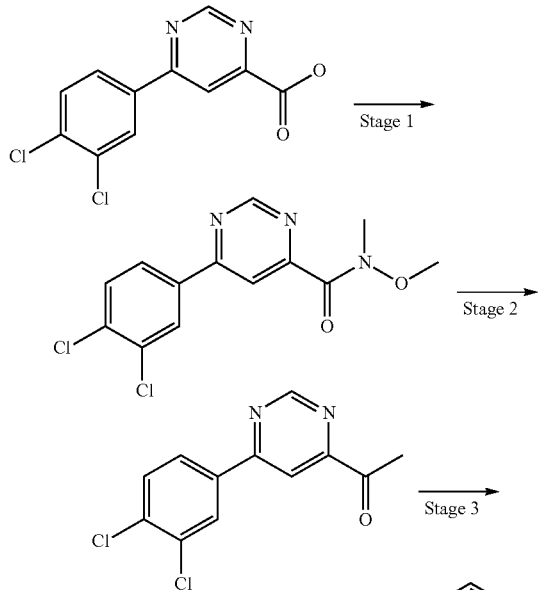

Referring to Reaction Scheme 18, Stage 1, to a stirred solution of 6-(3,4-dichloro-phenyl)-pyrimidine-4-carboxylic acid (1 eq) in DCM (20 vol) under an atmosphere of nitrogen were added oxalyl chloride (3 eq) and 1 drop of DMF (cat.). The reaction mixture was stirred at ambient temperature for 30 minutes after which time the solvents were removed in vacuo. The resulting residue was dissolved in THF (10 vol). Triethylamine (1.5 eq) and O,N-dimethylhydroxylamine hydrochloride salt (1.1 eq) were successively added to the reaction mixture, which was stirred at ambient temperature for 16 hours. The solvent was removed in vacuo and the resulting residue was dissolved in DCM and washed with water (2×). The organic phase was dried over $Na_2SO_4$, filtered and concentrated in vacuo to furnish the desired intermediate.

Referring to Reaction Scheme 18, Stage 2, to a stirred solution of 6-(3,4-dichloro-phenyl)-pyrimidine-4-carboxylic acid methoxy-methyl-amide (1 eq) at 0° C. in anhydrous THF (10 vol) was added a 1.4 M solution of methylmagnesium bromide in THF/toluene (1 eq). The reaction mixture was allowed to warm up to room temperature while stirring and monitored by LCMS until completion. Water and a solution of ammonium chloride were added to the reaction mixture, which was extracted with DCM (2×). The organic layers were combined, dried over $Na_2SO_4$, filtered and concentrated in vacuo to furnish the target compound as a solid, which was further purified by trituration with acetonitrile/water (1/1).

Referring to Reaction Scheme 18, Stage 3, to a stirred solution of 1-[6-(3,4-dichloro-phenyl)-pyrimidin-4-yl]-ethanone (1 eq) in ethanol (25 vol) was added methoxylamine hydrochloride (5 eq) and pyridine (3.3 eq). The reaction mixture was stirred at 95° C. and monitored by LCMS. After cooling, the reaction mixture was concentrated in vacuo. Purification by flash column chromatography (eluent: [1:9 to 1:4] EtOAc:heptane) afforded the required target compound.

| Structure | Molecular Weight | Mass Spec Result |
|---|---|---|
| 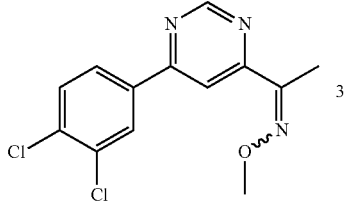 | 232.67 | [M + H]⁺ = 233, 98% @ rt = 4.53 min |
| 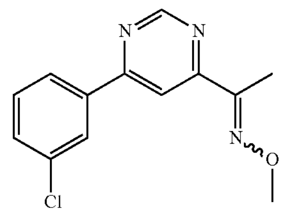 [SMILES: CON=C(C)c1cc(-c2cccc(Cl)c2)ncn1] | 261.71 | [M + H]⁺ = 262, 100% @ rt = 5.20 min |

Example 19

Reaction Scheme 19

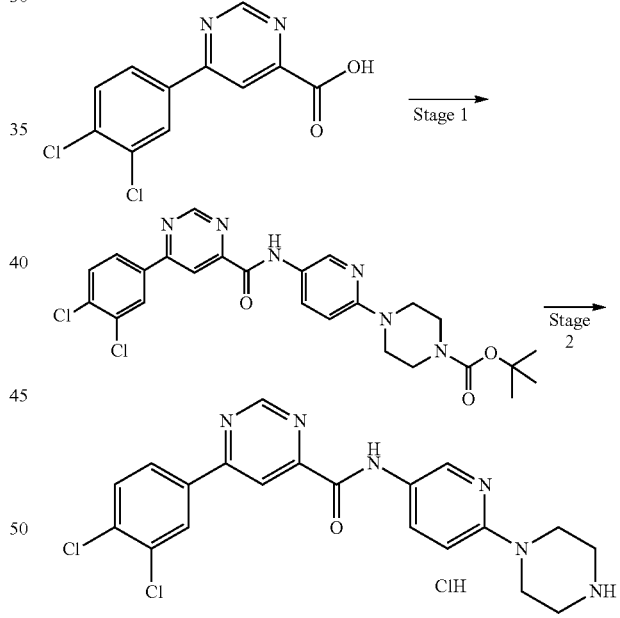

Referring to Reaction Scheme 19, Stage 1, 4-(5-{[6-(3,4-dichloro-phenyl)-pyrimidine-4-carbonyl]-amino}-pyridin-2-yl)-piperazine-1-carboxylic acid tert-butyl ester was prepared according to method B starting with 4-(5-aminopyridin-2-yl)-piperazine-1-carboxylic acid tert-butyl ester.

Referring to Reaction Scheme 19, Stage 2, to a suspension of 4-(5-{[6-(3,4-dichloro-phenyl)-pyrimidine-4-carbonyl]-amino}-pyridin-2-yl)-piperazine-1-carboxylic acid tert-butyl ester (1 eq) in 1,4-dioxane (43 vol) was added 4M HCl in 1,4-dioxane (16 vol) and the reaction mixture was stirred at room temperature for 1 hour 30 minutes. The solvent was evaporated in vacuo and the remaining solid was triturated with EtOAc, methanol, DCM and heptane. It was dried in a vacuum oven to furnish the desired molecule.

| Structure | Molecular Weight | Mass Spec Result |
|---|---|---|
| (structure shown) | 465.77 | [M + H]⁺ = 429/431, 100% @ rt = 3.33 min |

Example 20

Reaction Scheme 20

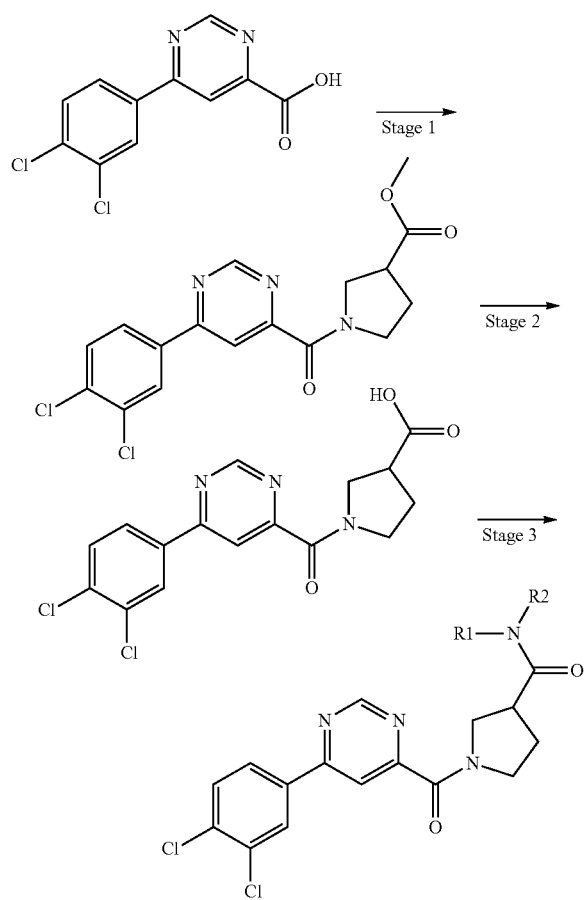

Referring to Reaction Scheme 20, Stage 1, 1-[6-(3,4-dichloro-phenyl)-pyrimidine-4-carbonyl]-pyrrolidine-3-carboxylic acid methyl ester was prepared according to method B (acid chloride method) using pyrrolidine-3-carboxylic acid methyl ester hydrochloride.

Referring to Reaction Scheme 20, Stage 2, to a solution of 1-[6-(3,4-dichloro-phenyl)-pyrimidine-4-carbonyl]-pyrrolidine-3-carboxylic acid methyl ester (1 eq) in THF:water (1:1, 46 vol) was added 1M NaOH (2 eq) and the mixture was stirred at room temperature for 30 minutes until completion of the reaction was observed by TLC. The reaction mixture was washed with EtOAc (2×15 vol) and then acidified with 1M HCl (5.3 vol) and extracted with EtOAc (3×15 vol) and dried over Na₂SO₄. The solvent was then evaporated to give the desired carboxylic acid.

Referring to Reaction Scheme 20, Stage 3, to a solution of 1-[6-(3,4-dichloro-phenyl)-pyrimidine-4-carbonyl]-pyrrolidine-3-carboxylic acid (1 eq) in DMF (20 vol) was added O-(7-azabenzotriazol-1-yl)-N,N,N',N'-tetramethyluronium hexafluorophosphate (1.1 eq) followed by the amine (1.2 eq) and the reaction mixture was stirred at room temperature for 1 hour 30 minutes. The reaction was monitored by LCMS. If the reaction was not complete, the appropriate amine (0.7 eq) was added and the reaction mixture was stirred at ambient temperature for another hour. EtOAc was added and the organic layer was washed with a saturated solution of sodium bicarbonate then with a saturated aqueous solution of NaCl, dried over Na₂SO₄, filtered and the solvent was removed in vacuo. The solid was then triturated with an appropriate solvent and dried in a Genevac to furnish the desired compounds.

| Structure | Molecular Weight | Mass Spec Result |
|---|---|---|
| (structure shown) | 366.21 | [M + H]⁺ = 366/368, 100% @ rt = 3.91 min |

-continued
| Structure | Molecular Weight | Mass Spec Result |
|---|---|---|
| 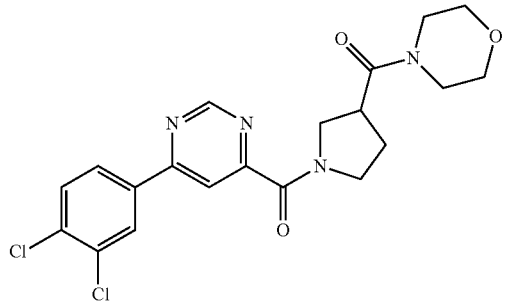 [SMILES: O=C(c1cc(-c2ccc(Cl)c(Cl)c2)ncn1)N1CCC(C(=O)N2CCOCC2)C1] | 435.31 | [M + H]⁺ = 435/437, 100% @ rt = 3.97 min |
| 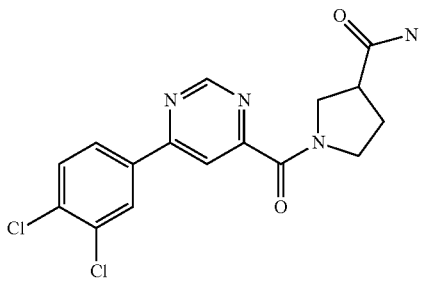 [SMILES: NC(=O)C1CCN(C(=O)c2cc(-c3ccc(Cl)c(Cl)c3)ncn2)C1] | 365.22 | [M + H]⁺ = 365/367, 100% @ rt = 3.63 min |
| 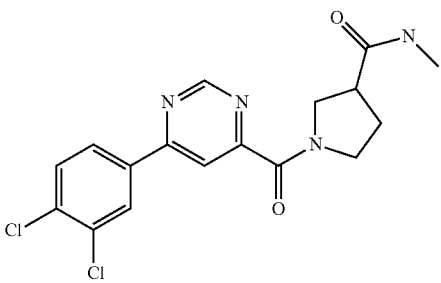 [SMILES: CNC(=O)C1CCN(C(=O)c2cc(-c3ccc(Cl)c(Cl)c3)ncn2)C1] | 379.25 | [M + H]⁺ = 379/381, 100% @ rt = 3.77 min |
| 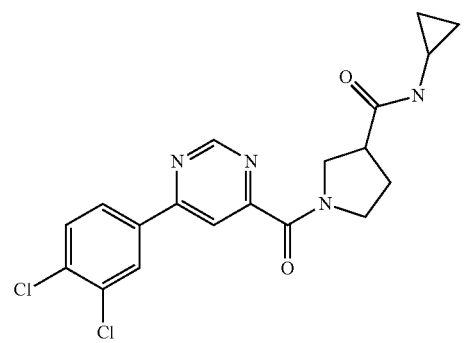 [SMILES: O=C(NC1CC1)C1CCN(C(=O)c2cc(-c3ccc(Cl)c(Cl)c3)ncn2)C1] | 405.29 | [M + H]⁺ = 405/407, 100% @ rt = 3.95 min |
| 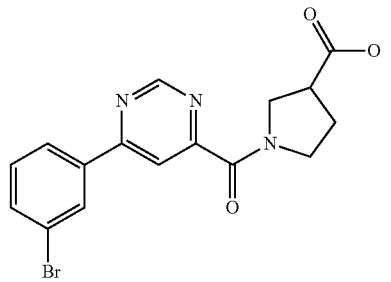 [SMILES: O=C(O)C1CCN(C(=O)c2cc(-c3cccc(Br)c3)ncn2)C1] | 376.21 | [M + H]⁺ = 360/362, 100% @ rt = 3.70 min |

Example 21

Reaction Scheme 21

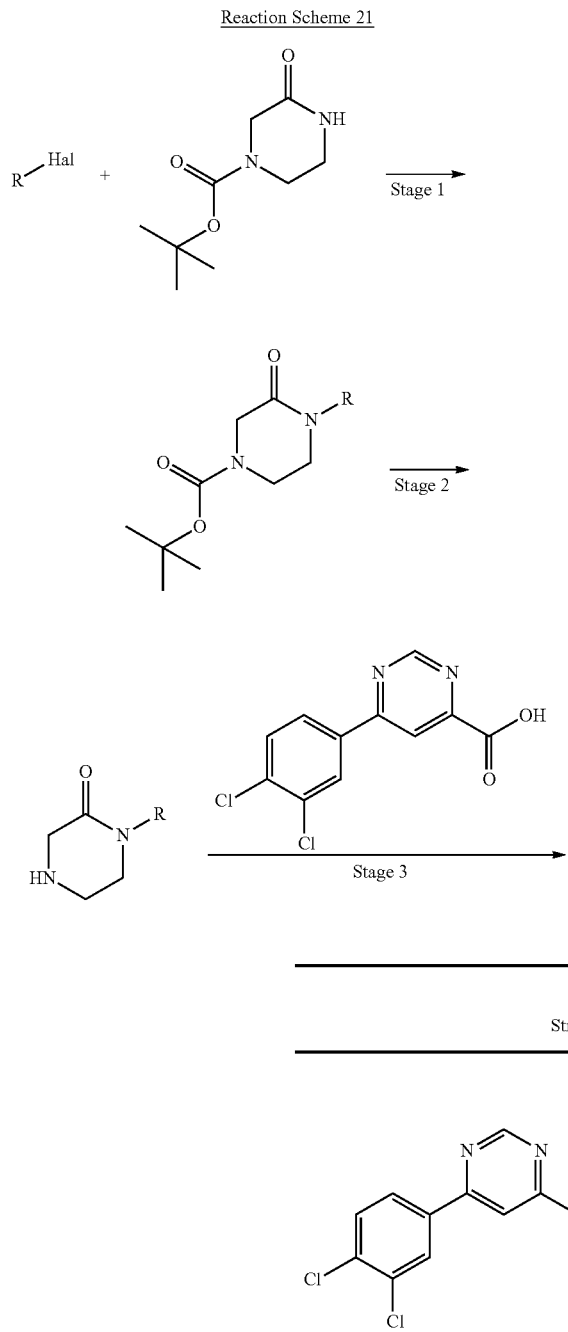

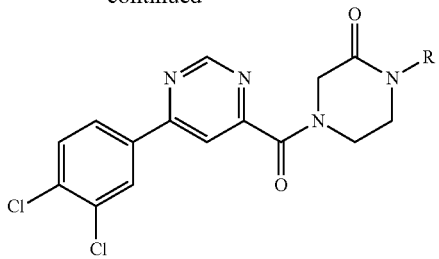

Referring to Reaction Scheme 21, Stage 1, to a solution of 3-oxo-piperazine-1-carboxylic acid tert-butyl ester (synthesis described in patent WO2004/35576, 1 eq) in dry THF (50 vol) was added sodium hydride (60% dispersion in mineral oil) (2 eq) followed by the alkyl halide (1.5 eq) and the reaction mixture was stirred under an atmosphere of nitrogen at reflux for 3 hours 30 minutes. Water was added and the compound was extracted with EtOAc, dried over $Na_2SO_4$. The solvent was evaporated to give crude material which was used without further purification in the next stage.

Referring to Reaction Scheme 21, Stage 2, to a suspension of 4-substituted-3-oxo-piperazine-1-carboxylic acid tert-butyl ester (1 eq) in 1,4-dioxane (6.25 vol) was added 4M HCl in 1,4-dioxane (10.4 vol) and the reaction mixture was stirred at room temperature for 5 hours. The solvent was evaporated in vacuo and the crude residue was used without further purification in the next stage.

Referring to Reaction Scheme 21, Stage 3, 4-[6-(3,4-dichloro-phenyl)-pyrimidine-4-carbonyl]-1-substituted-piperazin-2-one was prepared according method B (acid chloride method) starting with the previous intermediate described in Stage 2.

| Structure | Molecular Weight | Mass Spec Result |
|---|---|---|
| 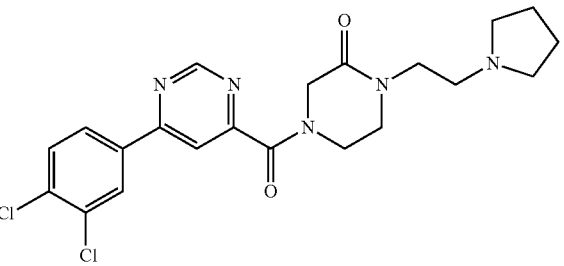 | 448.36 | $[M + H]^+$ = 448/450, 100% @ rt = 3.01 min |
| 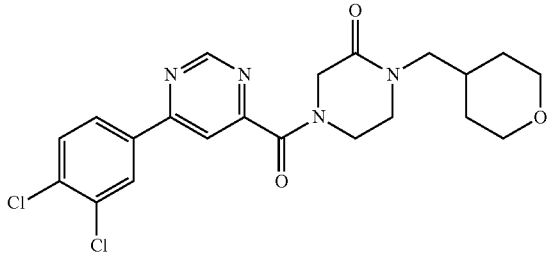 [SMILES: O=C1CN(C(=O)c2cc(-c3ccc(Cl)c(Cl)c3)ncn2)CCN1CC1CCOCC1] | 449.34 | $[M + H]^+$ = 449/451, 100% @ rt = 4.10 min |

| Structure | Molecular Weight | Mass Spec Result |
|---|---|---|
| 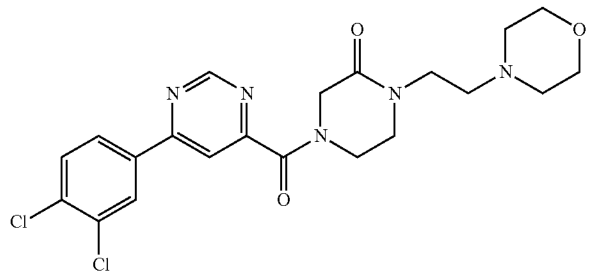 [SMILES: O=C1CN(C(=O)c2cc(-c3ccc(Cl)c(Cl)c3)ncn2)CCN1CCN1CCOCC1] | 464.36 | [M + H]⁺ = 464/466, 99% @ rt = 2.97 min |
| 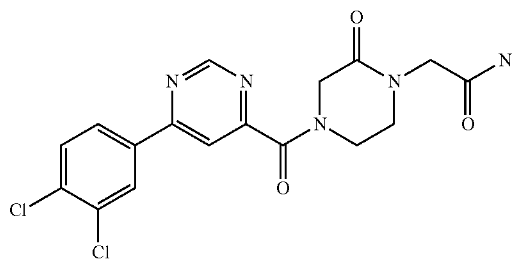 [SMILES: NC(=O)CN1CCN(C(=O)c2cc(-c3ccc(Cl)c(Cl)c3)ncn2)CC1=O] | 408.25 | [M + H]⁺ = 408/410, 100% @ rt = 3.54 min |

Example 22

Reaction Scheme 22

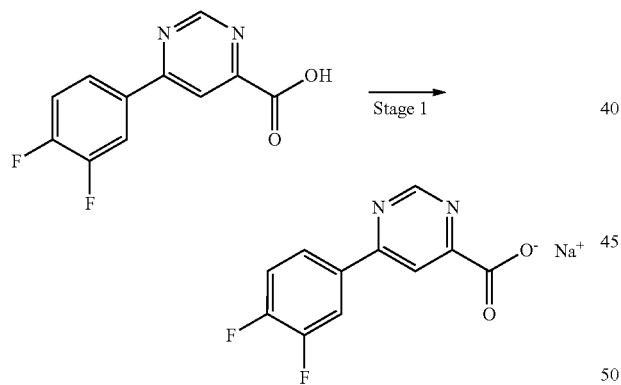

Referring to Reaction Scheme 22, Stage 1, to a solution of 6-(3,4-difluorophenyl)pyrimidine-4-carboxylic acid (synthesis described in Table 1, 1 eq) in THF (50 vol) was added 2M NaOH (0.95 eq) and the reaction mixture was stirred for 30 minutes. The precipitate was filtered off, washed with THF (50 vol) and dried in a vacuum oven at 40° C. to afford the desired product as a white solid.

| Structure | Molecular Weight | Mass Spec Result |
|---|---|---|
| 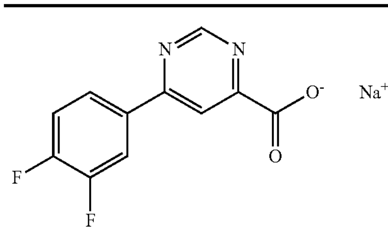 | 258.16 | [M + H]⁺ = 236, 100% @ rt = 3.60 min |

Example 23

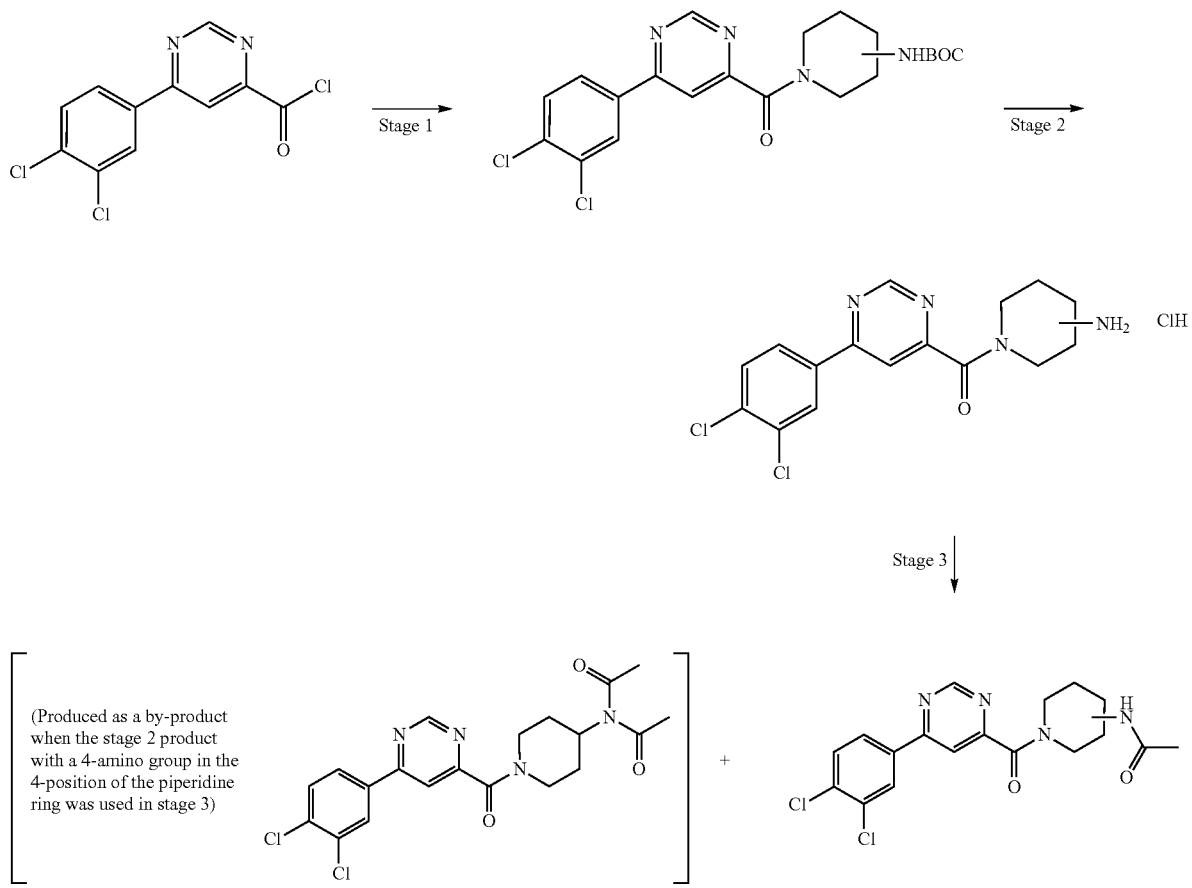

Referring to Reaction Scheme 23, Stage 1, {1-[6-(3,4-dichloro-phenyl)-pyrimidine-4-carbonyl]-substituted}-carbamic acid tert-butyl ester was prepared according to method B (acid chloride method) starting with piperidin-4-yl-carbamic acid tert-butyl ester or piperidin-3-yl-carbamic acid tert-butyl ester respectively.

Referring to Reaction Scheme 23, Stage 2, 4.0M hydrogen chloride in 1,4-dioxane (40 vol) was added to a solution of {1-[6-(3,4-dichloro-phenyl)-pyrimidine-4-carbonyl]-substituted}-carbamic acid tert-butyl ester (1 eq) in 1,4-dioxane (40 vol). After 1 hour 30 minutes the precipitate was filtered off and dried in vacuo. This was treated with water (15 vol), dichloromethane (15 vol) and shaken. The aqueous layer was evaporated in a Genevac to give the desired product.

Referring to Reaction Scheme 23, Stage 3, acetyl chloride (1.1 eq) was added to a stirred solution of the stage 2 product (1.0 eq) in dry THF (20 vol) under nitrogen at room temperature, followed by the addition of diisopropylethylamine (2.5 eq), and stirring continued for 1 hour. The mixture was evaporated in vacuo, treated with aqueous saturated sodium bicarbonate (100 vol) and extracted with ethyl acetate (3×150 vol). The organic extracts were combined, dried ($Na_2SO_4$) and evaporated in vacuo. The residue was purified by FCC to yield the target compounds.

| Structure | Molecular Weight | Mass Spec Result |
|---|---|---|
| 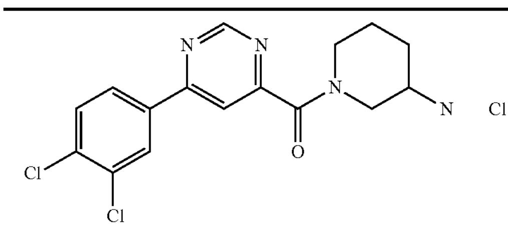 | 387.7 | $[M + H]^+$ = 351/353, 99% @ rt = 2.94 min |

-continued
| Structure | Molecular Weight | Mass Spec Result |
|---|---|---|
| (pyrimidine-3,4-dichlorophenyl-carbonyl-piperidine-NH, Cl salt) | 387.7 | [M + H]⁺ = 351/353, 100% @ rt = 2.95 min |
| (pyrimidine-3,4-dichlorophenyl-carbonyl-piperidine-4-NHAc) | 393.28 | [M + H]⁺ = 393/395, 100% @ rt = 3.86 min |
| (pyrimidine-3,4-dichlorophenyl-carbonyl-piperidine-3-NHAc) | 393.28 | [M + H]⁺ = 393/395, 100% @ rt = 3.94 min |
Example 24
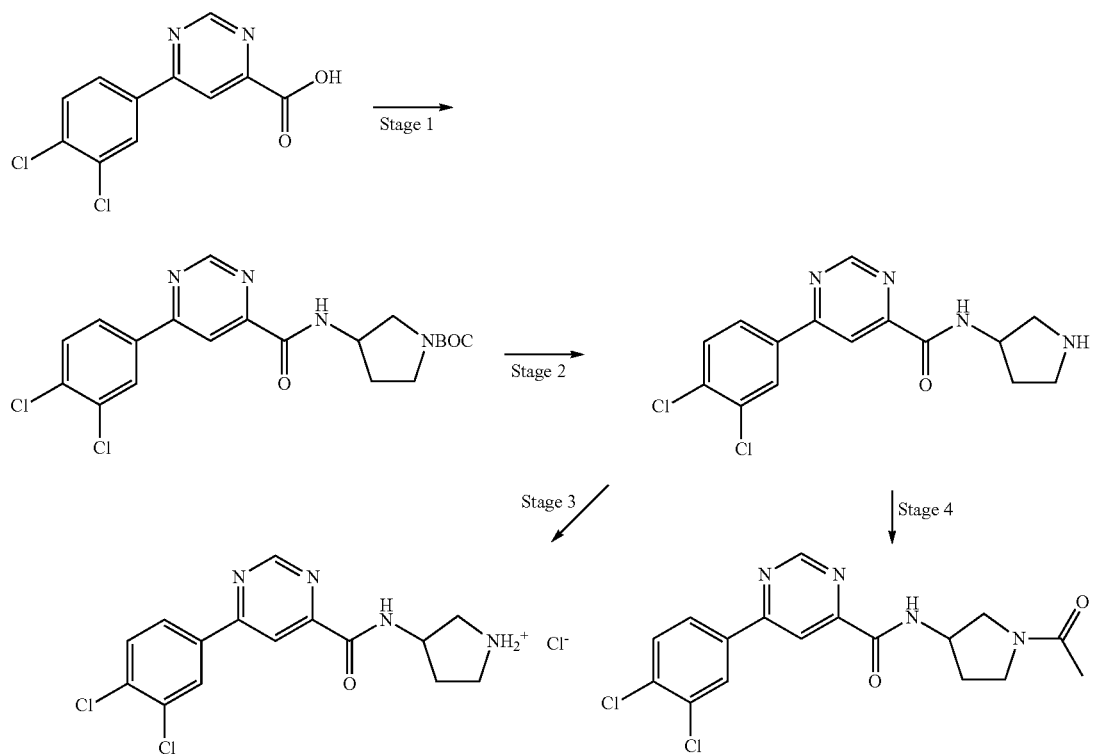
Reaction Scheme 24

Referring to Reaction Scheme 24, Stage 1, (R or S)-3-{[6-(3,4-Dichloro-phenyl)-pyrimidine-4-carbonyl]-amino}-pyrrolidine-1-carboxylic acid tert-butyl ester was prepared according to method B (acid chloride method) using (R or S)-3-amino-pyrrolidine-1-carboxylic acid tert-butyl ester hydrochloride.

Referring to Reaction Scheme 24, Stage 2, 4M hydrogen chloride in 1,4-dioxane (16 vol) was added slowly to a solution of (R or S)-3-{[6-(3,4-dichloro-phenyl)-pyrimidine-4-carbonyl]-amino}-pyrrolidine-1-carboxylic acid tert-butyl ester (1 eq) and stirred at room temperature for 1 hour. Further 4M hydrogen chloride in 1,4-dioxane (5 vol) was added, and after 1 hour, the reaction mixture was evaporated in vacuo. Water was added and the mixture filtered. The filtrate was treated with ethyl acetate, and the aqueous layer separated. The aqueous layer was basified with aqueous 2M NaOH until an emulsion formed. This was extracted with isopropyl alcohol/chloroform (1:1), and the dried ($MgSO_4$) organic extracts were evaporated in vacuo, to give the desired product.

Referring to Reaction Scheme 24, Stage 3, a solution of the stage 2 product (1 eq) in DCM (6 vol) was treated with 2M HCl (16 vol). After stirring at room temperature for 10 minutes, the precipitate was filtered off, washed with water, air-dried for 9 h, and dried in vacuo at 40° C., to give the desired product.

Referring to Reaction Scheme 24, Stage 4, diisopropyl-ethylamine (1.5 eq) was added to 6-(3,4-dichloro-phenyl)-pyrimidine-4-carboxylic acid (R)-pyrrolidin-3-ylamide (1 eq) in DCM (15 vol), followed by the slow addition of acetyl chloride (1.2 eq) under nitrogen with ice-cooling. After 1 hour, DCM was added, and the organic layer washed consecutively with water, aqueous sodium bicarbonate, and brine. The dried ($MgSO_4$) organic layer was evaporated in vacuo. Flash column chromatography yielded the target compound.

| Structure | Molecular Weight | Mass Spec Result |
|---|---|---|
|  | 373.67 | $[M + H]^+$ = 337/339, 100% @ rt = 3.02 min |
|  | 373.67 | $[M + H]^+$ = 337/339, 100% @ rt = 3.04 min |
|  | 379.25 | $[M + H]^+$ = 379/381, 100% @ rt = 3.85 min |
|  | 379.25 | $[M + H]^+$ = 379/381, 99% @ rt = 4.16 min |

Example 25

Reaction Scheme 25

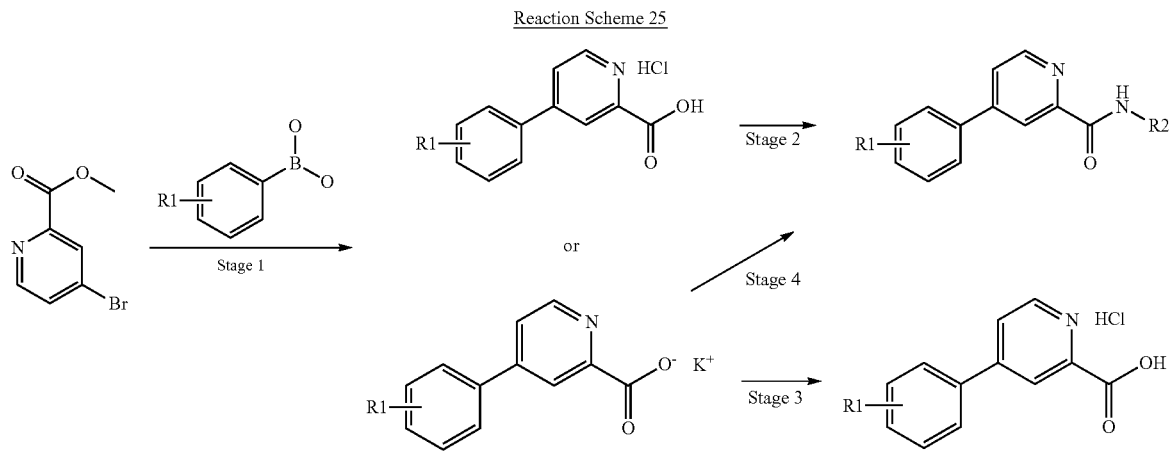

Referring to Reaction Scheme 25, Stage 1, to a stirred suspension of 4-bromo-pyridine-2-carboxylic acid methyl ester (1 eq) in 1,4-dioxane (20 vol) was added the appropriate substituted phenyl boronic acid (1.1 eq) and Pd(PPh$_3$)$_4$ (0.05 eq). A 2M K$_2$CO$_3$ solution (7.5 vol) was added and the reaction mixture was heated at 90° C. with stirring for 16 hours under an atmosphere of N$_2$. The reaction mixture was cooled to room temperature and the resulting precipitate was isolated by filtration to furnish the acid intermediate as the potassium salt, which was used without further purification in the stage. In the case of the 3-chlorophenyl analogue no precipitate was formed upon cooling, hence the solvent was removed in vacuo. The resulting residue was dissolved in EtOAc and water. Both phases were separated. EtOAc was removed in vacuo and the resulting residue was purified by flash column chromatography (eluent: [5:95] methanol:DCM) to furnish the desired 4-(3-chloro-phenyl)-pyridine-2-carboxylic acid methyl ester. The aqueous phase was acidified and the resulting precipitate was isolated by filtration and used as such in stage 2. Further purification was carried out by prep HPLC to furnish the required 4-(3-chloro-phenyl)-pyridine-2-carboxylic acid.

Referring to Reaction Scheme 25, Stage 2, the required amide analogues were prepared following the procedure described in method A from 4-(3-chloro-phenyl)-pyridine-2-carboxylic acid, hydrochloride salt and were purified by trituration in acetonitrile/water (1/1) or in water followed by heptane.

Referring to Reaction Scheme 25, Stage 3, the potassium salt isolated in stage 1 was suspended in HCl (2M) and stirred at ambient temperature for 2 hours. The solid was filtered and washed with water to furnish the desired target compound.

Referring to Reaction Scheme 25, Stage 4, the required amide analogues were prepared following the procedure described in method A from 4-(substituted-phenyl)-pyridine-2-carboxylic acid potassium salt and were purified by trituration in acetonitrile/water (1/1) or in water followed by heptane.

The following compounds were prepared substantially as described above.

| Structure | Molecular Weight | Mass Spec Result |
|---|---|---|
| 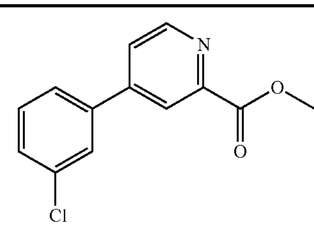 | 247.68 | [M + H]$^+$ = 248, 98% @ rt = 4.50 min |
| 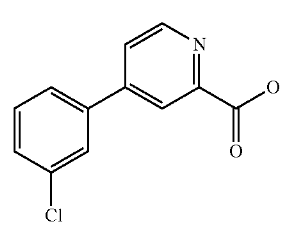 [SMILES: O=C(O)c1cc(-c2cccc(Cl)c2)ccn1] | 233.66 | [M + H]$^+$ = 234, 95% @ rt = 4.26 min |

-continued

| Structure | Molecular Weight | Mass Spec Result |
|---|---|---|
| (3,4-dichlorophenyl pyridine-2-carboxylic acid structure) | 304.56 | [M + H]⁺ = 268, 98% @ rt = 4.26 min |
| (4-(3-chlorophenyl)-N-(pyridin-3-yl)picolinamide) | 309.76 | [M + H]⁺ = 310, 100% @ rt = 4.12 min |
| (4-(3-chlorophenyl)-N-phenylpicolinamide) | 308.77 | [M + H]⁺ = 309, 100% @ rt = 5.15 min |
| (4-(3-chlorophenyl)pyridin-2-yl)(indolin-1-yl)methanone | 334.81 | [M + H]⁺ = 335, 100% @ rt = 4.91 min |
| (4-(3-chlorophenyl)-N-(p-tolyl)picolinamide) | 322.80 | [M + H]⁺ = 323, 100% @ rt = 5.37 min |
| (4-(3-chlorophenyl)-N-(5-methoxypyridin-3-yl)picolinamide) | 339.78 | [M + H]⁺ = 340, 99% @ rt = 4.32 min |
| (4-(3,5-dichlorophenyl)-N-phenylpicolinamide) | 343.22 | [M + H]⁺ = 343, 100% @ rt = 5.47 min |

225
-continued

| Structure | Molecular Weight | Mass Spec Result |
|---|---|---|
| (3,5-dichlorophenyl)-pyridine-2-carboxamide, N-(4-methylphenyl) | 357.24 | [M + H]⁺ = 357, 100% @ rt = 5.65 min |
| (3,5-dichlorophenyl)-pyridine-2-carboxamide, N-(pyridin-3-yl) | 344.20 | [M + H]⁺ = 346, 100% @ rt = 4.21 min |
| (3,5-dichlorophenyl)-pyridine-2-carboxamide, N-(5-methoxypyridin-3-yl) | 374.23 | [M + H]⁺ = 376, 100% @ rt = 4.72 min |
| (3,5-dichlorophenyl)-pyridine-2-carboxamide, N-(indolin-1-yl) | 369.25 | [M + H]⁺ = 369, 100% @ rt = 5.42 min |
| (3-chlorophenyl)-pyridine-2-carboxamide, N-(pyrimidin-5-yl) | 310.75 | [M + H]+ = 311, 100% @ rt = 4.23 min |
| (3,4-dichlorophenyl)-pyridine-2-carboxamide, N-phenyl | 343.22 | [M + H]⁺ = 343, 100% @ rt = 5.40 min |

| Structure | Molecular Weight | Mass Spec Result |
|---|---|---|
| 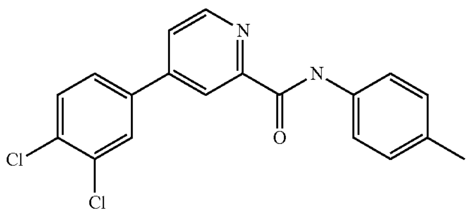 [SMILES: Cc1ccc(NC(=O)c2cc(-c3ccc(Cl)c(Cl)c3)ccn2)cc1] | 357.24 | [M + H]+ = 357, 100% @ rt = 5.59 min |
| 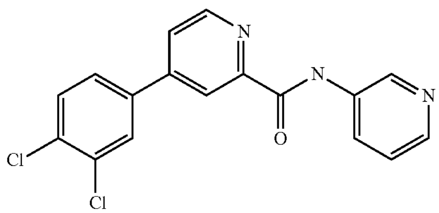 [SMILES: O=C(Nc1cccnc1)c1cc(-c2ccc(Cl)c(Cl)c2)ccn1] | 344.20 | [M + H]+ = 345, 98% @ rt = 4.13 min |
| 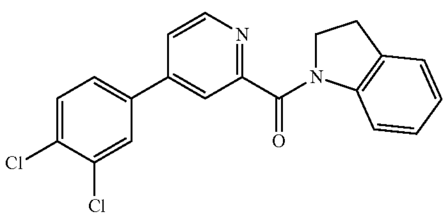 [SMILES: O=C(c1cc(-c2ccc(Cl)c(Cl)c2)ccn1)N1CCc2ccccc21] | 369.25 | [M + H]+ = 369, 100% @ rt = 5.14 min |
| 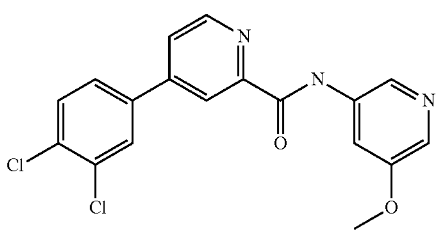 [SMILES: COc1cncc(NC(=O)c2cc(-c3ccc(Cl)c(Cl)c3)ccn2)c1] | 374.23 | [M + H]+ = 374/376, 100% @ rt = 4.66 min |
| | 345.19 | [M + H]+ = 344, 100% @ rt = 4.56 min |
| | 345.19 | [M + H]+ = 345, 100% @ rt = 4.67 min |

Example 26

Reaction Scheme 26

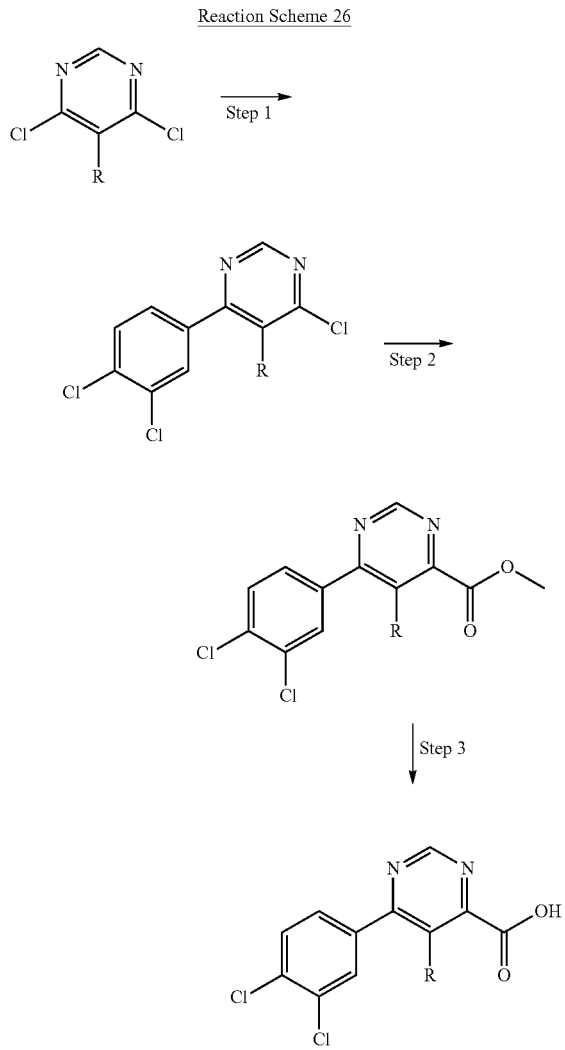

Referring to Reaction Scheme 26, Stage 1. Potassium carbonate (2M solution, 52.0 ml, 104.0 mmol) was added in one portion to a stirred solution of 3,4-dichlorophenyl boronic acid (6.9 g, 37.0 mmol) and 4,6-dichloro-5-methylpyrimidine (8.5 g, 52.0 mmol) in dioxane (150 ml). The mixture was degassed with nitrogen for 5 minutes, after which time palladium tetrakis triphenylphosphine (3.0 g, 3.0 mmol) was added in one portion, the mixture was then heated to 90° C. and stirred at this temperature for 16 hours under a nitrogen atmosphere. After this time the reaction mixture was cooled to room temperature and concentrated. The resulting residue was dissolved in DCM (500 ml), washed sequentially with water (500 ml) then brine (500 ml) before being dried (MgSO$_4$), filtered and concentrated. The resulting residue was purified by flash column chromatography (elution: 6% EtOAc, 94% Heptane) to give the desired compound (6.05 g, 42% yield) as a white solid. $\delta_H$ (500 MHz, DMSO) 8.91-9.00 (1 H, m) 7.88-7.96 (1 H, m) 7.76-7.88 (1 H, m) 7.58-7.69 (1 H, m) 2.36 (3 H, s). Tr=2.30 min m/z (ES$^+$) (M+H$^+$) 275, 277.

Referring to Reaction Scheme 26, Stage 2. Triethylamine (6.1 ml, 44.0 mmol) was added in one portion to a calorimeter containing a stirred solution of 4-chloro-6-(3,4-dichloro-phenyl)-5-methyl-pyrimidine (5.95 g, 22.0 mmol) in methanol (80 ml). The mixture was degassed with nitrogen for 5 minutes, after which time Pd(dppf)$_2$Cl$_2$ (0.9 g, 1.0 mmol) was added in one portion, the calorimeter was sealed, pressurised with carbon monoxide (5 bar) and was heated to 50° C. overnight. After this time the reaction mixture was cooled to room temperature, diluted with methanol and concentrated. The resulting residue was dissolved in DCM (300 ml) and washed sequentially with water (250 ml) and brine (250 ml). The organic layer was separated, dried (MgSO$_4$), filtered, concentrated and the resulting residue purified by flash column chromatography (elution: 40% EtOAc, 60% heptane) to give the desired compound (5.2 g, 80% yield) as a white solid. $\delta_H$ (500 MHz, DMSO) 9.19 (1 H, s) 7.92-7.97 (1 H, m) 7.79-7.85 (1 H, m) 7.63-7.70 (1 H, m) 3.95 (3 H, s) 2.30-2.42 (3 H, m). Tr=2.10 min m/z (ES$^+$) (M+H$^+$) 297, 299.

Referring to Reaction Scheme 26, Stage 3. NaOH (2M solution, 1.1 ml, 2.0 mmol) was added in one portion to a stirred solution of 6-(3,4-dichloro-phenyl)-5-methyl-pyrimidine-4-carboxylic acid methyl ester (0.32 g, 1.0 mmol) in THF (10 ml) and the mixture was stirred at room temperature for 16 hours. After this time, the resulting precipitate was collected by filtration, washed with water (1 ml) and DCM (20 ml) before being dried under vacuum. This solid was then suspended in HCl (2M solution, 60 ml) and acetonitrile (60 ml), heated to 80° C. until complete dissolution then cooled to room temperature. The acetonitrile was removed under reduced pressure and the solid precipitate was collected by filtration, washed with water (10 ml) before being dried in a vacuum over overnight to give the hydrochloride salt of the desired compound (0.22 g, 75% yield) as a white solid.

The following compounds were prepared substantially as described above.

| Structure | Molecular Weight | Mass Spec Result |
|---|---|---|
| (pyrimidine with 3,4-dichlorophenyl, OMe, COOH) | 298.01 | [M + H]+ = 299/301, 100% @ rt = 3.65 min |
| (pyrimidine with 3,4-dichlorophenyl, NH$_2$, COOH) | 283.09 | [M + H]+ = 284/286, 100% @ rt = 3.78 min |

Example 27

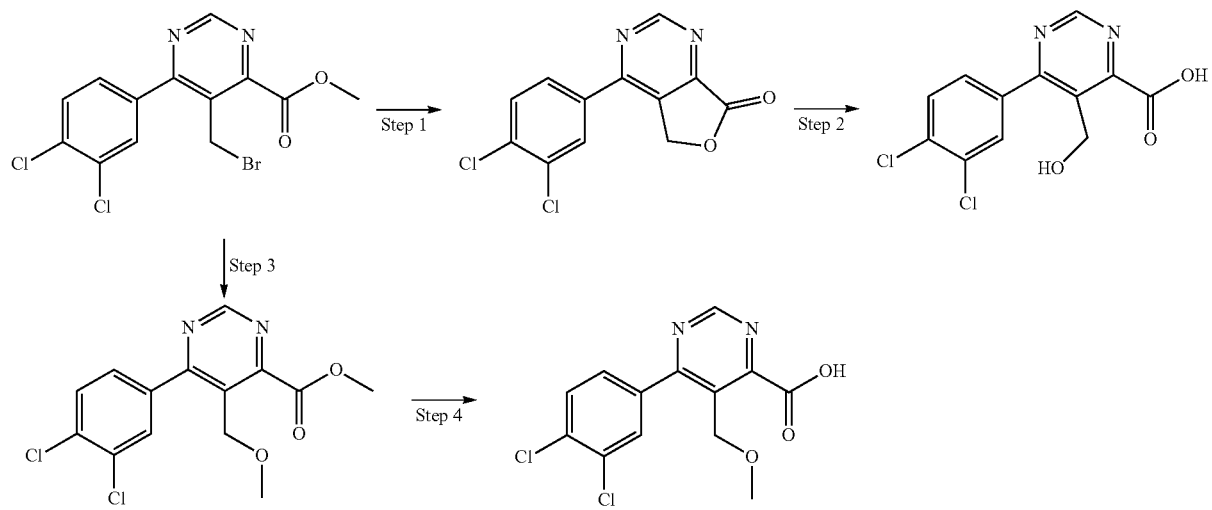

Reaction Scheme 27

Referring to Reaction Scheme 27, Stage 1. Sodium bicarbonate (0.46 g, 5.0 mmol) was added in one portion to a stirred solution of 5-bromomethyl-6-(3,4-dichloro-phenyl)-pyrimidine-4-carboxylic acid methyl ester (0.24 g, 0.64 mmol) in DMSO (5 ml), and the mixture was stirred at room temperature under a nitrogen atmosphere for 20 hours. After this time the mixture was partitioned between ethyl acetate (20 ml) and water (20 ml), the organic layer was separated and the aqueous layer extracted with ethyl acetate (2×20 ml). The organic layers were combined, dried (MgSO$_4$), filtered, concentrated and the resulting residue was triturated with diethyl ether. The resulting precipitate was collected by filtration and dried under vacuum to give the desired compound (0.08 g, 45% yield) as an orange solid.

Referring to Reaction Scheme 27, Stage 2. Sodium methoxide (0.02 g, 0.36 mmol) was added in one portion to a stirred solution of 4-(3,4-dichloro-phenyl)-5H-furo[3,4-d]pyrimidin-7-one (0.05 g, 0.18 mmol) in methanol (5 ml), and the mixture was stirred at room temperature under a nitrogen atmosphere for 20 hours. After this time, sodium hydroxide (2M solution, 0.05 ml, 0.89 mmol) was added and the mixture was heated to 70° C. and stirred at this temperature for a further 4 hours. After this time the reaction mixture was cooled to room temperature and the resulting precipitate was collected by filtration, washed with methanol (5 ml) and dried under vacuum to give the desired compound (0.01 g, 5% yield) as an off-white solid.

Referring to Reaction Scheme 27, Stage 3. Sodium methoxide (0.03 g, 0.53 mmol) was added in one portion to a stirred solution of 5-bromomethyl-6-(3,4-dichloro-phenyl)-pyrimidine-4-carboxylic acid methyl ester (0.1 g, 0.26 mmol) in methanol (5 ml), and the mixture was stirred at room temperature under a nitrogen atmosphere for 20 hours. After this time the mixture was concentrated and the resulting residue taken up in DCM (10 ml). The solution was washed consecutively with water (2×50 ml) and brine (2×50 ml), before being separated, dried (MgSO$_4$), filtered and concentrated. The resulting residue was purified by flash column chromatography (elution: 100% DCM to 99% DCM: 1% Methanol) to give the desired compound (0.02 g, 20% yield) as a white solid. Tr=2.11 min m/z (ES$^+$) (M+H$^+$) 327, 329.

Referring to Reaction Scheme 27, Stage 4. Sodium hydroxide (0.05 ml, 0.1 mmol) was added in one portion to a stirred solution of methyl 6-(3,4-dichlorophenyl)-5-(methoxymethyl)pyrimidine-4-carboxylate (0.1 g, 0.26 mmol) in THF (5 ml) and the mixture was stirred at room temperature under a nitrogen atmosphere for 20 hours. After this time the resulting precipitate was collected by filtration, washed with water (1 ml) and dried under vacuum to give the desired compound (0.004 g, 15% yield) as a white solid.

The following compounds were prepared substantially as described above.

| Structure | Molecular Weight | Mass Spec Result |
|---|---|---|
| 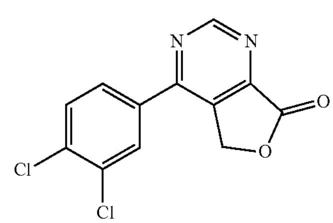 [SMILES: O=C1OCc2c1ncnc2-c1ccc(Cl)c(Cl)c1] | 281.1 | [M + H]+ = 281/283, 98% @ rt = 4.16 min |
| 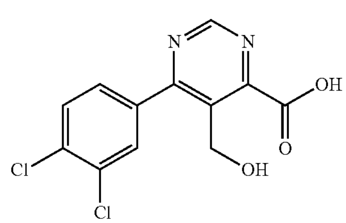 [SMILES: O=C(O)c1ncnc(-c2ccc(Cl)c(Cl)c2)c1CO] | 298.11 | [M + H]+ = 299/301, 96% @ rt = 3.31 min |

-continued

| Structure | Molecular Weight | Mass Spec Result |
|---|---|---|
| (structure shown) | 312.12 | [M + H]+ = 313/315, 100% @ rt = 3.79-3.87 min |

Example 28

Reaction Scheme 28

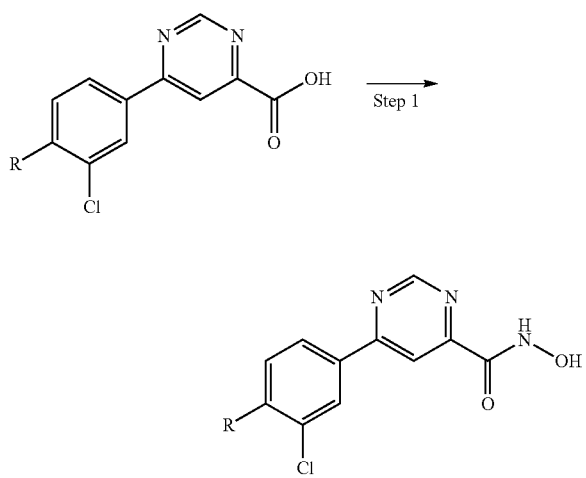

Referring to Reaction Scheme 28, Stage 1. Carbonyl diimidazole (0.46 g, 1.95 mmol) was added portionwise to a stirred solution of 6-(3,4-dichloro-phenyl)-pyrimidine-4-carboxylic acid (0.5 g, 1.78 mmol) in DCM (20 ml) and the mixture was stirred at room temperature for 30 minutes. After this time hydroxylamine hydrochloride (0.15 g, 2.13 mmol) was added in one portion and the reaction mixture was stirred at room temperature under a nitrogen atmosphere for 5 hours. The resulting mixture was washed with HCl (1M solution, 40 ml), followed by saturated sodium bicarbonate (40 ml), the organic layer was separated, dried (MgSO₄), filtered and concentrated. The resulting residue was then purified by prep HPLC to give the desired compound (0.026 g, 5% yield) as a beige powder.

| Structure | Molecular Weight | Mass Spec Result |
|---|---|---|
| (structure shown) | 284.1 | [M + Na]+ = 306/308, 100% @ rt = 3.75 min |

Example 29

Reaction Scheme 29

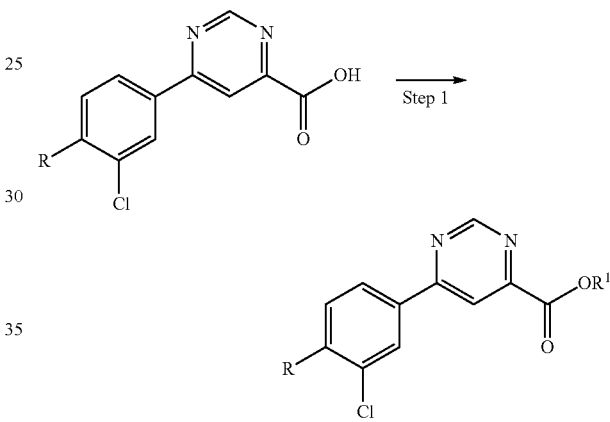

Referring to Reaction Scheme 29, Stage 1. Thionyl chloride (0.04 ml, 0.56 mmol) was added dropwise to a stirred solution of 6-(3,4-dichlorophenyl)pyrimidine-4-carboxylic acid (0.1 g, 0.33 mmol) in DCM (5 ml) and the mixture was stirred at room temperature for 1 hour. After this time the mixture was concentrated, re-dissolved in DCM and butan-1-ol (0.5 ml, 5.46 mmol) was added in one portion and stirring was continued for a further 72 hours. The resulting mixture was concentrated and purified by flash column chromatography (elution: 10% ethyl acetate, 90% heptanes) to give the desired compound (0.07 g, 58% yield) as a white powder.

The following compounds were prepared substantially as described above.

| Structure | Molecular Weight | Mass Spec Result |
|---|---|---|
| (structure shown) | 325.2 | [M + H]+ = 325/327, 100% @ rt = 5.37 min |

-continued

| Structure | Molecular Weight | Mass Spec Result |
|---|---|---|
| 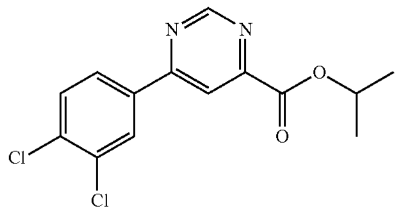 [SMILES: CC(C)OC(=O)c1cc(-c2ccc(Cl)c(Cl)c2)ncn1] | 311.17 | [M + H]+ = 311/313, 100% @ rt = 5.06 min |
| 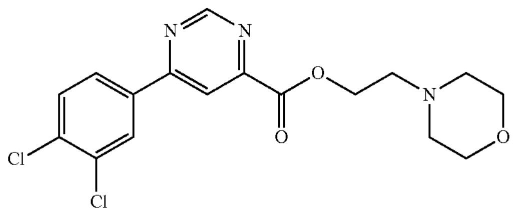 [SMILES: O=C(OCCN1CCOCC1)c1cc(-c2ccc(Cl)c(Cl)c2)ncn1] | 382.25 | [M + H]+ = 383, 99% @ rt = 3.25 min |

Example 30

Reaction Scheme 30

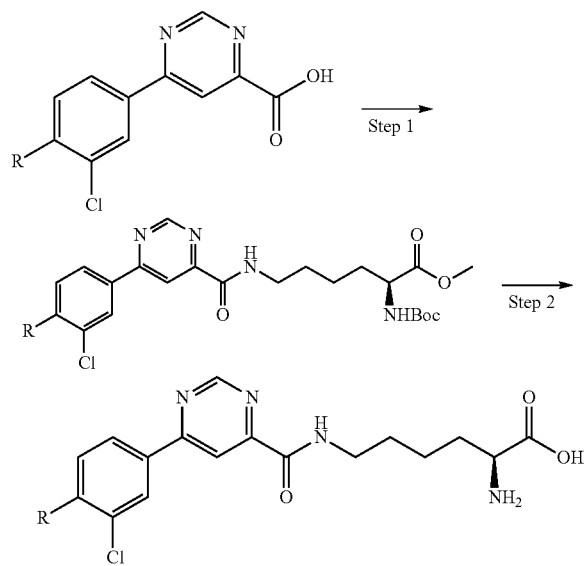

Referring to Reaction Scheme 30, Stage 1. Diisopropyl ethylamine (0.25 ml, 1.4 mmol) was added in one portion to a stirred solution of 6-(3,4-dichlorophenyl)pyrimidine-4-carboxylic acid (0.13 g, 0.47 mmol), methyl (2R)-6-amino-2-{[(tert-butoxy)carbonyl]amino}hexanoate (0.12 g, 0.47 mmol) and HATU (0.18 g, 0.47 mmol) in DMF (8 ml) and the mixture was stirred at room temperature for 2 hours. After this time the resulting mixture was concentrated, and purified by flash column chromatography (elution: 40% ethyl acetate, 60% heptanes) to give the desired compound (0.16 g, 64% yield) as a yellow solid. $\delta_H$ (250 MHz, CDCl$_3$) 9.25 (d, J=1.37 Hz, 1H), 8.51 (d, J=1.22 Hz, 1H), 8.36 (d, J=2.13 Hz, 1H), 7.94-8.15 (m, 2H), 7.62 (d, J=8.53 Hz, 1H), 5.08 (dd, J=1.98, 8.38 Hz, 1H), 4.18-4.44 (m, 1H), 3.75 (s, 3H), 3.52 (q, J=6.75 Hz, 2H), 1.61-2.00 (m, 4H), 1.46-1.55 (m, 2H), 1.44 (s, 9H). Tr=2.45 min m/z (ES$^+$) (M+Na$^+$) 533, 535.

Referring to Reaction Scheme 30, Stage 2. NaOH (2M solution, 2 ml, 4.0 mmol) was added in one portion to a stirred solution of methyl (2S)-2-{[(tert-butoxy)carbonyl]amino}-6-{[6-(3,4-dichlorophenyl)pyrimidin-4-yl]formamido}hexanoate (0.16 g, 0.31 mmol) in THF (2 ml) and the mixture was stirred at room temperature for 2 hours. After this time the resulting mixture was concentrated, and added in one portion to a stirred solution of HCl in dioxane (4M solution, 4 ml) and stirred at room temperature for 7 hours. After this time the resulting precipitate was collected by filtration and purified by prep HPLC to give the title compound (0.03 g, 25% yield) as a white powder.

| Structure | Molecular Weight | Mass Spec Result |
|---|---|---|
| 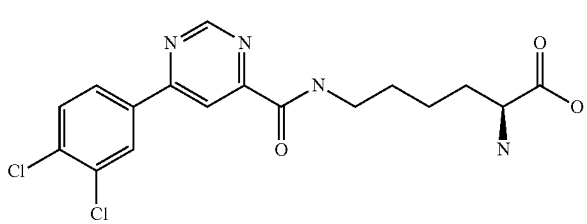 [SMILES: N[C@@H](CCCCNC(=O)c1cc(-c2ccc(Cl)c(Cl)c2)ncn1)C(=O)O] | 397.26 | [M + H]+ = 397/399, 98% @ rt = 3.29 min |

Example 31

Reaction Scheme 31

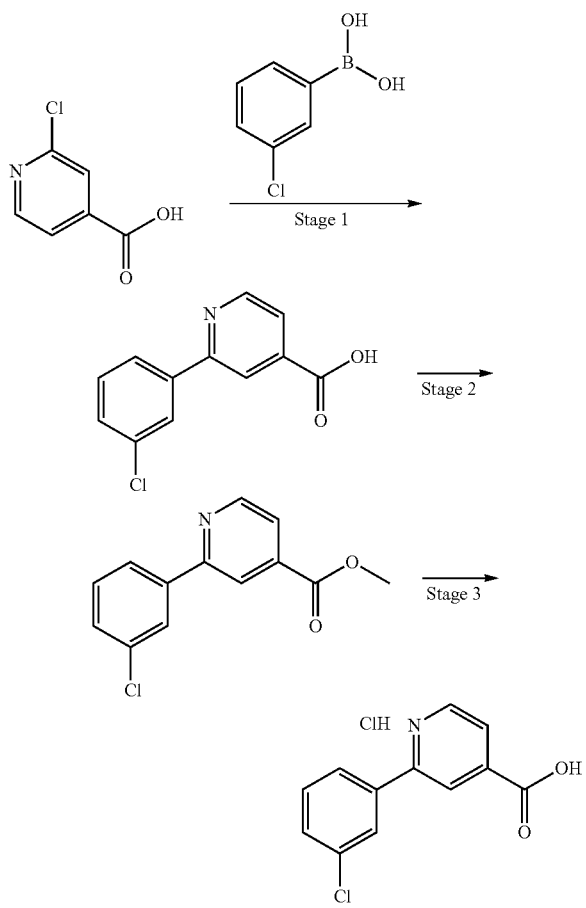

Referring to Reaction Scheme 31, Stage 1. 2-Chloroisonicotinic acid (1 eq), 3-chlorophenyl boronic acid (1.5 eq) and Pd(PPh$_3$)$_4$ (0.03 eq) were suspended in 1,4-dioxane (20 vol). A 2M K$_2$CO$_3$ solution (7.5 vol) was added to the reaction mixture, which was heated at 90° C. with stirring for 16 hours under an atmosphere of N$_2$. 3-Chlorophenyl boronic acid (0.5 eq), Pd(PPh$_3$)$_4$ (0.03 eq) and a 2M K$_2$CO$_3$ solution (7.5 vol) were added to the reaction mixture, which was heated at 90° C. for a further hour. The reaction mixture was cooled to room temperature and washed with EtOAc and dichloromethane. The aqueous layer was acidified with concentrated HCl and the resulting precipitate was isolated by filtration and used in the next step without further purification.

Referring to Reaction Scheme 31, Stage 2. To a stirred suspension of the intermediate obtained in Stage 1 in methanol (50 vol) was added concentrated HCl (4 drops) and the reaction mixture was stirred at 65° C. for 16 hours. The reaction mixture was concentrated in vacuo. The resulting residue was dissolved in DCM and water. The organic phase was collected and the solvent was removed in vacuo. Purification by flash column chromatography (eluent: [1:20] EtOAc:heptane), followed by prep HPLC yielded the target compound.

Referring to Reaction Scheme 31, Stage 3. To a stirred solution of 2-(3-chloro-phenyl)-isonicotinic acid methyl ester (1 eq) in THF (30 vol) was added 2M NaOH solution (8 vol) and the reaction mixture was stirred at ambient temperature for 3 hours. The reaction mixture was concentrated in vacuo. The residue was dissolved in a 2M solution of HCl and the resulting precipitate was filtered off and washed with water and heptane to furnish the desired target compound.

| Structure | Molecular Weight | Mass Spec Result |
|---|---|---|
| (methyl 2-(3-chlorophenyl)isonicotinate) | 247.68 | [M + H]$^+$ = 248, 95% @ rt = 4.52 min |
| (2-(3-chlorophenyl)isonicotinic acid) | 270.12 | [M + H]$^+$ = 234/236, 100% @ rt = 3.95 min |

Example 32

A generalized procedure for monitoring L-Kynurenine (KYN) hydroxylation to form product 3-Hydroxy-Kynurenine (3OH-KYN) by LC/MS is described below. Product is quantified by multiple reaction monitoring using MS.

Key Reagents:
Compound: Stock concentrations: 10 mM in 100% DMSO
Cell line: CHO GST HIS KMO cell line, 1E4 cells/well/100 µl in 96 well cell plate
Substrate: L-Kynurenine (Sigma: Cat #K3750, stock concentration: 10 mM in 100 mM potassium phosphate buffer, pH 7.4)

Assay Conditions:
Medium: OptiMem (Reduced Serum Medium 1×, +L-Glutamine+HEPES-Phenol Red; GIBCO: Cat #11058)
Assay Volume: 200 µl
Plate Format: 96 well plate, transparent (Corning)
Read-Out: product (3OH-KYN) quantification using product specific MRM
Reader: LC/MS/MS Assay Protocol:
  prepare serial dilution (factor 3) of compound in 100% DMSO (top concentration=6.67 mM, 100% DMSO)
    [8 points: 6.67 mM; 2.22 mM; 0.74 mM; 0.247 mM; 0.082 mM; 0.027 mM; 0.009 mM; 0.003 mM]
  prepare 300-fold concentrated solution of each compound concentration (top concentration 22.22 µM, 0.3% DMSO) in OptiMem medium
    [22.2 µM; 7.41 µM; 2.47 µM; 0.82 µM; 0.27 µM; 0.09 µM; 0.03 µM; 0.01 µM]
  prepare substrate (10 mM) at concentration of 1.1 mM in medium
  medium of cell plate is drawed off
  cells are washed with OptiMem (100 µl/well) and drawed off again assay mix: 90 µl OptiMem/well+90 µl compound/well of each concentration
  [final compound top concentration: 10 µM; 0.15% DMSO]
  [final compound bottom concentration: 0.004 µM; 0.15% DMSO]
pre-incubation: 30 min at 37° C.
add 20 µl/well of the 1.1 mM substrate solution (final assay concentration: 100 µM)
positive control: 200 µl OptiMem
negative control: 180 µl OptiMem+20 µl 1.1 mM substrate
incubate ~24 h at 37° C.
transfer 100 µl of each well in a transparent 96 well plate (Corning)
add 100 µl/well 10% trichloro acetic acid (TCA) in water
centrifugate plate for 3 min at 4000 rpm
detect product by LC/MS (injection of 50 µl/well; 2.5 fold overfill of the 20 µl sample loop)
Data Analysis: $IC_{50}$'s are calculated using automated fitting algorithm (A+Analysis).

Example 33

A method of monitoring L-Kynurenine (KYN) hydroxylation to form product 3-Hydroxy-Kynurenine (3OH-KYN) by LC/MS is described below. Product is quantified by multiple reaction monitoring.
Key Reagents:
Compound: Stock concentrations: 10 mM in 100% DMSO
Enzyme: KMO enzyme prepared at Evotec via mitochondria isolation from CHO-GST HIS KMO cells
Substrate: L-Kynurenine (Sigma: Cat #K3750)
  [stock concentration: 10 mM in 100 mM potassium phosphate buffer, pH 7.4]
Assay Conditions:
Buffer: 100 mM potassium phosphate, pH 7.4, 200 µM NADPH,
  0.4 U/ml G6P-DH (Glucose 6-phosphate dehydrogenase), 3 mM G6P (D-Glucose 6-phosphate)
Assay Volume: 40 µl
Plate Format: 384 well plate, transparent (Matrix)
Read-Out: product (3OH-KYN) quantification using product specific MRM
Reader: LC/MS/MS
Assay Protocol:
  prepare serial dilution (factor 3) of compound in 100% DMSO (top concentration=10 mM, 100% DMSO)
    [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
    [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assay buffer/well+8 µl KMO human enzyme+4 µl 1 mM substrate (final concentration=100 µM)
    [final compound top concentration: 30 µM; 0.3% DMSO]
    [final compound bottom concentration: 0.0137 µM; 0.3% DMSO]
  positive control: 4 µl 50 µM FCE28833 in assay buffer [0.5% DMSO] (final assay concentration=5 µM)+24 µl assay buffer/well+8 µl KMO human enzyme+4 µl 1 mM substrate (final concentration=100 µM)
  negative control: 28 µl assay buffer/well+8 µl KMO human enzyme+4 µl 1 mM substrate (final concentration=100 µM)
  incubate 400 min at RT
  add 40 µl/well 10% trichloro acetic acid in water to stop the assay and precipitate protein
  centrifuge plate for 3 min at 4000 rpm
  product detection by LC/MS (injection of 50 µl/well; 2.5 fold overfill of the 20 µl sample loop)
Data Analysis: $IC_{50}$'s are calculated using automated fitting algorithm (A+Analysis).

Example 34

A method of monitoring L-Kynurenine (KYN) hydroxylation to form 3-Hydroxy-Kynurenine (3OH-KYN) by LC/MS is described. Product is quantified by multiple reaction monitoring (MRM method).
Key Reagents:
Compound: Stock concentrations: 10 mM in 100% DMSO
Enzyme: KMO enzyme prepared at Evotec from mouse liver (4-6 weeks old) via mitochondria isolation as described in the literature
Substrate: L-Kynurenine (Sigma: Cat #K3750, stock concentration: 10 mM in 100 mM potassium phosphate buffer, pH 7.4)
Assay Conditions:
Buffer: 100 mM potassium phosphate, pH 7.4, 200 µM NADPH,
  0.4 U/ml G6P-DH (Glucose 6-phosphate Dehydrogenase), 3 mM G6P (D-Glucose 6-phosphate)
Assay Volume: 40 µl
Plate Format: 384 well plate, transparent (Matrix)
Read-Out: product (3OH-KYN) quantification using product specific MRM
Reader: LC/MS/MS
Assay Protocol:
  prepare serial dilution (factor 3) of compound in 100% DMSO (top concentration=10 mM, 100% DMSO)
    [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
    [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assaybuffer/well+8 µl KMO mouse enzyme+4 µl 1 mM substrate (final concentration=100 µM)
    [final compound top concentration: 30 µM; 0.3% DMSO]
    [final compound bottom concentration: 0.0137 µM; 0.3% DMSO]
  positive control: 4 µl 50 µM FCE28833 in assay buffer, 0.5% DMSO [final assay concentration=5 µM]+24 µl assaybuffer/well+8 µl KMO mouse enzyme+4 µl 1 mM substrate [final concentration=100 µM]
  negative control: 28 µl assay buffer/well+8 µl KMO mouse enzyme+4 µl 1 mM substrate [final concentration=100 µM]
  incubate 40 min at RT add 40 µl/well 10% trichloro acetic acid in water to stop the assay and precipitate protein
centrifuge plate for 3 min at 4000 rpm
product detection by LC/MS (injection of 20 µl/well, 2 fold overfill of the 10 µl sample loop)

Data Analysis: $IC_{50}$'s are calculated using automated fitting algorithm (A+Analysis).

Example 35

Using procedures similar to those described herein, the following compounds were assayed for activity.

TABLE 2

| IUPAC name | % Inhibition at 10 uM* |
|---|---|
| 6-(4-Chloro-3-fluoro-phenyl)-pyrimidine-4-carboxylic acid | 102.645 |
| 6-(4-Chloro-phenyl)-pyrimidine-4-carboxylic acid | 100.52 |
| 6-(4-Chloro-2-fluoro-phenyl)-pyrimidine-4-carboxylic acid | 100.97 |
| 6-(3-Chloro-phenyl)-pyrimidine-4-carboxylic acid (3,5-dimethyl-isoxazol-4-yl)-amide | 89.92 |
| 4-[6-(3,4-Dichloro-phenyl)-pyrimidine-4-carbonyl]-piperazin-2-one | 101.568333 |
| 6-(5-Chloro-2-fluoro-phenyl)-pyrimidine-4-carboxylic acid pyridin-3-yl-amide | 84.21 |
| 6-(3,4-Dichloro-phenyl)-pyrimidine-4-carboxylic acid methylamide | 100.31 |
| 6-(3,4-Dichloro-phenyl)-pyrimidine-4-carboxylic acid oxazol-2-yl-amide | 101.04 |
| 6-(3,4-Dichloro-phenyl)-pyrimidine-4-carboxylic acid (3-methyl-[1,2,4]-thiadiazol-5-yl)-amide | 100.16 |
| [6-(3,4-Dichloro-phenyl)-pyrimidin-4-yl]-(6-fluoro-2,3-dihydro-indol-1-yl)-methanone | 100.71 |
| (6-Chloro-2,3-dihydro-indol-1-yl)-[6-(3,4-dichloro-phenyl)-pyrimidin-4-yl]-methanone | 98.22 |
| 6-(4-Chloro-3-fluoro-phenyl)-pyrimidine-4-carboxylic acid pyridin-3-yl-amide | 94.48 |
| 6-(4-Chloro-3-fluoro-phenyl)-pyrimidine-4-carboxylic acid (2,6-dimethyl-pyridin-3-yl)-amide | 52.81 |
| 1-{4-[6-(3,4-Dichloro-phenyl)-pyrimidine-4-carbonyl]-piperazin-1-yl}-ethanone | 100.06 |
| [6-(3,4-Dichloro-phenyl)-pyrimidin-4-yl]-(4-methyl-piperazin-1-yl)-methanone | 94.86 |
| [6-(3,4-Dichloro-phenyl)-pyrimidin-4-yl]-piperazin-1-yl-methanone | 71.34 |
| 6-(3,4-Dichloro-phenyl)-pyrimidine-4-carboxylic acid ((R)-1-phenyl-ethyl)-amide | 101.25 |
| 6-(3,4-Dichloro-phenyl)-pyrimidine-4-carboxylic acid (tetrahydro-pyran-4-ylmethyl)-amide | 101.39 |
| (R)-1-[6-(3,4-Dichloro-phenyl)-pyrimidine-4-carbonyl]-pyrrolidine-2-carboxylic acid amide | 101.046667 |
| [6-(3,4-Dichloro-phenyl)-pyrimidin-4-yl]-((R)-3-hydroxy-pyrrolidin-1-yl)-methanone | 101.49 |
| 6-(3,4-Dichloro-phenyl)-pyrimidine-4-carboxylic acid ((S)-1-phenyl-ethyl)-amide | 102.29 |
| 6-(3,4-Dichloro-phenyl)-pyrimidine-4-carboxylic acid (1-phenyl-cyclopropyl)-amide | 96.68 |
| [6-(3,4-Dichloro-phenyl)-pyrimidin-4-yl]-((R)-3-hydroxy-piperidin-1-yl)-methanone | 99.86 |
| 6-(3,4-Dichloro-phenyl)-pyrimidine-4-carboxylic acid (2-hydroxy-ethyl)-amide | 76.68 |
| 6-(3,4-Dichloro-phenyl)-pyrimidine-4-carboxylic acid ((S)-2-hydroxy-propyl)-amide | 86.83 |
| 6-(3,4-Dichloro-phenyl)-pyrimidine-4-carboxylic acid ((R)-2-hydroxy-propyl)-amide | 100.71 |
| 4-[6-(3,4-Dichloro-phenyl)-pyrimidine-4-carbonyl]-1-methyl-piperazin-2-one | 87.44 |
| 6-(3,4-Dichloro-phenyl)-pyrimidine-4-carboxylic acid ((S)-2-hydroxy-1-methyl-ethyl)-amide | 99.59 |
| 6-(3,4-Dichloro-phenyl)-pyrimidine-4-carboxylic acid ((R)-2-hydroxy-1-methyl-ethyl)-amide | 97.775 |
| (S)-1-[6-(3,4-Dichloro-phenyl)-pyrimidine-4-carbonyl]-pyrrolidine-2-carboxylic acid amide | 99.05 |
| 6-(3,4-Dichloro-phenyl)-pyrimidine-4-carboxylic acid (2-amino-ethyl)-methyl-amide, trifluoro-acetic acid salt | 64.52 |
| 6-(3,4-Dichloro-phenyl)-pyrimidine-4-carboxylic acid (tetrahydro-pyran-4-yl)-amide | 55.35 |

TABLE 2-continued

| IUPAC name | % Inhibition at 10 uM* |
|---|---|
| N-{(S)-1-[6-(3,4-Dichloro-phenyl)-pyrimidine-4-carbonyl]-pyrrolidin-3-yl}-acetamide | 100.27 |
| [6-(3,4-Dichloro-phenyl)-pyrimidin-4-yl]-((S)-3-hydroxy-piperidin-1-yl)-methanone | 99.98 |
| N-{(R)-1-[6-(3,4-Dichloro-phenyl)-pyrimidine-4-carbonyl]-pyrrolidin-3-yl}-acetamide | 98.55 |
| 6-(3,4-Dichloro-phenyl)-pyrimidine-4-carboxylic acid (5-methyl-[1,3,4]oxadiazol-2-ylmethyl)-amide | 100.815 |
| 6-(3,4-Dichloro-phenyl)-pyrimidine-4-carboxylic acid [4-(2-morpholin-4-yl-ethoxy)-phenyl]-amide | 100.44 |
| 6-(3,4-Dichloro-phenyl)-pyrimidine-4-carboxylic acid [4-(2-morpholin-4-yl-ethoxy)-phenyl]-amide hydrochloride salt | 90.48 |
| 6-(3,4-Dichloro-phenyl)-pyrimidine-4-carboxylic acid (3-morpholin-4-yl-phenyl)-amide | 100.15 |
| 6-(3,4-Dichloro-phenyl)-pyrimidine-4-carboxylic acid (3-morpholin-4-yl-phenyl)-amide hydrochloride salt | 99.76 |
| 6-(3,4-Difluoro-phenyl)-pyrimidine-4-carboxylic acid ((S)-1-phenyl-ethyl)-amide | 100.39 |
| 6-(3-Chloro-4-fluoro-phenyl)-pyrimidine-4-carboxylic acid ((S)-1-phenyl-ethyl)-amide | 89.07 |
| 6-(5-Chloro-2-fluoro-phenyl)-pyrimidine-4-carboxylic acid ((S)-1-phenyl-ethyl)-amide | 68.66 |
| 6-(3,4-Dichloro-phenyl)-pyrimidine-4-carboxylic acid (1-methyl-1H-pyrazol-3-yl)-amide | 100.05 |
| 6-(3,4-Dichloro-phenyl)-pyrimidine-4-carboxylic acid pyridazin-3-yl-amide | 100.38 |
| 6-(3,4-Dichloro-phenyl)-pyrimidine-4-carboxylic acid pyrazin-2-yl-amide | 100.28 |
| 6-(3,4-Dichloro-phenyl)-pyrimidine-4-carboxylic acid (5-tert-butyl-[1,3,4]oxadiazol-2-yl)-amide | 101.373333 |
| 6-(4-Chloro-phenyl)-pyrimidine-4-carboxylic acid pyridin-3-yl-amide | 67.93 |
| 6-(4-Chloro-phenyl)-pyrimidine-4-carboxylic acid ((S)-1-phenyl-ethyl)-amide | 68.94 |
| 6-(3,4-Dichloro-phenyl)-pyrimidine-4-carboxylic acid ((1S,2R)-2-hydroxy-indan-1-yl)-amide | 97.78 |
| 6-(3,4-Dichloro-phenyl)-pyrimidine-4-carboxylic acid (1,2,3,4-tetrahydro-naphthalen-1S-yl)-amide | 95.92 |
| 6-(3,4-Dichloro-phenyl)-pyrimidine-4-carboxylic acid (4-morpholin-4-yl-phenyl)-amide | 101.19 |
| 6-(3,4-Dichloro-phenyl)-pyrimidine-4-carboxylic acid (4-morpholin-4-yl-phenyl)-amide hydrochloride salt | 76.95 |
| 6-(4-Chloro-phenyl)-pyrimidine-4-carboxylic acid pyrimidin-5-ylamide | 56.49 |
| 6-(3,4-Dichloro-phenyl)-pyrimidine-4-carboxylic acid ((S)-1-pyridin-4-yl-ethyl)-amide | 91.79 |
| 6-(3,4-Dichloro-phenyl)-pyrimidine-4-carboxylic acid ((R)-1-pyridin-3-yl-ethyl)-amide | 90.86 |
| 6-(3,4-Dichloro-phenyl)-pyrimidine-4-carboxylic acid [4-(4-methyl-piperazin-1-yl)-phenyl]-amide hydrochloride salt | 89.6 |
| 6-(3,4-Dichloro-phenyl)-pyrimidine-4-carboxylic acid [3-(4-methyl-piperazin-1-yl)-phenyl]-amide | 75.48 |
| 6-(3,4-Dichloro-phenyl)-pyrimidine-4-carboxylic acid [3-(4-methyl-piperazin-1-yl)-phenyl]-amide hydrochloride salt | 85.89 |
| 6-(4-Chloro-3-fluoro-phenyl)-pyrimidine-4-carboxylic acid ((S)-1-phenyl-ethyl)-amide | 46.62 |
| 6-(3-Chloro-phenyl)-pyrimidine-4-carboxylic acid ((S)-1-pyridin-4-yl-ethyl)-amide | 96.86 |
| 6-(3,4-Dichloro-phenyl)-pyrimidine-4-carboxylic acid ((S)-1-pyridin-3-yl-ethyl)-amide | 85.1 |
| 6-(3-Fluoro-phenyl)-pyrimidine-4-carboxylic acid ((S)-1-phenyl-ethyl)-amide | 90.15 |
| 6-(3,4-Dichloro-phenyl)-pyrimidine-4-carboxylic acid (1-methyl-1H-indazol-3-yl)-amide | 93.95 |
| 6-(3-Fluoro-phenyl)-pyrimidine-4-carboxylic acid pyrimidin-5-yl-amide | 81.88 |
| 6-(3,4-Dichloro-phenyl)-pyrimidine-4-carboxylic acid (2,2,6,6-tetramethyl-piperidin-4-yl)-amide | 100.11 |
| 6-(3,4-Dichloro-phenyl)-pyrimidine-4-carboxylic acid (2,2,6,6-tetramethyl-piperidin-4-yl)-amide hydrochloride salt | 99.59 |
| 6-(3,4-Dichloro-phenyl)-pyrimidine-4-carboxylic acid [6-(2-morpholin-4-yl-ethoxy)-pyridin-3-yl]-amide hydrochloride salt | 86.37 |
| 6-(3,4-Dichloro-phenyl)-pyrimidine-4-carboxylic acid (4-piperazin-1-yl-phenyl)-amide | 43.46 |
| 6-(3,4-Dichloro-phenyl)-pyrimidine-4-carboxylic acid (4-piperazin-1-yl-phenyl)-amide hydrochloride salt | 93.13 |

TABLE 2-continued

| IUPAC name | % Inhibition at 10 uM* |
|---|---|
| 6-(3,4-Dichloro-phenyl)-pyrimidine-4-carboxylic acid [4-(2,6-dimethyl-morpholin-4-yl)-phenyl]-amide | |
| 6-(3,4-Dichloro-phenyl)-pyrimidine-4-carboxylic acid [4-(2,6-dimethyl-morpholin-4-yl)-phenyl]-amide hydrochloride salt | 97.61 |
| [6-(3,4-Dichloro-phenyl)-pyrimidin-4-yl]-((3S,5R)-3,5-dimethyl-piperazin-1-yl)-methanone, trifluoro-acetic acid salt | 95.92 |
| 6-(3,4-Dichloro-phenyl)-pyrimidine-4-carboxylic acid (2-hydroxy-2-methyl-propyl)-amide | 57.19 |
| 6-(3,4-Dichloro-phenyl)-pyrimidine-4-carboxylic acid [3-(2,6-dimethyl-morpholin-4-yl)-phenyl]-amide | 57.56 |
| 6-(3,4-Dichloro-phenyl)-pyrimidine-4-carboxylic acid [1-(3-oxo-3,4-dihydro-2H-benzo[1,4]oxazin-6-yl)-ethyl]-amide | 99.66 |
| 6-(3,4-Dichloro-phenyl)-pyrimidine-4-carboxylic acid (tetrahydro-furan-3S-yl)-amide | 53.41 |
| 6-(3,4-Dichloro-phenyl)-pyrimidine-4-carboxylic acid (tetrahydro-furan-3R-yl)-amide | 41.5 |
| (S)-2-{[6-(3,4-Dichloro-phenyl)-pyrimidine-4-carbonyl]-amino}-3-hydroxy-propionic acid | 101.22 |
| [6-(3,4-Dichloro-phenyl)-pyrimidin-4-yl]-[4-(morpholine-4-carbonyl)-piperazin-1-yl]-methanone | 40.38 |
| 6-(3,4-Dichloro-phenyl)-pyrimidine-4-carboxylic acid (1-piperidin-4-yl-ethyl)-amide hydrochloride salt | 85.09 |
| 6-(3,4-Dichloro-phenyl)-pyrimidine-4-carboxylic acid (3-piperidin-4-yl-phenyl)-amide hydrochloride salt | 69.06 |
| 6-(3-Chloro-2-fluoro-phenyl)-pyrimidine-4-carboxylic acid pyridin-3-yl-amide | 100.83 |
| (R)-2-{[6-(3,4-Dichloro-phenyl)-pyrimidine-4-carbonyl]-amino}-3-hydroxy-propionic acid | 91.12 |
| 6-(3,4-Dichloro-phenyl)-pyrimidine-4-carboxylic acid (4-dimethylamino-tetrahydro-pyran-4-ylmethyl)-amide hydrochloride salt | 96.81 |
| 6-(3,4-Dichloro-phenyl)-pyrimidine-4-carboxylic acid (2,4,6-trimethyl-phenyl)-amide | 70.84 |
| 6-(3,4-Dichloro-phenyl)-pyrimidine-4-carboxylic acid (2,4-dimethyl-pyridin-3-yl)-amide | 85.37 |
| 6-(3,4-Dichloro-phenyl)-pyrimidine-4-carboxylic acid (6-methyl-pyridazin-3-yl)-amide | 77.125 |
| 6-(3,4-Dichloro-phenyl)-pyrimidine-4-carboxylic acid (1-aza-bicyclo[2.2.2]oct-3-yl)-amide | 100.905 |
| 6-(3,4-Dichloro-phenyl)-pyrimidine-4-carboxylic acid (3-tert-butyl-isothiazol-5-yl)-amide | |
| 4-[6-(3-Chloro-4-fluoro-phenyl)-pyrimidine-4-carbonyl]-piperazin-2-one | 100.85 |
| 4-[6-(3,4-Difluoro-phenyl)-pyrimidine-4-carbonyl]-piperazin-2-one | 100.995 |
| 6-(3,4-Dichloro-phenyl)-pyrimidine-4-carboxylic acid (3,5-dimethyl-pyrazin-2-yl)-amide | 97.84 |
| 6-(3,4-Dichloro-phenyl)-pyrimidine-4-carboxylic acid [1,3,4]oxadiazol-2-ylamide | 101.93 |
| 6-(3,4-Dichloro-phenyl)-pyrimidine-4-carboxylic acid (1-aza-bicyclo[2.2.2]oct-4-ylmethyl)-amide hydrochloride salt | 65.78 |
| 6-(3,4-Dichloro-phenyl)-pyrimidine-4-carboxylic acid (3-trifluoromethyl-isoxazol-5-yl)-amide | 101.875 |
| 2-[6-(3,4-Dichloro-phenyl)-pyrimidine-4-carbonyl]-hexahydro-pyrrolo[1,2-a]pyrazin-6-one | 97.22 |
| 6-(3,4-Dichloro-phenyl)-pyrimidine-4-carboxylic acid (5-oxo-pyrrolidin-3-yl)-amide | 83.73 |
| 6-(3,4-Dichloro-phenyl)-pyrimidine-4-carboxylic acid [5-(1-hydroxy-1-methyl-ethyl)-[1,3,4]oxadiazol-2-yl]-amide | 102.115 |
| 1-{4-[6-(3,4-Dichloro-phenyl)-pyrimidine-4-carbonyl]-piperazin-1-yl}-3-pyrrolidin-1-yl-propan-1-one | 68.48 |
| 6-(3,4-Dichloro-phenyl)-pyrimidine-4-carboxylic acid ((R)-2-hydroxy-1-methyl-propyl)-amide | 66.43 |
| 6-(3,4-Dichloro-phenyl)-pyrimidine-4-carboxylic acid ((S)-1-carbamoyl-propyl)-amide | 87.6 |
| 6-(3,4-Dichloro-phenyl)-pyrimidine-4-carboxylic acid ((S)-1-carbamoyl-ethyl)-amide | 47.73 |
| 6-(3,4-Dichloro-phenyl)-pyrimidine-4-carboxylic acid (5-oxo-pyrrolidin-2-yl)-amide | 93.08 |
| 4-[6-(3-Bromo-phenyl)-pyrimidine-4-carbonyl]-piperazin-2-one | 96.625 |
| 4-[6-(3,4-Dichloro-phenyl)-pyrimidine-4-carbonyl]-3-methyl-piperazin-2-one | 97.9 |
| (S)-2-{[6-(3,4-Dichloro-phenyl)-pyrimidine-4-carbonyl]-amino}-propionic acid | 100.865 |
| 1-[6-(3,4-Dichloro-phenyl)-pyrimidine-4-carbonyl]-2,2,5,5-tetramemyl-pyrrolidine-3-carboxylic acid amide | 98.27 |
| 6-(3,4-Dichloro-phenyl)-pyrimidine-4-carboxylic acid (5-trifluoromethyl-[1,3,4]oxadiazol-2-yl)-amide | 102.78 |
| 6-(3-Bromo-phenyl)-pyrimidine-4-carboxylic acid (5-methyl-[1,3,4]oxadiazol-2-yl)-amide | 102.59 |
| 6-(3,4-Dichloro-phenyl)-pyrimidine-4-carboxylic acid ((S)-1-acetyl-pyrrolidin-3-yl)-amide | 84.87 |
| (3aS,6aR)-5-[6-(3,4-Dichloro-phenyl)-pyrimidine-4-carbonyl]-tetrahydro-pyrrolo[3,4-c]pyrrole-1,3-dione | 95.73 |
| 6-(3,4-Dichloro-phenyl)-pyrimidine-4-carboxylic acid (4-hydroxy-tetrahydro-pyran-4-ylmethyl)-amide | 74.49 |
| 6-(3,4-Dichloro-phenyl)-pyrimidine-4-carboxylic acid [2-oxo-2-(3-oxo-piperazin-1-yl)-ethyl]-amide | 62.23 |
| ((S)-3-Amino-pyrrolidin-1-yl)-[6-(3,4-dichloro-phenyl)-pyrimidin-4-yl]-methanone | 93.99 |
| N-{(S)-1-[6-(3,4-Dichloro-phenyl)-pyrimidine-4-carbonyl]-pyrrolidin-3-yl}-3-dimethylamino-propionamide | 91.785 |
| 6-(3,4-Dichloro-phenyl)-pyrimidine-4-carboxylic acid (3-piperazin-2-yl-phenyl)-amide hydrochloride salt | 96.58 |
| 6-(3-Bromo-phenyl)-pyrimidine-4-carboxylic acid | 102.1 |
| 6-(3,4-Dichloro-phenyl)-pyrimidine-4-carboxylic acid methoxy-methyl-amide | 103.74 |
| 6-(3-Bromo-phenyl)-pyrimidine-4-carboxylic acid sodium salt | 101.5 |
| N-[6-(3-Chloro-phenyl)-pyrimidine-4-carbonyl]-benzenesulfonamide | 100.67 |
| 3-Chloro-N-[6-(3-chloro-phenyl)-pyrimidine-4-carbonyl]-benzenesulfonamide | 101.57 |
| 3-Chloro-N-[6-(3,4-dichloro-phenyl)-pyrimidine-4-carbonyl]-benzenesulfonamide | 102.26 |
| N-[6-(3,4-Dichloro-phenyl)-pyrimidine-4-carbonyl]-benzenesulfonamide | 100.73 |
| N-[6-(3-Chloro-phenyl)-pyrimidine-4-carbonyl]-methanesulfonamide | 101.58 |
| 1-[6-(3-Chloro-phenyl)-pyrimidin-4-yl]-ethanone | 97.49 |
| 1-[6-(3-Chloro-phenyl)-pyrimidin-4-yl]-ethanone O-methyl-oxime | 102.2 |
| 6-(3,4-Dichloro-phenyl)-pyrimidine-4-carboxylic acid (6-piperazin-1-yl-pyridin-3-yl)-amide hydrochloride salt | 87.82 |
| 1-[6-(3,4-Dichloro-phenyl)-pyrimidine-4-carbonyl]-pyrrolidine-3-carboxylic acid | 101.855 |
| [6-(3,4-Dichloro-phenyl)-pyrimidin-4-yl]-[3-(morpholine-4-carbonyl)-pyrrolidin-1-yl]-methanone | 90.83 |
| 1-[6-(3,4-Dichloro-phenyl)-pyrimidine-4-carbonyl]-pyrrolidine-3-carboxylic acid amide | 101.835 |
| 1-[6-(3,4-Dichloro-phenyl)-pyrimidine-4-carbonyl]-pyrrolidine-3-carboxylic acid methylamide | 83.065 |
| 1-[6-(3,4-Dichloro-phenyl)-pyrimidine-4-carbonyl]-pyrrolidine-3-carboxylic acid cyclopropylamide | 91.815 |
| 1-[6-(3-Bromo-phenyl)-pyrimidine-4-carbonyl]-pyrrolidine-3-carboxylic acid | 93.05 |
| 4-[6-(3,4-Dichloro-phenyl)-pyrimidine-4-carbonyl]-1-(2-pyrrolidin-1-yl-ethyl)-piperazin-2-one | 99.275 |
| 4-[6-(3,4-Dichloro-phenyl)-pyrimidine-4-carbonyl]-1-(tetrahydro-pyran-4-ylmethyl)-piperazin-2-one | 99.91 |
| 4-[6-(3,4-Dichloro-phenyl)-pyrimidine-4-carbonyl]-1-(2-morpholin-4-yl-ethyl)-piperazin-2-one | 98.703333 |
| 6-(3,4-Dichloro-phenyl)-pyrimidine-4-carboxylic acid (S)-pyrrolidin-3-ylamide hydrochloride salt | 89.355 |
| 6-(3,4-Dichloro-phenyl)-pyrimidine-4-carboxylic acid (R)-pyrrolidin-3-ylamide hydrochloride salt | 95.94 |
| 6-(3,4-Dichloro-phenyl)-pyrimidine-4-carboxylic acid ((S)-1-acetyl-pyrrolidin-3-yl)-amide | 98.54 |
| 6-(3,4-Difluoro-phenyl)-2-methyl-pyrimidine-4-carboxylic acid | 100 |
| 6-Naphthalen-2-yl-pyrimidine-4-carboxylic acid | 96 |
| 6-Biphenyl-3-yl-pyrimidine-4-carboxylic acid | 70 |
| N-[6-(3-Chloro-4-fluoro-phenyl)-pyrimidin-4-yl]-benzenesulfonamide | 98 |
| 5-amino-6-(3,4-dichlorophenyl)pyrimidine-4-carboxylate | 72 |
| N-[6-(3,4-dichlorophenyl)pyrimidin-4-yl]-2-fluorobenzene-1-sulfonamide | 103 |
| N-[6-(3,4-dichlorophenyl)pyrimidin-4-yl]-N-methylbenzenesulfonamide | 27 |

TABLE 2-continued

| IUPAC name | % Inhibition at 10 uM* |
|---|---|
| 4-(3,4-dichlorophenyl)-5H,7H-furo[3,4-d]pyrimidin-7-one | 94 |
| 6-(3,4-dichlorophenyl)-5-(hydroxymethyl)pyrimidine-4-carboxylate | 95 |
| N-[6-(3,4-dichlorophenyl)pyrimidin-4-yl]-3-(trifluoromethoxy)benzene-1-sulfonamide | 100 |
| N-[6-(3,4-dichlorophenyl)pyrimidin-4-yl]-2,4-dimethylbenzene-1-sulfonamide | 56 |
| N-[6-(3,4-dichlorophenyl)pyrimidin-4-yl]-3-fluorobenzene-1-sulfonamide | 102 |
| N-[6-(3-chloro-4-fluorophenyl)pyrimidin-4-yl]-2-fluorobenzene-1-sulfonamide | 100 |
| N-[4-(3,4-dichlorophenyl)pyridin-2-yl]benzenesulfonamide | 17 |
| 6-(3,4-dichlorophenyl)-5-(methoxymethyl)pyrimidine-4-carboxylate | 99 |
| 6-(3,4-dichlorophenyl)-5-methoxypyrimidine-4-carboxylate | 100 |
| 6-(3,4-dichlorophenyl)-N-hydroxypyrimidine-4-carboxamide | 73 |
| butyl 6-(3,4-dichlorophenyl)pyrimidine-4-carboxylate | 100 |
| 2-methylpropyl 6-(3,4-dichlorophenyl)pyrimidine-4-carboxylate | 100 |
| propan-2-yl 6-(3,4-dichlorophenyl)pyrimidine-4-carboxylate | 100 |
| 2-(morpholin-4-yl)ethyl 6-(3,4-dichlorophenyl)pyrimidine-4-carboxylate | 100 |
| (2S)-2-amino-6-{[6-(3,4-dichlorophenyl)pyrimidin-4-yl]formamido}hexanoic acid | 85 |

*Some portion of activity of amides may be due to contribution of acid precursor.

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A compound selected from the group consisting of:

6-Naphthalen-2-yl-pyrimidine-4-carboxylic acid; and

6-Biphenyl-3-yl-pyrimidine-4-carboxylic acid;

or a pharmaceutically acceptable salt thereof.

2. A pharmaceutical composition comprising a compound of claim 1, or a pharmaceutically acceptable salt thereof, and at least one pharmaceutically acceptable excipient.

3. A method of treating Huntington's disease in a subject in need of such a treatment which method comprises administering to the subject a therapeutically effective amount of a compound of claim 1 or a pharmaceutically acceptable salt thereof.

* * * * *